United States Patent
Jeffries et al.

(10) Patent No.: US 10,662,448 B2
(45) Date of Patent: May 26, 2020

(54) COMPOSITIONS AND METHODS FOR PRODUCING LIPIDS AND OTHER BIOMATERIALS FROM GRAIN ETHANOL STILLAGE AND STILLAGE DERIVATIVES

(71) Applicant: Xylome Corporation, Madison, WI (US)

(72) Inventors: Thomas W. Jeffries, Madison, WI (US); David Z. Mokry, Madison, WI (US); Christopher H. Calvey, Madison, WI (US)

(73) Assignee: XYLOME CORPORATION, Madison, WI (US)

( * ) Notice: Subject to any disclaimer, the term of this patent is extended or adjusted under 35 U.S.C. 154(b) by 136 days.

(21) Appl. No.: 15/679,825

(22) Filed: Aug. 17, 2017

(65) Prior Publication Data
US 2018/0245109 A1  Aug. 30, 2018

Related U.S. Application Data

(60) Provisional application No. 62/409,126, filed on Oct. 17, 2016.

(51) Int. Cl.
*C12N 1/16* (2006.01)
*C12P 7/64* (2006.01)
(Continued)

(52) U.S. Cl.
CPC ............... *C12P 7/649* (2013.01); *C12N 1/16* (2013.01); *C12N 15/81* (2013.01); *C12P 7/6463* (2013.01);
(Continued)

(58) Field of Classification Search
None
See application file for complete search history.

(56) References Cited

U.S. PATENT DOCUMENTS 8,110,670 B2  2/2012  Hu et al.
9,322,038 B2  4/2016  Yu et al.
(Continued)

FOREIGN PATENT DOCUMENTS

DE  102004052115 A1  4/2006
WO  WO 2007/136762 A2  11/2007
(Continued)

OTHER PUBLICATIONS

Geneseq Accession No. AXT55474, published Feb. 18, 2010 (Year: 2010).*
(Continued)

*Primary Examiner* — Richard C Ekstrom
(74) *Attorney, Agent, or Firm* — Daniel A. Blasiole; DeWitt LLP

(57) ABSTRACT

Lipogenic yeasts bioengineered to overexpress genes for lipid production, and methods of use thereof. The yeasts are modified to express, constitutively express, or overexpress an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, an auxiliary activity family 9 enzyme, or combinations thereof. The yeasts in some cases are also modified to reduce or ablate activity of certain proteins. The methods include cultivating the yeast to convert low value soluble organic stillage byproducts into lipids suitable for biodiesel production and other higher value uses.

14 Claims, 23 Drawing Sheets

Specification includes a Sequence Listing.

(51) Int. Cl.
  C12Q 1/48      (2006.01)
  C12N 15/81     (2006.01)
  C12Q 1/527     (2006.01)
  C12P 21/00     (2006.01)
  C12N 15/10     (2006.01)
  C12P 7/06      (2006.01)
  C12Q 1/40      (2006.01)

(52) U.S. Cl.
  CPC ............... *C12P 21/00* (2013.01); *C12Q 1/48* (2013.01); *C12Q 1/527* (2013.01); *C12N 15/1096* (2013.01); *C12P 7/06* (2013.01); *C12Q 1/40* (2013.01)

(56)         References Cited

U.S. PATENT DOCUMENTS

2010/0305341 A1   12/2010  Bailey et al.
  2012/0083023 A1    4/2012  Yu et al.
  2012/0264983 A1   10/2012  Hu
  2013/0137149 A1    5/2013  Phadnavis et al.
  2014/0234919 A1    8/2014  Yu et al.

FOREIGN PATENT DOCUMENTS

WO    WO 2010/118409 A1    10/2010
  WO    WO 2011/161317 A3    12/2011

OTHER PUBLICATIONS

Geneseq Accession No. BCG84303, published Dec. 17, 2015 (Year: 2015).*
UniProt Accession No. E2CWD2_LIPST, published Nov. 30, 2010 (Year: 2010).*
Matsuzawa T, Maehara T, Kamisaka Y, Ara S, Takaku H, Yaoi K. Identification and characterization of Δ12 and Δ12/Δ15 bifunctional fatty acid desaturases in the oleaginous yeast Lipomyces starkeyi. Applied microbiology and biotechnology. Oct. 1, 2018;102(20):8817-26.
Athenstaedt, Karin. "YALI0E32769g (DGA1) and YALI0E16797g (LRO1) encode major triacylglycerol synthases of the oleaginous yeast Yarrowia lipolytica." Biochimica et Biophysica Acta (BBA)—Molecular and Cell Biology of Lipids 1811.10 (2011): 587-596.
Barcia-Vieitez, Ramiro, and Juan Ignacio Ramos-Martínez. "The regulation of the oxidative phase of the pentose phosphate pathway: new answers to old problems." IUBMB life 66.11 (2014): 775-779.
Becker, Judith, et al. "Metabolic flux engineering of l-lysine production in Corynebacterium glutamicum—over expression and modification of G6P dehydrogenase." Journal of biotechnology 132.2 (2007): 99-109.
Beopoulos, Athanasios, et al. "Identification and characterization of DGA2, an acyltransferase of the DGAT1 acyl-CoA: diacylglycerol acyltransferase family in the oleaginous yeast Yarrowia lipolytica. New insights into the storage lipid metabolism of oleaginous yeasts." Applied microbiology and biotechnology 93.4 (2012): 1523-1537.
Bignell, Graham R., Ian J. Bruce, and Ivor H. Evans. "Amylolytic enzymes of Lipomyces starkeyi: purification and size-determination." Biotechnology letters 22.21 (2000): 1713-1718.
Bligh E. Graham, and W. Justin Dyer. "A rapid method of total lipid extraction and purification." Canadian journal of biochemistry and physiology 37.8 (1959): 911-917.
Boulton, Christopher A., and Colin Ratledge. "Use of transition studies in continuous cultures of Lipomyces starkeyi, an oleaginous yeast, to investigate the physiology of lipid accumulation." Microbiology 129.9 (1983): 2871-2876.
Calvey, Christopher H., Laura B. Willis, and Thomas W. Jeffries. "An optimized transformation protocol for Lipomyces starkeyi." Current genetics 60.3 (2014): 223-230.

Calvey, Christopher H., et al. "Nitrogen limitation, oxygen limitation, and lipid accumulation in Lipomyces starkeyi." Bioresource technology 200 (2016): 780-788.
Cannella, David, and Henning Jorgensen. "Do new cellulolytic enzyme preparations affect the industrial strategies for high solids lignocellulosic ethanol production?." Biotechnology and bioengineering 111.1 (2014): 59-68.
Cardenas, Javier, and Nancy A. Da Silva. "Engineering cofactor and transport mechanisms in Saccharomyces cerevisiae for enhanced acetyl-CoA and polyketide biosynthesis." Metabolic engineering 36 (2016): 80-89.
Chen, Lin, et al. "Expression, purification and characterization of a recombinant Lipomyces starkey dextranase in Pichia pastoris." Protein expression and purification 58.1 (2008): 87-93.
Choi, Jin Wook, and Nancy A. Da Silva. "Improving polyketide and fatty acid synthesis by engineering of the yeast acetyl-CoA carboxylase." Journal of biotechnology 187 (2014): 56-59.
Collett, James R., Pimphan A. Meyer, and Susanne B. Jones. Preliminary economics for hydrocarbon fuel production from cellulosic sugars. No. PNNL-23374. Pacific Northwest National Laboratory (PNNL), Richland, WA (US), Environmental Molecular Sciences Laboratory (EMSL), 2014.
Courchesne, Noémie Manuelle Dorval, et al. "Enhancement of lipid production using biochemical, genetic and transcription factor engineering approaches." Journal of biotechnology 141.1-2 (2009): 31-41.
Evans, Christopher Thomas, and Colin Ratledge. "Possible regulatory roles of ATP: citrate lyase, malic enzyme, and AMP deaminase in lipid accumulation by Rhodosporidium toruloides CBS 14." Canadian journal of microbiology 31.11 (1985): 1000-1005.
Flores, Carmen-Lisset, and Carlos Gancedo. "Yarrowia lipolytica mutants devoid of pyruvate carboxylase activity show an unusual growth phenotype." Eukaryotic cell 4.2 (2005): 356-364.
Gallagher, Anne M., Catherine T. Kelly, and William M. Fogarty. "A novel extracellular carbohydrase produced by Lipomyces tetrasporus." Applied microbiology and biotechnology 35.4 (1991): 455-460.
Garay, Luis A., et al. "Eighteen new oleaginous yeast species." Journal of industrial microbiology & biotechnology 43.7 (2016): 887-900.
Gibson, Daniel G., et al. "Enzymatic assembly of DNA molecules up to several hundred kilobases." Nature methods 6.5 (2009): 343.
Gietz, R. Daniel, and Robin A. Woods. "Transformation of yeast by lithium acetate/single-stranded carrier DNA/polyethylene glycol method." Methods in enzymology. vol. 350. Academic Press, 2002. 87-96.
Gomma, Ahmed E., et al. "Improvement in oil production by increasing Malonyl-CoA and Glycerol-3-Phosphate pools in Scenedesmus quadricauda." Indian journal of microbiology 55.4 (2015): 447-455.
Gong, Zhiwei, et al. "Co-fermentation of cellobiose and xylose by Lipomyces starkeyi for lipid production." Bioresource technology 117 (2012): 20-24.
Gorner, Christian, et al. "Genetic engineering and production of modified fatty acids by the non-conventional oleaginous yeast Trichosporon oleaginosus ATCC 20509." Green Chemistry 18.7 (2016): 2037-2046.
Hamid, Aidil Abdul, et al. "The role of ATP citrate lyase, malic enzyme and fatty acid synthase in the regulation of lipid accumulation in Cunninghamella sp. 2A1." Annals of Microbiology 61.3 (2011): 463-468.
Hammond, Earl G., et al. "Soybean oil." Bailey's industrial oil and fat products (2005).
Holdsworth, Jane E., and Colin Ratledge. "Lipid turnover in oleaginous yeasts." Microbiology 134.2 (1988): 339-346.
Holdsworth, Jane E., Marten Veenhuis, and Colin Ratledge. "Enzyme activities in oleaginous yeasts accumulating and utilizing exogenous or endogenous lipids." Microbiology 134.11 (1988): 2907-2915.
Kang, Hee-Kyoung, et al. "Cloning and characterization of a dextranase gene from Lipomyces starkeyi and its expression in Saccharomyces cerevisiae." Yeast 22.15 (2005): 1239-1248.
Kildegaard, Kanchana R., et al. "Engineering and systems-level analysis of Saccharomyces cerevisiae for production of

(56) References Cited

OTHER PUBLICATIONS 3-hydroxypropionic acid via malonyl-CoA reductase-dependent pathway." Microbial cell factories 15.1 (2016): 53.
Kim, Youngmi, et al. "Composition of corn dry-grind ethanol by-products: DDGS, wet cake, and thin stillage." Bioresource technology 99.12 (2008): 5165-5176.
Lee, So-Young, et al. "Demonstration of two independent dextranase and amylase active sites on a single enzyme elaborated by Lipomyces starkeyi KSM 22." Journal of microbiology and biotechnology 13.2 (2003): 313-316.
Li, Zhi, et al. "Overexpression of malic enzyme (ME) of Mucor circinelloides improved lipid accumulation in engineered Rhodotorula glutinis." Applied microbiology and biotechnology 97.11 (2012): 4927-4936.
Morgenstern, Ingo, Justin Powlowski, and Adrian Tsang. "Fungal cellulose degradation by oxidative enzymes: from dysfunctional GH61 family to powerful lytic polysaccharide monooxygenase family." Briefings in functional genomics 13.6 (2014): 471-481.
Moritz, Bernd, et al. "Kinetic properties of the glucose-6-phosphate and 6 phosphogluconate dehydrogenases from Corynebacterium glutamicum and their application for predicting pentose phosphate pathway flux in vivo." The FEBS Journal 267.12 (2000): 3442-3452.
Naganuma, T., et al. "Differences in enzyme activities of Lipomyces starkeyi between cells accumulating lipid and proliferating cells." Journal of basic microbiology 27.1 (1987): 35-42.
Oguro, Yoshifumi, et al. "Multicopy integration and expression of heterologous genes in the oleaginous yeast, Lipomyces starkeyi." Bioscience, biotechnology, and biochemistry 79.3 (2015): 512-515.
Ohnishi, Junko, et al. "A novel gnd mutation leading to increased L-lysine production in Corynebacterium glutamicum." FEMS microbiology letters 242.2 (2005): 265-274.
Pan, Li-Xia, et al. "Isolation of the oleaginous yeasts from the soil and studies of their lipid-producing capacities." Food technology and Biotechnology 47.2 (2009): 215-220.
Papanikolaou, Seraphim, et al. "Kinetic profile of the cellular lipid composition in an oleaginous Yarrowia lipolytica capable of producing a cocoa-butter substitute from industrial fats." Antonie van Leeuwenhoek 80.3-4 (2001): 215-224.
Punpeng, Boontiam, et al. "A novel raw-starch-digesting yeast α-amylase from Lipomyces starkeyi HN-606." Journal of fermentation and bioengineering 73.2 (1992): 108-111.
Rangasamy, Dhandapani, and Colin Ratledge. "Genetic enhancement of fatty acid synthesis by targeting rat liver ATP: citrate lyase into plastids of tobacco." Plant physiology 122.4 (2000): 1231-1238.
Ratledge, C. Lipid biotechnology—a wonderland for the microbial physiologist. Journal of the American Oil Chemists Society 64, 1647-1656 (1987).
Ratledge, Colin. "Regulation of lipid accumulation in oleaginous micro-organisms." (2002): 1047-1050.
Ratledge, Colin. "Fatty acid biosynthesis in microorganisms being used for single cell oil production." Biochimie 86.11 (2004): 807-815.
Ratledge, Colin. "The role of malic enzyme as the provider of NADPH in oleaginous microorganisms: a reappraisal and unsolved problems." Biotechnology letters 36.8 (2014): 1557-1568.
Riley Robert, et al. "Comparative genomics of biotechnologically important yeasts." Proceedings of the National Academy of Sciences 113.35 (2016): 9882-9887.
Rippa, Mario, et al. "6-Phosphogluconate dehydrogenase: the mechanism of action investigated by a comparison of the enzyme from different species1." Biochimica et Biophysica Acta (BBA)—Protein Structure and Molecular Enzymology 1429.1 (1998): 83-92.
Ruenwai, Rawisara, Supapon Cheevadhanarak, and Kobkul Laoteng. "Overexpression of acetyl-CoA carboxylase gene of Mucor rouxii enhanced fatty acid content in Hansenula polymorpha." Molecular biotechnology 42.3 (2009): 327-332.
Ryu, S.J. et al. "Purification and partial characterization of a novel glucanhydrolase from Lipomyces starkeyi KSM 22 and its use for inhibition of insoluble glucan formation." Bioscience, biotechnology, and biochemistry 64.2 (2000): 223-228.
Saenge, Chanika, et al. "Potential use of oleaginous red yeast Rhodotorula glutinis for the bioconversion of crude glycerol from biodiesel plant to lipids and carotenoids." Process Biochemistry 46.1 (2011): 210-218.
Shi, Shuobo, et al. "Improving production of malonyl coenzyme A-derived metabolites by abolishing Snf1-dependent regulation of Acc1." MBio 5.3 (2014): e01130-14.
Sitepu, I. R., et al. "An improved high-throughput Nile red fluorescence assay for estimating intracellular lipids in a variety of yeast species." Journal of microbiological methods 91.2 (2012): 321-328.
Steyn, Andries JC, Julius Marmur, and Isak S. Pretorius. "Cloning, sequence analysis and expression in yeasts of a cDNA containing a Lipomyces kononenkoae α-amylase-encoding gene." Gene 166.1 (1995): 65-71.
Tai, Mitchell, and Gregory Stephanopoulos. "Engineering the push and pull of lipid biosynthesis in oleaginous yeast Yarrowia lipolytica for biofuel production." Metabolic engineering 15 (2013): 1-9.
Tang, Wei, et al. "The isocitrate dehydrogenase gene of oleaginous yeast Lipomyces starkeyi is linked to lipid accumulation." Canadian journal of microbiology 55.9 (2009): 1062-1069.
Tang, Xiaoling, Huixing Feng, and Wei Ning Chen. "Metabolic engineering for enhanced fatty acids synthesis in Saccharomyces cerevisiae." Metabolic engineering 16 (2013): 95-102.
Tang, Xiaoling, and Wei Ning Chen. "Investigation of fatty acid accumulation in the engineered Saccharomyces cerevisiae under nitrogen limited culture condition." Bioresource technology 162 (2014): 200-206.
Van Rossum, Harmen M., et al. "Engineering cytosolic acetyl-coenzyme A supply in Saccharomyces cerevisiae: pathway stoichiometry, free-energy conservation and redox-cofactor balancing." Metabolic engineering 36 (2016): 99-115.
Velasco, Pilar, et al. "The modulation of the oxidative phase of the pentose phosphate pathway in mouse liver." The international journal of biochemistry & cell biology 27.10 (1995): 1015-1019.
Vicente, Gemma, et al. "Direct transformation of fungal biomass from submerged cultures into biodiesel." Energy & Fuels 24.5 (2010): 3173-3178.
Wang, Zhi-Peng, et al. "Disruption of the MIG1 gene enhances lipid biosynthesis in the oleaginous yeast Yarrowia lipolytica ACA-DC 50109." Biochimica et Biophysica Acta (BBA)—Molecular and Cell Biology of Lipids 1831.4 (2013): 675-682.
Wang, Jiancai, et al. "Overexpression of ACC gene from oleaginous yeast Lipomyces starkeyi enhanced the lipid accumulation in Saccharomyces cerevisiae with increased levels of glycerol 3-phosphate substrates." Bioscience, biotechnology, and biochemistry 80.6 (2016): 1214-1222.
Wilkie, Ann C., Kelly J. Riedesel, and John M. Owens. "Stillage characterization and anaerobic treatment of ethanol stillage from conventional and cellulosic feedstocks." Biomass and Bioenergy 19.2 (2000): 63-102.
Wynn, James P., Aidil bin Abdul Hamid, and Colin Ratledge. "The role of malic enzyme in the regulation of lipid accumulation in filamentous fungi." Microbiology 145.8 (1999): 1911-1917.
Xuan, Jian-Wu, Philippe Fournier, and Claude Gaillardin. "Cloning of the LYS5 gene encoding saccharopine dehydrogenase from the yeast Yarrowia lipolytica by target integration." Current Genetics 14.1 (1988): 15-21.
Yen, Hong-Wei, Ya-Chun Yang, and Yi-Huan Yu. "Using crude glycerol and thin stillage for the production of microbial lipids through the cultivation of Rhodotorula glutinis." Journal of bioscience and bioengineering 114.4 (2012): 453-456.
Zha, Jian, et al. "Enhanced expression of genes involved in initial xylose metabolism and the oxidative pentose phosphate pathway in the improved xylose-utilizing Saccharomyces cerevisiae through evolutionary engineering." Journal of industrial microbiology & biotechnology 41.1 (2014): 27-39.
Zhang, Ying, Ian P. Adams, and Colin Ratledge. "Malic enzyme: the controlling activity for lipid production? Overexpression of malic enzyme in Mucor circinelloides leads to a 2.5-fold increase in lipid accumulation." Microbiology 153.7 (2007): 2013-2025.

(56) References Cited

OTHER PUBLICATIONS

Zhang, Yong, et al. "New industrial brewing yeast strains with ILV2 disruption and LSD1 expression." International Journal of Food Microbiology 123 (2008): 18-24.

Zhang, Man, Luciano Galdieri, and Ales Vancura. "The yeast AMPK homolog SNF1 regulates acetyl coenzyme A homeostasis and histone acetylation." Molecular and cellular biology 33.23 (2013): 4701-4717.

Zhao, Xin, et al. "Medium optimization for lipid production through co-fermentation of glucose and xylose by the oleaginous yeast Lipomyces starkeyi." European Journal of Lipid Science and Technology 110.5 (2008): 405-412.

Zhou, Yongjin J., et al. "Production of fatty acid-derived oleochemicals and biofuels by synthetic yeast cell factories." Nature communications 7 (2016): ncomms11709.

Zhu, Z.W. et al. in Nature Communications, vol. 3 (2012).

\* cited by examiner

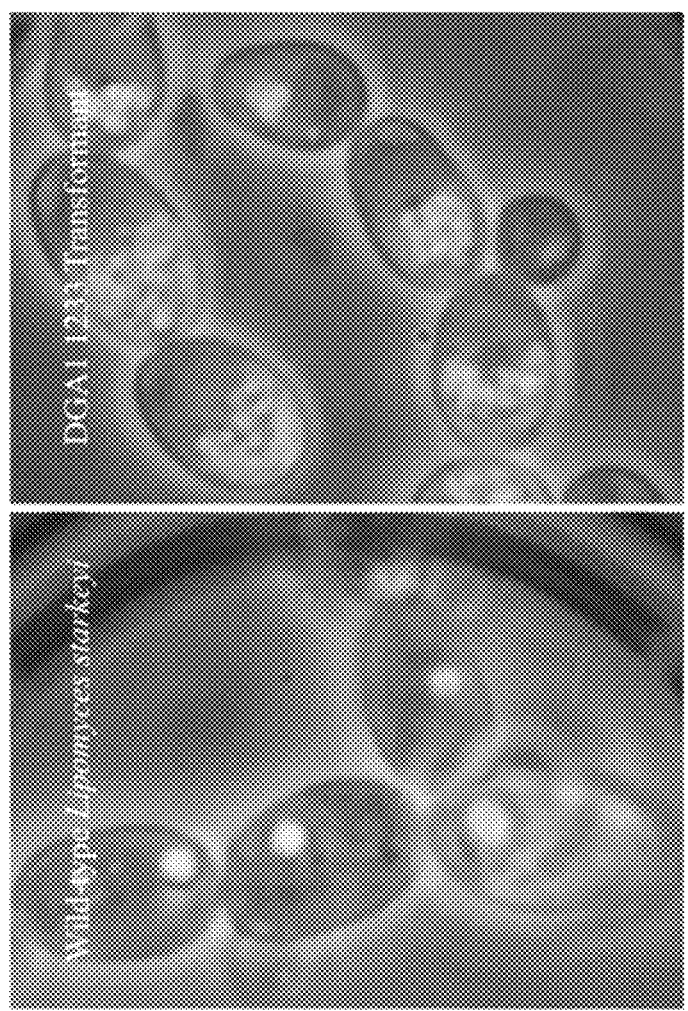
FIG. 11C
FIG. 11B
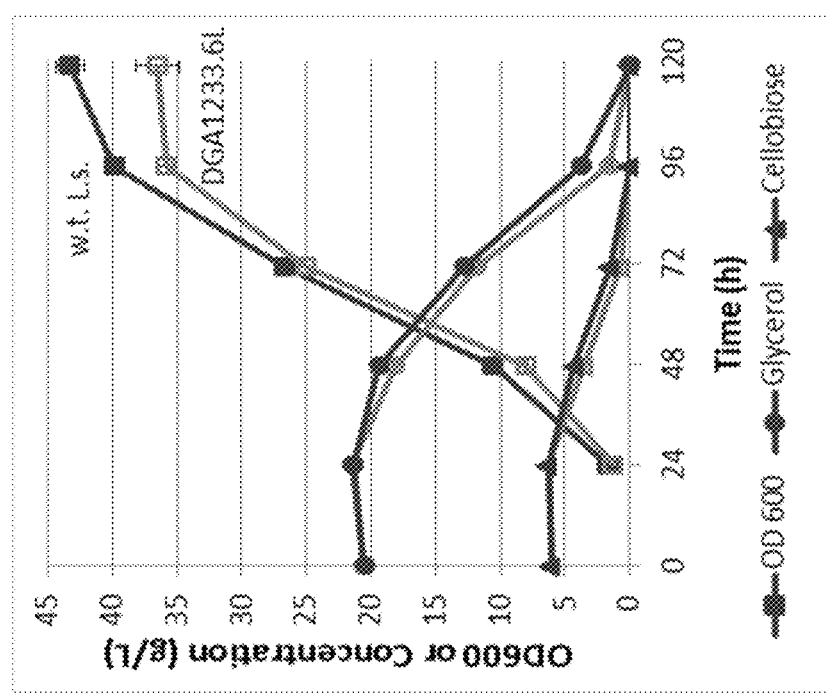
FIG. 11A

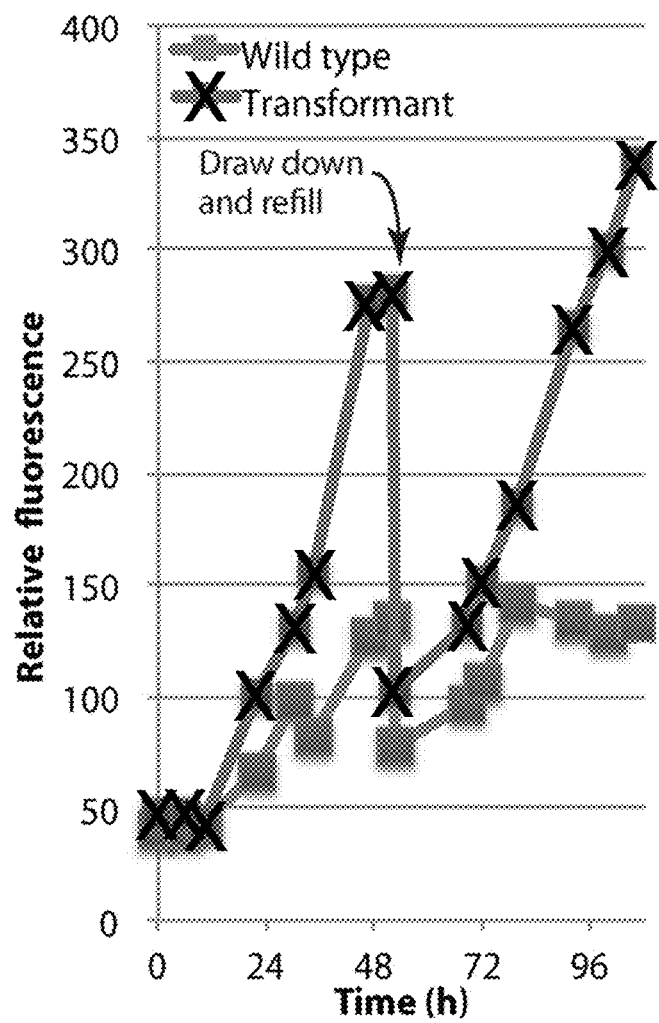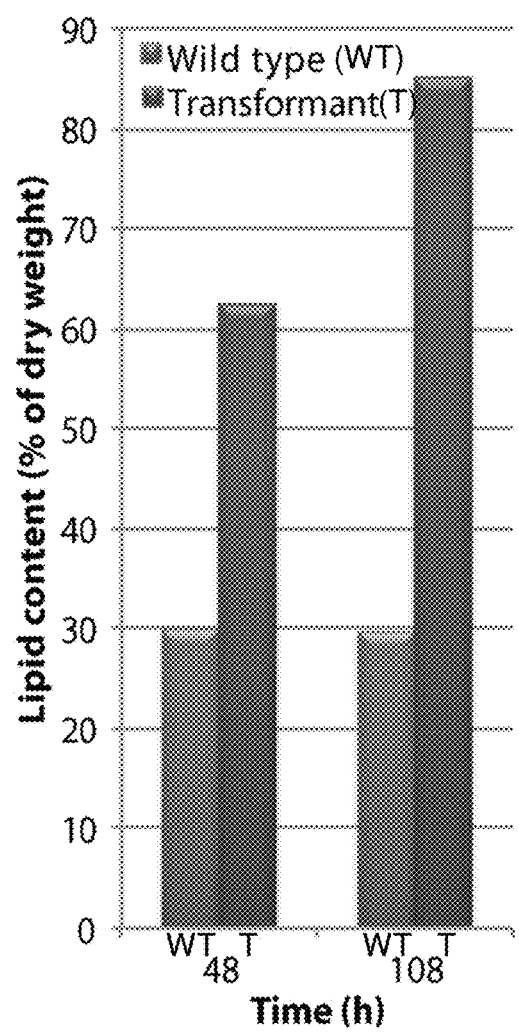
FIG. 12A  FIG. 12B

Rescue of GUT1 Growth Defect

Average Fluorescence GUT1/GUT2 Transformants

SEQUENCE LISTING

<160> NUMBER OF SEQ ID NOS: 91

<210> SEQ ID NO 1
<211> LENGTH: 6932
<212> TYPE: DNA
<213> ORGANISM: Lipomyces starkeyi
<220> FEATURE:
<221> NAME/KEY: Intron
<222> LOCATION: (124)..(189)
<220> FEATURE:
<221> NAME/KEY: Intron
<222> LOCATION: (2833)..(2889)
<220> FEATURE:
<221> NAME/KEY: Intron
<222> LOCATION: (2972)..(3027)
<220> FEATURE:
<221> NAME/KEY: Intron
<222> LOCATION: (4522)..(4569)

<400> SEQUENCE: 1

```
atgtctgctg cggccagtag cctccctcc cactttatcg gccttaacac cgtcgatgtg      60
gcggccaata gccccgttaa ggattttgtc cagaatcatg gtggtcacac cgtcatcact     120
tccgtacgtg accgatctgt ttcctctttg atctttgtcg catcatgact gacgatctaa     180
tccatttagg ttctcatagc gaacaacggt atcgccgctg tcaaggaaat ccgcagtgtc     240
cggaaatggg cctacgagac tttcggcgac gagcgcgcca tctccttcac cgtcatggcc     300
acgcctgagg atctcaaggc aaacgcggat tacatccgca tggcagatca gtacgtcgaa     360
gttcccggcg ggacaaacaa caacaatttc gccaacgtcg agctcatcgt cgatatcgcc     420
gagcgcatga acgtccacgc cgtctgggcc ggctgggac atgcctccga aaacccaaag      480
ctcccagagt ctctcgcgca gtcgccaaag aagatcgtct tcatcggccc gcccggatcc     540
gccatgcggt ctctcggtga caagatctcg tccaccatag ttgcccagca cgcaaaagtc     600
ccctgtattc cctggtctgg aaccggcgtg gacgaagtcc agattgattc tgttagcggt     660
ctcgtcaccg tgtccgatga gatatacgca aagggttgta cttccaccgc ggaagaggct     720
ctcgagaagg cccgcatcat cggcttcccc gtcatgatca aggcttccga aggtggcggt     780
ggcaaaggta ttcgaaaggt cgagagcgag gacaacttcc attctttgta cagccaggtt     840
gccaatgagg tccctggatc tcccatcttc gtcatgaagc ttgccggcaa cgcgcgacat     900
cttgaggtcc aattgcttgc cgatcaatac ggaaacaaca tctctctctt tggcagagat     960
tgctcagtcc agcgtcgtca ccagaagatt atcgaagagg cgcctgtcac tgttgccaac    1020
cccgcaacat tctcggcaat ggaacacgcc gctgttcgac ttggccagct tgtcggctat    1080
gtctccgccg gtacagtcga gtacctctac tctcacgacg acgacaaatt ctacttcttg    1140
gagctcaatc cccgtcttca ggtagagcat cctactaccg agatggtcac cggtgtcaac    1200
ttacccgccg ctcagctcca aatcgcgatg ggtgtgtctc tccaccgaat cagagatatc    1260
cggctcttct acggcgtcga tcctcacact tcgaccgaaa tcgactttga tttctccaag    1320
gagggctctc ttcaaaactca gcgccgtcca gtgcccaagg ccacaccac ggcctgccga     1380
atcacgtccg aagatcctgg cgaaggtttc aaaccatcta gtggtgtcat gcacgaactg    1440
aactttagat cgagctccaa tgtctggggt tacttctccg tcggaaatca gggcggaatc    1500
```

```
cactcgttct ccgattccca gttcggtcat atctttgcat tcggcgaaaa cagaagcgcg    1560
agtcgcaagc acatggttgt cgcgttgaag gaattgtcta ttcgtggtga cttccgcact    1620
acggtcgaat atctcattaa gctgcttgag actcctgatt tcgagtctaa caagatcacc    1680
accggatggc tcgatgagct aatttccaag aagctcaccg ccgagcgccc tgatcctgtc    1740
gtcgctgttg tctgcggcgc tgtcacgaag gcacatcttg cttcagaggc ttgcttccag    1800
gagtacaaga attccctaga gaagggccag gtcccgtcga aggacatcct aaagactttg    1860
ttccctgtcg actttatcta cgagggcagc cgatacaagt tcactgtcac gcgatcgtcc    1920
atggatttgt atcagatttt catcaacggt tccaagtgcc tggtcggtgt caaatcactc    1980
agtgacggtg gtcttttggt tttgctcgga ggcaagtccc acaatgtgta ctggaaggac    2040
gaagttggaa ccaccagact cagtgtcgac tccaagactt gcttgttgga gcaggagaat    2100
gatcctaccc agctccgcac tccttccccc ggtaagctcg tcaagttctt ggtcgagaac    2160
ggtgagcacg tcaagactgg acagccgttt gctgaagttg aggtcatgaa gatgtacatg    2220
cccctgattg ctcaggagga cggtatcgtg caattgatca gcagcctgg agctactctc    2280 gaggctggcg atattctcgg catttagct ctagatgatc catcccgcgt caaacacgcc    2340
aagcccttcg agggtcaact gcctgatttc ggttcgccat tggttctagg cagcaagcct    2400
tcgcagcgat tcaatctgtt gctaagcacc ctcaggaaca ttctggctgg ttttgacaac    2460
caggtcttgt tggcgtcgac tctcaaggat ctgagccaag tattaaagga cgacgcgctg    2520
ccctatagtg agtggaacgc tcagttctcc gcccttcaca gtcgtatccc gcagaagctc    2580
gacgcgactc tttccagtct tatcgagcgc tccaagtcca aggacgctga attcccggca    2640
aagttgctgt tgcgcgctat tgagcgattt gctgaagagt tcatccagcc gcaggatcta    2700
tttgtcttca gcaacaggt cgagcctctt gttaccattg ctacgagata ccaggctggt    2760
ttgaaagcac atgagtatgg tgtcattgct gaattgttgg agcagtattt ggctgtcgag    2820
aaattgtttt cggtgagccg cacacttttc tgttgctgtt atggacgggc cgcgtactaa    2880
catttgtagg gcgccaatat tcgggatgag gatgttttc tcagacttag agatgaaaat    2940
aaggatgata ttttcaaggt tgtcatgact ggtatgttaa tttgttgtcg cgccggcttt    3000
cgagtaccag tatgttgatg tcactagtat tctctcacgg tcgcgttgga gctaagaaca    3060
acctcatcct cgcaattta gccgcacttc gatccgacag atctgaggtt tccgaggtcg    3120
ctaaatactt gcggcctgct ctcaagacat taacggagct tgactcaggt gtcactgccc    3180
ctgtggctct caaggctcgt gaactattga tccagtgcgc acttccatct ctcgaggagc    3240
gaaccgccca gctcgaacat atattgcgct cgtctgttgt tgagtcgcga tacggtgagg    3300
tgggctttga gcacagtgct cccagaattg acgtcttgaa ggaggtcatt gactcgcaat    3360
acatcgtttt tgacgttctg ccaaagtttt tcgcgcactc ggatcgttat gtcacccttag    3420 ccgcactcga gctctacgtc cgtcgcgctt atcgcgcgta taacgtcatg agcatggagt    3480
accacaacga aggcgatctt gtgcccgtcg tcacgttcaa gttttttgctt gccgctattg    3540 gcaatcccgc ttacaacatc gtcggacagg gtgctccgtc aggcgattcg cgcattgatt    3600
tccagcgtgc tgcggcggtt tcggatctca catttatgat gagcaagtcc gacagcgagt    3660
ccttgcgatc cggtgtgatt gttcccgtgg ctgatattgc tgatattgac gaagttctcc    3720
ctcgtgcttt ggattacctc ccacagcgag ccggtgcggg atcgggaggc ttctccttct    3780
cggctaaatc tgatttggac tcgaagcgac gaccagcacc gccaaagcca gagtctttga    3840
gcaatatctg caacgttttg atccgcaaga cggcaaaaac cgacgacgct gcacttgtct    3900
```

```
cggatatcaa gttcatcgtc gatgagtaca aggaggagtt cttgcttcga tctattcgac    3960
gagttacatt cgtttgcggc cgcgaggacg gttcgtatcc tggttatttt acgttccgcg    4020
gtcctgacta cgtcgaggac gagagtatcc gacatattga gcctgcgttg gcgtaccagc    4080
ttgagttggg acgtttgtcg aactttaact ataagccgat tttcacggat aaccgcaaca    4140
ttcacgtcta ccaggccatc ggcaaggacg ttcctagcga caagcgtttc ttcgtgagag    4200
gtatcgtcag acccggccgt ctacgtgatg aaattccgac gtcggaatac cttatctctg    4260
aaaccgaccg actgatgtcg gacattttgg acgctctcga ggttatcggt cctaataaca    4320
cggatatgaa ccacatttc atcaactttt cgcccatttt ccatttggta ccggaagagg    4380
tcgaggcagc atttggacag ttcttggaga gatttggacg cagattgtgg agattgagag    4440
tgactggtgc ggagatccgg attatgtgca ccgacccgga gactaatgtg ccgtaccct    4500 tgcgtgcgat tatcacgaat ggtgagtatc tttcatactt ttttttcggc tgctgctaat    4560
tttcgttagt gtccggctat gtcgtccaga gtgagttgta cacggaggtc aagaatgata    4620
agggccaatg ggtgttcaag tcgttgggta agccaggtaa catgcacttg cgctcgatca    4680
cgactccata cgcgaccaag gaatggctac agccgaagag atacaaggca cacttgatgg    4740
gcacgacatt cgtgtacgat ttcccagagc ttttcaacca agctattcgt gctagttggc    4800
gtgcagcgca gcagcagtcg cccgagaatg tgcttacgta caaggagctt atcatggatg    4860
acagtggaga gttgtcggag gtttctcgag agccaggtgc gaatacttgc ggaatggttg    4920
cctggttgtt cacggcgctc actcccgaat atccaacggg ccgtcaattc atcgtggtcg    4980
ccaatgatat cacttacaag attggctcct tcggtcctca ggaggataag tacttccaca    5040
ctgtgaccca gctcgccgtc aaacttggca ttccccgaat ctatctctct gcaaactctg    5100
gtgcgcgaat tggcgttgcg gacgaatttg tgtcattgtt ctcggtcgcc tggaatgatt    5160
cttccaatcc tgaaaaggga ttcaagtact tgtacctcac gcctgcgatc tacaacggtc    5220
tttcggacgc ggccaagaag actgtgctta ccgaacgcat tgttgaggag ggcgaggagc    5280
gatatgttat caccaccatt atcggcgctg aagacggtct tggtgtcgag tgtcttcgtg    5340
gatcgggtct cattgccggc gctacttcga aggcttataa agacattttc acgattactt    5400
tggtcacttg ccgttcggtt ggtattggtg cttatctcgt ccgtctcgga cagcgtgcga    5460
tccagattga gggccagcct atcatactta ctggtgctcc tgcgatcaac aaactccttg    5520
gtcgggaagt ttacagttcg aatttgcagc tcggtggcac gcagatcatg tacaagaacg    5580
gtgtatcgca tcttaccgct aatgatgacc ttgctggtgt catgaagatt atcgagtgga    5640
tgtcatacgt accgtataag aaaggtggtc agctgccaat ttatccatca tcagatacct    5700
gggatcgtga tgtcacttat actcctccca aacaggtccc gtacgatgtc cgatggctga    5760
tcgctggtcg cgaggacgag gagggcggtt tcgagtacgg tttgttcgac aaagactcgt    5820
tccaggagac ccttagcggc tgggctcgaa ctgtcgttgt cggtcgtgcg cggttaggcg    5880
gcatccctgt cggcgtaatt ggcgttgaag tccgctcggt cgagaacatt ttccccgccg    5940
atcctgccaa tcccgattcg acagaaatgg tcgtccagga agccggccag gtttggtacc    6000
ccaactcggc atttaagact gctcaggcga ttaacgattt caaccacggt gaggagcttc    6060
cgctcgtaat cctcgccaac tggagaggtt tctctggcgg tcagcgtgat atgtacaacg    6120
aggtcttgaa gtacgttcg ttcatcgtgg atgcgctcgt tggttacaag cagcctattt    6180
tcgtctacat tccgccgcat gcagagctcc gtggtggttc atgggttgtt atcgatccca    6240
```

```
ccatcaactc tgatcagatg gagatgtacg cggatgacga ggcacgtgct ggtgtgttgg    6300
agcccgaggg tatggttggc atcaagtacc gtcgtgaccg tctcttggag accatgactc    6360
gtctcgaccc ggtctatgcc tcgctcaagc gccaggccga caagaaagat ctcgctccgg    6420
caatcgctca ggatctcaaa gtcaagttga gcgaacggga agcacattg atgccaatct     6480 accgacagat cagcttacag ttcgccgact gcatgaccg gcaggacga atgaaggcga      6540 agggaactat ccgtgaagtc cttcactggc gtgaggctag acgtttcttc tactggcgtg    6600
ttagacgtcg tgttggcgag agctatattc ttcgtgatct ggaggctgct aacccgaaat    6660 cgacagagact agaacgcgtc gcgcgattga agtcttggta tgctgaggct ggtatcaacg   6720
aatcttccga cgcagacgtc gcaagctgga tcgagaagtc tggtgccgct atcaccagca    6780
aagtcaaaca ggttagaaag gatgcaaaga tccaggactt gttggctctt gtgcgcgcgg    6840
ataaggatgt cgctttgcag ggcctggttg agtccctcaa ggctttgtct actgaggaac    6900
gggatgcgat tttcaagcag gcttctaatt aa                                  6932

<210> SEQ ID NO 2
<211> LENGTH: 2234
<212> TYPE: PRT
<213> ORGANISM: Lipomyces starkeyi

<400> SEQUENCE: 2

Met Ser Ala Ala Ala Ser Ser Leu Pro Ser His Phe Ile Gly Leu Asn
1               5                   10                  15

Thr Val Asp Val Ala Ala Asn Ser Pro Val Lys Asp Phe Val Gln Asn
            20                  25                  30

His Gly Gly His Thr Val Ile Thr Ser Val Leu Ile Ala Asn Asn Gly
        35                  40                  45

Ile Ala Ala Val Lys Glu Ile Arg Ser Val Arg Lys Trp Ala Tyr Glu
    50                  55                  60

Thr Phe Gly Asp Glu Arg Ala Ile Ser Phe Thr Val Met Ala Thr Pro
65                  70                  75                  80

Glu Asp Leu Lys Ala Asn Ala Asp Tyr Ile Arg Met Ala Asp Gln Tyr
                85                  90                  95

Val Glu Val Pro Gly Gly Thr Asn Asn Asn Phe Ala Asn Val Glu
            100                 105                 110

Leu Ile Val Asp Ile Ala Glu Arg Met Asn Val His Ala Val Trp Ala
        115                 120                 125

Gly Trp Gly His Ala Ser Glu Asn Pro Lys Leu Pro Glu Ser Leu Ala
    130                 135                 140

Gln Ser Pro Lys Lys Ile Val Phe Ile Gly Pro Pro Gly Ser Ala Met
145                 150                 155                 160

Arg Ser Leu Gly Asp Lys Ile Ser Ser Thr Ile Val Ala Gln His Ala
                165                 170                 175

Lys Val Pro Cys Ile Pro Trp Ser Gly Thr Gly Val Asp Glu Val Gln
            180                 185                 190

Ile Asp Ser Val Ser Gly Leu Val Thr Val Ser Asp Glu Ile Tyr Ala
        195                 200                 205

Lys Gly Cys Thr Ser Thr Ala Glu Glu Ala Leu Glu Lys Ala Arg Ile
    210                 215                 220

Ile Gly Phe Pro Val Met Ile Lys Ala Ser Glu Gly Gly Gly Gly Lys
225                 230                 235                 240

Gly Ile Arg Lys Val Glu Ser Glu Asp Asn Phe His Ser Leu Tyr Ser
                245                 250                 255
```

```
Gln Val Ala Asn Glu Val Pro Gly Ser Pro Ile Phe Val Met Lys Leu
            260                 265                 270

Ala Gly Asn Ala Arg His Leu Glu Val Gln Leu Leu Ala Asp Gln Tyr
        275                 280                 285

Gly Asn Asn Ile Ser Leu Phe Gly Arg Asp Cys Ser Val Gln Arg Arg
    290                 295                 300

His Gln Lys Ile Ile Glu Glu Ala Pro Val Thr Val Ala Asn Pro Ala
305                 310                 315                 320

Thr Phe Ser Ala Met Glu His Ala Ala Val Arg Leu Gly Gln Leu Val
                325                 330                 335

Gly Tyr Val Ser Ala Gly Thr Val Glu Tyr Leu Tyr Ser His Asp Asp
            340                 345                 350

Asp Lys Phe Tyr Phe Leu Glu Leu Asn Pro Arg Leu Gln Val Glu His
        355                 360                 365

Pro Thr Thr Glu Met Val Thr Gly Val Asn Leu Pro Ala Ala Gln Leu
    370                 375                 380

Gln Ile Ala Met Gly Val Ser Leu His Arg Ile Arg Asp Ile Arg Leu
385                 390                 395                 400

Phe Tyr Gly Val Asp Pro His Thr Ser Thr Glu Ile Asp Phe Asp Phe
                405                 410                 415

Ser Lys Glu Gly Ser Leu Gln Thr Gln Arg Arg Pro Val Pro Lys Gly
            420                 425                 430

His Thr Thr Ala Cys Arg Ile Thr Ser Glu Asp Pro Gly Glu Gly Phe
        435                 440                 445

Lys Pro Ser Ser Gly Val Met His Glu Leu Asn Phe Arg Ser Ser Ser
    450                 455                 460

Asn Val Trp Gly Tyr Phe Ser Val Gly Asn Gln Gly Gly Ile His Ser
465                 470                 475                 480

Phe Ser Asp Ser Gln Phe Gly His Ile Phe Ala Phe Gly Glu Asn Arg
                485                 490                 495

Ser Ala Ser Arg Lys His Met Val Val Ala Leu Lys Glu Leu Ser Ile
            500                 505                 510

Arg Gly Asp Phe Arg Thr Thr Val Glu Tyr Leu Ile Lys Leu Leu Glu
        515                 520                 525

Thr Pro Asp Phe Glu Ser Asn Lys Ile Thr Thr Gly Trp Leu Asp Glu
    530                 535                 540

Leu Ile Ser Lys Lys Leu Thr Ala Glu Arg Pro Asp Pro Val Val Ala
545                 550                 555                 560

Val Val Cys Gly Ala Val Thr Lys Ala His Leu Ala Ser Glu Ala Cys
                565                 570                 575

Phe Gln Glu Tyr Lys Asn Ser Leu Glu Lys Gly Gln Val Pro Ser Lys
            580                 585                 590

Asp Ile Leu Lys Thr Leu Phe Pro Val Asp Phe Ile Tyr Glu Gly Ser
        595                 600                 605

Arg Tyr Lys Phe Thr Val Thr Arg Ser Ser Met Asp Leu Tyr Gln Ile
    610                 615                 620

Phe Ile Asn Gly Ser Lys Cys Leu Val Gly Val Lys Ser Leu Ser Asp
625                 630                 635                 640

Gly Gly Leu Leu Val Leu Leu Gly Gly Lys Ser His Asn Val Tyr Trp
                645                 650                 655

Lys Asp Glu Val Gly Thr Thr Arg Leu Ser Val Asp Ser Lys Thr Cys
            660                 665                 670
```

-continued

Leu Leu Glu Gln Glu Asn Asp Pro Thr Gln Leu Arg Thr Pro Ser Pro
    675                 680                 685

Gly Lys Leu Val Lys Phe Leu Val Glu Asn Gly Glu His Val Lys Thr
690                 695                 700

Gly Gln Pro Phe Ala Glu Val Glu Val Met Lys Met Tyr Met Pro Leu
705                 710                 715                 720

Ile Ala Gln Glu Asp Gly Ile Val Gln Leu Ile Lys Gln Pro Gly Ala
                725                 730                 735

Thr Leu Glu Ala Gly Asp Ile Leu Gly Ile Leu Ala Leu Asp Asp Pro
                740                 745                 750

Ser Arg Val Lys His Ala Lys Pro Phe Glu Gly Gln Leu Pro Asp Phe
            755                 760                 765

Gly Ser Pro Leu Val Leu Gly Ser Lys Pro Ser Gln Arg Phe Asn Leu
770                 775                 780

Leu Leu Ser Thr Leu Arg Asn Ile Leu Ala Gly Phe Asp Asn Gln Val
785                 790                 795                 800

Leu Leu Ala Ser Thr Leu Lys Asp Leu Ser Gln Val Leu Lys Asp Asp
                805                 810                 815

Ala Leu Pro Tyr Ser Glu Trp Asn Ala Gln Phe Ser Ala Leu His Ser
                820                 825                 830

Arg Ile Pro Gln Lys Leu Asp Ala Thr Leu Ser Ser Leu Ile Glu Arg
            835                 840                 845

Ser Lys Ser Lys Asp Ala Glu Phe Pro Ala Lys Leu Leu Leu Arg Ala
850                 855                 860

Ile Glu Arg Phe Ala Glu Glu Phe Ile Gln Pro Gln Asp Leu Phe Val
865                 870                 875                 880

Phe Lys Gln Gln Val Glu Pro Leu Val Thr Ile Ala Thr Arg Tyr Gln
                885                 890                 895

Ala Gly Leu Lys Ala His Glu Tyr Gly Val Ile Ala Glu Leu Leu Glu
                900                 905                 910

Gln Tyr Leu Ala Val Glu Lys Leu Phe Ser Gly Ala Asn Ile Arg Asp
            915                 920                 925

Glu Asp Val Phe Leu Arg Leu Arg Asp Glu Asn Lys Asp Asp Ile Phe
930                 935                 940

Lys Val Val Met Thr Val Phe Ser His Gly Arg Val Gly Ala Lys Asn
945                 950                 955                 960

Asn Leu Ile Leu Ala Ile Leu Ala Ala Leu Arg Ser Asp Arg Ser Glu
                965                 970                 975

Val Ser Glu Val Ala Lys Tyr Leu Arg Pro Ala Leu Lys Thr Leu Thr
            980                 985                 990

Glu Leu Asp Ser Gly Val Thr Ala Pro Val Ala Leu Lys Ala Arg Glu
        995                 1000                1005

Leu Leu Ile Gln Cys Ala Leu Pro Ser Leu Glu Glu Arg Thr Ala
    1010                1015                1020

Gln Leu Glu His Ile Leu Arg Ser Ser Val Glu Ser Arg Tyr
    1025                1030                1035

Gly Glu Val Gly Phe Glu His Ser Ala Pro Arg Ile Asp Val Leu
    1040                1045                1050

Lys Glu Val Ile Asp Ser Gln Tyr Ile Val Phe Asp Val Leu Pro
    1055                1060                1065

Lys Phe Phe Ala His Ser Asp Arg Tyr Val Thr Leu Ala Ala Leu
    1070                1075                1080

Glu Leu Tyr Val Arg Arg Ala Tyr Arg Ala Tyr Asn Val Met Ser

-continued

```
            1085                1090                1095
Met Glu Tyr His Asn Glu Gly Asp Leu Val Pro Val Val Thr Phe
    1100                1105                1110
Lys Phe Leu Leu Ala Ala Ile Gly Asn Pro Ala Tyr Asn Ile Val
    1115                1120                1125
Gly Gln Gly Ala Pro Ser Gly Asp Ser Arg Ile Asp Phe Gln Arg
    1130                1135                1140
Ala Ala Ser Val Ser Asp Leu Thr Phe Met Met Ser Lys Ser Asp
    1145                1150                1155
Ser Glu Ser Leu Arg Ser Gly Val Ile Val Pro Val Ala Asp Ile
    1160                1165                1170
Ala Asp Ile Asp Glu Val Leu Pro Arg Ala Leu Asp Tyr Leu Pro
    1175                1180                1185
Gln Arg Ala Gly Ala Gly Ser Gly Gly Phe Ser Phe Ser Ala Lys
    1190                1195                1200
Ser Asp Leu Asp Ser Lys Arg Arg Pro Ala Pro Pro Lys Pro Glu
    1205                1210                1215
Ser Leu Ser Asn Ile Cys Asn Val Leu Ile Arg Lys Thr Ala Lys
    1220                1225                1230
Thr Asp Asp Ala Ala Leu Val Ser Asp Ile Lys Phe Ile Val Asp
    1235                1240                1245
Glu Tyr Lys Glu Glu Phe Leu Leu Arg Ser Ile Arg Arg Val Thr
    1250                1255                1260
Phe Val Cys Gly Arg Glu Asp Gly Ser Tyr Pro Gly Tyr Phe Thr
    1265                1270                1275
Phe Arg Gly Pro Asp Tyr Val Glu Asp Glu Ser Ile Arg His Ile
    1280                1285                1290
Glu Pro Ala Leu Ala Tyr Gln Leu Glu Leu Gly Arg Leu Ser Asn
    1295                1300                1305
Phe Asn Tyr Lys Pro Ile Phe Thr Asp Asn Arg Asn Ile His Val
    1310                1315                1320
Tyr Gln Ala Ile Gly Lys Asp Val Pro Ser Asp Lys Arg Phe Phe
    1325                1330                1335
Val Arg Gly Ile Val Arg Pro Gly Arg Leu Arg Asp Glu Ile Pro
    1340                1345                1350
Thr Ser Glu Tyr Leu Ile Ser Glu Thr Asp Arg Leu Met Ser Asp
    1355                1360                1365
Ile Leu Asp Ala Leu Glu Val Ile Gly Pro Asn Asn Thr Asp Met
    1370                1375                1380
Asn His Ile Phe Ile Asn Phe Ser Pro Ile Phe His Leu Val Pro
    1385                1390                1395
Glu Glu Val Glu Ala Ala Phe Gly Gln Phe Leu Glu Arg Phe Gly
    1400                1405                1410
Arg Arg Leu Trp Arg Leu Arg Val Thr Gly Ala Glu Ile Arg Ile
    1415                1420                1425
Met Cys Thr Asp Pro Glu Thr Asn Val Pro Tyr Pro Leu Arg Ala
    1430                1435                1440
Ile Ile Thr Asn Val Ser Gly Tyr Val Val Gln Ser Glu Leu Tyr
    1445                1450                1455
Thr Glu Val Lys Asn Asp Lys Gly Gln Trp Val Phe Lys Ser Leu
    1460                1465                1470
Gly Lys Pro Gly Asn Met His Leu Arg Ser Ile Thr Thr Pro Tyr
    1475                1480                1485
```

```
Ala Thr Lys Glu Trp Leu Gln Pro Lys Arg Tyr Lys Ala His Leu
    1490            1495                1500

Met Gly Thr Thr Phe Val Tyr Asp Phe Pro Glu Leu Phe Asn Gln
    1505            1510                1515

Ala Ile Arg Ala Ser Trp Arg Ala Ala Gln Gln Gln Ser Pro Glu
    1520            1525                1530

Asn Val Leu Thr Tyr Lys Glu Leu Ile Met Asp Asp Ser Gly Glu
    1535            1540                1545

Leu Ser Glu Val Ser Arg Glu Pro Gly Ala Asn Thr Cys Gly Met
    1550            1555                1560

Val Ala Trp Leu Phe Thr Ala Leu Thr Pro Glu Tyr Pro Thr Gly
    1565            1570                1575

Arg Gln Phe Ile Val Val Ala Asn Asp Ile Thr Tyr Lys Ile Gly
    1580            1585                1590

Ser Phe Gly Pro Gln Glu Asp Lys Tyr Phe His Thr Val Thr Gln
    1595            1600                1605

Leu Ala Val Lys Leu Gly Ile Pro Arg Ile Tyr Leu Ser Ala Asn
    1610            1615                1620

Ser Gly Ala Arg Ile Gly Val Ala Asp Glu Phe Val Ser Leu Phe
    1625            1630                1635

Ser Val Ala Trp Asn Asp Ser Ser Asn Pro Glu Lys Gly Phe Lys
    1640            1645                1650

Tyr Leu Tyr Leu Thr Pro Ala Ile Tyr Asn Gly Leu Ser Asp Ala
    1655            1660                1665

Ala Lys Lys Thr Val Leu Thr Glu Arg Ile Val Glu Glu Gly Glu
    1670            1675                1680

Glu Arg Tyr Val Ile Thr Thr Ile Ile Gly Ala Glu Asp Gly Leu
    1685            1690                1695

Gly Val Glu Cys Leu Arg Gly Ser Gly Leu Ile Ala Gly Ala Thr
    1700            1705                1710

Ser Lys Ala Tyr Lys Asp Ile Phe Thr Ile Thr Leu Val Thr Cys
    1715            1720                1725

Arg Ser Val Gly Ile Gly Ala Tyr Leu Val Arg Leu Gly Gln Arg
    1730            1735                1740

Ala Ile Gln Ile Glu Gly Gln Pro Ile Ile Leu Thr Gly Ala Pro
    1745            1750                1755

Ala Ile Asn Lys Leu Leu Gly Arg Glu Val Tyr Ser Ser Asn Leu
    1760            1765                1770

Gln Leu Gly Gly Thr Gln Ile Met Tyr Lys Asn Gly Val Ser His
    1775            1780                1785

Leu Thr Ala Asn Asp Asp Leu Ala Gly Val Met Lys Ile Ile Glu
    1790            1795                1800

Trp Met Ser Tyr Val Pro Tyr Lys Lys Gly Gly Gln Leu Pro Ile
    1805            1810                1815

Tyr Pro Ser Ser Asp Thr Trp Asp Arg Asp Val Thr Tyr Thr Pro
    1820            1825                1830

Pro Lys Gln Val Pro Tyr Asp Val Arg Trp Leu Ile Ala Gly Arg
    1835            1840                1845

Glu Asp Glu Glu Gly Gly Phe Glu Tyr Gly Leu Phe Asp Lys Asp
    1850            1855                1860

Ser Phe Gln Glu Thr Leu Ser Gly Trp Ala Arg Thr Val Val Val
    1865            1870                1875
```

Gly Arg Ala Arg Leu Gly Gly Ile Pro Val Gly Val Ile Gly Val
     1880              1885              1890

Glu Val Arg Ser Val Glu Asn Ile Phe Pro Ala Asp Pro Ala Asn
     1895              1900              1905

Pro Asp Ser Thr Glu Met Val Val Gln Glu Ala Gly Gln Val Trp
     1910              1915              1920

Tyr Pro Asn Ser Ala Phe Lys Thr Ala Gln Ala Ile Asn Asp Phe
     1925              1930              1935

Asn His Gly Glu Glu Leu Pro Leu Val Ile Leu Ala Asn Trp Arg
     1940              1945              1950

Gly Phe Ser Gly Gly Gln Arg Asp Met Tyr Asn Glu Val Leu Lys
     1955              1960              1965

Tyr Gly Ser Phe Ile Val Asp Ala Leu Val Gly Tyr Lys Gln Pro
     1970              1975              1980

Ile Phe Val Tyr Ile Pro Pro His Ala Glu Leu Arg Gly Gly Ser
     1985              1990              1995

Trp Val Val Ile Asp Pro Thr Ile Asn Ser Asp Gln Met Glu Met
     2000              2005              2010

Tyr Ala Asp Asp Glu Ala Arg Ala Gly Val Leu Glu Pro Glu Gly
     2015              2020              2025

Met Val Gly Ile Lys Tyr Arg Arg Asp Arg Leu Leu Glu Thr Met
     2030              2035              2040

Thr Arg Leu Asp Pro Val Tyr Ala Ser Leu Lys Arg Gln Ala Asp
     2045              2050              2055

Lys Lys Asp Leu Ala Pro Ala Ile Ala Gln Asp Leu Lys Val Lys
     2060              2065              2070

Leu Ser Glu Arg Glu Ser Thr Leu Met Pro Ile Tyr Arg Gln Ile
     2075              2080              2085

Ser Leu Gln Phe Ala Asp Leu His Asp Arg Ala Gly Arg Met Lys
     2090              2095              2100

Ala Lys Gly Thr Ile Arg Glu Val Leu His Trp Arg Glu Ala Arg
     2105              2110              2115

Arg Phe Phe Tyr Trp Arg Val Arg Arg Arg Val Gly Glu Ser Tyr
     2120              2125              2130

Ile Leu Arg Asp Leu Glu Ala Ala Asn Pro Lys Ser Thr Arg Leu
     2135              2140              2145

Glu Arg Val Ala Arg Leu Lys Ser Trp Tyr Ala Glu Ala Gly Ile
     2150              2155              2160

Asn Glu Ser Ser Asp Ala Asp Val Ala Ser Trp Ile Glu Lys Ser
     2165              2170              2175

Gly Ala Ala Ile Thr Ser Lys Val Lys Gln Val Arg Lys Asp Ala
     2180              2185              2190

Lys Ile Gln Asp Leu Leu Ala Leu Val Arg Ala Asp Lys Asp Val
     2195              2200              2205

Ala Leu Gln Gly Leu Val Glu Ser Leu Lys Ala Leu Ser Thr Glu
     2210              2215              2220

Glu Arg Asp Ala Ile Phe Lys Gln Ala Ser Asn
     2225              2230

<210> SEQ ID NO 3
<211> LENGTH: 2406
<212> TYPE: DNA
<213> ORGANISM: Lipomyces starkeyi
<220> FEATURE:
<221> NAME/KEY: Intron

<222> LOCATION: (1408)..(1461)

<400> SEQUENCE: 3

```
atgttgccga tcagctcgtt aatcgctctt ctgggagcga tatcattgtc tcctgctgtc    60
gttgctcgtc atattcttcg gcgagattgc agtacagtta ccgtgttgtc gtcgcctgag   120
actgtgacta gttcgaacca cgttcagcta gccagttatg agatgtgcga cggtaccttg   180
tcagcgtccc tttatatcta caatgatgat tacgataaga ttgtgacact ttattatctt   240
acatcgtcgg gcaatactgg gtctgcaaca gcctcttatt cttctggttt gagcaacaac   300
tgggaattat ggaccttatc cactaccgct acaggtgctg tcgaaattac tgaggctagc   360
tatattgata gtgatgcatc tgtgacatac acaacgtcgt gaacgtgcc tctcacaacc   420
actacaacgt catcatcaat tactagtgca tattcaacgt ctagcattac tacatctagt   480
acgtcgacgt ctgcttgtgc cacagttact gtcttgtcgt cgcctgagac tgtgacgagt   540
tcgaaccatg ttcagctagc cagtcatgag atgtgcgaca gtaccttgtc agcgtcccct   600
tatatctaca atgatgatta tgataagatt gtgacacttt attatcttac atcgtcgggc   660
acaactgggt ccgtaacagc gtcttattct tctagtttga gtaacaactg gaattgtgg    720
tctctctcgg ctccggctgc agatgctgtc gagatcactg gagctagtta gtagacagc    780
gatgcatctg cgacatacgc cacgtctttt gatataccctc ttactaccac gacaacgtcg   840
tcgtcttctg ctagtgcgac ttcaacatct agtctaacca acatctag tgtttccatt     900
tcggtgtccg tccctacagg aacagctgca aattggcgag taggctat ctatcagatc     960
gtgactgata gatttgcacg cactgacggc tccaccacat atttatgcga tgttaccgat  1020
agggtctatt gcggagggtc ttatcagggg attatcaata tgctggatta catccaaggc  1080
atgggcttta ctgctatttg gatttctcct atagtggaaa atattcccga tgacaccgga  1140
tacggttacg catatcatgg ttattggatg aaagatatct tcgccctgaa tacaaatttt  1200
ggtactgcag acgatttgat agcgttggct acggaattgc ataatcgcgg catgtacttg  1260
atggttgata ttgttgtcaa tcactttgct ttctcaggaa gtcatgccga cgtggactac  1320
tctgaatatt tcccgtattc gtcccaggat tattttcatt cattttgctg gattacagat  1380
tactcgaatc agacaaacgt tgaggtggta tgtatctaag catatttgta gcattctatc  1440
ttggaactga ccggccctca gtgctggctt ggcgacgata ctgttcctct cgtgacgtc   1500
aatacccaac ttgacaccgt gaaaagtgaa tatcaatcct gggttcaaga acttatagct  1560
aattactcta ttgacggcct aagaattgac accgtcaagc acgtgcagat ggattttt gg  1620
gcaccatttc aagaggctgc agggatttac gccgttggtg aagtattcga cggtgatcca  1680
tcctacacat gtccatatca ggaaaatctt gacggtgtct tgaattatcc tgtttattat  1740
cctgtcgtct ctgcgtttga gagtgttagt gggtcggtct cctcgttagt cgatatgatt  1800
gatacgctca gtctgaatg caccgacact actctcctag gctcctttct agagaatcaa  1860
gataatccgc gattccctag ctacacttct gatgagtctt aattaaaaa tgcgatcgct  1920
ttcactatgc tctcagacgg cattcccata atttattacg gtcaggagca aggcctcaat  1980
ggtgaaaacg atccctataa tcgagaggcg ctttggctta cggctactc cacaacgtcg  2040
acgttctaca aatacattgc gtcgttgaat cagattagaa atcaggctat atacaaagat  2100
gatacttatc tcacatatca gaactgggtt atttattcgg attccacgac aatagcaatg  2160
cggaaaggtt ttacagggaa ccaaataatt acgttctgt caaatcttgg gaccagtggc  2220
agttcgtaca ctttgacgct ttcgaatacg ggatataccg catctagcgt tgtatatgag  2280
```

-continued

```
atcttgacat gcacagctgt gactgtggat tcgtctggga atttggcagt gccgatgtcc    2340
agtggcctac caaaagtctt ttatcaggaa tcgcaactgg ttggctctgg aatctgctcc    2400
ttgtag                                                                2406
```

<210> SEQ ID NO 4
<211> LENGTH: 783
<212> TYPE: PRT
<213> ORGANISM: Lipomyces starkeyi

<400> SEQUENCE: 4

```
Met Leu Pro Ile Ser Ser Leu Ile Ala Leu Leu Gly Ala Ile Ser Leu
1               5                   10                  15

Ser Pro Ala Val Val Ala Arg His Ile Leu Arg Arg Asp Cys Ser Thr
            20                  25                  30

Val Thr Val Leu Ser Ser Pro Glu Thr Val Thr Ser Ser Asn His Val
        35                  40                  45

Gln Leu Ala Ser Tyr Glu Met Cys Asp Gly Thr Leu Ser Ala Ser Leu
    50                  55                  60

Tyr Ile Tyr Asn Asp Asp Tyr Asp Lys Ile Val Thr Leu Tyr Tyr Leu
65                  70                  75                  80

Thr Ser Ser Gly Asn Thr Gly Ser Ala Thr Ala Ser Tyr Ser Ser Gly
                85                  90                  95

Leu Ser Asn Asn Trp Glu Leu Trp Thr Leu Ser Thr Thr Ala Thr Gly
            100                 105                 110

Ala Val Glu Ile Thr Glu Ala Ser Tyr Ile Asp Ser Asp Ala Ser Val
        115                 120                 125

Thr Tyr Thr Thr Ser Leu Asn Val Pro Leu Thr Thr Thr Thr Thr Ser
    130                 135                 140

Ser Ser Ile Thr Ser Ala Tyr Ser Thr Ser Ser Ile Thr Thr Ser Ser
145                 150                 155                 160

Thr Ser Thr Ser Ala Cys Ala Thr Val Thr Val Leu Ser Ser Pro Glu
                165                 170                 175

Thr Val Thr Ser Ser Asn His Val Gln Leu Ala Ser His Glu Met Cys
            180                 185                 190

Asp Ser Thr Leu Ser Ala Ser Leu Tyr Ile Tyr Asn Asp Asp Tyr Asp
        195                 200                 205

Lys Ile Val Thr Leu Tyr Tyr Leu Thr Ser Ser Gly Thr Thr Gly Ser
    210                 215                 220

Val Thr Ala Ser Tyr Ser Ser Leu Ser Asn Asn Trp Glu Leu Trp
225                 230                 235                 240

Ser Leu Ser Ala Pro Ala Asp Ala Val Glu Ile Thr Gly Ala Ser
                245                 250                 255

Tyr Val Asp Ser Asp Ala Ser Ala Thr Tyr Ala Thr Ser Phe Asp Ile
            260                 265                 270

Pro Leu Thr Thr Thr Thr Ser Ser Ser Ala Ser Ala Thr Ser
        275                 280                 285

Thr Ser Ser Leu Thr Thr Thr Ser Ser Val Ser Ile Ser Val Ser Val
    290                 295                 300

Pro Thr Gly Thr Ala Ala Asn Trp Arg Gly Arg Ala Ile Tyr Gln Ile
305                 310                 315                 320

Val Thr Asp Arg Phe Ala Arg Thr Asp Gly Ser Thr Thr Tyr Leu Cys
                325                 330                 335

Asp Val Thr Asp Arg Val Tyr Cys Gly Gly Ser Tyr Gln Gly Ile Ile
```

```
                340             345             350
Asn Met Leu Asp Tyr Ile Gln Gly Met Gly Phe Thr Ala Ile Trp Ile
        355                 360                 365

Ser Pro Ile Val Glu Asn Ile Pro Asp Asp Thr Gly Tyr Gly Tyr Ala
    370                 375                 380

Tyr His Gly Tyr Trp Met Lys Asp Ile Phe Ala Leu Asn Thr Asn Phe
385                 390                 395                 400

Gly Thr Ala Asp Asp Leu Ile Ala Leu Ala Thr Glu Leu His Asn Arg
                405                 410                 415

Gly Met Tyr Leu Met Val Asp Ile Val Val Asn His Phe Ala Phe Ser
                420                 425                 430

Gly Ser His Ala Asp Val Asp Tyr Ser Glu Tyr Phe Pro Tyr Ser Ser
            435                 440                 445

Gln Asp Tyr Phe His Ser Phe Cys Trp Ile Thr Asp Tyr Ser Asn Gln
        450                 455                 460

Thr Asn Val Glu Val Cys Trp Leu Gly Asp Asp Thr Val Pro Leu Val
465                 470                 475                 480

Asp Val Asn Thr Gln Leu Asp Thr Val Lys Ser Glu Tyr Gln Ser Trp
                485                 490                 495

Val Gln Glu Leu Ile Ala Asn Tyr Ser Ile Asp Gly Leu Arg Ile Asp
            500                 505                 510

Thr Val Lys His Val Gln Met Asp Phe Trp Ala Pro Phe Gln Glu Ala
        515                 520                 525

Ala Gly Ile Tyr Ala Val Gly Glu Val Phe Asp Gly Asp Pro Ser Tyr
    530                 535                 540

Thr Cys Pro Tyr Gln Glu Asn Leu Asp Gly Val Leu Asn Tyr Pro Val
545                 550                 555                 560

Tyr Tyr Pro Val Val Ser Ala Phe Glu Ser Val Ser Gly Ser Val Ser
                565                 570                 575

Ser Leu Val Asp Met Ile Asp Thr Leu Lys Ser Glu Cys Thr Asp Thr
            580                 585                 590

Thr Leu Leu Gly Ser Phe Leu Glu Asn Gln Asp Asn Pro Arg Phe Pro
        595                 600                 605

Ser Tyr Thr Ser Asp Glu Ser Leu Ile Lys Asn Ala Ile Ala Phe Thr
    610                 615                 620

Met Leu Ser Asp Gly Ile Pro Ile Ile Tyr Tyr Gly Gln Glu Gln Gly
625                 630                 635                 640

Leu Asn Gly Gly Asn Asp Pro Tyr Asn Arg Glu Ala Leu Trp Leu Thr
                645                 650                 655

Gly Tyr Ser Thr Thr Ser Thr Phe Tyr Lys Tyr Ile Ala Ser Leu Asn
            660                 665                 670

Gln Ile Arg Asn Gln Ala Ile Tyr Lys Asp Asp Thr Tyr Leu Thr Tyr
        675                 680                 685

Gln Asn Trp Val Ile Tyr Ser Asp Ser Thr Thr Ile Ala Met Arg Lys
    690                 695                 700

Gly Phe Thr Gly Asn Gln Ile Ile Thr Val Leu Ser Asn Leu Gly Thr
705                 710                 715                 720

Ser Gly Ser Ser Tyr Thr Leu Thr Leu Ser Asn Thr Gly Tyr Thr Ala
                725                 730                 735

Ser Ser Val Val Tyr Glu Ile Leu Thr Cys Thr Ala Val Thr Val Asp
            740                 745                 750

Ser Ser Gly Asn Leu Ala Val Pro Met Ser Ser Gly Leu Pro Lys Val
        755                 760                 765
```

```
Phe Tyr Gln Glu Ser Gln Leu Val Gly Ser Gly Ile Cys Ser Leu
    770                 775                 780

<210> SEQ ID NO 5
<211> LENGTH: 1845
<212> TYPE: DNA
<213> ORGANISM: Lipomyces starkeyi
<220> FEATURE:
<221> NAME/KEY: Intron
<222> LOCATION: (74)..(123)
<220> FEATURE:
<221> NAME/KEY: Intron
<222> LOCATION: (140)..(193)
<220> FEATURE:
<221> NAME/KEY: Intron
<222> LOCATION: (302)..(348)
<220> FEATURE:
<221> NAME/KEY: Intron
<222> LOCATION: (372)..(419)
<220> FEATURE:
<221> NAME/KEY: Intron
<222> LOCATION: (516)..(564)
<220> FEATURE:
<221> NAME/KEY: Intron
<222> LOCATION: (643)..(697)

<400> SEQUENCE: 5
atggccgaag agaacaagat tcctaccgag gaaaacgcga caatgctcca ggcatttgag     60
tggtacatcc ccggtacgtc cccatccata ttgccagttt tgctcagact aacgtgcgta    120
tagacgacca cacacattgg tattccgtga ctctttcgac attttacaga atgaataagc    180
tcacaaggta taggaaacga ctcgctcgtg atatcgagaa gtatcgcgac atcggcatca    240
ctgctttgtg gatcccgccc ccatgcaagg cttcgtcacc atctgggaat ggatatgata    300
tgtatgtcct attgtattcg ttataggtga tgcgtctaac gggaatagat acgatctgtg    360
ggatctcgga ggtacgatct tcgagttgtc gtcattgatg cctgtctgac catgcccaga    420
gttcgatcag aaaggttccg ttccgacaaa atggggcgat aaggacgatt tggtcaggct    480
agcccacaat gccgagaaag ccggtgtctt gctttgtaag atctcgctga tcagaatgct    540
ggatgcatgt tgctaaacac gcagacgccg acgccgtgct caaccacaaa gcagcagccg    600
acgaaactga gcgctgccga gtcgccgaag tcgacccaga gagtatgtct gtccgcatta    660 tcttttttgta ttcccttggg gtcataacat ctggtagacc gcacgcggtt catctccgat    720
gagtacgaaa tcgacggctg gctaggcttc actttctctg gccgcggcga caagtattct    780
tccatgaaat ggcactggga gcatttctcc ggcacggatt acaacgccga gaataacaag    840
acggcgattt acaagattct tggagacttt aagtcttggg cgcagtcagt cgacaacgag    900
aaaggtaact tgattactt gatgtttgcc gacattgatc attcgcatcc agacgtgaaa    960
aaggatatca acgattgggg aatctggatc gcggagctgc tgtcgttgag agggtttcga   1020
tttgatgccg tgaagcattt ctcggaggag tatttaaagg agtttatcac tcaattgaaa   1080
acgaacgtga acgaagattt tttctttgtg ggcgagtttt ggaaagattc gttgtcggac   1140
atgttgggat acctcgatcg tcttgatggc cacaagttca gcttgtttga cgcgccgctg   1200
gtgtacaatt tttcggaagc atcaaagacg gaatcctttg atctacgcgc gatctttgac   1260
ggcacgcttg tgcaagcgcg tcccatttcc gcagtgacgc tggtcatgaa ccatgacaca   1320
caaccgcacc aggcactcga ggcgccgatc gagggatttt tcaagccgat tgcgtacggt   1380
ttgatcctcc tccgtcagga ggggtatcca tgtgtgtttt ggggcgattt ggagggcatt   1440
tcaggggagt ataagagga gccgagttgt ggggggccagc tttcggatat tattctggca   1500
```

```
aggaagttgt atgcgtatgg cgagcaggac gattatttcg attaccctac gtgcttgggg    1560
tgggttcgtc gcggcgcgtg ggatagatta aacggatgcg cggtcattgt ttcgaacgcg    1620
ggtcccggtg agaagcgcat gtttgttggc gaagagcata aggggagat ctggaccgac     1680 gttcttgggt gggaacaggg cgaggtgcat attggcgagg acggaaatgc ggatttcaaa    1740
tgtcctgcta ctagtatggc gatctgggtt aacaaggacg cgccaggccg tgatcagttt    1800
ggaaagttca agcccggcaa ggggattttg caaggagtag tctag                    1845

<210> SEQ ID NO 6
<211> LENGTH: 513
<212> TYPE: PRT
<213> ORGANISM: Lipomyces starkeyi

<400> SEQUENCE: 6
```

Met Ala Glu Glu Asn Lys Ile Pro Thr Glu Asn Ala Thr Met Leu
1               5                   10                  15

Gln Ala Phe Glu Trp Tyr Ile Pro Asp Asp His Thr His Trp Lys Arg
            20                  25                  30

Leu Ala Arg Asp Ile Glu Lys Tyr Arg Asp Ile Gly Ile Thr Ala Leu
        35                  40                  45

Trp Ile Pro Pro Cys Lys Ala Ser Ser Pro Ser Gly Asn Gly Tyr
    50                  55                  60

Asp Ile Tyr Asp Leu Trp Asp Leu Gly Glu Phe Asp Gln Lys Gly Ser
65                  70                  75                  80

Val Pro Thr Lys Trp Gly Asp Lys Asp Leu Val Arg Leu Ala His
            85                  90                  95

Asn Ala Glu Lys Ala Gly Val Leu Leu Tyr Ala Asp Ala Val Leu Asn
            100                 105                 110

His Lys Ala Ala Ala Asp Glu Thr Glu Arg Cys Arg Val Ala Glu Val
        115                 120                 125

Asp Pro Glu Asn Arg Thr Arg Phe Ile Ser Asp Glu Tyr Glu Ile Asp
        130                 135                 140

Gly Trp Leu Gly Phe Thr Phe Ser Gly Arg Gly Asp Lys Tyr Ser Ser
145                 150                 155                 160

Met Lys Trp His Trp Glu His Phe Ser Gly Thr Asp Tyr Asn Ala Glu
                165                 170                 175

Asn Asn Lys Thr Ala Ile Tyr Lys Ile Leu Gly Asp Phe Lys Ser Trp
            180                 185                 190

Ala Gln Ser Val Asp Asn Glu Lys Gly Asn Phe Asp Tyr Leu Met Phe
        195                 200                 205

Ala Asp Ile Asp His Ser His Pro Asp Val Lys Lys Asp Ile Asn Asp
    210                 215                 220

Trp Gly Ile Trp Ile Ala Glu Leu Leu Ser Leu Arg Gly Phe Arg Phe
225                 230                 235                 240

Asp Ala Val Lys His Phe Ser Glu Glu Tyr Leu Lys Glu Phe Ile Thr
                245                 250                 255

Gln Leu Lys Thr Asn Val Asn Glu Asp Phe Phe Val Gly Glu Phe
            260                 265                 270

Trp Lys Asp Ser Leu Ser Asp Met Leu Gly Tyr Leu Asp Arg Leu Asp
        275                 280                 285

Gly His Lys Phe Ser Leu Phe Asp Ala Pro Leu Val Tyr Asn Phe Ser
    290                 295                 300

Glu Ala Ser Lys Thr Glu Ser Phe Asp Leu Arg Ala Ile Phe Asp Gly

```
                305                 310                 315                 320
Thr Leu Val Gln Ala Arg Pro Ile Ser Ala Val Thr Leu Val Met Asn
                    325                 330                 335

His Asp Thr Gln Pro His Gln Ala Leu Glu Ala Pro Ile Glu Gly Phe
                340                 345                 350

Phe Lys Pro Ile Ala Tyr Gly Leu Ile Leu Arg Gln Glu Gly Tyr
            355                 360                 365

Pro Cys Val Phe Trp Gly Asp Leu Glu Gly Ile Ser Gly Glu Tyr Lys
370                 375                 380

Glu Glu Pro Ser Cys Gly Gly Gln Leu Ser Asp Ile Ile Leu Ala Arg
385                 390                 395                 400

Lys Leu Tyr Ala Tyr Gly Glu Gln Asp Asp Tyr Phe Asp Tyr Pro Thr
                405                 410                 415

Cys Leu Gly Trp Val Arg Arg Gly Ala Trp Asp Arg Leu Asn Gly Cys
                420                 425                 430

Ala Val Ile Val Ser Asn Ala Gly Pro Gly Glu Lys Arg Met Phe Val
                435                 440                 445

Gly Glu Glu His Lys Gly Glu Ile Trp Thr Asp Val Leu Gly Trp Glu
            450                 455                 460

Gln Gly Glu Val His Ile Gly Glu Asp Gly Asn Ala Asp Phe Lys Cys
465                 470                 475                 480

Pro Ala Thr Ser Met Ala Ile Trp Val Asn Lys Asp Ala Pro Gly Arg
                485                 490                 495

Asp Gln Phe Gly Lys Phe Lys Pro Gly Lys Gly Ile Leu Gln Gly Val
                500                 505                 510

Val

<210> SEQ ID NO 7
<211> LENGTH: 1920
<212> TYPE: DNA
<213> ORGANISM: Artificial Sequence
<220> FEATURE:
<223> OTHER INFORMATION: Chimeric Thermostable Secreted Alpha-Amylase
<220> FEATURE:
<221> NAME/KEY: Intron
<222> LOCATION: (149)..(198)
<220> FEATURE:
<221> NAME/KEY: Intron
<222> LOCATION: (215)..(268)
<220> FEATURE:
<221> NAME/KEY: Intron
<222> LOCATION: (377)..(423)
<220> FEATURE:
<221> NAME/KEY: Intron
<222> LOCATION: (447)..(494)
<220> FEATURE:
<221> NAME/KEY: Intron
<222> LOCATION: (591)..(639)
<220> FEATURE:
<221> NAME/KEY: Intron
<222> LOCATION: (718)..(772)

<400> SEQUENCE: 7
atgttgccga tcagctcgtt aatcgctctt ctgggagcga tatcattgtc tcctgctgtc      60
gttgctcgtc atattcttgc cgaagagaac aagattccta ccgaggaaaa cgcgacaatg     120
ctccaggcat ttgagtggta catccccggt acgtccccat ccatattgcc agttttgctc     180
agactaacgt gcgtatagac gaccacacac attggtattc cgtgactctt tcgacatttt     240
acagaatgaa taagctcaca aggtatagga acgactcgc tcgtgatatc gagaagtatc     300
gcgacatcgg catcactgct tgtggatcc cgccccatg caaggcttcg tcaccatctg      360
```

-continued

```
ggaatggata tgatatgtat gtcctattgt attcgttata ggtgatgcgt ctaacgggaa    420
tagatacgat ctgtgggatc tcggaggtac gatcttcgag ttgtcgtcat tgatgcctgt    480
ctgaccatgc ccagagttcg atcagaaagg ttccgttccg acaaaatggg gcgataagga    540
cgatttggtc aggctagccc acaatgccga gaaagccggt gtcttgcttt gtaagatctc    600
gctgatcaga atgctggatg catgttgcta acacgcaga cgccgacgcc gtgctcaacc    660
acaaagcagc agccgacgaa actgagcgct gccgagtcgc cgaagtcgac ccagagagta    720
tgtctgtccg cattatcttt ttgtattccc tttgggtcat aacatctggt agaccgcacg    780
cggttcatct ccgatgagta cgaaatcgac ggctggctag gcttcacttt ctctggccgc    840
ggcgacaagt attcttccat gaaatggcac tgggagcatt tctccggcac ggattacaac    900
gccgagaata caagacggc gatttacaag attcttggag actttaagtc ttgggcgcag    960
tcagtcgaca acgagaaagg taactttgat tacttgatgt ttgccgacat tgatcattcg   1020
catccagacg tgaaaaagga tatcaacgat tggggaatct ggatcgcgga gctgctgtcg   1080
ttgagagggt ttcgatttga tgccgtgaag catttctcgg aggagtattt aaaggagttt   1140
atcactcaat tgaaaacgaa cgtgaacgaa gattttttct ttgtgggcga gttttggaaa   1200
gattcgttgt cggacatgtt gggataccte gatcgtcttg atggccacaa gttcagcttg   1260
tttgacgcgc cgctggtgta caattttttcg gaagcatcaa agacggaatc ctttgatcta   1320
cgcgcgatct ttgacggcac gcttgtgcaa gcgcgtccca tttccgcagt gacgctggtc   1380
atgaaccatg acacacaacc gcaccaggca ctcgaggcgc cgatcgaggg atttttcaag   1440
ccgattgcgt acggtttgat cctcctccgt caggaggggt atccatgtgt gttttggggc   1500
gatttggagg gcatttcagg ggagtataaa gaggagccga gttgtggggg ccagcttcg    1560
gatattattc tggcaaggaa gttgtatgcg tatggcgagc aggacgatta tttcgattac   1620
cctacgtgct gggggtgggt tcgtcgcggc gcgtgggata gattaaacgg atgcgcggtc   1680
attgttcga acgcgggtcc cggtgagaag cgcatgtttg ttggcgaaga gcataagggg   1740
gagatctgga ccgacgttct tgggtgggaa cagggcgagg tgcatattgg cgaggacgga   1800
aatgcggatt tcaaatgtcc tgctactagt atggcgatct gggttaacaa ggacgcgcca   1860
ggccgtgatc agtttggaaa gttcaagccc ggcaagggga ttttgcaagg agtagtctag   1920
```

<210> SEQ ID NO 8
<211> LENGTH: 538
<212> TYPE: PRT
<213> ORGANISM: Artificial Sequence
<220> FEATURE:
<223> OTHER INFORMATION: Chimeric Thermostable Secreted Alpha-Amylase

<400> SEQUENCE: 8

```
Met Leu Pro Ile Ser Ser Leu Ile Ala Leu Leu Gly Ala Ile Ser Leu
1               5                   10                  15

Ser Pro Ala Val Val Ala Arg His Ile Leu Ala Glu Glu Asn Lys Ile
            20                  25                  30

Pro Thr Glu Glu Asn Ala Thr Met Leu Gln Ala Phe Glu Trp Tyr Ile
        35                  40                  45

Pro Asp Asp His Thr His Trp Lys Arg Leu Ala Arg Asp Ile Glu Lys
    50                  55                  60

Tyr Arg Asp Ile Gly Ile Thr Ala Leu Trp Ile Pro Pro Cys Lys
65                  70                  75                  80

Ala Ser Ser Pro Ser Gly Asn Gly Tyr Asp Ile Tyr Asp Leu Trp Asp
```

```
                    85                  90                  95
Leu Gly Glu Phe Asp Gln Lys Gly Ser Val Pro Thr Lys Trp Gly Asp
                100                 105                 110

Lys Asp Asp Leu Val Arg Leu Ala His Asn Ala Glu Lys Ala Gly Val
            115                 120                 125

Leu Leu Tyr Ala Asp Ala Val Leu Asn His Lys Ala Ala Asp Glu
130                 135                 140

Thr Glu Arg Cys Arg Val Ala Glu Val Asp Pro Glu Asn Arg Thr Arg
145                 150                 155                 160

Phe Ile Ser Asp Glu Tyr Glu Ile Asp Gly Trp Leu Gly Phe Thr Phe
                165                 170                 175

Ser Gly Arg Gly Asp Lys Tyr Ser Ser Met Lys Trp His Trp Glu His
                180                 185                 190

Phe Ser Gly Thr Asp Tyr Asn Ala Glu Asn Asn Lys Thr Ala Ile Tyr
                195                 200                 205

Lys Ile Leu Gly Asp Phe Lys Ser Trp Ala Gln Ser Val Asp Asn Glu
            210                 215                 220

Lys Gly Asn Phe Asp Tyr Leu Met Phe Ala Asp Ile Asp His Ser His
225                 230                 235                 240

Pro Asp Val Lys Lys Asp Ile Asn Asp Trp Gly Ile Trp Ile Ala Glu
                245                 250                 255

Leu Leu Ser Leu Arg Gly Phe Arg Phe Asp Ala Val Lys His Phe Ser
                260                 265                 270

Glu Glu Tyr Leu Lys Glu Phe Ile Thr Gln Leu Lys Thr Asn Val Asn
            275                 280                 285

Glu Asp Phe Phe Val Gly Glu Phe Trp Lys Asp Ser Leu Ser Asp
290                 295                 300

Met Leu Gly Tyr Leu Asp Arg Leu Asp Gly His Lys Phe Ser Leu Phe
305                 310                 315                 320

Asp Ala Pro Leu Val Tyr Asn Phe Ser Glu Ala Ser Lys Thr Glu Ser
                325                 330                 335

Phe Asp Leu Arg Ala Ile Phe Asp Gly Thr Leu Val Gln Ala Arg Pro
                340                 345                 350

Ile Ser Ala Val Thr Leu Val Met Asn His Asp Thr Gln Pro His Gln
                355                 360                 365

Ala Leu Glu Ala Pro Ile Glu Gly Phe Phe Lys Pro Ile Ala Tyr Gly
                370                 375                 380

Leu Ile Leu Leu Arg Gln Glu Gly Tyr Pro Cys Val Phe Trp Gly Asp
385                 390                 395                 400

Leu Glu Gly Ile Ser Gly Glu Tyr Lys Glu Pro Ser Cys Gly Gly
                405                 410                 415

Gln Leu Ser Asp Ile Ile Leu Ala Arg Lys Leu Tyr Ala Tyr Gly Glu
                420                 425                 430

Gln Asp Asp Tyr Phe Asp Tyr Pro Thr Cys Leu Gly Trp Val Arg Arg
                435                 440                 445

Gly Ala Trp Asp Arg Leu Asn Gly Cys Ala Val Ile Val Ser Asn Ala
            450                 455                 460

Gly Pro Gly Glu Lys Arg Met Phe Val Gly Glu His Lys Gly Glu
465                 470                 475                 480

Ile Trp Thr Asp Val Leu Gly Trp Glu Gln Gly Glu Val His Ile Gly
                485                 490                 495

Glu Asp Gly Asn Ala Asp Phe Lys Cys Pro Ala Thr Ser Met Ala Ile
                500                 505                 510
```

Trp Val Asn Lys Asp Ala Pro Gly Arg Asp Gln Phe Gly Lys Phe Lys
        515                 520                 525

Pro Gly Lys Gly Ile Leu Gln Gly Val Val
        530                 535

<210> SEQ ID NO 9
<211> LENGTH: 1996
<212> TYPE: DNA
<213> ORGANISM: Lipomyces starkeyi
<220> FEATURE:
<221> NAME/KEY: Intron
<222> LOCATION: (385)..(436)

<400> SEQUENCE: 9

| | | | | |
|---|---|---|---|---|
| atgtctcctc | cttctgccga | cgccaacatc | acacgcttcg | cgccgccaac cgcgccagcg | 60 |
| tcgccgctgc | cggcgtacca | gctcttccac | aacaagacgc | gtgcgttcgt ttatggcctg | 120 |
| cagccgcgtg | cttgccaggg | tatgctcgat | ttcgacttca | tctgcaagcg cacgaccccg | 180 |
| tcggtcgccg | ctatcatcta | tcctttcggc | ggccagtttg | tgtctaagat gtattggggc | 240 |
| acgaaggaga | ccctcctccc | tgtctaccag | agcgccaaga | aggccgcaga gaagcatccc | 300 |
| gaagtcgacg | tcgtcgtcaa | cttttgcctct | tcccgatccg | tctactcctc aacgatggag | 360 |
| cttctggaat | taccccagat | tagggtgtgt | tttggtctaa | gtttacttac tcaattgatg | 420 |
| ctaatatact | gattagacaa | ttgcgatcat | tgcggaaggt | gtgcctgagc gtcgcgctcg | 480 |
| cgagattctt | ttcaaggcca | aggaaaaggg | cgtcgtcatc | atcggccctg ctactgtcgg | 540 |
| cggtatcaaa | cctggctgct | taagatcgg | caacaccggc | ggtatgatgg acaacatcgt | 600 |
| tgcctccaaa | ctctaccgac | ctggatccgt | cggctacgtc | tccaagtccg gtggtatgtc | 660 |
| taacgaactc | aataacatca | tctctcagac | caccgatggt | gtctacgaag gtgtcgctat | 720 |
| tggcggtgac | cgttatcccg | gcaccacctt | catcgaccac | ctcctccgct acgaggccga | 780 |
| tcccgattgt | aagatcctgg | tgttgcttgg | tgaggttggt | ggtgtgagg aataccgcgt | 840 |
| catcgatgct | gtcaagtctg | gcacgatcac | aaagccaatt | gtcgcctggg ccatcggcac | 900 |
| ttgcgcatct | atgttcacga | ctgaggttca | gtttggccac | gctggttcgt tcgccaactc | 960 |
| ccagctcgag | actgctaagg | ccaagaatgc | cgccatgaag | gccgccggtt tttacgttcc | 1020 |
| tgacaccttc | gaggatatgc | cagatgtctt | gggtgatctc | tacaagagtc tcgtcaagaa | 1080 |
| gggtgtcatt | gttccgaagc | ccgagcccga | gcctccaaag | atcccgattg actacgcctg | 1140 |
| ggcccaggaa | cttggcctca | tccgtaagcc | ggccgcgttc | atctcgacca tttctgacga | 1200 |
| tcgtggccaa | gagctgctct | acgccggcat | gcccattacc | gacgtcttca aggagaatat | 1260 |
| tggcatcggt | ggcgtcatgt | cgcttctgtg | gttccgtcgt | cgtctgcccg actacgcttc | 1320 |
| caagttcctc | gagatggtcc | ttatgctcac | tgcagaccac | ggaccagctg tctcaggcgc | 1380 |
| catgaacacc | atcatcacta | ctcgtgctgg | caaggacttg | atctccgctc tcgtgtccgg | 1440 |
| tctgttgacc | atcggtgagc | gattcggtgg | tgcgctcgac | ggcgccgctc aggaattcac | 1500 |
| caatgcgttc | gacaagggcc | tttcgccccg | ccagtttgtc | gacaccatgc gcaagcagaa | 1560 |
| caagctcatc | cccggtattg | gccacaagat | caagtcccgc | aacaatccag atatgcgggt | 1620 |
| tgagttagtc | aaggaatttg | cccgcaacag | cttcccatcc | accaaacttc tcgactacgc | 1680 |
| gctcgccgtc | gagactgtta | ccacttccaa | gaaggacaac | ttgatcctca acgtcgacgg | 1740 |
| ctgtgtcgcc | gtctgcttca | tcgatttgat | ccgccactgc | ggtgctttca cccctgaaga | 1800 |
| agctgaagac | tacctgaaga | tgggagttct | gaacggcctg | ttcgttcttg gccgatccat | 1860 |

-continued

```
tggtttgatc gcgcactatc tggatcagaa gcgcctgcgc actggcttgt acagacaccc    1920
ttgggatgat attacatatc tgctccccag tgttgactct ttgggcggca gcagtcgcgt    1980
tgaagtcacg gtctag                                                    1996
```

<210> SEQ ID NO 10
<211> LENGTH: 647
<212> TYPE: PRT
<213> ORGANISM: Lipomyces starkeyi

<400> SEQUENCE: 10

```
Met Ser Pro Pro Ser Ala Asp Ala Asn Ile Thr Arg Phe Ala Pro Pro
1               5                   10                  15

Thr Ala Pro Ala Ser Pro Leu Pro Ala Tyr Gln Leu Phe His Asn Lys
            20                  25                  30

Thr Arg Ala Phe Val Tyr Gly Leu Gln Pro Arg Ala Cys Gln Gly Met
        35                  40                  45

Leu Asp Phe Asp Phe Ile Cys Lys Arg Thr Thr Pro Ser Val Ala Ala
    50                  55                  60

Ile Ile Tyr Pro Phe Gly Gly Gln Phe Val Ser Lys Met Tyr Trp Gly
65                  70                  75                  80

Thr Lys Glu Thr Leu Leu Pro Val Tyr Gln Ser Ala Lys Lys Ala Ala
                85                  90                  95

Glu Lys His Pro Glu Val Asp Val Val Asn Phe Ala Ser Ser Arg
            100                 105                 110

Ser Val Tyr Ser Ser Thr Met Glu Leu Leu Glu Leu Pro Gln Ile Arg
        115                 120                 125

Thr Ile Ala Ile Ile Ala Glu Gly Val Pro Glu Arg Arg Ala Arg Glu
    130                 135                 140

Ile Leu Phe Lys Ala Lys Glu Lys Gly Val Val Ile Ile Gly Pro Ala
145                 150                 155                 160

Thr Val Gly Gly Ile Lys Pro Gly Cys Phe Lys Ile Gly Asn Thr Gly
                165                 170                 175

Gly Met Met Asp Asn Ile Val Ala Ser Lys Leu Tyr Arg Pro Gly Ser
            180                 185                 190

Val Gly Tyr Val Ser Lys Ser Gly Gly Met Ser Asn Glu Leu Asn Asn
        195                 200                 205

Ile Ile Ser Gln Thr Thr Asp Gly Val Tyr Glu Gly Val Ala Ile Gly
    210                 215                 220

Gly Asp Arg Tyr Pro Gly Thr Thr Phe Ile Asp His Leu Leu Arg Tyr
225                 230                 235                 240

Glu Ala Asp Pro Asp Cys Lys Ile Leu Val Leu Leu Gly Glu Val Gly
                245                 250                 255

Gly Val Glu Glu Tyr Arg Val Ile Asp Ala Val Lys Ser Gly Thr Ile
            260                 265                 270

Thr Lys Pro Ile Val Ala Trp Ala Ile Gly Thr Cys Ala Ser Met Phe
        275                 280                 285

Thr Thr Glu Val Gln Phe Gly His Ala Gly Ser Phe Ala Asn Ser Gln
    290                 295                 300

Leu Glu Thr Ala Lys Ala Lys Asn Ala Ala Met Lys Ala Ala Gly Phe
305                 310                 315                 320

Tyr Val Pro Asp Thr Phe Glu Asp Met Pro Asp Val Leu Gly Asp Leu
                325                 330                 335

Tyr Lys Ser Leu Val Lys Lys Gly Val Ile Val Pro Lys Pro Glu Pro
```

```
            340              345              350
Glu Pro Pro Lys Ile Pro Ile Asp Tyr Ala Trp Ala Gln Glu Leu Gly
        355              360              365

Leu Ile Arg Lys Pro Ala Ala Phe Ile Ser Thr Ile Ser Asp Asp Arg
    370              375              380

Gly Gln Glu Leu Leu Tyr Ala Gly Met Pro Ile Thr Asp Val Phe Lys
385              390              395              400

Glu Asn Ile Gly Ile Gly Gly Val Met Ser Leu Leu Trp Phe Arg Arg
                405              410              415

Arg Leu Pro Asp Tyr Ala Ser Lys Phe Leu Glu Met Val Leu Met Leu
            420              425              430

Thr Ala Asp His Gly Pro Ala Val Ser Gly Ala Met Asn Thr Ile Ile
        435              440              445

Thr Thr Arg Ala Gly Lys Asp Leu Ile Ser Ala Leu Val Ser Gly Leu
    450              455              460

Leu Thr Ile Gly Glu Arg Phe Gly Gly Ala Leu Asp Gly Ala Ala Gln
465              470              475              480

Glu Phe Thr Asn Ala Phe Asp Lys Gly Leu Ser Pro Arg Gln Phe Val
                485              490              495

Asp Thr Met Arg Lys Gln Asn Lys Leu Ile Pro Gly Ile Gly His Lys
            500              505              510

Ile Lys Ser Arg Asn Asn Pro Asp Met Arg Val Glu Leu Val Lys Glu
        515              520              525

Phe Ala Arg Asn Ser Phe Pro Ser Thr Lys Leu Leu Asp Tyr Ala Leu
    530              535              540

Ala Val Glu Thr Val Thr Thr Ser Lys Lys Asp Asn Leu Ile Leu Asn
545              550              555              560

Val Asp Gly Cys Val Ala Val Cys Phe Ile Asp Leu Ile Arg His Cys
                565              570              575

Gly Ala Phe Thr Pro Glu Glu Ala Glu Asp Tyr Leu Lys Met Gly Val
            580              585              590

Leu Asn Gly Leu Phe Val Leu Gly Arg Ser Ile Gly Leu Ile Ala His
        595              600              605

Tyr Leu Asp Gln Lys Arg Leu Arg Thr Gly Leu Tyr Arg His Pro Trp
    610              615              620

Asp Asp Ile Thr Tyr Leu Leu Pro Ser Val Asp Ser Leu Gly Gly Ser
625              630              635              640

Ser Arg Val Glu Val Thr Val
                645

<210> SEQ ID NO 11
<211> LENGTH: 1540
<212> TYPE: DNA
<213> ORGANISM: Lipomyces starkeyi
<220> FEATURE:
<221> NAME/KEY: Intron
<222> LOCATION: (445)..(496)

<400> SEQUENCE: 11
atgtccgcaa agtccatcca cgaggccgac ggaaaggcac tactctctta cttcctccca      60
cggtcaccgc tgctcacaaa ggaaggtact tcgaccgagt tcgtgcctgc tccaccgcgt     120
ctcgcgtcgc tcaccttccc tgacgactcc ccagcaaccg ttaaggccgt cctagatgct     180
gcagaatcga cctacggggtg gctgcttgcg ccgggtgcga agttcgtcgc caagcctgac     240
caattgatca agcgtcgtgg caagtccggt ctgctctcgc ttaacgtcac ctggcaacag     300
```

```
gctcgcgact ggatcacagt ccgcgctggt aagaagcttg ttgtcgaggg catccctggc    360
tacctgcgta ctttccttgt cgagcctttc gttccccatc cgcaagagac ggaatactac    420
atcaacatca actctgttcg tgaagtacgt attgtttgat cgcaactccg gggtgttatc    480
aatctaactt ttgtagggcg actggatttt gttttatcac gagggtggtg tcgatgtcgg    540
tgacgttgac tccaaggcct ctaagctgtt gatcccggtc gatctcgaca aggagtaccc    600
gacgaatgct actataatct ccactctcct ctccaaagtg ccagaggcac agcacgctac    660
gcttgtcgac ttcatcaacc gcctgtacgc cgtctatgtc gacctgcaat tcacgtacct    720
cgagattaac ccactcgtcg tcatcccgac cgcgtctggc gtcgaggtcc actatcttga    780
tctcgcggcc aagctcgacc aaacagcgga gttcgagtgc ggcgccaagt gggcaggtgc    840
ccgcgctcct actgcgctcg gaatcactcc ggccaagaac ggcgcctcga tcaacatcga    900
tgccggtccc ccaatggttt ccctgcgcc gtttggtcgt gagctttcgg acgaggaggc    960
ctacatcgcc gagcttgatg ccaaaaccgg tgcgtcgctc aagcttactg tgctcaatcc   1020
actaggccgc gtgtggacac tcgtcgcggg cggcggtgcg tccgtcgtgt acgccgatgc   1080
catcgcgtct gccggctacg ctaacgacat tgccaactac ggtgaatact ctggtgcacc   1140
taccgagacg caaacttacg agtacgcgaa gactgtgctg gatctgatga cccgcggtac   1200
tcccgtcgaa ggtggtaagg tcctgttcat tggcggtggt atcgcgaact tcacacaggt   1260
cggctcgaca ttcaagggca taattcgcgc gttcaaggac taccagtccc aactccacct   1320
ccatggcgtg aagatgtacg tccgccgcgg tgggcctaac tggcaggaag gtctccgtct   1380
gatcaaatcc tgcggcgagg agctctctat ccctatggag gtctacggac agacatgca   1440
cgtatctggt attgtccctc tcgcactgct caaaaagcga cctgctggca tctatccgtt   1500
tggctcttct gccagcagca gtgccgtcag tgtgctgtaa                         1540
```

<210> SEQ ID NO 12
<211> LENGTH: 495
<212> TYPE: PRT
<213> ORGANISM: Lipomyces starkeyi

<400> SEQUENCE: 12

Met Ser Ala Lys Ser Ile His Glu Ala Asp Gly Lys Ala Leu Leu Ser
1               5                   10                  15

Tyr Phe Leu Pro Arg Ser Pro Leu Leu Thr Lys Glu Gly Thr Ser Thr
                20                  25                  30

Glu Phe Val Pro Ala Pro Pro Arg Leu Ala Ser Leu Thr Phe Pro Asp
            35                  40                  45

Asp Ser Pro Ala Thr Val Lys Ala Val Leu Asp Ala Ala Glu Ser Thr
        50                  55                  60

Tyr Gly Trp Leu Leu Ala Pro Gly Ala Lys Phe Val Ala Lys Pro Asp
65                  70                  75                  80

Gln Leu Ile Lys Arg Arg Gly Lys Ser Gly Leu Leu Ser Leu Asn Val
                85                  90                  95

Thr Trp Gln Gln Ala Arg Asp Trp Ile Thr Val Arg Ala Gly Lys Lys
            100                 105                 110

Leu Val Val Glu Gly Ile Pro Gly Tyr Leu Arg Thr Phe Leu Val Glu
            115                 120                 125

Pro Phe Val Pro His Pro Gln Glu Thr Glu Tyr Tyr Ile Asn Ile Asn
        130                 135                 140

Ser Val Arg Glu Gly Asp Trp Ile Leu Phe Tyr His Glu Gly Gly Val

```
                145                 150                 155                 160
Asp Val Gly Asp Val Asp Ser Lys Ala Ser Lys Leu Leu Ile Pro Val
            165                 170                 175
Asp Leu Asp Lys Glu Tyr Pro Thr Asn Ala Thr Ile Ile Ser Thr Leu
        180                 185                 190
Leu Ser Lys Val Pro Glu Ala Gln His Ala Thr Leu Val Asp Phe Ile
    195                 200                 205
Asn Arg Leu Tyr Ala Val Tyr Val Asp Leu Gln Phe Thr Tyr Leu Glu
210                 215                 220
Ile Asn Pro Leu Val Val Ile Pro Thr Ala Ser Gly Val Glu Val His
225                 230                 235                 240
Tyr Leu Asp Leu Ala Ala Lys Leu Asp Gln Thr Ala Glu Phe Glu Cys
            245                 250                 255
Gly Ala Lys Trp Ala Gly Ala Arg Ala Pro Thr Ala Leu Gly Ile Thr
        260                 265                 270
Pro Ala Lys Asn Gly Ala Ser Ile Asn Ile Asp Ala Gly Pro Pro Met
    275                 280                 285
Val Phe Pro Ala Pro Phe Gly Arg Glu Leu Ser Asp Glu Glu Ala Tyr
290                 295                 300
Ile Ala Glu Leu Asp Ala Lys Thr Gly Ala Ser Leu Lys Leu Thr Val
305                 310                 315                 320
Leu Asn Pro Leu Gly Arg Val Trp Thr Leu Val Ala Gly Gly Gly Ala
            325                 330                 335
Ser Val Val Tyr Ala Asp Ala Ile Ala Ser Ala Gly Tyr Ala Asn Asp
        340                 345                 350
Ile Ala Asn Tyr Gly Glu Tyr Ser Gly Ala Pro Thr Glu Thr Gln Thr
    355                 360                 365
Tyr Glu Tyr Ala Lys Thr Val Leu Asp Leu Met Thr Arg Gly Thr Pro
370                 375                 380
Val Glu Gly Gly Lys Val Leu Phe Ile Gly Gly Gly Ile Ala Asn Phe
385                 390                 395                 400
Thr Gln Val Gly Ser Thr Phe Lys Gly Ile Ile Arg Ala Phe Lys Asp
            405                 410                 415
Tyr Gln Ser Gln Leu His Leu His Gly Val Lys Met Tyr Val Arg Arg
        420                 425                 430
Gly Gly Pro Asn Trp Gln Glu Gly Leu Arg Leu Ile Lys Ser Cys Gly
    435                 440                 445
Glu Glu Leu Ser Ile Pro Met Glu Val Tyr Gly Pro Asp Met His Val
450                 455                 460
Ser Gly Ile Val Pro Leu Ala Leu Leu Lys Lys Arg Pro Ala Gly Ile
465                 470                 475                 480
Tyr Pro Phe Gly Ser Ser Ala Ser Ser Ala Val Ser Val Leu
            485                 490                 495

<210> SEQ ID NO 13
<211> LENGTH: 1387
<212> TYPE: DNA
<213> ORGANISM: Lipomyces starkeyi
<220> FEATURE:
<221> NAME/KEY: Intron
<222> LOCATION: (42)..(89)
<220> FEATURE:
<221> NAME/KEY: Intron
<222> LOCATION: (168)..(220)
<220> FEATURE:
<221> NAME/KEY: Intron
<222> LOCATION: (747)..(799)
```

<400> SEQUENCE: 13

```
atgagtgaga aggcagagat cgaggttccg ccgcaaaaat cgtgagtacg tcggatgctt      60
gcttaggaca gatgctgatt gctatttagg acattccctc gcagtgtgca cttcgctcca     120
cttcatattc cactggagag acgcctacag actttggcag tcttattgta agtctcgtct     180
accttacggt gacatggagt cgctaatgat atgagggtag ccacactgtc gcgctaccat     240
actgcatcgg tctgttcttt ctcatgctcg cgttccctcc ttttttggcca ttattggtaa     300
tgtatgtcat atacgcatac gggttcgacc actcgagctc gaacggagag atctcccgcc     360
ggcgatcgcc gctgtttcga agactcccgt gttcaggct gtattgtgat acttccccca     420
tccacattca ccgggaggtt ccgctcgagc cgacgtttcc tggtcgcctt cgcgaaccga     480
gtggccttgt cgagcggtgg attgcgaaga tgttcggcgt gcaggacgct gttgtcgagg     540
gaaatgaatc tgacgttaag gccacggcca acggcaatgg gacgacgaaa gaaatcggac     600
cgacgtatgt tttcggctat catccgcatg gaattgttag cttgggtgcg tttggtgcta     660
ttggtacgga aggcgctgga tgggagaagc tctttcctgg gatcccggtg tcactgctga     720
ctctcgaaac aaatttcagc cttccagtag gttgatgttt gggtttgtct gccatgggat     780
agtactaata acagattagt tttacagaga gtatttgctg tcacttggga ttgcttcagt     840
atctcgacgg tcttgtacca atctcctcaa acacgaccaa tccatctgca tcgttatcgg     900
cggcgcccaa gagtcgctct tagcggaacc aggcactcta gatctgatcc tcgttaaacg     960
tcgcggtttt gtcaaacttg caatgtcaac ggcgcgggta tctgaccaac cgatttgtct    1020
tgttccgatc ctcagtttcg gcgagaacga cgtgtacgac caagtccgcg gggaccgatc    1080
gtcgaagttg tataagatcc agactttat caagaaagcg gccgggttta cgctaccatt    1140
gatgtatgcg cgcggtatat ttaattacga ctttgggctg atgccgtacc gcaggcaaat    1200
gacgctcgtg gtcggcaagc cgattgcagt gccgtacgtg gcccagccta cggaggctga    1260
aatcgaagtg tatcacaagc agtacatgga tgaattgagg aggttatggg acacgtataa    1320
ggacgactat tttgtagacc acaagggcaa gggggtcaag aattccgaga tgcgttttgt    1380
ggagtaa                                                               1387
```

<210> SEQ ID NO 14
<211> LENGTH: 410
<212> TYPE: PRT
<213> ORGANISM: Lipomyces starkeyi

<400> SEQUENCE: 14

```
Met Ser Glu Lys Ala Glu Ile Glu Val Pro Pro Gln Lys Ser Thr Phe
1               5                   10                  15

Pro Arg Ser Val His Phe Ala Pro Leu His Ile Pro Leu Glu Arg Arg
            20                  25                  30

Leu Gln Thr Leu Ala Val Leu Phe His Thr Val Ala Leu Pro Tyr Cys
        35                  40                  45

Ile Gly Leu Phe Phe Leu Met Leu Ala Phe Pro Pro Phe Trp Pro Leu
    50                  55                  60

Leu Val Met Tyr Val Ile Tyr Ala Tyr Gly Phe Asp His Ser Ser Ser
65                  70                  75                  80

Asn Gly Glu Ile Ser Arg Arg Arg Ser Pro Leu Phe Arg Arg Leu Pro
                85                  90                  95

Leu Phe Arg Leu Tyr Cys Asp Tyr Phe Pro Ile His Ile His Arg Glu
            100                 105                 110
```

Val Pro Leu Glu Pro Thr Phe Pro Gly Arg Leu Arg Glu Pro Ser Gly
         115                 120                 125
Leu Val Glu Arg Trp Ile Ala Lys Met Phe Gly Val Gln Asp Ala Val
130                 135                 140
Val Glu Gly Asn Glu Ser Asp Val Lys Ala Thr Ala Asn Gly Asn Gly
145                 150                 155                 160
Thr Thr Lys Glu Ile Gly Pro Thr Tyr Val Phe Gly Tyr His Pro His
                 165                 170                 175
Gly Ile Val Ser Leu Gly Ala Phe Gly Ala Ile Gly Thr Glu Gly Ala
                 180                 185                 190
Gly Trp Glu Lys Leu Phe Pro Gly Ile Pro Val Ser Leu Leu Thr Leu
                 195                 200                 205
Glu Thr Asn Phe Ser Leu Pro Phe Tyr Arg Glu Tyr Leu Leu Ser Leu
210                 215                 220
Gly Ile Ala Ser Val Ser Arg Arg Ser Cys Thr Asn Leu Leu Lys His
225                 230                 235                 240
Asp Gln Ser Ile Cys Ile Val Ile Gly Gly Ala Gln Glu Ser Leu Leu
                 245                 250                 255
Ala Glu Pro Gly Thr Leu Asp Leu Ile Leu Val Lys Arg Arg Gly Phe
                 260                 265                 270
Val Lys Leu Ala Met Ser Thr Ala Arg Val Ser Asp Gln Pro Ile Cys
                 275                 280                 285
Leu Val Pro Ile Leu Ser Phe Gly Glu Asn Asp Val Tyr Asp Gln Val
                 290                 295                 300
Arg Gly Asp Arg Ser Ser Lys Leu Tyr Lys Ile Gln Thr Phe Ile Lys
305                 310                 315                 320
Lys Ala Ala Gly Phe Thr Leu Pro Leu Met Tyr Ala Arg Gly Ile Phe
                 325                 330                 335
Asn Tyr Asp Phe Gly Leu Met Pro Tyr Arg Arg Gln Met Thr Leu Val
                 340                 345                 350
Val Gly Lys Pro Ile Ala Val Pro Tyr Val Ala Gln Pro Thr Glu Ala
                 355                 360                 365
Glu Ile Glu Val Tyr His Lys Gln Tyr Met Asp Glu Leu Arg Arg Leu
370                 375                 380
Trp Asp Thr Tyr Lys Asp Asp Tyr Phe Val Asp His Lys Gly Lys Gly
385                 390                 395                 400
Val Lys Asn Ser Glu Met Arg Phe Val Glu
                 405                 410

<210> SEQ ID NO 15
<211> LENGTH: 1543
<212> TYPE: DNA
<213> ORGANISM: Lipomyces starkeyi
<220> FEATURE:
<221> NAME/KEY: Intron
<222> LOCATION: (198)..(245)
<220> FEATURE:
<221> NAME/KEY: Intron
<222> LOCATION: (324)..(376)
<220> FEATURE:
<221> NAME/KEY: Intron
<222> LOCATION: (903)..(955)

<400> SEQUENCE: 15
atgcatggcg tcgcagtgcc ccaccttcct cccctctcg ctcccgattt ccgcttcgtc    60
cggctgcccg tcgactgcct cttcgctgtg ctggccttta catatttaga acaaacggat   120

```
catcggacaa gcggcatttt ctgtatcatt ttagcaatga gtgagaaggc agagatcgag    180
gttccgccgc aaaaatcgtg agtacgtcgg atgcttgctt aggacagatg ctgattgcta    240
tttaggacat tccctcgcag tgtgcacttc gctccacttc atattccact ggagagacgc    300
ctacagactt tggcagtctt attgtaagtc tcgtctacct tacggtgaca tggagtcgct    360
aatgatatga gggtagccac actgtcgcgc taccatactg catcggtctg ttctttctca    420
tgctcgcgtt ccctcctttt tggccattat tggtaatgta tgtcatatac gcatacgggt    480
tcgaccactc gagctcgaac ggagagatct cccgccggcg atcgccgctg tttcgaagac    540
tcccgttgtt caggctgtat tgtgattact tccccatcca cattcaccgg gaggttccgc    600
tcgagccgac gtttcctggt cgccttcgcg aaccgagtgg ccttgtcgag cggtggattg    660
cgaagatgtt cggcgtgcag gacgctgttg tcgagggaaa tgaatctgac gttaaggcca    720
cggccaacgg caatgggacg acgaaagaaa tcggaccgac gtatgttttc ggctatcatc    780
cgcatggaat tgttagcttg ggtgcgtttg gtgctattgg tacggaaggc gctggatggg    840
agaagctctt tcctgggatc ccggtgtcac tgctgactct cgaaacaaat ttcagccttc    900
cagtaggttg atgtttgggt ttgtctgcca tgggatagta ctaataacag attagtttta    960
cagagagtat ttgctgtcac ttgggattgc ttcagtatct cgacggtctt gtaccaatct   1020
cctcaaacac gaccaatcca tctgcatcgt tatcggcggc gcccaagagt cgctcttagc   1080
ggaaccaggc actctagatc tgatcctcgt aaacgtcgc ggttttgtca acttgcaat    1140
gtcaacggcg cgggtatctg accaaccgat ttgtcttgtt ccgatcctca gtttcggcga   1200
gaacgacgtg tacgaccaag tccgcgggga ccgatcgtcg aagttgtata agatccagac   1260
ttttatcaag aaagcggccg ggtttacgct accattgatg tatgcgcgcg gtatatttaa   1320
ttacgacttt gggctgatgc cgtaccgcag gcaaatgacg ctcgtggtcg caagccgat    1380
tgcagtgccg tacgtggccc agcctacgga ggctgaaatc gaagtgtatc acaagcagta   1440
catggatgaa ttgaggaggt tatgggacac gtataaggac gactattttg tagaccacaa   1500
gggcaagggg gtcaagaatt ccgagatgcg ttttgtggag taa                     1543
```

<210> SEQ ID NO 16
<211> LENGTH: 462
<212> TYPE: PRT
<213> ORGANISM: Lipomyces starkeyi

<400> SEQUENCE: 16

Met His Gly Val Ala Val Pro His Leu Pro Pro Leu Ala Pro Asp
1               5                   10                  15

Phe Arg Phe Val Arg Leu Pro Val Asp Cys Leu Phe Ala Val Leu Ala
                20                  25                  30

Phe Thr Tyr Leu Glu Gln Thr Asp His Arg Thr Ser Gly Ile Phe Cys
            35                  40                  45

Ile Ile Leu Ala Met Ser Glu Lys Ala Glu Ile Glu Val Pro Pro Gln
50                  55                  60

Lys Ser Thr Phe Pro Arg Ser Val His Phe Ala Pro Leu His Ile Pro
65                  70                  75                  80

Leu Glu Arg Arg Leu Gln Thr Leu Ala Val Leu Phe His Thr Val Ala
                85                  90                  95

Leu Pro Tyr Cys Ile Gly Leu Phe Phe Leu Met Leu Ala Phe Pro Pro
            100                 105                 110

Phe Trp Pro Leu Leu Val Met Tyr Val Ile Tyr Ala Tyr Gly Phe Asp
        115                 120                 125

```
His Ser Ser Ser Asn Gly Glu Ile Ser Arg Arg Ser Pro Leu Phe
    130                 135                 140
Arg Arg Leu Pro Leu Phe Arg Leu Tyr Cys Asp Tyr Phe Pro Ile His
145                 150                 155                 160
Ile His Arg Glu Val Pro Leu Glu Pro Thr Phe Pro Gly Arg Leu Arg
                165                 170                 175
Glu Pro Ser Gly Leu Val Glu Arg Trp Ile Ala Lys Met Phe Gly Val
            180                 185                 190
Gln Asp Ala Val Val Glu Gly Asn Glu Ser Asp Val Lys Ala Thr Ala
        195                 200                 205
Asn Gly Asn Gly Thr Thr Lys Glu Ile Gly Pro Thr Tyr Val Phe Gly
    210                 215                 220
Tyr His Pro His Gly Ile Val Ser Leu Gly Ala Phe Gly Ala Ile Gly
225                 230                 235                 240
Thr Glu Gly Ala Gly Trp Glu Lys Leu Phe Pro Gly Ile Pro Val Ser
                245                 250                 255
Leu Leu Thr Leu Glu Thr Asn Phe Ser Leu Pro Phe Tyr Arg Glu Tyr
            260                 265                 270
Leu Leu Ser Leu Gly Ile Ala Ser Val Ser Arg Arg Ser Cys Thr Asn
        275                 280                 285
Leu Leu Lys His Asp Gln Ser Ile Cys Ile Val Ile Gly Gly Ala Gln
    290                 295                 300
Glu Ser Leu Leu Ala Glu Pro Gly Thr Leu Asp Leu Ile Leu Val Lys
305                 310                 315                 320
Arg Arg Gly Phe Val Lys Leu Ala Met Ser Thr Ala Arg Val Ser Asp
                325                 330                 335
Gln Pro Ile Cys Leu Val Pro Ile Leu Ser Phe Gly Glu Asn Asp Val
            340                 345                 350
Tyr Asp Gln Val Arg Gly Asp Arg Ser Ser Lys Leu Tyr Lys Ile Gln
        355                 360                 365
Thr Phe Ile Lys Lys Ala Ala Gly Phe Thr Leu Pro Leu Met Tyr Ala
    370                 375                 380
Arg Gly Ile Phe Asn Tyr Asp Phe Gly Leu Met Pro Tyr Arg Arg Gln
385                 390                 395                 400
Met Thr Leu Val Val Gly Lys Pro Ile Ala Val Pro Tyr Val Ala Gln
                405                 410                 415
Pro Thr Glu Ala Glu Ile Glu Val Tyr His Lys Gln Tyr Met Asp Glu
            420                 425                 430
Leu Arg Arg Leu Trp Asp Thr Tyr Lys Asp Asp Tyr Phe Val Asp His
        435                 440                 445
Lys Gly Lys Gly Val Lys Asn Ser Glu Met Arg Phe Val Glu
    450                 455                 460

<210> SEQ ID NO 17
<211> LENGTH: 5724
<212> TYPE: DNA
<213> ORGANISM: Lipomyces starkeyi
<220> FEATURE:
<221> NAME/KEY: Intron
<222> LOCATION: (1927)..(1977)
<220> FEATURE:
<221> NAME/KEY: Intron
<222> LOCATION: (2192)..(2245)
<220> FEATURE:
<221> NAME/KEY: Intron
<222> LOCATION: (4798)..(4848)
```

```
<400> SEQUENCE: 17
atgcgtcccg agactgagca agagctcgcc catatcctac tcgtcgagct actcgcctac       60
cagttcgcgt cccccgtccg ctggatcgaa actcaggatg tcatcttcca ggagttcaac      120
tccgagcgtc tcgtcgaaat cggtccgtcc ccgacccttg cgggaatggc acagcgcact      180
ctaaaggcaa atacgagtc atacgatgct gcactctcac ttcagcgcca ggttctctgc       240
tactctaagg acgccaagga gatctactac accccagatc ccgtcgtcgt cgaagccgct      300
ccagagcctg ctgcggctac tgctggcgct cctgctactg ctgctcctgc tgcagctgca      360
gcagccgttg cagctgctcc atccggacca gttgccgctg tttctgatga gcctgtcaag      420
gctgtcgaaa tcttgcgctc gctcgtcgct cagaaactca agaagcctta cgaccaggtg      480
ccacttgcaa aggccattaa agatcttgtc ggcggcaagt ccactctcca gaacgaaatt      540
ctgggtgatc tgggcaagga gttcggctcg gctcctgaga aggcagagga gactcctcta      600
gaagagctag gcgccgctat ccagggttcc ggcttcaatg ccagctcgg caaacagtca       660
ctctcgctca tcggtcgact agtcgcttct aagatgcctg gtggcttcaa cctcacctcc      720
actcgcaagt atctccagga cagatggggt cttggacctg gtcgccagga cggtgttttg      780
ctcctcgcca tcacgatcga gccacctgcg cgtctcgcgg ccgaagccga tgcaaagaaa      840
tatctcgacg aagtcgctgc caagtacgct tccttcgccg gcatctcgct ctcgtccggc      900
agtggtgacg ccggtgccgg tggtgccgga ggcggcgcta ttgccatcga ctctgccgcg      960
ttcgaggagc tcaccaagga ccaaacccat ctcgttcgcc agcaaatgga attgtttgcc     1020
aagtacctca aggtcgacct ccgggccggc gataagcttt tcgtcgacga gcaggacgcg     1080
tcctccgaac tccgcaagga acttgacctc tggattgccg aacatggcga cttttacgcg     1140
accggcatca ttccctcctt ctcgccgctc aaggcccgcg tgtacgactc gtcttggaat     1200
tgggctcgcc aggatgcgct taccatgtac tacgacatca tctttggccg tctctctgtt     1260
gtcgataggg agattgtgtc ccactgcatt ctcctcatga accgctcgaa ccctactttta    1320
ctcgaattca tgcagtatca tatcgaccat gcccggagaa agcgtgggga cacataccag     1380
ctcgcgaagc agcttggcca gcagctcatc gacaactgcc gagatgcact cggcgtggag     1440
ccagtctata aggacgtcat gtacccaaca gctccccaga ccgccattga tgttaaagga     1500
aatatcaagt acgacgaagt ccctcgtgtc gcagtccgca agctcgagca atacgtcaag     1560
gaaatggccg ccggtggcaa gatcacggag aatcgcagcc gcacgaagtt gcacgccggc     1620
cttgcccgca tctacaaaat aatccgccag caacaaaagc ttagcaagag ttccaagctt     1680
cagatcaaga ccttgtacga ggacgtcatc caatctctct cgcttgaatc cggtcttgcc     1740
aacggcagtc cctcacccga tggcacaggc cgcccaactt cgcctaagcg caggaagggc     1800
ggcaagggaa agaaatacac cgaaacgatt ccgttcttgc acttgaagaa gaaggatatg     1860
cacggttggg actacagcaa gcctctgact ggcatctatc tcgagtgcct cgagcaggcc     1920
gcaaaagtaa gttttctcca catttgtata ctgcgagcat catacttact tatctagtcc     1980
ggtgtctcat ttaaagacaa gtacgctttg atgaccggtg ctggcgctgg ctctattggt     2040
gccgctgtct tgcagggact tttgtccggt ggtgcgaagg ttgttgtcac tacgtcgcga     2100
tattcgaagg aagtgaccga gtactatcaa tctatctacg cgaagtacgg cgccagcaac     2160
agtacattga ttgtcgttcc tttcaatcag ggtatgttta ttgaagagtt catttatcga     2220
aatttgttgc tgacaggttt gtcaggctct aagcaggacg ttgacgctct cgttgactac     2280
gtttacgaca ccaagaaggg tctcggctgg gatcttgatt atgtcattcc gtttgccgcc     2340
```

```
attccagaga acggccgtga gatcgacggc attgactcca agtccgagct tgctcaccga   2400
atgatgctta ctaacttact ccgcattctc ggcaatgtta agactcagaa gctcgctcac   2460
ggctacgcga ctcgtccggc tcaggtcatc ctaccgatgt cccccaacca cggtactttc   2520
gggtccgacg gcttgtattc ggagtctaag cttgcactcg agacattgtt caacagatgg   2580
tactccgagt cctggggtcc gtacctcacg atctgcggtg ccgtcattgg ctggactcgt   2640
ggcaccggtc ttatgaacca gaacaacttg atcgctgaac gtattgagag tcttggtgtc   2700
cgcaccttct ctcagcagga gatggctttc aacatcctcg gtcttatgtc ccccgcgatc   2760
gtcaacctt gccagatgga gcctgttttc gcggacttga atggtggcat gcagtatatt    2820
cccaatctca aggaggcctc agcccagatt cgtcaggagc tcctccagac gtccgagatt   2880
cgccgggcag tttcagcaga gagtgcgatc gagtacaagc ttgtcaatgg cgcagaagct   2940
gagcgtctgc aaaagtctgt cgtcatccag ccgcgtgcca atattaaatt cgagttcccg   3000
aggctcaagg agtactcaga aatcgctcac cttgccgaaa acctcaaggg catggtcgac   3060
ctcgagaaag tcgtcgtcgt cactggtttc gccgaagtcg gtccttgggg caacgctcgc   3120
acgcggtggg agatggaagc ctatggccag ttctctcttg aaggttgcat cgaaatggct   3180
tggattatgg gtctcattaa gcaccacaat ggtcaattga agggcaagat gtactctggc   3240
tgggtcgata ccaagagcaa cgagcctgtc gacgactttg acgtcaagtc gaagtacgag   3300
aaacatattc ttgagcactc cggcatccgg ttgattgagg ctgagttgtt tgacggctat   3360
gaccccaaga agaagaagat gcttcaggaa gttgttatcg agcatgatct cgagcctttc   3420
gagacctcga aggagaccgc gtacgagttt aagcgcgagc acggcgacaa ggtcgagatt   3480
ttcgagattg ctgagacagg gcagtggact gtccgactgc tcaagggcgc cagtctgcta   3540
attcccaagg cgctccagtt cgatcgtttg gttgctggtc agatcccgac cggctgggac   3600
gctcgacgat acggtatcgg ggaggacatc atttcgcagg tcgatccgat cactctctat   3660
gttcttgtct ccactgtcga ggcactgctt tctgccggtg ttaccgaccc gtacgagttc   3720
tacaagtacg tccatgtttc tgaggtcggt aactgcaccg gttccggtgt cggtggcatg   3780
agcgctcttc gcggcatgta caaggaccga tttatggaca agccggtcca gaaagatatt   3840
cttcaggaat ctttcatcaa cactatgtct gcatgggtta acatgttgct cctctcctcg   3900
tccggtccaa tcaagactcc tgtcggtgcc tgcgctactt ccattgagtc tgtcgatatt   3960
ggctacgaga ccatcatttc cggcaaggcc aagatatgtc tggtcggcgg ctacgacgat   4020
ttccaggaag aaggttcatt cgagttcggc aacatgggtg ccacatccaa ctccgagacc   4080
gagattgccc atgggcgtac cccagctgag atgtcccgtc cgacgacgac tacgcgtgcc   4140
ggtttcatgg agtcccatgg tgctggtatc cagttgatta tgacgccaa gctcgctctc    4200
gcaatgggtg tcccggtcta cggtatcatt ggtatgaccg ccaccgcgac cgacaagatc   4260
ggccgatccg tgccggcgcc tggtaagggt atcctcacca cagcgcgtga acagggag    4320
tccaagttcc cgtcgccact gcttgacatc aagtaccgac gccgccagct tgagaagcgt   4380
cagtcccaga tccgcgagtg gaccgagtcc gagatcttgt attttgcagca ggaagtcaat   4440
tccatgcgcg accaatatga gaatttcgat gagagggagt atttgaccga cgccttgcc    4500
catgttgagc gtgaggctgc gcgacaggag aaggacgcct tggcgcagtg gggtaatgat   4560
ttctacaagc aagatgcaag aatcgcgcct ctgcgtggtg cgcttgctgt ttggaatctt   4620
acggttgatg atcttggtgt tgcgtcgttc catggcacgt ccactgttgc aaatgataag   4680
```

-continued

```
aacgagagca tgacaattgc caacatgatg actcatctcg gacgatcaaa gggtaatgcc    4740
atcctcggca ttttccagaa gtatttgacc ggtcaccta  agggtgccgc aggtgctgta    4800
agtttcaagc attttttatta catttcagga gtgggctaac aatgacagtg gatgttgaac   4860
ggtgcgctcc aggtcctcaa cactggtctg gtgcccggta accgcaatgc cgacaatgtt    4920
gacaaggttc tcgaacagtt cgactcgatt ttgtatccgt cacgcagtat ccaaacggac    4980
ggtatcaagg ccgcgtccgt gacgtcgttc ggtttcggcc agaagggtgc ccaggcaatc    5040
atcattaact ctgattacct tttcgccact ctcgatgagg acgcatacaa cgcctacacc    5100
gcgaaggtcg tggcgcgtca caagagggcg tacagataca tccatcatgc catggccact    5160
aacaccatgt tcgtcgccaa gaacgatccg ccatatgcca aggacctcga gagcactgtc    5220
tatctcgacc cgcttgtgcg cgttgagccg ataagaaagg ctggcacgta cgcgtacccg    5280
gcaaagaagc ccgctcagcc atccaataag gagactgagg atgtgttgct gaagttaacc    5340
cagtccaccg cgtcaactgg caccaacgtc ggagtcgacg tagaggcttt gtcggccatc    5400
ccgattgaca acgagaccttt tatcgagcgt aactacactc ccgccgaaat cagttactgc    5460
tcttcttctg ctgatccccg ggcaagcttt gctggcactt ggtgcgcgaa ggaagctgtc    5520
ttcaagagct gggcgttaa  atccgacggc gcgggtgcgg cgttgaaaga atcgagatc    5580
gttcggaaat cgggcaagcc cgaggtcgtg ttctcaggcg ttgcgaagca acgggcggaa    5640
gaaaagggcg tcaaggacgt cagtgttagt atcagtcata acgaattcca ggcggtcgcg    5700
gttgctgttg cagagttggt ttaa                                          5724
```

<210> SEQ ID NO 18
<211> LENGTH: 1855
<212> TYPE: PRT
<213> ORGANISM: Lipomyces starkeyi

<400> SEQUENCE: 18

```
Met Arg Pro Glu Thr Glu Gln Glu Leu Ala His Ile Leu Leu Val Glu
1               5                   10                  15

Leu Leu Ala Tyr Gln Phe Ala Ser Pro Val Arg Trp Ile Glu Thr Gln
            20                  25                  30

Asp Val Ile Phe Gln Glu Phe Asn Ser Glu Arg Leu Val Glu Ile Gly
        35                  40                  45

Pro Ser Pro Thr Leu Ala Gly Met Ala Gln Arg Thr Leu Lys Ala Lys
    50                  55                  60

Tyr Glu Ser Tyr Asp Ala Ala Leu Ser Leu Gln Arg Gln Val Leu Cys
65                  70                  75                  80

Tyr Ser Lys Asp Ala Lys Glu Ile Tyr Tyr Thr Pro Asp Pro Val Val
                85                  90                  95

Val Glu Ala Ala Pro Glu Pro Ala Ala Thr Ala Gly Ala Pro Ala
            100                 105                 110

Thr Ala Pro Ala Ala Ala Ala Ala Val Ala Ala Ala Pro Ser
        115                 120                 125

Gly Pro Val Ala Ala Val Ser Asp Glu Pro Val Lys Ala Val Glu Ile
    130                 135                 140

Leu Arg Ser Leu Val Ala Gln Lys Leu Lys Pro Tyr Asp Gln Val
145                 150                 155                 160

Pro Leu Ala Lys Ala Ile Lys Asp Leu Val Gly Gly Lys Ser Thr Leu
                165                 170                 175

Gln Asn Glu Ile Leu Gly Asp Leu Gly Lys Glu Phe Gly Ser Ala Pro
            180                 185                 190
```

```
Glu Lys Ala Glu Glu Thr Pro Leu Glu Glu Leu Gly Ala Ala Ile Gln
        195                 200                 205

Gly Ser Gly Phe Asn Gly Gln Leu Gly Lys Gln Ser Leu Ser Leu Ile
        210                 215                 220

Gly Arg Leu Val Ala Ser Lys Met Pro Gly Gly Phe Asn Leu Thr Ser
225                 230                 235                 240

Thr Arg Lys Tyr Leu Gln Asp Arg Trp Gly Leu Gly Pro Gly Arg Gln
                245                 250                 255

Asp Gly Val Leu Leu Leu Ala Ile Thr Ile Glu Pro Pro Ala Arg Leu
                260                 265                 270

Ala Ala Glu Ala Asp Ala Lys Lys Tyr Leu Asp Glu Val Ala Ala Lys
                275                 280                 285

Tyr Ala Ser Phe Ala Gly Ile Ser Leu Ser Ser Gly Ser Gly Asp Ala
                290                 295                 300

Gly Ala Gly Gly Ala Gly Gly Ala Ile Ala Ile Asp Ser Ala Ala
305                 310                 315                 320

Phe Glu Glu Leu Thr Lys Asp Gln Thr His Leu Val Arg Gln Gln Met
                325                 330                 335

Glu Leu Phe Ala Lys Tyr Leu Lys Val Asp Leu Arg Ala Gly Asp Lys
                340                 345                 350

Leu Phe Val Asp Glu Gln Asp Ala Ser Ser Glu Leu Arg Lys Glu Leu
                355                 360                 365

Asp Leu Trp Ile Ala Glu His Gly Asp Phe Tyr Ala Thr Gly Ile Ile
                370                 375                 380

Pro Ser Phe Ser Pro Leu Lys Ala Arg Val Tyr Asp Ser Ser Trp Asn
385                 390                 395                 400

Trp Ala Arg Gln Asp Ala Leu Thr Met Tyr Tyr Asp Ile Ile Phe Gly
                405                 410                 415

Arg Leu Ser Val Val Asp Arg Glu Ile Val Ser His Cys Ile Leu Leu
                420                 425                 430

Met Asn Arg Ser Asn Pro Thr Leu Leu Glu Phe Met Gln Tyr His Ile
                435                 440                 445

Asp His Cys Pro Glu Lys Arg Gly Asp Thr Tyr Gln Leu Ala Lys Gln
                450                 455                 460

Leu Gly Gln Gln Leu Ile Asp Asn Cys Arg Asp Ala Leu Gly Val Glu
465                 470                 475                 480

Pro Val Tyr Lys Asp Val Met Tyr Pro Thr Ala Pro Gln Thr Ala Ile
                485                 490                 495

Asp Val Lys Gly Asn Ile Lys Tyr Asp Glu Val Pro Arg Val Ala Val
                500                 505                 510

Arg Lys Leu Glu Gln Tyr Val Lys Glu Met Ala Ala Gly Gly Lys Ile
                515                 520                 525

Thr Glu Asn Arg Ser Arg Thr Lys Leu His Ala Gly Leu Ala Arg Ile
                530                 535                 540

Tyr Lys Ile Ile Arg Gln Gln Lys Leu Ser Lys Ser Ser Lys Leu
545                 550                 555                 560

Gln Ile Lys Thr Leu Tyr Glu Asp Val Ile Gln Ser Leu Ser Leu Glu
                565                 570                 575

Ser Gly Leu Ala Asn Gly Ser Pro Ser Pro Asp Gly Thr Gly Arg Pro
                580                 585                 590

Thr Ser Pro Lys Arg Arg Lys Gly Gly Lys Gly Lys Lys Tyr Thr Glu
                595                 600                 605
```

```
Thr Ile Pro Phe Leu His Leu Lys Lys Lys Asp Met His Gly Trp Asp
    610             615             620
Tyr Ser Lys Pro Leu Thr Gly Ile Tyr Leu Glu Cys Leu Glu Gln Ala
625             630              635             640
Ala Lys Ser Gly Val Ser Phe Lys Asp Lys Tyr Ala Leu Met Thr Gly
                645             650             655
Ala Gly Ala Gly Ser Ile Gly Ala Ala Val Leu Gln Gly Leu Leu Ser
            660             665             670
Gly Gly Ala Lys Val Val Thr Thr Ser Arg Tyr Ser Lys Glu Val
            675             680             685
Thr Glu Tyr Tyr Gln Ser Ile Tyr Ala Lys Tyr Gly Ala Ser Asn Ser
690             695             700
Thr Leu Ile Val Val Pro Phe Asn Gln Gly Ser Lys Gln Asp Val Asp
705             710             715             720
Ala Leu Val Asp Tyr Val Tyr Asp Thr Lys Lys Gly Leu Gly Trp Asp
                725             730             735
Leu Asp Tyr Val Ile Pro Phe Ala Ala Ile Pro Glu Asn Gly Arg Glu
            740             745             750
Ile Asp Gly Ile Asp Ser Lys Ser Glu Leu Ala His Arg Met Met Leu
            755             760             765
Thr Asn Leu Leu Arg Ile Leu Gly Asn Val Lys Thr Gln Lys Leu Ala
770             775             780
His Gly Tyr Ala Thr Arg Pro Ala Gln Val Ile Leu Pro Met Ser Pro
785             790             795             800
Asn His Gly Thr Phe Gly Ser Asp Gly Leu Tyr Ser Glu Ser Lys Leu
                805             810             815
Ala Leu Glu Thr Leu Phe Asn Arg Trp Tyr Ser Glu Ser Trp Gly Pro
            820             825             830
Tyr Leu Thr Ile Cys Gly Ala Val Ile Gly Trp Thr Arg Gly Thr Gly
            835             840             845
Leu Met Asn Gln Asn Asn Leu Ile Ala Glu Arg Ile Glu Ser Leu Gly
            850             855             860
Val Arg Thr Phe Ser Gln Gln Glu Met Ala Phe Asn Ile Leu Gly Leu
865             870             875             880
Met Ser Pro Ala Ile Val Asn Leu Cys Gln Met Glu Pro Val Phe Ala
                885             890             895
Asp Leu Asn Gly Gly Met Gln Tyr Ile Pro Asn Leu Lys Glu Ala Ser
            900             905             910
Ala Gln Ile Arg Gln Glu Leu Leu Gln Thr Ser Glu Ile Arg Arg Ala
            915             920             925
Val Ser Ala Glu Ser Ala Ile Glu Tyr Lys Leu Val Asn Gly Ala Glu
930             935             940
Ala Glu Arg Leu Gln Lys Ser Val Val Ile Gln Pro Arg Ala Asn Ile
945             950             955             960
Lys Phe Glu Phe Pro Arg Leu Lys Glu Tyr Ser Glu Ile Ala His Leu
                965             970             975
Ala Glu Asn Leu Lys Gly Met Val Asp Leu Glu Lys Val Val Val Val
            980             985             990
Thr Gly Phe Ala Glu Val Gly Pro Trp Gly Asn Ala Arg Thr Arg Trp
            995             1000            1005
Glu Met Glu Ala Tyr Gly Gln Phe Ser Leu Glu Gly Cys Ile Glu
    1010            1015            1020
Met Ala Trp Ile Met Gly Leu Ile Lys His His Asn Gly Gln Leu
```

```
            1025                1030                1035
Lys Gly Lys Met Tyr Ser Gly Trp Val Asp Thr Lys Ser Asn Glu
        1040                1045                1050

Pro Val Asp Asp Phe Asp Val Lys Ser Lys Tyr Glu Lys His Ile
        1055                1060                1065

Leu Glu His Ser Gly Ile Arg Leu Ile Glu Ala Glu Leu Phe Asp
        1070                1075                1080

Gly Tyr Asp Pro Lys Lys Lys Met Leu Gln Glu Val Val Ile
        1085                1090                1095

Glu His Asp Leu Glu Pro Phe Glu Thr Ser Lys Glu Thr Ala Tyr
        1100                1105                1110

Glu Phe Lys Arg Glu His Gly Asp Lys Val Glu Ile Phe Glu Ile
        1115                1120                1125

Ala Glu Thr Gly Gln Trp Thr Val Arg Leu Leu Lys Gly Ala Ser
        1130                1135                1140

Leu Leu Ile Pro Lys Ala Leu Gln Phe Asp Arg Leu Val Ala Gly
        1145                1150                1155

Gln Ile Pro Thr Gly Trp Asp Ala Arg Arg Tyr Gly Ile Gly Glu
        1160                1165                1170

Asp Ile Ile Ser Gln Val Asp Pro Ile Thr Leu Tyr Val Leu Val
        1175                1180                1185

Ser Thr Val Glu Ala Leu Leu Ser Ala Gly Val Thr Asp Pro Tyr
        1190                1195                1200

Glu Phe Tyr Lys Tyr Val His Val Ser Glu Val Gly Asn Cys Thr
        1205                1210                1215

Gly Ser Gly Val Gly Gly Met Ser Ala Leu Arg Gly Met Tyr Lys
        1220                1225                1230

Asp Arg Phe Met Asp Lys Pro Val Gln Lys Asp Ile Leu Gln Glu
        1235                1240                1245

Ser Phe Ile Asn Thr Met Ser Ala Trp Val Asn Met Leu Leu Leu
        1250                1255                1260

Ser Ser Ser Gly Pro Ile Lys Thr Pro Val Gly Ala Cys Ala Thr
        1265                1270                1275

Ser Ile Glu Ser Val Asp Ile Gly Tyr Glu Thr Ile Ile Ser Gly
        1280                1285                1290

Lys Ala Lys Ile Cys Leu Val Gly Gly Tyr Asp Asp Phe Gln Glu
        1295                1300                1305

Glu Gly Ser Phe Glu Phe Gly Asn Met Gly Ala Thr Ser Asn Ser
        1310                1315                1320

Glu Thr Glu Ile Ala His Gly Arg Thr Pro Ala Glu Met Ser Arg
        1325                1330                1335

Pro Thr Thr Thr Thr Arg Ala Gly Phe Met Glu Ser His Gly Ala
        1340                1345                1350

Gly Ile Gln Leu Ile Met Thr Ala Lys Leu Ala Leu Ala Met Gly
        1355                1360                1365

Val Pro Val Tyr Gly Ile Ile Gly Met Thr Ala Thr Ala Thr Asp
        1370                1375                1380

Lys Ile Gly Arg Ser Val Pro Ala Pro Gly Lys Gly Ile Leu Thr
        1385                1390                1395

Thr Ala Arg Glu Asn Arg Glu Ser Lys Phe Pro Ser Pro Leu Leu
        1400                1405                1410

Asp Ile Lys Tyr Arg Arg Arg Gln Leu Glu Lys Arg Gln Ser Gln
        1415                1420                1425
```

```
Ile Arg Glu Trp Thr Glu Ser Glu Ile Leu Tyr Leu Gln Gln Glu
    1430                1435                1440

Val Asn Ser Met Arg Asp Gln Tyr Glu Asn Phe Asp Glu Arg Glu
    1445                1450                1455

Tyr Leu Thr Glu Arg Leu Ala His Val Glu Arg Glu Ala Ala Arg
    1460                1465                1470

Gln Glu Lys Asp Ala Leu Ala Gln Trp Gly Asn Asp Phe Tyr Lys
    1475                1480                1485

Gln Asp Ala Arg Ile Ala Pro Leu Arg Gly Ala Leu Ala Val Trp
    1490                1495                1500

Asn Leu Thr Val Asp Asp Leu Gly Val Ala Ser Phe His Gly Thr
    1505                1510                1515

Ser Thr Val Ala Asn Asp Lys Asn Glu Ser Met Thr Ile Ala Asn
    1520                1525                1530

Met Met Thr His Leu Gly Arg Ser Lys Gly Asn Ala Ile Leu Gly
    1535                1540                1545

Ile Phe Gln Lys Tyr Leu Thr Gly His Pro Lys Gly Ala Ala Gly
    1550                1555                1560

Ala Trp Met Leu Asn Gly Ala Leu Gln Val Leu Asn Thr Gly Leu
    1565                1570                1575

Val Pro Gly Asn Arg Asn Ala Asp Asn Val Asp Lys Val Leu Glu
    1580                1585                1590

Gln Phe Asp Ser Ile Leu Tyr Pro Ser Arg Ser Ile Gln Thr Asp
    1595                1600                1605

Gly Ile Lys Ala Ala Ser Val Thr Ser Phe Gly Phe Gly Gln Lys
    1610                1615                1620

Gly Ala Gln Ala Ile Ile Ile Asn Ser Asp Tyr Leu Phe Ala Thr
    1625                1630                1635

Leu Asp Glu Asp Ala Tyr Asn Ala Tyr Thr Ala Lys Val Val Ala
    1640                1645                1650

Arg His Lys Arg Ala Tyr Arg Tyr Ile His His Ala Met Ala Thr
    1655                1660                1665

Asn Thr Met Phe Val Ala Lys Asn Asp Pro Pro Tyr Ala Lys Asp
    1670                1675                1680

Leu Glu Ser Thr Val Tyr Leu Asp Pro Leu Val Arg Val Glu Pro
    1685                1690                1695

Asp Lys Lys Ala Gly Thr Tyr Ala Tyr Pro Ala Lys Lys Pro Ala
    1700                1705                1710

Gln Pro Ser Asn Lys Glu Thr Glu Asp Val Leu Leu Lys Leu Thr
    1715                1720                1725

Gln Ser Thr Ala Ser Thr Gly Thr Asn Val Gly Val Asp Val Glu
    1730                1735                1740

Ala Leu Ser Ala Ile Pro Ile Asp Asn Glu Thr Phe Ile Glu Arg
    1745                1750                1755

Asn Tyr Thr Pro Ala Glu Ile Ser Tyr Cys Ser Ser Ser Ala Asp
    1760                1765                1770

Pro Arg Ala Ser Phe Ala Gly Thr Trp Cys Ala Lys Glu Ala Val
    1775                1780                1785

Phe Lys Ser Leu Gly Val Lys Ser Asp Gly Ala Gly Ala Ala Leu
    1790                1795                1800

Lys Glu Ile Glu Ile Val Arg Lys Ser Gly Lys Pro Glu Val Val
    1805                1810                1815
```

```
Phe Ser Gly Val Ala Lys Gln Arg Ala Glu Glu Lys Gly Val Lys
    1820            1825                1830

Asp Val Ser Val Ser Ile Ser His Asn Glu Phe Gln Ala Val Ala
    1835            1840                1845

Val Ala Val Ala Glu Leu Val
    1850            1855

<210> SEQ ID NO 19
<211> LENGTH: 6456
<212> TYPE: DNA
<213> ORGANISM: Lipomyces starkeyi
<220> FEATURE:
<221> NAME/KEY: Intron
<222> LOCATION: (821)..(866)
<220> FEATURE:
<221> NAME/KEY: Intron
<222> LOCATION: (2665)..(2722)
<220> FEATURE:
<221> NAME/KEY: Intron
<222> LOCATION: (5302)..(5355)
<220> FEATURE:
<221> NAME/KEY: Intron
<222> LOCATION: (5425)..(5473)

<400> SEQUENCE: 19
atgtacgctg gcgctgagac tggcgtcgca acgcctcaca ctcaggcctc tctgcgtccg      60
ctctcgctcc agcatggctc gctggagcac accgtgtttg taccaaccgc gctctatctc     120
tcaatcctcc atctacggga cgaattcgcc gccactcttc ctactccaac tgaagacttc     180
gccggagacg aagagcctgc atccaactgc gagcttgttg cccgattcct cgccttttta     240
gtcgctcagg tcgaggaaga gccagaccag tatgatgacg ttctcgcgct cgtccttgcc     300
gactttgaat ctcgcttcct ccgtgcaaat gaagtccatg ccgtcgcagc tgcgcttcct     360
ggggatctgg ccaagcgtga ggtcgtcatc agcgcctact acgcagccag gctcgctgcc     420
aatcgtccaa tcaaaggcca cgattcagcg ctgcttcgtg cctccgctga cggtcgtgct     480 tccatttttcg caattttcgg cggccaggga aatatcgagg aatattttga tgagctccgc     540
aatgtctact ccctctatca tggtcttatt gacgactttg ttcagcactg cgctcgcgac     600
ttgctcaagc ttgcttccga cgatcgcacc atgaaagtct actcgaatgg cctcgacatc     660
atgcgatggc tccgcgagcc cgagtcgact cctgacctcg attatcttgt ttcggcacct     720
gtctcacttc ctttgatcgg tgtcactcag ctcactcatt acgctgccac ttgcaagatc     780
ctcggcaagg agccaggtga atttagatca cacttgtccg gtatgtattg attagtctga     840
caagtgacat ttgctaacgt cgacaggaac aaccggtcac tctcaaggtg tcgtcacggc     900
cgctgccatt tcggcctcga ctacatggga gtccttcttc gacgtcgcgt ccaagactct     960
ccagatcctg ttctggatcg gttgccgcgc tcagcagacc tatcctcgca cctctctcgc    1020
gccttccgtc ctccaggact cggtcaacga aggcgaaggc aaaccatcgc ctatgctttc    1080
ggtgcgcgac cttgtcaagt cccaggtcca gaagcacgtt gatttgacaa attcccatct    1140
tccaccagag aagcacgtct cgatctcgct cgagaacggt gcccgtaact ttgtcgtcac    1200
cggtccgcct cagtcgctct acggtctcag cttgtcgctc cgcaagtccc gtgcgccgcc    1260
cggactcgag cagaacagag tcccatattc ccagcgcaag ctcaagttct ccaatagatt    1320
cttacccatc actgctcctt tccactcgcc gtacgttcat gaggcatacg aaactatcgt    1380
cgatgatctc aaatctgcca atgtttcgtt tgcgccggag gagctcggca tcccagtcta    1440
cgatacatac gatggacatg acttacgcaa gcttacggac gaggacggct ccgttgtcga    1500
```

```
gcgtctcgtc aagatggtta ccagcctgcc tgtcaactgg gagcaagcca cagccttcgg    1560
caaggtcacg cacattctcg actttgggcc tggcggtgtg tctggcctag gtgtcttgac    1620
acatcgcaat aaggagggaa ctggtgtccg tgtcatcttg gccggcactt tggagggtac    1680
tctatcggag cttggttaca agtccgaatt gtttgatcgc gaggacgacg ctgtcaaatt    1740
tgccgctgac tggggtcttg agttcgcacc caaacttgtc aagactgcgc aagggcagac    1800
ctatgttgac acgaagtttt cgcgtttact tggacagccg cccatcatgg ttgctggtat    1860
gactccgtca accgttccgc ctgatttcgt tgctgccact atgaacgccg gataccacat    1920
cgaacttggc ggtggtggct actttaacgc cagtggtctc acccaagcgt tctacaagat    1980
cgaaaaatct actttccctg cgccggtat tacagtcaat ttgatctatg tcaacccccg    2040
ggccatggga tggcaatcc ctctcattca gaagctccgc gctgaaggcg ttccgatcga    2100
aggtctcacc atcggcgcag gtgttccatc gaccgaagtc gcgaacgagt acatcgaaac    2160
tctcggcatc aagcacctgg gtctcaaacc tgggtctata gacgcgatcc agcaggtcat    2220
taccatcgcg caggccaacc caacattccc gatcgtcttg cagtggacag gtggtcgtgg    2280
tggcggtcat cattcgttcg aggacttcca cagcccgatc ttgcagatgt acccgcgcat    2340
ccgtcggtgc agcaacatca tcctcctcgc gggctcaggt ttcggtggtg ccgaagacac    2400
gtacccgtac ttgactggtc agtgggcgac caggttcgcg tacccgccaa tgccatttga    2460
cggtgtctta tttggcagca gaatcatgac tgcgaaggaa gcgcacacgt cactaggggc    2520
aaagcaagct attgttgatg cgcctggtgt ggatgagttg cagtgggaga aaacgtataa    2580
tggtgctgct ggtggcgtca ttacagtctt gtccgagatg ggcgagccca ttcacaagtt    2640
ggctacgcga ggtgttgtgt tttggtaagt tccacagttt atatacctcc ctgggaaaaa    2700
tagctctgac gtacttgtgc aggaaggaga tggataccac gattttcagt ctgcccaaga    2760
acaagcgcgt cgatgccctc aaggccaaga aggactacat catcaagaag ctcaatgccg    2820
acttccaaaa ggtttggttc ggtaagaact ctgccggtga ggtagtcgaa ctcgaggaca    2880
tgacctacgg tgagattctc aagcgccttg ttgaactcat gtttgttgcc cacgagaagc    2940
gctggatcga ccttccgctg cgcaacatga ccggtgacta tatccgccgt attgaggagc    3000
gcttcacgca tgagacaggt cgcccatcgc tcctgcagtc gtacaccgag ctggatgagc    3060
cgacgccgac ggttgacaga atcctggcgg cgtatcccga ggccactgag cagattatca    3120
acgtgcaaga caaggagttt ttccttatgc tgaccctccg acctggtcag aagccggttc    3180
cgtttgttcc ggcgttggat gataattttg agttgtactt caagaaggac tcgctctggc    3240
agtctgagga ccttgctgcc gtcgtcggtc aggatgtgca gcgcacatgt gttctgcaag    3300
gtcctgtcgc tgtcaagtac gccaagatcg tcaacgaacc cgtgaaggac attttggatg    3360
gcattcacga caaacatatc gagttcttga ccaaggacat ttatggaggc gaggagtcga    3420
agattccggt tatcgaatac tttggaggca aagatattgt tccatctgtc tttgagaccg    3480
cattgaaggt agacagtttg actgttaccg aggccgacga ctccatcacc tatgtgctcg    3540
atgccggtgt cagcggcaac gctactcttc ccgacgttga gtcgtggttg agtttgcttg    3600
gtggtgaatg ttatgctgg cgccacgcat tcttcaccac cgatgttttt ggttcagggca    3660 cgaagtatga gacgagcccg cttaagcggt tgttcaagcc ggcttttggg gtcaaggtca    3720
ccattcagca tccggaagat ttggaaaaga ctcgcattat cgtttccgag aaaatcaacg    3780
gcaaggatgt cgtcgttatt gacaccttca agcgtccgga ttctaatacc atcgaaatga    3840
cgatttatga tgatcgtact gcagagggca agtctgttgg catgctgctg ttgttcacat    3900
```

```
atcaccctga agtcggattt gcgccaatcc gcgaggtcat ggccggccgc aacgacagaa    3960
tcaaggagtt ttactggaag ctgtggttcg gttctgagga gtacccggcc aacttatccg    4020
tcaccgacgc attcgaaggt ggctcgacca ccgtcactgg caaggcaatt gctgactttg    4080
tatatgctgt cgggaacaac ggtgaggcat ttgtcgaccg gcctggtaag actacattcg    4140
cacctatgga ttttgctatt gtagtagggt ggaaggctat tactaaggcg ctcttcccca    4200
aggccatcga cggtgacttg ttgaagctgg tccatctttc gaactcgttc aaaatgtacc    4260
ctggtgcaga gccgctcaag aaggacgacg tcgttaccac cactgccaag atcaatgctg    4320
tgttgaacca ggattccggt aagatggttg aagtcagcgg cgttatctcc cgtgattaca    4380
tgccagtcat ggaggtcacc tcccagttct tttacagagg cgcgtacacc gactacgaga    4440
acacgttcca gcgcaagtcg gagttgccga tggaggtcac gctcaagtct cccaaggatg    4500
ttgcggtttt gcgatcgaag gactggttcg agctcaatga cgatcctcac gttgacctac    4560
tcaaccagac tctcacattc cggctcgaaa ccttcgtcag atacaaaaac aagactgtct    4620
tttcgtctgt ccgcaccact ggtcaggttt tgcttgaatt gcctacgcgt gagattatcc    4680
agatcggcac cgttgagtac gaggccagtg aatcccatgg aaacccggtc atcgactatc    4740
ttgagcgcca cggcagcacg attgaacagc cgattatgtt cgaaaactcg atcccattga    4800
acgcctcgac ggagcttgtc taccgcgcgc ctgcttccaa cgaaggctac gctcgtgtgt    4860
ctggtgacta caacccgatc catgtgtccc gtgtgttcgc agagtatgcc aacctccgag    4920
gcaacatcac tcacggcatg tactcctccg ctgccgtccg gtcgctcgtc gagacctggg    4980
cagcggagaa ccacgtcgca cgcgtgcgtg ggtttaattg ctctttcgtc ggtatggtcc    5040
tgcctaacga gaatatcgag acgaaattgc accatgtcgg tatgattgcg ggccggaaga    5100
ttatcaaggt tgagaccacg aacaaggact caggtgatgt cgtcttgatc ggccaggcag    5160
aggtcgagca gcccgtgtcg acgtatatct tcactggcca gggttcgcag gagcagggta    5220
tgggaatgga tctatacgag tctagcgctg tagcgcgtga ggtttgggac cgcgctgata    5280
gacatttcct caataactat ggtatgtttt aatccgaagt agctcgaagg tgaattgaac    5340
taatgtcgtg aacaggcttt tcaattatca atattgttaa gaacaatcct aaagagttta    5400
ctgttcactt tggtggtcca cgaggtgcgt attctctcct ttgataaaat taatgatatc    5460
tgacatttcg caggcaaggc aattaggcac aactacacat cgatgatgtt cgagtctgtt    5520
gatgcggacg gtcagctcaa gtccgagaag atcttcaagg acatcacgga gaacacatct    5580
tcttacacct tccgttcgcc tactggcttg ttgtcagcca ctcagttcac gcagccggct    5640
ttgacgctta tggagaaggc ttcgttcgag gacatgaacg ccaagggtct tgtcccggct    5700
gactgctcgt acgcaggcca ctcgttgggc gaatactctg cgctcgcggc actcggcgac    5760
gtcatgccga tcgagtctct tgtcgatgtc gtgttctacc gtggtatgac catgcaagtc    5820
gcagtcccgc gtgacgcgct aggacgatcg aattatggta tgtgtgctgt caacccgtct    5880
cgtatctcgc cgaccttcaa cgatgccgca ctccgctatg tcgtcgaaca catatcctct    5940
cagaccaagt ggctcttgga gattgtcaat tacaatgttg agaacacgca atacgtcacc    6000
gccggagatc tccgtggact tgactgtctt accaacgtgc tcaatttcat gaaggtacag    6060
aagatcgacc tcgacaagct catgaagacc atgtcgatgg aagacgttaa ggagcagctc    6120
accgacattg tcgaagaaat agcgaagaag agcatcgcaa agccgcagcc gatcgagctc    6180
gaccgtggtt tcgccactat ccctctcaaa ggtatttcgg tgccgttcca ctccagttat    6240
```

```
ctgcgcagcg gtgtcaagcc gtttaaccgg ttcttgatca agaagttgcc acagcaggcg    6300
ctcaagccgg ccaatttaat tggaaagtat attcccaatt tgactgccaa gccattctcg    6360
atctcgaagg agtatttcca ggaagtgtat gacttgaccg gtagcgccaa gatcaggagc    6420
attttggaca actgggagaa gtatgagact gcttag                              6456
```

<210> SEQ ID NO 20
<211> LENGTH: 2082
<212> TYPE: PRT
<213> ORGANISM: Lipomyces starkeyi

<400> SEQUENCE: 20

```
Met Tyr Ala Gly Ala Glu Thr Gly Val Ala Thr Pro His Thr Gln Ala
1               5                   10                  15

Ser Leu Arg Pro Leu Ser Leu Gln His Gly Ser Leu Glu His Thr Val
            20                  25                  30

Phe Val Pro Thr Ala Leu Tyr Leu Ser Ile Leu His Leu Arg Asp Glu
        35                  40                  45

Phe Ala Ala Thr Leu Pro Thr Pro Thr Glu Asp Phe Ala Gly Asp Glu
    50                  55                  60

Glu Pro Ala Ser Asn Cys Glu Leu Val Ala Arg Phe Leu Ala Phe Leu
65                  70                  75                  80

Val Ala Gln Val Glu Glu Pro Asp Gln Tyr Asp Asp Val Leu Ala
                85                  90                  95

Leu Val Leu Ala Asp Phe Glu Ser Arg Phe Leu Arg Ala Asn Glu Val
            100                 105                 110

His Ala Val Ala Ala Ala Leu Pro Gly Asp Leu Ala Lys Arg Glu Val
        115                 120                 125

Val Ile Ser Ala Tyr Tyr Ala Ala Arg Leu Ala Ala Asn Arg Pro Ile
    130                 135                 140

Lys Gly His Asp Ser Ala Leu Leu Arg Ala Ser Ala Asp Gly Arg Ala
145                 150                 155                 160

Ser Ile Phe Ala Ile Phe Gly Gly Gln Gly Asn Ile Glu Glu Tyr Phe
                165                 170                 175

Asp Glu Leu Arg Asn Val Tyr Ser Leu Tyr His Gly Leu Ile Asp Asp
            180                 185                 190

Phe Val Gln His Cys Ala Arg Asp Leu Leu Lys Leu Ala Ser Asp Asp
        195                 200                 205

Arg Thr Met Lys Val Tyr Ser Asn Gly Leu Asp Ile Met Arg Trp Leu
    210                 215                 220

Arg Glu Pro Glu Ser Thr Pro Asp Leu Asp Tyr Leu Val Ser Ala Pro
225                 230                 235                 240

Val Ser Leu Pro Leu Ile Gly Val Thr Gln Leu Thr His Tyr Ala Ala
                245                 250                 255

Thr Cys Lys Ile Leu Gly Lys Glu Pro Gly Glu Phe Arg Ser His Leu
            260                 265                 270

Ser Gly Thr Thr Gly His Ser Gln Gly Val Val Thr Ala Ala Ala Ile
        275                 280                 285

Ser Ala Ser Thr Thr Trp Glu Ser Phe Phe Asp Val Ala Ser Lys Thr
    290                 295                 300

Leu Gln Ile Leu Phe Trp Ile Gly Cys Arg Ala Gln Gln Thr Tyr Pro
305                 310                 315                 320

Arg Thr Ser Leu Ala Pro Ser Val Leu Gln Asp Ser Val Asn Glu Gly
                325                 330                 335
```

```
Glu Gly Lys Pro Ser Pro Met Leu Ser Val Arg Asp Leu Val Lys Ser
            340             345                 350

Gln Val Gln Lys His Val Asp Leu Thr Asn Ser His Leu Pro Pro Glu
        355                 360                 365

Lys His Val Ser Ile Ser Leu Glu Asn Gly Ala Arg Asn Phe Val Val
    370                 375                 380

Thr Gly Pro Pro Gln Ser Leu Tyr Gly Leu Ser Leu Ser Leu Arg Lys
385                 390                 395                 400

Ser Arg Ala Pro Pro Gly Leu Glu Gln Asn Arg Val Pro Tyr Ser Gln
                405                 410                 415

Arg Lys Leu Lys Phe Ser Asn Arg Phe Leu Pro Ile Thr Ala Pro Phe
            420                 425                 430

His Ser Pro Tyr Val His Glu Ala Tyr Glu Thr Ile Val Asp Asp Leu
        435                 440                 445

Lys Ser Ala Asn Val Ser Phe Ala Pro Glu Leu Gly Ile Pro Val
    450                 455                 460

Tyr Asp Thr Tyr Asp Gly His Asp Leu Arg Lys Leu Thr Asp Glu Asp
465                 470                 475                 480

Gly Ser Val Val Glu Arg Leu Val Lys Met Val Thr Ser Leu Pro Val
                485                 490                 495

Asn Trp Glu Gln Ala Thr Ala Phe Gly Lys Val Thr His Ile Leu Asp
            500                 505                 510

Phe Gly Pro Gly Gly Val Ser Gly Leu Gly Val Leu Thr His Arg Asn
        515                 520                 525

Lys Glu Gly Thr Gly Val Arg Val Ile Leu Ala Gly Thr Leu Glu Gly
    530                 535                 540

Thr Leu Ser Glu Leu Gly Tyr Lys Ser Glu Leu Phe Asp Arg Glu Asp
545                 550                 555                 560

Asp Ala Val Lys Phe Ala Ala Asp Trp Gly Leu Glu Phe Ala Pro Lys
                565                 570                 575

Leu Val Lys Thr Ala Gln Gly Gln Thr Tyr Val Asp Thr Lys Phe Ser
            580                 585                 590

Arg Leu Leu Gly Gln Pro Pro Ile Met Val Ala Gly Met Thr Pro Ser
        595                 600                 605

Thr Val Pro Pro Asp Phe Val Ala Ala Thr Met Asn Ala Gly Tyr His
    610                 615                 620

Ile Glu Leu Gly Gly Gly Gly Tyr Phe Asn Ala Ser Gly Leu Thr Gln
625                 630                 635                 640

Ala Phe Tyr Lys Ile Glu Lys Ser Thr Phe Pro Gly Ala Gly Ile Thr
                645                 650                 655

Val Asn Leu Ile Tyr Val Asn Pro Arg Ala Met Gly Trp Ala Ile Pro
            660                 665                 670

Leu Ile Gln Lys Leu Arg Ala Glu Gly Val Pro Ile Glu Gly Leu Thr
        675                 680                 685

Ile Gly Ala Gly Val Pro Ser Thr Glu Val Ala Asn Glu Tyr Ile Glu
    690                 695                 700

Thr Leu Gly Ile Lys His Leu Gly Leu Lys Pro Gly Ser Ile Asp Ala
705                 710                 715                 720

Ile Gln Gln Val Ile Thr Ile Ala Gln Ala Asn Pro Thr Phe Pro Ile
                725                 730                 735

Val Leu Gln Trp Thr Gly Gly Arg Gly Gly Gly His His Ser Phe Glu
            740                 745                 750

Asp Phe His Ser Pro Ile Leu Gln Met Tyr Pro Arg Ile Arg Arg Cys
```

```
                    755                 760                 765
Ser Asn Ile Ile Leu Leu Ala Gly Ser Gly Phe Gly Gly Ala Glu Asp
        770                 775                 780

Thr Tyr Pro Tyr Leu Thr Gly Gln Trp Ala Thr Arg Phe Ala Tyr Pro
785                 790                 795                 800

Pro Met Pro Phe Asp Gly Val Leu Phe Gly Ser Arg Ile Met Thr Ala
                805                 810                 815

Lys Glu Ala His Thr Ser Leu Gly Ala Lys Gln Ala Ile Val Asp Ala
        820                 825                 830

Pro Gly Val Asp Glu Leu Gln Trp Glu Lys Thr Tyr Asn Gly Ala Ala
                835                 840                 845

Gly Gly Val Ile Thr Val Leu Ser Glu Met Gly Glu Pro Ile His Lys
        850                 855                 860

Leu Ala Thr Arg Gly Val Val Phe Trp Lys Glu Met Asp Thr Thr Ile
865                 870                 875                 880

Phe Ser Leu Pro Lys Asn Lys Arg Val Asp Ala Leu Lys Ala Lys Lys
                885                 890                 895

Asp Tyr Ile Ile Lys Lys Leu Asn Ala Asp Phe Gln Lys Val Trp Phe
                900                 905                 910

Gly Lys Asn Ser Ala Gly Glu Val Val Glu Leu Glu Asp Met Thr Tyr
        915                 920                 925

Gly Glu Ile Leu Lys Arg Leu Val Glu Leu Met Phe Val Ala His Glu
        930                 935                 940

Lys Arg Trp Ile Asp Leu Ser Leu Arg Asn Met Thr Gly Asp Tyr Ile
945                 950                 955                 960

Arg Arg Ile Glu Glu Arg Phe Thr His Glu Thr Gly Arg Pro Ser Leu
                965                 970                 975

Leu Gln Ser Tyr Thr Glu Leu Asp Glu Pro Thr Pro Thr Val Asp Arg
        980                 985                 990

Ile Leu Ala Ala Tyr Pro Glu Ala Thr Glu Gln Ile Ile Asn Val Gln
        995                 1000                1005

Asp Lys Glu Phe Phe Leu Met Leu Thr Leu Arg Pro Gly Gln Lys
        1010                1015                1020

Pro Val Pro Phe Val Pro Ala Leu Asp Asp Asn Phe Glu Leu Tyr
        1025                1030                1035

Phe Lys Lys Asp Ser Leu Trp Gln Ser Glu Asp Leu Ala Ala Val
        1040                1045                1050

Val Gly Gln Asp Val Gln Arg Thr Cys Val Leu Gln Gly Pro Val
        1055                1060                1065

Ala Val Lys Tyr Ala Lys Ile Val Asn Glu Pro Val Lys Asp Ile
        1070                1075                1080

Leu Asp Gly Ile His Asp Lys His Ile Glu Phe Leu Thr Lys Asp
        1085                1090                1095

Ile Tyr Gly Gly Glu Glu Ser Lys Ile Pro Val Ile Glu Tyr Phe
        1100                1105                1110

Gly Gly Lys Asp Ile Val Pro Ser Val Phe Glu Thr Ala Leu Lys
        1115                1120                1125

Val Asp Ser Leu Thr Val Thr Glu Ala Asp Asp Ser Ile Thr Tyr
        1130                1135                1140

Val Leu Asp Ala Gly Val Ser Gly Asn Ala Thr Leu Pro Asp Val
        1145                1150                1155

Glu Ser Trp Leu Ser Leu Leu Gly Gly Glu Cys Tyr Gly Trp Arg
        1160                1165                1170
```

-continued

```
His Ala Phe Phe Thr Thr Asp Val Phe Val Gln Gly Thr Lys Tyr
    1175                1180                1185

Glu Thr Ser Pro Leu Lys Arg Leu Phe Lys Pro Ala Phe Gly Val
    1190                1195                1200

Lys Val Thr Ile Gln His Pro Glu Asp Leu Glu Lys Thr Arg Ile
    1205                1210                1215

Ile Val Ser Glu Lys Ile Asn Gly Lys Asp Val Val Ile Asp
    1220                1225                1230

Thr Phe Lys Arg Pro Asp Ser Asn Thr Ile Glu Met Thr Ile Tyr
    1235                1240                1245

Asp Asp Arg Thr Ala Glu Gly Lys Ser Val Gly Met Leu Leu Leu
    1250                1255                1260

Phe Thr Tyr His Pro Glu Val Gly Phe Ala Pro Ile Arg Glu Val
    1265                1270                1275

Met Ala Gly Arg Asn Asp Arg Ile Lys Glu Phe Tyr Trp Lys Leu
    1280                1285                1290

Trp Phe Gly Ser Glu Glu Tyr Pro Ala Asn Leu Ser Val Thr Asp
    1295                1300                1305

Ala Phe Glu Gly Gly Ser Thr Thr Val Thr Gly Lys Ala Ile Ala
    1310                1315                1320

Asp Phe Val Tyr Ala Val Gly Asn Asn Gly Glu Ala Phe Val Asp
    1325                1330                1335

Arg Pro Gly Lys Thr Thr Phe Ala Pro Met Asp Phe Ala Ile Val
    1340                1345                1350

Val Gly Trp Lys Ala Ile Thr Lys Ala Leu Phe Pro Lys Ala Ile
    1355                1360                1365

Asp Gly Asp Leu Leu Lys Leu Val His Leu Ser Asn Ser Phe Lys
    1370                1375                1380

Met Tyr Pro Gly Ala Glu Pro Leu Lys Lys Asp Val Val Thr
    1385                1390                1395

Thr Thr Ala Lys Ile Asn Ala Val Leu Asn Gln Asp Ser Gly Lys
    1400                1405                1410

Met Val Glu Val Ser Gly Val Ile Ser Arg Asp Tyr Met Pro Val
    1415                1420                1425

Met Glu Val Thr Ser Gln Phe Phe Tyr Arg Gly Ala Tyr Thr Asp
    1430                1435                1440

Tyr Glu Asn Thr Phe Gln Arg Lys Ser Glu Leu Pro Met Glu Val
    1445                1450                1455

Thr Leu Lys Ser Pro Lys Asp Val Ala Val Leu Arg Ser Lys Asp
    1460                1465                1470

Trp Phe Glu Leu Asn Asp Asp Pro His Val Asp Leu Leu Asn Gln
    1475                1480                1485

Thr Leu Thr Phe Arg Leu Glu Thr Phe Val Arg Tyr Lys Asn Lys
    1490                1495                1500

Thr Val Phe Ser Ser Val Arg Thr Thr Gly Gln Val Leu Leu Glu
    1505                1510                1515

Leu Pro Thr Arg Glu Ile Ile Gln Ile Gly Thr Val Glu Tyr Glu
    1520                1525                1530

Ala Ser Glu Ser His Gly Asn Pro Val Ile Asp Tyr Leu Glu Arg
    1535                1540                1545

His Gly Ser Thr Ile Glu Gln Pro Ile Met Phe Glu Asn Ser Ile
    1550                1555                1560
```

-continued

Pro Leu Asn Ala Ser Thr Glu Leu Val Tyr Arg Ala Pro Ala Ser
1565                1570                1575

Asn Glu Gly Tyr Ala Arg Val Ser Gly Asp Tyr Asn Pro Ile His
1580                1585                1590

Val Ser Arg Val Phe Ala Glu Tyr Ala Asn Leu Arg Gly Asn Ile
1595                1600                1605

Thr His Gly Met Tyr Ser Ser Ala Ala Val Arg Ser Leu Val Glu
1610                1615                1620

Thr Trp Ala Ala Glu Asn His Val Ala Arg Val Arg Gly Phe Asn
1625                1630                1635

Cys Ser Phe Val Gly Met Val Leu Pro Asn Glu Asn Ile Glu Thr
1640                1645                1650

Lys Leu His His Val Gly Met Ile Ala Gly Arg Lys Ile Ile Lys
1655                1660                1665

Val Glu Thr Thr Asn Lys Asp Ser Gly Asp Val Val Leu Ile Gly
1670                1675                1680

Gln Ala Glu Val Glu Gln Pro Val Ser Thr Tyr Ile Phe Thr Gly
1685                1690                1695

Gln Gly Ser Gln Glu Gln Gly Met Gly Met Asp Leu Tyr Glu Ser
1700                1705                1710

Ser Ala Val Ala Arg Glu Val Trp Asp Arg Ala Asp Arg His Phe
1715                1720                1725

Leu Asn Asn Tyr Gly Phe Ser Ile Ile Asn Ile Val Lys Asn Asn
1730                1735                1740

Pro Lys Glu Phe Thr Val His Phe Gly Gly Pro Arg Gly Lys Ala
1745                1750                1755

Ile Arg His Asn Tyr Thr Ser Met Met Phe Glu Ser Val Asp Ala
1760                1765                1770

Asp Gly Gln Leu Lys Ser Glu Lys Ile Phe Lys Asp Ile Thr Glu
1775                1780                1785

Asn Thr Ser Ser Tyr Thr Phe Arg Ser Pro Thr Gly Leu Leu Ser
1790                1795                1800

Ala Thr Gln Phe Thr Gln Pro Ala Leu Thr Leu Met Glu Lys Ala
1805                1810                1815

Ser Phe Glu Asp Met Asn Ala Lys Gly Leu Val Pro Ala Asp Cys
1820                1825                1830

Ser Tyr Ala Gly His Ser Leu Gly Glu Tyr Ser Ala Leu Ala Ala
1835                1840                1845

Leu Gly Asp Val Met Pro Ile Glu Ser Leu Val Asp Val Val Phe
1850                1855                1860

Tyr Arg Gly Met Thr Met Gln Val Ala Val Pro Arg Asp Ala Leu
1865                1870                1875

Gly Arg Ser Asn Tyr Gly Met Cys Ala Val Asn Pro Ser Arg Ile
1880                1885                1890

Ser Pro Thr Phe Asn Asp Ala Ala Leu Arg Tyr Val Val Glu His
1895                1900                1905

Ile Ser Ser Gln Thr Lys Trp Leu Leu Glu Ile Val Asn Tyr Asn
1910                1915                1920

Val Glu Asn Thr Gln Tyr Val Thr Ala Gly Asp Leu Arg Gly Leu
1925                1930                1935

Asp Cys Leu Thr Asn Val Leu Asn Phe Met Lys Val Gln Lys Ile
1940                1945                1950

Asp Leu Asp Lys Leu Met Lys Thr Met Ser Met Glu Asp Val Lys

| | | | | | | | | | | | |
|---|---|---|---|---|---|---|---|---|---|---|---|
| | | 1955 | | | | 1960 | | | | 1965 | |
| Glu | Gln | Leu | Thr | Asp | Ile | Val | Glu | Glu | Ile | Ala | Lys Lys Ser Ile |
| | | 1970 | | | | 1975 | | | | 1980 | |
| Ala | Lys | Pro | Gln | Pro | Ile | Glu | Leu | Asp | Arg | Gly | Phe Ala Thr Ile |
| | | 1985 | | | | 1990 | | | | 1995 | |
| Pro | Leu | Lys | Gly | Ile | Ser | Val | Pro | Phe | His | Ser | Ser Tyr Leu Arg |
| | | 2000 | | | | 2005 | | | | 2010 | |
| Ser | Gly | Val | Lys | Pro | Phe | Asn | Arg | Phe | Leu | Ile | Lys Lys Leu Pro |
| | | 2015 | | | | 2020 | | | | 2025 | |
| Gln | Gln | Ala | Leu | Lys | Pro | Ala | Asn | Leu | Ile | Gly | Lys Tyr Ile Pro |
| | | 2030 | | | | 2035 | | | | 2040 | |
| Asn | Leu | Thr | Ala | Lys | Pro | Phe | Ser | Ile | Ser | Lys | Glu Tyr Phe Gln |
| | | 2045 | | | | 2050 | | | | 2055 | |
| Glu | Val | Tyr | Asp | Leu | Thr | Gly | Ser | Ala | Lys | Ile | Arg Ser Ile Leu |
| | | 2060 | | | | 2065 | | | | 2070 | |
| Asp | Asn | Trp | Glu | Lys | Tyr | Glu | Thr | Ala | | | |
| | | 2075 | | | | 2080 | | | | | |

```
<210> SEQ ID NO 21
<211> LENGTH: 5159
<212> TYPE: DNA
<213> ORGANISM: Lipomyces starkeyi
<220> FEATURE:
<221> NAME/KEY: Intron
<222> LOCATION: (63)..(216)
<220> FEATURE:
<221> NAME/KEY: Intron
<222> LOCATION: (244)..(365)
<220> FEATURE:
<221> NAME/KEY: Intron
<222> LOCATION: (827)..(882)

<400> SEQUENCE: 21
atgacttcgg tttcagacga agagagagcg cgcactcaca cattggtatt ggagctcttg      60
gcgtaagtct tctacccttg gtccaagttt tcccaatttg gcagttagcc ctaaatgctg     120
ggctgggcga tctcgacacg agaagctgta atatcgacta cagcaaggat agaaaacata     180
taggagcaag agctaatagt tattctttcc tgacagtcat cagttcgcat atcctgtaca     240
atggtaagct tcccattctt tcccaccact tcaaagacgc tgtcatgtca tgtgctcgat     300
catgttgacc tcgtacattg attttgttca cccaaaggca atatgctgac aggtggatgg     360
tgaaggattg atacacaaga tgccctcttg ggggaagaaa agatcgagcg attcgtcgag     420
attgggccat cgaacacact cactggactg gctaaacaaa ctatccaaac gaaatatcaa     480
gaccatgaca ctgccctgtc aatccaaagg cagcttttaa gcatcaaaca gactgagagt     540
gacatctact atgcaactgg agaggccgtg gaggtgccaa acaagcacc tgctaaaacc      600
gacgcaaaac ctactgctcc agctccgtcg ccagagcctg ctgcaaccgc gcccgcgcca     660
tctgctccct cgcccgcacc gagtggagct ggtgccagat cgattgcaac agctgaggat     720
gtcccagtga agtcagaaga tatagttctt actattattg ctcaaaagtt gaagaagtcc     780
accaaggata tttcgctcag cagtaatatc aaagcgctcg ttggaggtat gaaatccatc     840
gaatgaaact tcagtgacat aaaactgatt tgaatatttt aggtcgctca actttggaga     900
atgagattgt cggagaccct cttagtgaat tcggcaacct acctgaaaga tccgaggaac     960
tcagtttgac cgagctggga gaaacccttca acagcgcaaa tgctcaaaga cgactcggca    1020
agcagacaaa tacccctagta caacgtctta ttgctgcgtc aatgccggga gattttagca    1080
```

```
tgacaagggt cagaaaatat cttgaggatc gttggggctt tcaagctggc cgccaagatt    1140
ccgtgcttct atctgcaatt ccctcgcctc ctaaaaaccg acttgggat ccaaaggaag    1200 tcaatgctta tctggattca ttggttaagg agtatgcgca agccgctgga ttggcactgg    1260
aagaagcacc acagcagcag cagcagtctg ccgtccaagt caatccggaa gccataaatg    1320
ctgttgttcg gagacaagag caactggcag aacagcagct caaagtctac gctcaatttc    1380
tggatgttga tctccatgct gatggcaagt ctgcagagca atcggaaagc gccatgtcgg    1440
ctcttcagaa acagttagat tgtgggtag ctgaacatgg tgaggcgtat gctagtggta    1500
tcactccagt ctttgatgcc aagaagcttc gagagtactc ctcttactgg acttgggcct    1560
tgcaagacct cacagctact ttctacgata tcagtcgcgg aacattaaaa gtcgaccctg    1620
aggtgattga tgatatttct taccggctgg ccaacaaatc aagcccaccg ttagtggact    1680
caatcagata cctgttgacg caatgtcatg atgaaaaatc aaaggccttc taccaactcc    1740
ttctcaatac tgttgcgcag tcaattggat ctattcccgt tttcaagacc tccacgaatt    1800
tccttggccc tcgaacaact atcgacgagc tgggcaatat cacatactct gaacacccga    1860
ggtctgaaga cggatcaaag gagcatttgg gtgaaccgac tcgtcttcca catattaaac    1920
gcaagaatga caaagaatgg acattcgatt cggcaacgac cgcattgtac aacaaagcta    1980
tcgatcaaat ctcaagcaca ggtctctcac tcgccaataa aacgattctc ctaactggag    2040
ccggaacgaa ctccatcggt gaagagcttc tgaaaggcct tctcgctggt ggtgcacaag    2100
tcattgttac gaccaatagc ttttcatcca agacagctct caagtatcag aagatctacc    2160
agggtcacgg ctctaaaggg tccaaactgg ttttggttcc atttaaccaa ggtagccagc    2220
aggatgtcga atctctggtt gattatatct acaaccagaa acaaggcctc ggttgggatc    2280
ttgatgttgt catcccattc gccgcaattt ctgttacagg gcgacaaata gacgagattg    2340
actccaagag tgagatagca cagcgtatca tgctgacaaa tactattcga cttctcggag    2400
ctatcaagag acataaggag gctgcaggct accgaacccg gcccacccat gctatacttc    2460
ccctgtcacc caaccatggt gtctttggtg gtgatggtct atactctgag tcgaagatgg    2520
cactcgaaag tctgttcgca aaatggcatt ctgaaggttg gagcgattat ctctccatct    2580
gtggtacttc aatcggttgg actcgcggca ccggtctgat gcatcagaac gatacagtgg    2640
ccgagggcgt cgaaaaactt ggcgtgagaa cattctcccg accagaaatg gctctctgca    2700
ttctcgcctt attgagtcgt ccttttggtcg agttttctca agaagaaccc ctgtacgccg    2760
acttcagcgt tggtatggat aaagtaccag atttcccgag tgagttgaac gcgatccagg    2820
ataacatcaa agcctgagc gagatccgaa gagctgttgc agcggaatta gcgcttgaca    2880
acggatctga tcttaaagcg acaaagtcag ccaaaaatga acaggatgcc ataaaaaaac    2940
gtgcgaagat cgagcttgga tttccgacct tgccaaacta tgaaacagag attcagccgc    3000
tccgctccca attggattcc atggtctcgc ttgaacacac tgttgtgatt gtaggcttt    3060 cggagctagg accttgcgga aattctcgta ctcgctggga aatggaagcc tatgatgaac    3120
tctcgctcga aggatgcacc gaaatggctt ggatcatggg cctcataaaa tattccaagg    3180
cctctggtaa taaaccagcc ggatggatcg atgtcaagac aaaagagccc gttgaggaat    3240
ttgacgtgaa aaagcgttac gagtcatata ttcgcgagca tacgggcatt cgactaattg    3300
agccgactct tttcgacaag tacaatcctg aaaagaagca aatgactcaa gagattgtcg    3360
tccaagaaga tcttgcacca ttcgaaacat ctaaggatgc tgcactcagc tttaagagag    3420
aacacggaga caaggtggaa atattcccag gcgtggagtc tgactcttac agtgtcgtca    3480
```

```
tgaaaaaggg ggcagtgata catgttccca aggccgtgaa gttcagacaa actgtcgcgg    3540
cacagattcc tacaggatgg gatccacgga cgtatggcat ttcagacgat attatcaacc    3600
aggtcgatcc ggtcaccttca tatacacttg taacaactgt cgaaggcctt ctttcagcgg    3660
gtatcacgga tccttacgag atctacaagt acatccatgt ctccgaactt ggcaattgct    3720
ttggaagcgg tttgggtggt acaaactcct cagaaaagat gtaccgggat cggttggcag    3780
acaagcctgt gcagaatgat atcttgcaag agacattttt gaacacagtt ggagcttggg    3840
tgaacatgct cttgctctca tcaagtggac caaacaagac atccgttgga gcctgcgcaa    3900
cttctgtgga atcacttgac acagcctacg atctcattct tgctggcaag gcaaagatgt    3960
gtttcgttgg tagcgttgac gagttctcag aatacacgtc tttggagttt cgaacatga    4020 aagcaactat caatgccgag acggagcgtg aggctggtcg ggacccgaag agatgtcac    4080 gtcctgcagc ctcttcaagg aaaggtttca tggaatccca cggcgctggt ctccatatag    4140
cttgcacgga aaagcttgcc attgagatgg gactgcctat atatggtgtc atcgccttca    4200
caggcatctc cagtgacaag gtcggccgct ctgttcccgc tccgggcaag ggagtcctgt    4260
caaatgcaag agaatcgaca gctggggttcc catcgccact tcttgatatc gaatatcgtc    4320
gacgacagat tgatatacga cgacagcaaa tcaccaactt cagagaggtg gagctcagta    4380
accttgagga cacgattctg catcttatgg ccaataataa tcatttcaat gcatctgaat    4440
atcgagcata tatggtcaag cagattgatc tcaaattcca gatgcaggaa caagatatgc    4500
ttgcctcctt tggaaatcac ttttggcgta accaccctga atcgcaccc atcaagggag    4560 cgttggcaac ctggggtctt agtgtcgacg atgtgaccgt ggcttctttc cacggaacct    4620
caactgtcct gaacgagaag aacgagtgct ctattatcca aaaccagctt tctcatctcg    4680
gacgtaccaa aggaagtcgc actctcggtg tattccagaa gagcgtcacc gggcacccga    4740
aaggtcctgc aagttcctgg atgctcaatg gctgcctgca gatcatgagc acggggctcg    4800
tgccaggaaa ccgaaatcta gataatttgg atcccgggtt tgaacagtac gatcatatca    4860
cgttcctgaa ccagaatgtt caaacggctg gcatcaaggc cttctctttg acctcatttg    4920
gcttcggcca gaagggtggt caggtgattg gtgtgcaccc caaatatctg tttgcgacaa    4980
ttccgaagga tgtgttcgac gactacgcga agaggttgaa gaagaggcgg gcgattgcga    5040
ctgtcgcatt ccatgaggca ttgctcgaga taacatgtt tgtggcgaag gacgacccgc    5100
cgtacgatgt tgtacaggag atgaagacgc tactggatcc aaatgctagg tgggagtag    5159
```

<210> SEQ ID NO 22
<211> LENGTH: 1608
<212> TYPE: PRT
<213> ORGANISM: Lipomyces starkeyi

<400> SEQUENCE: 22

```
Met Thr Ser Val Ser Asp Glu Glu Arg Ala Arg Thr His Thr Leu Val
1               5                   10                  15

Leu Glu Leu Leu Ala His Gln Phe Ala Tyr Pro Val Gln Trp Ile Asp
            20                  25                  30

Thr Gln Asp Ala Leu Leu Gly Glu Glu Lys Ile Glu Arg Phe Val Glu
        35                  40                  45

Ile Gly Pro Ser Asn Thr Leu Thr Gly Ser Ala Lys Gln Thr Ile Gln
    50                  55                  60

Thr Lys Tyr Gln Asp His Asp Thr Ala Ser Ser Ile Gln Arg Gln Leu
65                  70                  75                  80
```

```
Leu Ser Ile Lys Gln Thr Glu Ser Asp Ile Tyr Tyr Ala Thr Gly Glu
                85              90                  95
Ala Val Glu Val Pro Lys Gln Ala Pro Ala Lys Thr Asp Ala Lys Pro
            100                 105                 110
Thr Ala Pro Ala Pro Ser Pro Glu Pro Ala Ala Thr Ala Pro Ala Pro
            115                 120                 125
Ser Ala Pro Ser Pro Ala Pro Ser Gly Ala Gly Ala Arg Ser Ile Ala
    130                 135                 140
Thr Ala Glu Asp Val Pro Val Lys Ser Glu Asp Ile Val Leu Thr Ile
145                 150                 155                 160
Ile Ala Gln Lys Leu Lys Lys Ser Thr Lys Asp Ile Ser Leu Ser Ser
                165                 170                 175
Asn Ile Lys Ala Leu Val Gly Gly Arg Ser Thr Leu Glu Asn Glu Ile
            180                 185                 190
Val Gly Asp Leu Leu Ser Glu Phe Gly Asn Leu Pro Glu Arg Ser Glu
            195                 200                 205
Glu Leu Ser Leu Thr Glu Ser Gly Glu Thr Leu Asn Ser Ala Asn Ala
    210                 215                 220
Gln Arg Arg Leu Gly Lys Gln Thr Asn Thr Leu Val Gln Arg Leu Ile
225                 230                 235                 240
Ala Ala Ser Met Pro Gly Asp Phe Ser Met Thr Arg Val Arg Lys Tyr
                245                 250                 255
Leu Glu Asp Arg Trp Gly Phe Gln Ala Gly Arg Gln Asp Ser Val Leu
            260                 265                 270
Leu Ser Ala Ile Pro Ser Pro Lys Asn Arg Leu Gly Asp Pro Lys
    275                 280                 285
Glu Val Asn Ala Tyr Ser Asp Ser Leu Val Lys Glu Tyr Ala Gln Ala
    290                 295                 300
Ala Gly Leu Ala Ser Glu Glu Ala Pro Gln Gln Gln Gln Gln Ser Ala
305                 310                 315                 320
Val Gln Val Asn Pro Glu Ala Ile Asn Ala Val Val Arg Arg Gln Glu
                325                 330                 335
Gln Ser Ala Glu Gln Leu Lys Val Tyr Ala Gln Phe Ser Asp Val
            340                 345                 350
Asp Leu His Ala Asp Gly Lys Ser Ala Glu Gln Ser Glu Ser Ala Met
            355                 360                 365
Ser Ala Leu Gln Lys Gln Leu Asp Leu Trp Val Ala Glu His Gly Glu
    370                 375                 380
Ala Tyr Ala Ser Gly Ile Thr Pro Val Phe Asp Ala Lys Lys Leu Arg
385                 390                 395                 400
Glu Tyr Ser Ser Tyr Trp Thr Trp Ala Leu Gln Asp Leu Thr Ala Thr
                405                 410                 415
Phe Tyr Asp Ile Ser Arg Gly Thr Leu Lys Val Asp Pro Glu Val Ile
            420                 425                 430
Asp Asp Ile Ser Tyr Arg Ser Ala Asn Lys Ser Ser Pro Leu Val
            435                 440                 445
Asp Ser Ile Arg Tyr Ser Leu Thr Gln Cys His Asp Glu Lys Ser Lys
    450                 455                 460
Ala Phe Tyr Gln Leu Leu Leu Asn Thr Val Ala Gln Ser Ile Gly Ser
465                 470                 475                 480
Ile Pro Val Phe Lys Thr Ser Thr Asn Phe Leu Gly Pro Arg Thr Thr
                485                 490                 495
```

```
Ile Asp Glu Ser Gly Asn Ile Thr Tyr Ser Glu His Pro Arg Ser Glu
            500                 505                 510

Asp Gly Ser Lys Glu His Leu Gly Pro Thr Arg Leu Pro His Ile
        515                 520                 525

Lys Arg Lys Asn Asp Lys Glu Trp Thr Phe Asp Ser Ala Thr Thr Ala
        530                 535                 540

Leu Tyr Asn Lys Ala Ile Asp Gln Ile Ser Ser Thr Gly Leu Ser Leu
545                 550                 555                 560

Ala Asn Lys Thr Ile Leu Leu Thr Gly Ala Gly Thr Asn Ser Ile Gly
                565                 570                 575

Glu Glu Leu Ser Lys Gly Leu Leu Ala Gly Gly Ala Gln Val Ile Val
            580                 585                 590

Thr Thr Asn Ser Phe Ser Ser Lys Thr Ala Leu Lys Tyr Gln Lys Ile
        595                 600                 605

Tyr Gln Gly His Gly Ser Lys Gly Ser Lys Ser Val Leu Val Pro Phe
        610                 615                 620

Asn Gln Gly Ser Gln Gln Asp Val Glu Ser Ser Val Asp Tyr Ile Tyr
625                 630                 635                 640

Asn Gln Lys Gln Gly Leu Gly Trp Asp Leu Asp Val Val Ile Pro Phe
                645                 650                 655

Ala Ala Ile Ser Val Thr Gly Arg Gln Ile Asp Glu Ile Asp Ser Lys
                660                 665                 670

Ser Glu Ile Ala Gln Arg Ile Met Ser Thr Asn Thr Ile Arg Leu Leu
            675                 680                 685

Gly Ala Ile Lys Arg His Lys Glu Ala Ala Gly Tyr Arg Thr Arg Pro
        690                 695                 700

Thr His Ala Ile Leu Pro Ser Ser Pro Asn His Gly Val Phe Gly Gly
705                 710                 715                 720

Asp Gly Leu Tyr Ser Glu Ser Lys Met Ala Leu Glu Ser Ser Phe Ala
                725                 730                 735

Lys Trp His Ser Glu Gly Trp Ser Asp Tyr Leu Ser Ile Cys Gly Thr
            740                 745                 750

Ser Ile Gly Trp Thr Arg Gly Thr Gly Ser Met His Gln Asn Asp Thr
        755                 760                 765

Val Ala Glu Gly Val Glu Lys Leu Gly Val Arg Thr Phe Ser Arg Pro
        770                 775                 780

Glu Met Ala Leu Cys Ile Leu Ala Leu Leu Ser Arg Pro Leu Val Glu
785                 790                 795                 800

Phe Ser Gln Glu Glu Pro Ser Tyr Ala Asp Phe Ser Gly Gly Met Asp
                805                 810                 815

Lys Val Pro Asp Phe Pro Ser Glu Leu Asn Ala Ile Gln Asp Asn Ile
                820                 825                 830

Lys Ser Ser Ser Glu Ile Arg Arg Ala Val Ala Ala Glu Leu Ala Leu
        835                 840                 845

Asp Asn Gly Ser Asp Leu Lys Ala Thr Lys Ser Ala Lys Asn Glu Gln
        850                 855                 860

Asp Ala Ile Lys Lys Arg Ala Lys Ile Glu Leu Gly Phe Pro Thr Leu
865                 870                 875                 880

Pro Asn Tyr Glu Thr Glu Ile Gln Pro Leu Arg Ser Gln Leu Asp Ser
                885                 890                 895

Met Val Ser Leu Glu His Thr Val Val Ile Val Gly Phe Ser Glu Leu
            900                 905                 910

Gly Pro Cys Gly Asn Ser Arg Thr Arg Trp Glu Met Glu Ala Tyr Asp
```

```
                915                 920                 925
Glu Leu Ser Leu Glu Gly Cys Thr Glu Met Ala Trp Ile Met Gly Leu
    930                 935                 940
Ile Lys Tyr Ser Lys Ala Ser Gly Asn Lys Pro Ala Gly Trp Ile Asp
945                 950                 955                 960
Val Lys Thr Lys Glu Pro Val Glu Glu Phe Asp Val Lys Lys Arg Tyr
                965                 970                 975
Glu Ser Tyr Ile Arg Glu His Thr Gly Ile Arg Leu Ile Glu Pro Thr
            980                 985                 990
Leu Phe Asp Lys Tyr Asn Pro Glu Lys Lys Gln Met Thr Gln Glu Ile
        995                 1000                1005
Val Val Gln Glu Asp Leu Ala Pro Phe Glu Thr Ser Lys Asp Ala
    1010                1015                1020
Ala Leu Ser Phe Lys Arg Glu His Gly Asp Lys Val Glu Ile Phe
    1025                1030                1035
Pro Gly Val Glu Ser Asp Ser Tyr Ser Val Val Met Lys Lys Gly
    1040                1045                1050
Ala Val Ile His Val Pro Lys Ala Val Lys Phe Arg Gln Thr Val
    1055                1060                1065
Ala Ala Gln Ile Pro Thr Gly Trp Asp Pro Arg Thr Tyr Gly Ile
    1070                1075                1080
Ser Asp Asp Ile Ile Asn Gln Val Asp Pro Val Thr Leu Tyr Thr
    1085                1090                1095
Leu Val Thr Thr Val Glu Gly Leu Leu Ser Ala Gly Ile Thr Asp
    1100                1105                1110
Pro Tyr Glu Ile Tyr Lys Tyr Ile His Val Ser Glu Leu Gly Asn
    1115                1120                1125
Cys Phe Gly Ser Gly Leu Gly Gly Thr Asn Ser Ser Glu Lys Met
    1130                1135                1140
Tyr Arg Asp Arg Leu Ala Asp Lys Pro Val Gln Asn Asp Ile Leu
    1145                1150                1155
Gln Glu Thr Phe Leu Asn Thr Val Gly Ala Trp Val Asn Met Leu
    1160                1165                1170
Leu Leu Ser Ser Ser Gly Pro Asn Lys Thr Ser Val Gly Ala Cys
    1175                1180                1185
Ala Thr Ser Val Glu Ser Leu Asp Thr Ala Tyr Asp Leu Ile Leu
    1190                1195                1200
Ala Gly Lys Ala Lys Met Cys Phe Val Gly Ser Val Asp Glu Phe
    1205                1210                1215
Ser Glu Tyr Thr Ser Leu Glu Phe Ser Asn Met Lys Ala Thr Ile
    1220                1225                1230
Asn Ala Glu Thr Glu Arg Glu Ala Gly Arg Asp Pro Lys Glu Met
    1235                1240                1245
Ser Arg Pro Ala Ala Ser Ser Arg Lys Gly Phe Met Glu Ser His
    1250                1255                1260
Gly Ala Gly Leu His Ile Ala Cys Thr Ala Lys Leu Ala Ile Glu
    1265                1270                1275
Met Gly Ser Pro Ile Tyr Gly Val Ile Ala Phe Thr Gly Ile Ser
    1280                1285                1290
Ser Asp Lys Val Gly Arg Ser Val Pro Ala Pro Gly Lys Gly Val
    1295                1300                1305
Ser Ser Asn Ala Arg Glu Ser Thr Ala Gly Phe Pro Ser Pro Leu
    1310                1315                1320
```

```
Leu Asp Ile Glu Tyr Arg Arg Arg Gln Ile Asp Ile Arg Arg Gln
    1325                1330                1335

Gln Ile Thr Asn Phe Arg Glu Val Glu Leu Ser Asn Leu Glu Asp
    1340                1345                1350

Thr Ile Ser His Leu Met Ala Asn Asn Asn His Phe Asn Ala Ser
    1355                1360                1365

Glu Tyr Arg Ala Tyr Met Val Lys Gln Ile Asp Leu Lys Phe Gln
    1370                1375                1380

Met Gln Glu Gln Asp Met Leu Ala Ser Phe Gly Asn His Phe Trp
    1385                1390                1395

Arg Asn His Pro Glu Ile Ala Pro Ile Lys Gly Ala Leu Ala Thr
    1400                1405                1410

Trp Gly Leu Ser Val Asp Asp Val Thr Val Ala Ser Phe His Gly
    1415                1420                1425

Thr Ser Thr Val Ser Asn Glu Lys Asn Glu Cys Ser Ile Ile Gln
    1430                1435                1440

Asn Gln Leu Ser His Leu Gly Arg Thr Lys Gly Ser Arg Thr Leu
    1445                1450                1455

Gly Val Phe Gln Lys Ser Val Thr Gly His Pro Lys Gly Pro Ala
    1460                1465                1470

Ser Ser Trp Met Leu Asn Gly Cys Ser Gln Ile Met Ser Thr Gly
    1475                1480                1485

Leu Val Pro Gly Asn Arg Asn Leu Asp Asn Leu Asp Pro Gly Phe
    1490                1495                1500

Glu Gln Tyr Asp His Ile Thr Phe Ser Asn Gln Asn Val Gln Thr
    1505                1510                1515

Ala Gly Ile Lys Ala Phe Ser Leu Thr Ser Phe Gly Phe Gly Gln
    1520                1525                1530

Lys Gly Gly Gln Val Ile Gly Val His Pro Lys Tyr Ser Phe Ala
    1535                1540                1545

Thr Ile Pro Lys Asp Val Phe Asp Asp Tyr Ala Lys Arg Leu Lys
    1550                1555                1560

Lys Arg Arg Ala Ile Ala Thr Val Ala Phe His Glu Ala Leu Leu
    1565                1570                1575

Glu Asn Asn Met Phe Val Ala Lys Asp Asp Pro Tyr Asp Val
    1580                1585                1590

Val Gln Glu Met Lys Thr Leu Ser Asp Pro Asn Ala Arg Trp Glu
    1595                1600                1605

<210> SEQ ID NO 23
<211> LENGTH: 6132
<212> TYPE: DNA
<213> ORGANISM: Lipomyces starkeyi
<220> FEATURE:
<221> NAME/KEY: Intron
<222> LOCATION: (5030)..(5080)

<400> SEQUENCE: 23
atgagggatc gatttttca acatatcggc acgacggcgg ccagtgatga gctgttacct      60
caggagtcac tggtagagct tatcacagac tttctggact tcaaatcaaa gcttttgctt    120
aattggccag gtgccgatag aacatccagg cagaggcttc ttcgagcttt gctcgaccat    180
ctggagagaa atgccttac agatgacatc cacaccattg cggcgatatc gtccgacgac     240
cccgagcgac ctgctaaaat cattcgatca tactactctg cgtgccatgc atcaggtcgc    300
```

```
cccatagcca agcgccagtc tgcactgctg gattccgttt cgagtggtga ctccaagttg    360
tacgccgtgc tcggtggtca aggaatcact actgcttatc tggatgagct gcgcgaaatc    420
catacaatgt atcacagttt cttggtagat tatatcgaga cattggggga gttcttgaaa    480
tcccttgcat cccagccaga tgtgtctcga tattacccag aaggcctgga tatcatcaac    540
tggctgcgaa acccggaagc aacaccagat gtaagctacc ttgcttcatc ccgagtcagc    600
ttccctatta ttggcatact ccagctcgcg caatatatgg tcagcctgaa ggttttgggt    660
caaaatccct caactttcaa tcccagtctt agcggcatag ctggccactc tcagggttg    720 gtcattgctg cagtaatcgc tggcgctgtc gactggtcgt cttcatcga cttgagtcgt    780 acagccgtgg agatactgtt ttcgattgga gttgtcagcc agcagatcta tcctgagaca    840
tcaccagacc caagatagt ctccgattct atctccaatg atgaaggcac cccttcctct    900
atgctcagca ttcgtggcat ctccgaagct caagtccagg agcacgtgga tgtgtccaac    960
aaatctctac ccgaagatag aaagatttcg attgctctag caaatgggcc acgtaatttc   1020
gtggttgctg gacctgccac atccttgtgt gggctgaacg cacgtttgag gcggtttaaa   1080
gtgtccgcag aagtcgacca gaaccgaatc ccatcaaagg agcgaaaatc gactctcacg   1140
aaccactttc tccctataag tgtgcctttc cacaccaact atctacttcc tgcacttccg   1200
atcttgagaa agcgtctcgg ccatattttc ctacccagta acagtctgca aattccggta   1260
tacgacacaa acactggcga agaccttagc gccttgggta gtgagaatct acttgatagg   1320
ctagtatacc tgatcacagt cgcccctgtt cgctggctca aggcttcaac ctgtgaatcg   1380
gcgtctcata tcgttgactt tggtcctgga ggcagttccg gtattggcgt cgttactagc   1440
cacaacaagc aaggaacggg tgttcgtgtt atgatggctg gcgctttagc tggaaaatcc   1500
tccgaagtcg gttacaaggc cgaacttttc agttggaaca agcttccat tgtggatagc   1560 aagaattggg caagaagctt tagcccaaga ctgattcggg cgaccgatgg gcaaattcac   1620
ctcgagacca aaatgagcaa gcttttacac atgccaccca tcatggttgc tggcatgacg   1680
ccaactactg tatcctggag atttgtttca gctaccatca atgctggata tcacattgag   1740
ttagctggcg gaggctaccg tgacgaagcc atgttgacaa cagccttgaa caacatcgtg   1800
gctacgattc cacctggacg aggagtttgc atcaacatca tatatgtcga ccccgtgca   1860 gtagcatggc agatcccact tctggagaag ctccatgcgg aaggaatacc aattgatggt   1920
ttgaccattg gcgctggagt gccttcagtc gagatttccc aaagctatat caacgacctt   1980
ggattgaaat atattgcctt caaacctggt tcggtcaatt caatcaagca ggttattagc   2040
attgctaaag ccaattccac cttccccgtc attttgcagt ggactggcgg ccgagccgga   2100
ggccatcact ctttcgaaga cttccacacg ccgattttgg aagtctatgg ccagatccgc   2160
gattgcgaaa atattattct cgtcgctggt agtggctttg gctcagctga ggatgcttat   2220
ccatacttca ctggagcatg gtccaaggct ttcggttatc cccccatgcc ctttgatggt   2280
gtgttgcttg gaagtcgcat gatgacggca aggaagcct ccaccagtgt ggggtccaag   2340
aagaagatcg ttgagactga cggtcttcct gatggccaat gggagaaaac attcaaaggc   2400
gcagctggag gtgtgattac tgtcatctca gagatgggag agccaatgca cgttctagca   2460
actcgcggta tgagattctg ggctgaaatg gacactatct tcaagatgcc caaggatcag   2520
atggttgcta cgctacagaa gagaagcagc tacatcatca aaaagctcaa cgacgacttc   2580
caaaagtttt ggttcggcaa gaacacggct gaggaagctg tgctactgaa ggagatgact   2640
tatcacgaag tagttgcccg aatggtcgag ctgatgtata tcagtgcaag gggtgtatgg   2700
```

```
atcgataagt cattgaagac ccttacaggt gacttcattc gtcgggttga ggaaagattc    2760
gcaacgagca gcggcagtgg attcgttctt tcggattatg ccgacctcga tgctcctcaa    2820
gtggtgctgg acaccttgt caaaacctac cccgatatca gtgatgatat cattactcct     2880
ttggatgttc agttcttctt gtcgctctgt ctgcgtccag gcaagaaacc agttcctttt    2940
gttccggtcc tcgatgaaaa cttgtcattc tatttcaaga agattcgct gtggcagtct     3000 gagaaccttt gggcggttgt tggtaatgat gcagatcgta cacagatctt gcacggaccg    3060
gtagcagctc aacattcgaa gacctacgac gaacctgtcc aggacatcct cgacggcatc    3120
aagaatgggc tggtttcttc attgctcaaa gaagcttaca atggagagat caggaatctt    3180
cccgttcaga aggctccatt ggaaataacg ccacaagctc attggtctga ctccgaacgc    3240
aatgtgtcta tcaccgagtc ttcagagtca gtcgtctacg caatctcttc ggcgcgtgat    3300
gatttaccct cgccaagttc gtggtataga atgatcgcag gtgaccaata cacatggcgt    3360
tatgcgctcc tcagttcaga aactgtcatt tccggcaaca gcggttacc aaaccctatt      3420 cgcaaaatct gcacgccttc cagtgacctt cgtgtaactg ttgaaaacca taccgagcca    3480
tcgaaaatgg ttatcaccat ccaagctgca tcagatacgg agaaccccga tactgttgtg    3540
aagataaggt tgcagggatc ctgcatagtt gctgattgca tattgagtcc aacaactact    3600
catgtatcgc caaccttgcg attggcgttc tcataccacc cggatgcggt gtacgcgccg    3660
atacgggaga actcagatgg cttactcgat gaggtttcag aattctacag aaaactttgg    3720
tttggcgatg aacaactcga cttttgatgcg cagcctaccc aagatttctc gggagaaaca    3780
atgaccatta ctcgggaggc aatcagctct tttctccaag ccaccggcag tagttgcgag    3840
acataccgta gccgcgcaaa tcaggaactg cctgcacctt tggactttgg cattgttatt     3900
gcttggaaag ctctcctgaa accaatcttt ttgagaaaga atggtggcaa tattctcaag    3960
cttgtacatc tctccaacaa gttcaagcgt gtggatggag cagcttcttt aagcgctggc    4020
gacaaagtgt cgacttcttc ccgcatcaca gcggttcgca ttcaggatgc aggcaaagtg    4080
gttgaggtac ttgcggtcat taccaaggat ggaagtcctg tgatgaagt tgtctcgcaa     4140 ttcatgtatc gcggaaaata cactgacttc gaaacaactt ttgaacgaaa agttgaagtc    4200
ccgatgcagg tccatttggg ttcacgaaag gacgtcgcaa tcctcaaatc caagccttgg    4260
ttccaattaa ccaaccccga ctccgaattg ttggacagga ccttcatttt ccgtctcgaa    4320
actacgcaag tgaagtctac cgctactgct ggcaccgttt tggtggttgg cactgtttct    4380
gagaagcacg ctacagatgg tgaacgctca gtagcttcaa tcaactatac tactgcgctc    4440
tcctccgtca atcccatttt gcgctatctc aacacgcatg gtagcggagt cgaaggtcct    4500
gttttgctcg aaaatgcaat tccagttcat ggtgccagtg gaattccact caagaggccg    4560
atgtctagcg ctgcttatgc aaaggtctcc ggggattaca atcctatcca cgtgtcgaac    4620
acctttgcat tgctcgccaa cttaccaggc tcgattgttc atggcatgca tacaagctct    4680
gccattggat cattgcttga aacttggact gccaaaggtc gcgtgggcgc agtgcgcagt    4740
tttgaagctt cttttgtcgg tatggttctt ccggatgatc tggtagatgt cgagttttgg    4800
catacggcta tgatgaaagg ccgcaaagtg atcaagatta cagccaagaa gacagacagt    4860
ggtgagatgg tgttgaaggg cgaagccgag gtggaggaac agagatctgc ctacctgttc    4920
accggccagg gttcacagga acccaacatg ggcatggacc tttatgcaag cagcccaatt    4980
gctcgatctg tgtgggatat tgccgacaag ttctacttga agacttatgg ttcgttatcc    5040
```

```
tttcctgtat acgatacccca gttattaatt cttttttctag gttttgagat cacaaagatc    5100
gtcagagaga atcccaagga gatgactatt cattttggag gcgtcaatgg cagacgtatt    5160
cgccagaact acctttcatt gactctgcaa actactggtg atgacggtca gccaatcttg    5220
gagaaagtct tcaaggacat caacgaggac tcagagtcct acactttcaa gtcgcccaag    5280
ggtcttctcc atgcaacgca gttcacgcaa gcggctatta ccctggtaga actcgcacgg    5340
tacaaggaca tggaagcccg aggtcttatt tcggagaatt acaactttgc gggccactcc    5400
cttggagagt atccagccct agcatcattc gcacaaataa tgtcgattga gcagttagtc    5460
gcaatttgtt tctaccgtgg tatggcgatg caagttaccg tcaaacgtga cgagcaaggc    5520
gcttcagact actccttgtg tgctgtcaac ccgagtcgag tttcaaagac tttcaacgaa    5580
aagatgttgc gcttcattac caagaccatt tcgcaacaga ctgggtggct tctggagatt    5640
gtgaatttca acatctcaaa cagacaatat gtctgtgcag gagaactcat agcactcgat    5700
tgtcttacga aactacttga ccgcatcgca aagggcctga atgtcgactg gatcaatcga    5760
cctggaagtg gattagatgg taagactgtg ttccttatcaa ctgtccgttc catcatacaa    5820
gaggcacaag caaagaaaac acgcgtcgaa ttgaaacgag gtacgggcat tacacctctg    5880
gaaggcattg acgtgccgtt ccactcgact ctccttcgtc caggtgttgc cacattccgt    5940
gacttttttgg catcaaagat tgatccgtca aatatcgatg cgaaaaagct cgttaataaa    6000
tgggtcccta atctcacagg gaagccattt aggaatgacc ggaagtattt tgaatatgtc    6060
tacaatctta cagggtctgt gcctcttcag aagctgttgg gagaatggag ggaaatagat    6120
ttggttatgt ag                                                         6132
```

<210> SEQ ID NO 24
<211> LENGTH: 2026
<212> TYPE: PRT
<213> ORGANISM: Lipomyces starkeyi

<400> SEQUENCE: 24

```
Met Arg Asp Arg Phe Phe Gln His Ile Gly Thr Thr Ala Ala Ser Asp
1               5                   10                  15

Glu Ser Leu Pro Gln Glu Ser Ser Val Glu Leu Ile Thr Asp Phe Ser
            20                  25                  30

Asp Phe Lys Ser Lys Leu Leu Leu Asn Trp Pro Gly Ala Asp Arg Thr
        35                  40                  45

Ser Arg Gln Arg Leu Leu Arg Ala Leu Leu Asp His Ser Glu Arg Asn
    50                  55                  60

Val Leu Thr Asp Asp Ile His Thr Ile Ala Ala Ile Ser Ser Asp Asp
65                  70                  75                  80

Pro Glu Arg Pro Ala Lys Ile Ile Arg Ser Tyr Tyr Ser Ala Cys His
                85                  90                  95

Ala Ser Gly Arg Pro Ile Ala Lys Arg Gln Ser Ala Ser Ser Asp Ser
            100                 105                 110

Val Ser Ser Gly Asp Ser Lys Leu Tyr Ala Val Leu Gly Gly Gln Gly
        115                 120                 125

Ile Thr Thr Ala Tyr Ser Asp Glu Ser Arg Glu Ile His Thr Met Tyr
    130                 135                 140

His Ser Phe Leu Val Asp Tyr Ile Glu Thr Leu Gly Glu Phe Leu Lys
145                 150                 155                 160

Ser Leu Ala Ser Gln Pro Asp Val Ser Arg Tyr Tyr Pro Glu Gly Ser
                165                 170                 175
```

```
Asp Ile Ile Asn Trp Ser Arg Asn Pro Glu Ala Thr Pro Asp Val Ser
                180                 185                 190

Tyr Leu Ala Ser Ser Arg Val Ser Phe Pro Ile Ile Gly Ile Leu Gln
        195                 200                 205

Leu Ala Gln Tyr Met Val Ser Ser Lys Val Leu Gly Gln Asn Pro Ser
    210                 215                 220

Thr Phe Asn Pro Ser Leu Ser Gly Ile Ala Gly His Ser Gln Gly Leu
225                 230                 235                 240

Val Ile Ala Ala Val Ile Ala Gly Ala Val Asp Trp Ser Ser Phe Ile
                245                 250                 255

Asp Leu Ser Arg Thr Ala Val Glu Ile Ser Phe Ser Ile Gly Val Val
                260                 265                 270

Ser Gln Gln Ile Tyr Pro Glu Thr Ser Pro Asp Pro Lys Ile Val Ser
        275                 280                 285

Asp Ser Ile Ser Asn Asp Glu Gly Thr Pro Ser Ser Met Leu Ser Ile
290                 295                 300

Arg Gly Ile Ser Glu Ala Gln Val Gln Glu His Val Asp Val Ser Asn
305                 310                 315                 320

Lys Ser Leu Pro Glu Asp Arg Lys Ile Ser Ile Ala Leu Ala Asn Gly
                325                 330                 335

Pro Arg Asn Phe Val Val Ala Gly Pro Ala Thr Ser Leu Cys Gly Ser
                340                 345                 350

Asn Ala Arg Leu Arg Arg Phe Lys Val Ser Ala Glu Val Asp Gln Asn
        355                 360                 365

Arg Ile Pro Ser Lys Glu Arg Lys Ser Thr Leu Thr Asn His Phe Leu
    370                 375                 380

Pro Ile Ser Val Pro Phe His Thr Asn Tyr Leu Leu Pro Ala Leu Pro
385                 390                 395                 400

Ile Leu Arg Lys Arg Leu Gly His Ile Phe Leu Pro Ser Asn Ser Ser
                405                 410                 415

Gln Ile Pro Val Tyr Asp Thr Asn Thr Gly Asp Leu Ser Ala Leu
        420                 425                 430

Gly Ser Glu Asn Leu Leu Asp Arg Leu Val Tyr Ser Ile Thr Val Ala
        435                 440                 445

Pro Val Arg Trp Leu Lys Ala Ser Thr Cys Glu Ser Ala Ser His Ile
450                 455                 460

Val Asp Phe Gly Pro Gly Gly Ser Ser Gly Ile Gly Val Val Thr Ser
465                 470                 475                 480

His Asn Lys Gln Gly Thr Gly Val Arg Val Met Met Ala Gly Ala Leu
                485                 490                 495

Ala Gly Lys Ser Ser Glu Val Gly Tyr Lys Ala Glu Leu Phe Ser Trp
        500                 505                 510

Asn Lys Ala Ser Ile Val Asp Ser Lys Asn Trp Ala Arg Ser Phe Ser
    515                 520                 525

Pro Arg Ser Ile Arg Ala Thr Asp Gly Gln Ile His Leu Glu Thr Lys
530                 535                 540

Met Ser Lys Leu Leu His Met Pro Pro Ile Met Val Ala Gly Met Thr
545                 550                 555                 560

Pro Thr Thr Val Ser Trp Arg Phe Val Ser Ala Thr Ile Asn Ala Gly
                565                 570                 575

Tyr His Ile Glu Leu Ala Gly Gly Gly Tyr Arg Asp Glu Ala Met Leu
        580                 585                 590

Thr Thr Ala Leu Asn Asn Ile Val Ala Thr Ile Pro Pro Gly Arg Gly
```

-continued

```
            595                 600                 605
Val Cys Ile Asn Ile Ile Tyr Val Asp Pro Arg Ala Val Ala Trp Gln
610                 615                 620

Ile Pro Leu Ser Glu Lys Leu His Ala Glu Gly Ile Pro Ile Asp Gly
625                 630                 635                 640

Leu Thr Ile Gly Ala Gly Val Pro Ser Val Glu Ile Ser Gln Ser Tyr
                    645                 650                 655

Ile Asn Asp Leu Gly Leu Lys Tyr Ile Ala Phe Lys Pro Gly Ser Val
                660                 665                 670

Asn Ser Ile Lys Gln Val Ile Ser Ile Ala Lys Ala Asn Ser Thr Phe
                675                 680                 685

Pro Val Ile Leu Gln Trp Thr Gly Arg Ala Gly His His Ser
690                 695                 700

Phe Glu Asp Phe His Thr Pro Ile Leu Glu Val Tyr Gly Gln Ile Arg
705                 710                 715                 720

Asp Cys Glu Asn Ile Ile Leu Val Ala Gly Ser Gly Phe Gly Ser Ala
                    725                 730                 735

Glu Asp Ala Tyr Pro Tyr Phe Thr Gly Ala Trp Ser Lys Ala Phe Gly
                740                 745                 750

Tyr Pro Pro Met Pro Phe Asp Gly Val Leu Leu Gly Ser Arg Met Met
                755                 760                 765

Thr Ala Lys Glu Ala Ser Thr Ser Val Gly Ser Lys Lys Lys Ile Val
770                 775                 780

Glu Thr Asp Gly Leu Pro Asp Gly Gln Trp Glu Lys Thr Phe Lys Gly
785                 790                 795                 800

Ala Ala Gly Gly Val Ile Thr Val Ile Ser Glu Met Gly Glu Pro Met
                    805                 810                 815

His Val Leu Ala Thr Arg Gly Met Arg Phe Trp Ala Glu Met Asp Thr
                820                 825                 830

Ile Phe Lys Met Pro Lys Asp Gln Met Val Ala Thr Leu Gln Lys Arg
                835                 840                 845

Ser Ser Tyr Ile Ile Lys Lys Leu Asn Asp Asp Phe Gln Lys Val Trp
850                 855                 860

Phe Gly Lys Asn Thr Ala Glu Glu Ala Val Leu Ser Lys Glu Met Thr
865                 870                 875                 880

Tyr His Glu Val Val Ala Arg Met Val Glu Ser Met Tyr Ile Ser Ala
                    885                 890                 895

Arg Gly Val Trp Ile Asp Lys Ser Leu Lys Thr Leu Thr Gly Asp Phe
                900                 905                 910

Ile Arg Arg Val Glu Glu Arg Phe Ala Thr Ser Ser Gly Ser Gly Phe
                915                 920                 925

Val Leu Ser Asp Tyr Ala Asp Leu Asp Ala Pro Gln Val Val Ser Asp
                930                 935                 940

Thr Leu Val Lys Thr Tyr Pro Asp Ile Ser Asp Ile Ile Thr Pro
945                 950                 955                 960

Leu Asp Val Gln Phe Phe Leu Ser Leu Cys Ser Arg Pro Gly Lys Lys
                    965                 970                 975

Pro Val Pro Phe Val Pro Val Leu Asp Glu Asn Leu Ser Phe Tyr Phe
                980                 985                 990

Lys Lys Asp Ser Ser Trp Gln Ser  Glu Asn Leu Trp Ala  Val Val Gly
            995                 1000                1005

Asn Asp  Ala Asp Arg Thr Gln  Ile Leu His Gly Pro  Val Ala Ala
            1010                1015                1020
```

```
Gln His Ser Lys Thr Tyr Asp Glu Pro Val Gln Asp Ile Leu Asp
1025                1030                1035

Gly Ile Lys Asn Gly Ser Val Ser Ser Leu Leu Lys Glu Ala Tyr
1040                1045                1050

Asn Gly Glu Ile Arg Asn Leu Pro Val Gln Lys Ala Pro Leu Glu
1055                1060                1065

Ile Thr Pro Gln Ala His Trp Ser Asp Ser Glu Arg Asn Val Ser
1070                1075                1080

Ile Thr Glu Ser Ser Glu Ser Val Val Tyr Ala Ile Ser Ser Ala
1085                1090                1095

Arg Asp Asp Leu Pro Ser Pro Ser Ser Trp Tyr Arg Met Ile Ala
1100                1105                1110

Gly Asp Gln Tyr Thr Trp Arg Tyr Ala Leu Leu Ser Ser Glu Thr
1115                1120                1125

Val Ile Ser Gly Asn Lys Arg Leu Pro Asn Pro Ile Arg Lys Ile
1130                1135                1140

Cys Thr Pro Ser Ser Asp Leu Arg Val Thr Val Glu Asn His Thr
1145                1150                1155

Glu Pro Ser Lys Met Val Ile Thr Ile Gln Ala Ala Ser Asp Thr
1160                1165                1170

Glu Asn Pro Asp Thr Val Val Lys Ile Arg Leu Gln Gly Ser Cys
1175                1180                1185

Ile Val Ala Asp Cys Ile Leu Ser Pro Thr Thr Thr His Val Ser
1190                1195                1200

Pro Thr Leu Arg Leu Ala Phe Ser Tyr His Pro Asp Ala Val Tyr
1205                1210                1215

Ala Pro Ile Arg Glu Asn Ser Asp Gly Leu Leu Asp Glu Val Ser
1220                1225                1230

Glu Phe Tyr Arg Lys Leu Trp Phe Gly Asp Glu Gln Leu Asp Phe
1235                1240                1245

Asp Ala Gln Pro Thr Gln Asp Phe Ser Gly Glu Thr Met Thr Ile
1250                1255                1260

Thr Arg Glu Ala Ile Ser Ser Phe Leu Gln Ala Thr Gly Ser Ser
1265                1270                1275

Cys Glu Thr Tyr Arg Ser Arg Ala Asn Gln Glu Ser Pro Ala Pro
1280                1285                1290

Leu Asp Phe Gly Ile Val Ile Ala Trp Lys Ala Leu Ser Lys Pro
1295                1300                1305

Ile Phe Leu Arg Lys Asn Gly Gly Asn Ile Leu Lys Leu Val His
1310                1315                1320

Leu Ser Asn Lys Phe Lys Arg Val Asp Gly Ala Ala Ser Leu Ser
1325                1330                1335

Ala Gly Asp Lys Val Ser Thr Ser Ser Arg Ile Thr Ala Val Arg
1340                1345                1350

Ile Gln Asp Ala Gly Lys Val Val Glu Val Leu Ala Val Ile Thr
1355                1360                1365

Lys Asp Gly Ser Pro Val Met Glu Val Val Ser Gln Phe Met Tyr
1370                1375                1380

Arg Gly Lys Tyr Thr Asp Phe Glu Thr Thr Phe Glu Arg Lys Val
1385                1390                1395

Glu Val Pro Met Gln Val His Leu Gly Ser Arg Lys Asp Val Ala
1400                1405                1410
```

```
Ile Leu Lys Ser Lys Pro Trp Phe Gln Leu Thr Asn Pro Asp Ser
    1415            1420                1425

Glu Leu Leu Asp Arg Thr Phe Ile Phe Arg Leu Glu Thr Thr Gln
    1430            1435                1440

Val Lys Ser Thr Ala Thr Ala Gly Thr Val Leu Val Val Gly Thr
    1445            1450                1455

Val Ser Glu Lys His Ala Thr Asp Gly Glu Arg Ser Val Ala Ser
    1460            1465                1470

Ile Asn Tyr Thr Thr Ala Leu Ser Ser Val Asn Pro Ile Leu Arg
    1475            1480                1485

Tyr Leu Asn Thr His Gly Ser Gly Val Glu Gly Pro Val Leu Leu
    1490            1495                1500

Glu Asn Ala Ile Pro Val His Gly Ala Ser Gly Ile Pro Leu Lys
    1505            1510                1515

Arg Pro Met Ser Ser Ala Ala Tyr Ala Lys Val Ser Gly Asp Tyr
    1520            1525                1530

Asn Pro Ile His Val Ser Asn Thr Phe Ala Leu Leu Ala Asn Leu
    1535            1540                1545

Pro Gly Ser Ile Val His Gly Met His Thr Ser Ser Ala Ile Gly
    1550            1555                1560

Ser Leu Leu Glu Thr Trp Thr Ala Lys Gly Arg Val Gly Ala Val
    1565            1570                1575

Arg Ser Phe Glu Ala Ser Phe Val Gly Met Val Leu Pro Asp Asp
    1580            1585                1590

Ser Val Asp Val Glu Phe Trp His Thr Ala Met Met Lys Gly Arg
    1595            1600                1605

Lys Val Ile Lys Ile Thr Ala Lys Lys Thr Asp Ser Gly Glu Met
    1610            1615                1620

Val Leu Lys Gly Glu Ala Glu Val Glu Gln Arg Ser Ala Tyr
    1625            1630                1635

Ser Phe Thr Gly Gln Gly Ser Gln Glu Pro Asn Met Gly Met Asp
    1640            1645                1650

Leu Tyr Ala Ser Ser Pro Ile Ala Arg Ser Val Trp Asp Ile Ala
    1655            1660                1665

Asp Lys Phe Tyr Leu Lys Thr Tyr Gly Phe Glu Ile Thr Lys Ile
    1670            1675                1680

Val Arg Glu Asn Pro Lys Glu Met Thr Ile His Phe Gly Gly Val
    1685            1690                1695

Asn Gly Arg Arg Ile Arg Gln Asn Tyr Leu Ser Leu Thr Ser Gln
    1700            1705                1710

Thr Thr Gly Asp Asp Gly Gln Pro Ile Leu Glu Lys Val Phe Lys
    1715            1720                1725

Asp Ile Asn Glu Asp Ser Glu Ser Tyr Thr Phe Lys Ser Pro Lys
    1730            1735                1740

Gly Leu Leu His Ala Thr Gln Phe Thr Gln Ala Ala Ile Thr Ser
    1745            1750                1755

Val Glu Leu Ala Arg Tyr Lys Asp Met Glu Ala Arg Gly Leu Ile
    1760            1765                1770

Ser Glu Asn Tyr Asn Phe Ala Gly His Ser Leu Gly Glu Tyr Pro
    1775            1780                1785

Ala Leu Ala Ser Phe Ala Gln Ile Met Ser Ile Glu Gln Leu Val
    1790            1795                1800

Ala Ile Cys Phe Tyr Arg Gly Met Ala Met Gln Val Thr Val Lys
```

```
Arg Asp Glu Gln Gly Ala Ser Asp Tyr Ser Leu Cys Ala Val Asn
    1820            1825                1830

Pro Ser Arg Val Ser Lys Thr Phe Asn Glu Lys Met Leu Arg Phe
    1835            1840                1845

Ile Thr Lys Thr Ile Ser Gln Gln Thr Gly Trp Leu Ser Glu Ile
    1850            1855                1860

Val Asn Phe Asn Ile Ser Asn Arg Gln Tyr Val Cys Ala Gly Glu
    1865            1870                1875

Leu Ile Ala Leu Asp Cys Leu Thr Lys Leu Leu Asp Arg Ile Ala
    1880            1885                1890

Lys Gly Ser Asn Val Asp Trp Ile Asn Arg Pro Gly Ser Gly Leu
    1895            1900                1905

Asp Gly Lys Thr Val Phe Leu Ser Thr Val Arg Ser Ile Ile Gln
    1910            1915                1920

Glu Ala Gln Ala Lys Lys Thr Arg Val Glu Leu Lys Arg Gly Thr
    1925            1930                1935

Gly Ile Thr Pro Ser Glu Gly Ile Asp Val Pro Phe His Ser Thr
    1940            1945                1950

Leu Leu Arg Pro Gly Val Ala Thr Phe Arg Asp Phe Leu Ala Ser
    1955            1960                1965

Lys Ile Asp Pro Ser Asn Ile Asp Ala Lys Lys Leu Val Asn Lys
    1970            1975                1980

Trp Val Pro Asn Leu Thr Gly Lys Pro Phe Arg Asn Asp Arg Lys
    1985            1990                1995

Tyr Phe Glu Tyr Val Tyr Asn Leu Thr Gly Ser Val Pro Leu Gln
    2000            2005                2010

Lys Ser Leu Gly Glu Trp Arg Glu Ile Asp Leu Val Met
    2015            2020                2025

<210> SEQ ID NO 25
<211> LENGTH: 1827
<212> TYPE: DNA
<213> ORGANISM: Lipomyces starkeyi
<220> FEATURE:
<221> NAME/KEY: Intron
<222> LOCATION: (51)..(162)
<220> FEATURE:
<221> NAME/KEY: Intron
<222> LOCATION: (241)..(296)
<220> FEATURE:
<221> NAME/KEY: Intron
<222> LOCATION: (436)..(492)

<400> SEQUENCE: 25
atgccaaggg tcttcatcgg tgcactggat gccggcacca cgtctacaag gtgaggactg      60
ggccatttga gccgaggacg tcgtgcacgc tcacgctcac ccggccatat cctctgggaa     120
ctctttgaaa ggttccgtta gtgcatatgc taacaaccgc agattcatta tatttgacga     180
tgctggtagg ccttacgcta cacaccagat tgaattcgag cagcattatc cacatgctgg     240
gtgagttgcg ctgttaaata cgccttctgg aaaacaatac gctgaccgag taatagctgg     300
cacgagcaat acccttacga gattatcaag tgcgcgaatg actgtattga gggcgctgtc     360
aagaagtttg tcgcagatgg atacaatgtc tccgacataa aggcggttgg aattacaaac     420
cagcgtgaat ccactgtaaa tccttgttcc ttcttacaga tattaagaac agtctaacaa     480
aaaataacat aggtcgtctg ggattctgag acggggaagc cactgtataa tgcaattgct     540
```

```
tggcctgaca cgcgtactgc gcgactagta catcacttca agaacaagaa cggcgccgaa    600
gacctagtgc gaatctgcgg tctgccactg tctacctatc cgtccgcgct caagctggtg    660
tggctgttag aaaacgttca cggcgtccag gaggcacgaa agcgtggaac tttgatgttc    720
ggtaccgttg acacctggtt agtgtacaat ctgaccggtg gcggtaagac tggaaccgac    780
accaggtttg tgacagatac caccaatgcc tcgcgaacta tgttcctaaa tattaactct    840
ctcaagtacg atgatttcct ccttgatttc tttggagttt ctcaaggagt gagactccct    900
gacgttgtgt gctccgcaga cgacaaagct tacggtaata tcgcttccgg tgtcctcgct    960
ggtgtaccaa ttgcgtcgtg tctcggtgac cagtcagccg cgttggtcgg acagcgggcg   1020
ttcagtgtgg gcatgggcaa gaacacgtac ggaactggtt tgttcttgct gtacaacact   1080
ggtgaggagc cagtcttctc gaagaacggt ctcttaacca ctgtcggata tcatttcaag   1140
ggaaagaagc ctatatacgc tctggaaggg tccattgctg tcggtggcgc tgcagttaag   1200
ttcttgcgag ataatttacg gttgatttcg ttctccgatg aggtcgggca attggcagcg   1260
aaggtccccg acgctggtgg ggtcattttt gtcacggcct tctcgggact gttcgcgcct   1320
tactggattg acgataccca gggaaccatc tacggtatca cgaactacac aaccaaagaa   1380
cacattgctc gagcaaccat tgaggccacc tgttatcaga ctagagcagt tttggaagct   1440
atggctaagg attctggcta cgagttgaag acgctcaagg tcgacggtgg catgagtaac   1500
tcggatatat gcatgcaaat ccaatccgac attattggca ttgacgtcgt tcggccggag   1560
tatagggaga ctaccgcatt gggggcagcc attgcagcag ttttgcagt  tggagtctat   1620
agtagctttg aggagttgaa gcgagtgaac acggatggag agaccacatt caagccttcc   1680
atcactgaga agaagcgcga gaagttgtat aacctctggc agcgtgctgt atcgcgatgt   1740
ggtggttggt gcgggatga  ggatgacgac tctgagattg aggaggagac aagagttggg   1800
gatgggaccc aaaagcagtt tgcatag                                        1827
```

<210> SEQ ID NO 26
<211> LENGTH: 533
<212> TYPE: PRT
<213> ORGANISM: Lipomyces starkeyi

<400> SEQUENCE: 26

```
Met Pro Arg Val Phe Ile Gly Ala Leu Asp Ala Gly Thr Thr Ser Thr
1               5                   10                  15

Arg Phe Ile Ile Phe Asp Asp Ala Gly Arg Pro Tyr Ala Thr His Gln
            20                  25                  30

Ile Glu Phe Glu Gln His Tyr Pro His Ala Gly Trp His Glu Gln Tyr
        35                  40                  45

Pro Tyr Glu Ile Ile Lys Cys Ala Asn Asp Cys Ile Glu Gly Ala Val
    50                  55                  60

Lys Lys Phe Val Ala Asp Gly Tyr Asn Val Ser Asp Ile Lys Ala Val
65                  70                  75                  80

Gly Ile Thr Asn Gln Arg Glu Ser Thr Val Val Trp Asp Ser Glu Thr
                85                  90                  95

Gly Lys Pro Leu Tyr Asn Ala Ile Ala Trp Pro Asp Thr Arg Thr Ala
            100                 105                 110

Arg Leu Val His His Phe Lys Asn Lys Asn Gly Ala Glu Asp Leu Val
        115                 120                 125

Arg Ile Cys Gly Leu Pro Leu Ser Thr Tyr Pro Ser Ala Leu Lys Leu
    130                 135                 140
```

Val Trp Leu Leu Glu Asn Val His Gly Val Gln Glu Ala Arg Lys Arg
145                 150                 155                 160

Gly Thr Leu Met Phe Gly Thr Val Asp Thr Trp Leu Val Tyr Asn Leu
            165                 170                 175

Thr Gly Gly Lys Thr Gly Thr Asp Thr Arg Phe Val Thr Asp Thr
        180                 185                 190

Thr Asn Ala Ser Arg Thr Met Phe Leu Asn Ile Asn Ser Leu Lys Tyr
    195                 200                 205

Asp Asp Phe Leu Leu Asp Phe Phe Gly Val Ser Gln Gly Val Arg Leu
210                 215                 220

Pro Asp Val Val Cys Ser Ala Asp Lys Ala Tyr Gly Asn Ile Ala
225                 230                 235                 240

Ser Gly Val Leu Ala Gly Val Pro Ile Ala Ser Cys Leu Gly Asp Gln
            245                 250                 255

Ser Ala Ala Leu Val Gly Gln Arg Ala Phe Ser Val Gly Met Gly Lys
            260                 265                 270

Asn Thr Tyr Gly Thr Gly Leu Phe Leu Leu Tyr Asn Thr Gly Glu Glu
        275                 280                 285

Pro Val Phe Ser Lys Asn Gly Leu Leu Thr Thr Val Gly Tyr His Phe
290                 295                 300

Lys Gly Lys Lys Pro Ile Tyr Ala Leu Glu Gly Ser Ile Ala Val Gly
305                 310                 315                 320

Gly Ala Ala Val Lys Phe Leu Arg Asp Asn Leu Arg Leu Ile Ser Phe
                325                 330                 335

Ser Asp Glu Val Gly Gln Leu Ala Ala Lys Val Pro Asp Ala Gly Gly
            340                 345                 350

Val Ile Phe Val Thr Ala Phe Ser Gly Leu Phe Ala Pro Tyr Trp Ile
        355                 360                 365

Asp Asp Thr Gln Gly Thr Ile Tyr Gly Ile Thr Asn Tyr Thr Thr Lys
        370                 375                 380

Glu His Ile Ala Arg Ala Thr Ile Glu Ala Thr Cys Tyr Gln Thr Arg
385                 390                 395                 400

Ala Val Leu Glu Ala Met Ala Lys Asp Ser Gly Tyr Glu Leu Lys Thr
                405                 410                 415

Leu Lys Val Asp Gly Gly Met Ser Asn Ser Asp Ile Cys Met Gln Ile
            420                 425                 430

Gln Ser Asp Ile Ile Gly Ile Asp Val Val Arg Pro Glu Tyr Arg Glu
        435                 440                 445

Thr Thr Ala Leu Gly Ala Ala Ile Ala Ala Gly Phe Ala Val Gly Val
        450                 455                 460

Tyr Ser Ser Phe Glu Glu Leu Lys Arg Val Asn Thr Asp Gly Glu Thr
465                 470                 475                 480

Thr Phe Lys Pro Ser Ile Thr Glu Lys Lys Arg Glu Lys Leu Tyr Asn
            485                 490                 495

Leu Trp Gln Arg Ala Val Ser Cys Gly Gly Trp Leu Arg Asp Glu
        500                 505                 510

Asp Asp Asp Ser Glu Ile Glu Glu Glu Thr Arg Val Gly Asp Gly Thr
        515                 520                 525

Gln Lys Gln Phe Ala
    530

<210> SEQ ID NO 27
<211> LENGTH: 1842
<212> TYPE: DNA

<213> ORGANISM: Lipomyces starkeyi
<220> FEATURE:
<221> NAME/KEY: Intron
<222> LOCATION: (66)..(177)
<220> FEATURE:
<221> NAME/KEY: Intron
<222> LOCATION: (256)..(311)
<220> FEATURE:
<221> NAME/KEY: Intron
<222> LOCATION: (451)..(507)

<400> SEQUENCE: 27

| | | | | |
|---|---|---|---|---|
| atgactaccg | attccatgcc | aagggtcttc | atcggtgcac | tggatgccgg caccacgtct | 60 |
| acaaggtgag | gactgggcca | tttgagccga | ggacgtcgtg | cacgctcacg ctcacccggc | 120 |
| catatcctct | gggaactctt | tgaaaggttc | cgttagtgca | tatgctaaca accgcagatt | 180 |
| cattatattt | gacgatgctg | gtaggcctta | cgctacacac | cagattgaat tcgagcagca | 240 |
| ttatccacat | gctgggtgag | ttgcgctgtt | aaatacgcct | tctggaaaac aatacgctga | 300 |
| ccgagtaata | gctggcacga | gcaataccct | tacgagatta | tcaagtgcgc gaatgactgt | 360 |
| attgagggcg | ctgtcaagaa | gtttgtcgca | gatggataca | atgtctccga cataaaggcg | 420 |
| gttggaatta | caaccagcg | tgaatccact | gtaaatcctt | gttccttctt acagatatta | 480 |
| agaacagtct | aacaaaaaat | aacataggtc | gtctgggatt | ctgagacggg gaagccactg | 540 |
| tataatgcaa | ttgcttggcc | tgacacgcgt | actgcgcgac | tagtacatca cttcaagaac | 600 |
| aagaacggcg | ccgaagacct | agtgcgaatc | tgcggtctgc | cactgtctac ctatccgtcc | 660 |
| gcgctcaagc | tggtgtggct | gttagaaaac | gttcacggcg | tccaggaggc acgaaagcgt | 720 |
| ggaactttga | tgttcggtac | cgttgacacc | tggttagtgt | acaatctgac cggtggcggt | 780 |
| aagactggaa | ccgacaccag | gtttgtgaca | gataccacca | atgcctcgcg aactatgttc | 840 |
| ctaaatatta | actctctcaa | gtacgatgat | ttcctccttg | atttctttgg agtttctcaa | 900 |
| ggagtgagac | tccctgacgt | tgtgtgctcc | gcagacgaca | aagcttacgg taatatcgct | 960 |
| tccggtgtcc | tcgctggtgt | accaattgcg | tcgtgtctcg | gtgaccagtc agccgcgttg | 1020 |
| gtcggacagc | gggcgttcag | tgtgggcatg | gcaagaaca | cgtacggaac tggtttgttc | 1080 |
| ttgctgtaca | cactggtga | ggagccagtc | ttctcgaaga | acggtctctt aaccactgtc | 1140 |
| ggatatcatt | tcaagggaaa | gaagcctata | tacgctctgg | aagggtccat tgctgtcggt | 1200 |
| ggcgctgcag | ttaagttctt | gcgagataat | ttacggttga | tttcgttctc cgatgaggtc | 1260 |
| gggcaattgg | cagcgaaggt | ccccgacgct | ggtggggtca | tttttgtcac ggccttctcg | 1320 |
| ggactgttcg | cgccttactg | gattgacgat | acccagggaa | ccatctacgg tatcacgaac | 1380 |
| tacacaacca | agaacacat | tgctcgagca | accattgagg | ccacctgtta tcagactaga | 1440 |
| gcagttttgg | aagctatggc | taaggattct | ggctacgagt | tgaagacgct caaggtcgac | 1500 |
| ggtggcatga | gtaactcgga | tatatgcatg | caaatccaat | ccgacattat tggcattgac | 1560 |
| gtcgttcggc | cggagtatag | ggagactacc | gcattggggg | cagccattgc agcaggtttt | 1620 |
| gcagttggag | tctatagtag | ctttgaggag | ttgaagcgag | tgaacacgga tggagagacc | 1680 |
| acattcaagc | cttccatcac | tgagaagaag | cgcgagaagt | tgtataacct ctggcagcgt | 1740 |
| gctgtatcgc | gatgtggtgg | ttggttgcgg | gatgaggatg | acgactctga gattgaggag | 1800 |
| gagacaagag | ttgggatgg | gacccaaaag | cagtttgcat | ag | 1842 |

<210> SEQ ID NO 28
<211> LENGTH: 538
<212> TYPE: PRT

<213> ORGANISM: Lipomyces starkeyi

<400> SEQUENCE: 28

```
Met Thr Thr Asp Ser Met Pro Arg Val Phe Ile Gly Ala Leu Asp Ala
1               5                   10                  15

Gly Thr Thr Ser Thr Arg Phe Ile Ile Phe Asp Asp Ala Gly Arg Pro
            20                  25                  30

Tyr Ala Thr His Gln Ile Glu Phe Glu Gln His Tyr Pro His Ala Gly
        35                  40                  45

Trp His Glu Gln Tyr Pro Tyr Glu Ile Ile Lys Cys Ala Asn Asp Cys
    50                  55                  60

Ile Glu Gly Ala Val Lys Lys Phe Val Ala Asp Gly Tyr Asn Val Ser
65                  70                  75                  80

Asp Ile Lys Ala Val Gly Ile Thr Asn Gln Arg Glu Ser Thr Val Val
                85                  90                  95

Trp Asp Ser Glu Thr Gly Lys Pro Leu Tyr Asn Ala Ile Ala Trp Pro
            100                 105                 110

Asp Thr Arg Thr Ala Arg Leu Val His His Phe Lys Asn Lys Asn Gly
        115                 120                 125

Ala Glu Asp Leu Val Arg Ile Cys Gly Leu Pro Leu Ser Thr Tyr Pro
    130                 135                 140

Ser Ala Leu Lys Leu Val Trp Leu Leu Glu Asn Val His Gly Val Gln
145                 150                 155                 160

Glu Ala Arg Lys Arg Gly Thr Leu Met Phe Gly Thr Val Asp Thr Trp
                165                 170                 175

Leu Val Tyr Asn Leu Thr Gly Gly Lys Thr Gly Thr Asp Thr Arg
            180                 185                 190

Phe Val Thr Asp Thr Thr Asn Ala Ser Arg Thr Met Phe Leu Asn Ile
        195                 200                 205

Asn Ser Leu Lys Tyr Asp Asp Phe Leu Leu Asp Phe Phe Gly Val Ser
    210                 215                 220

Gln Gly Val Arg Leu Pro Asp Val Val Cys Ser Ala Asp Asp Lys Ala
225                 230                 235                 240

Tyr Gly Asn Ile Ala Ser Gly Val Leu Ala Gly Val Pro Ile Ala Ser
                245                 250                 255

Cys Leu Gly Asp Gln Ser Ala Ala Leu Val Gly Gln Arg Ala Phe Ser
            260                 265                 270

Val Gly Met Gly Lys Asn Thr Tyr Gly Thr Gly Leu Phe Leu Leu Tyr
        275                 280                 285

Asn Thr Gly Glu Glu Pro Val Phe Ser Lys Asn Gly Leu Leu Thr Thr
    290                 295                 300

Val Gly Tyr His Phe Lys Gly Lys Lys Pro Ile Tyr Ala Leu Glu Gly
305                 310                 315                 320

Ser Ile Ala Val Gly Gly Ala Ala Val Lys Phe Leu Arg Asp Asn Leu
                325                 330                 335

Arg Leu Ile Ser Phe Ser Asp Glu Val Gly Gln Leu Ala Ala Lys Val
            340                 345                 350

Pro Asp Ala Gly Gly Val Ile Phe Val Thr Ala Phe Ser Gly Leu Phe
        355                 360                 365

Ala Pro Tyr Trp Ile Asp Asp Thr Gln Gly Thr Ile Tyr Gly Ile Thr
    370                 375                 380

Asn Tyr Thr Thr Lys Glu His Ile Ala Arg Ala Thr Ile Glu Ala Thr
385                 390                 395                 400
```

```
Cys Tyr Gln Thr Arg Ala Val Leu Glu Ala Met Ala Lys Asp Ser Gly
                405                 410                 415
Tyr Glu Leu Lys Thr Leu Lys Val Asp Gly Gly Met Ser Asn Ser Asp
            420                 425                 430
Ile Cys Met Gln Ile Gln Ser Asp Ile Ile Gly Ile Asp Val Val Arg
        435                 440                 445
Pro Glu Tyr Arg Glu Thr Thr Ala Leu Gly Ala Ala Ile Ala Ala Gly
    450                 455                 460
Phe Ala Val Gly Val Tyr Ser Ser Phe Glu Glu Leu Lys Arg Val Asn
465                 470                 475                 480
Thr Asp Gly Glu Thr Thr Phe Lys Pro Ser Ile Thr Glu Lys Lys Arg
                485                 490                 495
Glu Lys Leu Tyr Asn Leu Trp Gln Arg Ala Val Ser Arg Cys Gly Gly
            500                 505                 510
Trp Leu Arg Asp Glu Asp Asp Ser Glu Ile Glu Glu Glu Thr Arg
        515                 520                 525
Val Gly Asp Gly Thr Gln Lys Gln Phe Ala
    530                 535
```

<210> SEQ ID NO 29
<211> LENGTH: 1831
<212> TYPE: DNA
<213> ORGANISM: Lipomyces starkeyi
<220> FEATURE:
<221> NAME/KEY: Intron
<222> LOCATION: (10)..(234)
<220> FEATURE:
<221> NAME/KEY: Intron
<222> LOCATION: (332)..(393)
<220> FEATURE:
<221> NAME/KEY: Intron
<222> LOCATION: (846)..(901)
<220> FEATURE:
<221> NAME/KEY: Intron
<222> LOCATION: (1168)..(1227)

<400> SEQUENCE: 29

```
atgggtcagg taagtcaatt ctgctatttt acgtccactc attcgagcag cgccaatttc    60
ttactgtttg cgattggaat tgattatcaa attcctttat gtgtttcagt gatcgaaata   120
tggcgcgctt gcttggtaac cgaagatgat gcgctagtcc caattgggtt agcgtctttt   180
cttaacgggt ctctcttctc cgaccgtggc agcctcgcta cacccaagg acagaacttg    240
atcctcaacg ctgctgacca cggctacaca gtggttgctt caatcgtac tgtttccaag    300
gttgatcact tccttgccaa tgaagccaag ggtatgttaa tttgagctaa atttggctca   360
attgagtgtg gaggttgacg ccgattggaa taggcaagag cgttgttggt gctcactcca   420
ttgcggagct ctgcgccaag ttgaagaagc cccgtcgagt tattcttctc gttaaggctg   480
gtaaggctgt tgacgatttc attgacttgc tcttgccaca catggagcct ggtgacatca   540
tcatcgacgg tggtaactct tatttccccg actccaaccg ccgctgcaag gagctggctg   600
ctaagggctt cctctttgtc ggctctggcg tttccggtgg tgaggagggt gcccgctatg   660
gtcccagttt gatgcctggt ggtaacgagg ctgcctggcc gtacatcaag aacatcttcc   720
aggatattgc tgccaagtct gacgtgagc cttgctgcga ctgggtcggt gacgaaggcg   780
ctggtcactt cgtcaagatg gtgcacaatg gtattgagta tggtgatatg cagttgattt   840
gcgaggtatg ttggtagttt agtggtccct ccaattaaac acgcattaac aattcctcta   900
ggcgtacgat attttgaagc gcggtgctgg attcaccgac aaggagattg gcgatgtttt   960
```

```
cactcagtgg aacaagggtg tccttgactc tttcttgatc gagattacgc gtgacatttt   1020
gtacttcaat gacgacgatg gaactcctct cgttgagaag attctcgaca ctgccggtca   1080
gaagggtacc ggcaagtgga ctgccattaa cgctctcgac cttggtatgc ccgttacctt   1140
gatcggcgag gctgtcttcg ctcgaacgta agctgatagg tctcctatat tgaatgcttt   1200
gaggcaaaaa gactaatctc tggtcagttt gtccgctatc aagcccgaac gtgtccgcgc   1260
cagcaagatc ttgaccggcc ctgtccccgc cttcaagggt gacaagaagg aacttgtcga   1320
ccaactcgag caggctctct atgcttccaa gattatctcc tatgcgcagg gtttcatgtt   1380
gatcagagag gctggccgag agtacggctg gacgttgaat aaccccgcca ttgcccttat   1440
gtggagaggt ggttgcatta tccggtctgt cttcttggcg gatatcaccc gtgcctaccg   1500
ccagaaacct gacttggaga accttctatt cgacgaattc ttccacaccg ccattgacaa   1560
ggcacagcca tcgtggcgcc agacggttgc caatgctgct ctctggggta ttcccactcc   1620
cgctttctct accgctcttt ccttctacga cggttacagg agcgagagac ttccggccaa   1680
tcttctccag gcacagcgtg actacttcgg tgctcacacc ttccacatct tgcccgaatt   1740
ctcgagcgag aagtacccta aggatactga cgtccatgtt aactggactg cagaggtgg    1800 caatgtttct gcctccacct accttgctta a                                  1831
```

<210> SEQ ID NO 30
<211> LENGTH: 475
<212> TYPE: PRT
<213> ORGANISM: Lipomyces starkeyi

<400> SEQUENCE: 30

```
Met Gly Gln Asn Leu Ile Leu Asn Ala Ala Asp His Gly Tyr Thr Val
1               5                   10                  15

Val Ala Phe Asn Arg Thr Val Ser Lys Val Asp His Phe Leu Ala Asn
            20                  25                  30

Glu Ala Lys Gly Lys Ser Val Val Gly Ala His Ser Ile Ala Glu Leu
        35                  40                  45

Cys Ala Lys Leu Lys Lys Pro Arg Arg Val Ile Leu Leu Val Lys Ala
    50                  55                  60

Gly Lys Ala Val Asp Asp Phe Ile Asp Leu Leu Leu Pro His Met Glu
65                  70                  75                  80

Pro Gly Asp Ile Ile Ile Asp Gly Gly Asn Ser Tyr Phe Pro Asp Ser
                85                  90                  95

Asn Arg Arg Cys Lys Glu Leu Ala Ala Lys Gly Phe Leu Phe Val Gly
            100                 105                 110

Ser Gly Val Ser Gly Gly Glu Glu Gly Ala Arg Tyr Gly Pro Ser Leu
        115                 120                 125

Met Pro Gly Gly Asn Glu Ala Ala Trp Pro Tyr Ile Lys Asn Ile Phe
    130                 135                 140

Gln Asp Ile Ala Ala Lys Ser Asp Gly Glu Pro Cys Cys Asp Trp Val
145                 150                 155                 160

Gly Asp Glu Gly Ala Gly His Phe Val Lys Met Val His Asn Gly Ile
                165                 170                 175

Glu Tyr Gly Asp Met Gln Leu Ile Cys Glu Ala Tyr Asp Ile Leu Lys
            180                 185                 190

Arg Gly Ala Gly Phe Thr Asp Lys Glu Ile Gly Asp Val Phe Thr Gln
        195                 200                 205

Trp Asn Lys Gly Val Leu Asp Ser Phe Leu Ile Glu Ile Thr Arg Asp
    210                 215                 220
```

```
Ile Leu Tyr Phe Asn Asp Asp Gly Thr Pro Leu Val Glu Lys Ile
225                 230                 235                 240

Leu Asp Thr Ala Gly Gln Lys Gly Thr Gly Lys Trp Thr Ala Ile Asn
            245                 250                 255

Ala Leu Asp Leu Gly Met Pro Val Thr Leu Ile Gly Glu Ala Val Phe
        260                 265                 270

Ala Arg Thr Leu Ser Ala Ile Lys Pro Glu Arg Val Arg Ala Ser Lys
    275                 280                 285

Ile Leu Thr Gly Pro Val Pro Ala Phe Lys Gly Asp Lys Lys Glu Leu
290                 295                 300

Val Asp Gln Leu Glu Gln Ala Leu Tyr Ala Ser Lys Ile Ile Ser Tyr
305                 310                 315                 320

Ala Gln Gly Phe Met Leu Ile Arg Glu Ala Gly Arg Glu Tyr Gly Trp
                325                 330                 335

Thr Leu Asn Asn Pro Ala Ile Ala Leu Met Trp Arg Gly Gly Cys Ile
            340                 345                 350

Ile Arg Ser Val Phe Leu Ala Asp Ile Thr Arg Ala Tyr Arg Gln Lys
        355                 360                 365

Pro Asp Leu Glu Asn Leu Leu Phe Asp Glu Phe Phe His Thr Ala Ile
    370                 375                 380

Asp Lys Ala Gln Pro Ser Trp Arg Gln Thr Val Ala Asn Ala Ala Leu
385                 390                 395                 400

Trp Gly Ile Pro Thr Pro Ala Phe Ser Thr Ala Leu Ser Phe Tyr Asp
                405                 410                 415

Gly Tyr Arg Ser Glu Arg Leu Pro Ala Asn Leu Leu Gln Ala Gln Arg
            420                 425                 430

Asp Tyr Phe Gly Ala His Thr Phe His Ile Leu Pro Glu Phe Ser Ser
        435                 440                 445

Glu Lys Tyr Pro Lys Asp Thr Asp Val His Val Asn Trp Thr Gly Arg
    450                 455                 460

Gly Gly Asn Val Ser Ala Ser Thr Tyr Leu Ala
465                 470                 475

<210> SEQ ID NO 31
<211> LENGTH: 1121
<212> TYPE: DNA
<213> ORGANISM: Lipomyces starkeyi
<220> FEATURE:
<221> NAME/KEY: Intron
<222> LOCATION: (42)..(94)

<400> SEQUENCE: 31
atgcttaacc tcaaagtatc tgttatcggt tctggcaact ggtaggcgcc tcctttttca    60
attcattaaa ttgctttact gactgtctcc atagggggcag cgccattgcg aaaatagtgg   120
ccgagaacgc ggctgagaac agcgacattt tcgagaccga cgttcgcatg tgggttttcg   180
aggagcttgt tgctggccag aagctcaccg aaattatcaa tacccagcac gagaacgtca   240
agtacttgcc aggcatcaaa ctgccgtcca acgtcgtggc tgtgccagac cttttggacg   300
ccgtcaagga tgccaacctc ttagtcttca acgtgcctca tcagtttctt ccacggatat   360
gtagccagct gaaaggcaaa gtgccgtcca ccgtcagagc tgtgtcttgc atcaaaggtg   420
tcgaggtttc tggcgatggc atcaccatca tcgcagacta tatctctcag gaactcggca   480
tttactgcgg tgccttgtct ggcgccaatc ttgctcccga agttgcgcaa gagaaatttt   540
ccgagacgac aatcgcgtac aaagttcccg atccaagcga ctccattgac gcacgcgtcg   600
```

```
taaggacgct cttccacaga ccttacttcc acgtaaacgt cgttggtgat gtcgccggtg    660
tgtctctttg tggtgcttta aaaaacattg tggcattggc atcaggattt gtagacggaa    720
tggcatgggg cgataatgcc aaggctgcca ttattcgaag aggattgtta gagatgacca    780
agtttggccg tgaattcttc ccggaatgca atgccagtac cttcaccgaa gaatcatgtg    840
gtgttgccga tgtcattact tcctgctctg gtgggcgcaa taacaagctt ggtgcggcga    900
tgattaagac caggcgaccc atttttgagc ttgaggaaga gttgctcaag ggtcagaagg    960
ctcaaggagt tacgactgcc caggaggtgc acgaattttt ggagcggcgg ggcaagttgg   1020
aagacttccc tcttttcacc gcagtccacg acattatttt caacggactc gacagctatg   1080
ctctgccgca gattctcgaa gatgtcgagc agaagttcta a                       1121
```

<210> SEQ ID NO 32
<211> LENGTH: 355
<212> TYPE: PRT
<213> ORGANISM: Lipomyces starkeyi

<400> SEQUENCE: 32

```
Met Leu Asn Leu Lys Val Ser Val Ile Gly Ser Gly Asn Trp Gly Ser
1               5                   10                  15

Ala Ile Ala Lys Ile Val Ala Glu Asn Ala Ala Glu Asn Ser Asp Ile
            20                  25                  30

Phe Glu Thr Asp Val Arg Met Trp Val Phe Glu Leu Val Ala Gly
        35                  40                  45

Gln Lys Leu Thr Glu Ile Ile Asn Thr Gln His Glu Asn Val Lys Tyr
    50                  55                  60

Leu Pro Gly Ile Lys Ser Pro Ser Asn Val Val Ala Val Pro Asp Leu
65                  70                  75                  80

Leu Asp Ala Val Lys Asp Ala Asn Leu Leu Val Phe Asn Val Pro His
            85                  90                  95

Gln Phe Leu Pro Arg Ile Cys Ser Gln Ser Lys Gly Lys Val Pro Ser
        100                 105                 110

Thr Val Arg Ala Val Ser Cys Ile Lys Gly Val Glu Val Ser Gly Asp
    115                 120                 125

Gly Ile Thr Ile Ile Ala Asp Tyr Ile Ser Gln Glu Leu Gly Ile Tyr
130                 135                 140

Cys Gly Ala Leu Ser Gly Ala Asn Leu Ala Pro Glu Val Ala Gln Glu
145                 150                 155                 160

Lys Phe Ser Glu Thr Thr Ile Ala Tyr Lys Val Pro Asp Pro Ser Asp
                165                 170                 175

Ser Ile Asp Ala Arg Val Val Arg Thr Leu Phe His Arg Pro Tyr Phe
            180                 185                 190

His Val Asn Val Val Gly Asp Val Ala Gly Val Ser Leu Cys Gly Ala
        195                 200                 205

Leu Lys Asn Ile Val Ala Leu Ala Ser Gly Phe Val Asp Gly Met Ala
    210                 215                 220

Trp Gly Asp Asn Ala Lys Ala Ala Ile Ile Arg Arg Gly Leu Leu Glu
225                 230                 235                 240

Met Thr Lys Phe Gly Arg Glu Phe Phe Pro Glu Cys Asn Ala Ser Thr
                245                 250                 255

Phe Thr Glu Glu Ser Cys Gly Val Ala Asp Val Ile Thr Ser Cys Ser
            260                 265                 270

Gly Gly Arg Asn Asn Lys Leu Gly Ala Ala Met Ile Lys Thr Arg Arg
```

|  |  | 275 |  |  | 280 |  |  | 285 |  |  |  |
|--|--|--|--|--|--|--|--|--|--|--|--|

Pro Ile Phe Glu Leu Glu Glu Leu Leu Lys Gly Gln Lys Ala Gln
    290                 295                 300

Gly Val Thr Thr Ala Gln Glu Val His Glu Phe Leu Glu Arg Arg Gly
305                 310                 315                 320

Lys Leu Glu Asp Phe Pro Leu Phe Thr Ala Val His Asp Ile Ile Phe
                325                 330                 335

Asn Gly Leu Asp Ser Tyr Ala Ser Pro Gln Ile Leu Glu Asp Val Glu
            340                 345                 350

Gln Lys Phe
    355

<210> SEQ ID NO 33
<211> LENGTH: 1930
<212> TYPE: DNA
<213> ORGANISM: Lipomyces starkeyi
<220> FEATURE:
<221> NAME/KEY: Intron
<222> LOCATION: (67)..(121)
<220> FEATURE:
<221> NAME/KEY: Intron
<222> LOCATION: (398)..(447)
<220> FEATURE:
<221> NAME/KEY: Intron
<222> LOCATION: (598)..(652)
<220> FEATURE:
<221> NAME/KEY: Intron
<222> LOCATION: (852)..(902)

<400> SEQUENCE: 33

| atggctccta | aatcgtcgac | tcgtgtgcca | ttgtcggtta | aagggcccat | tgattgtcca | 60 |
|---|---|---|---|---|---|---|
| tatgaggtaa | ttccagatca | actctgagat | gctgtccaac | tactaacaaa | ccatgattca | 120 |
| gggcaaagaa | atgctcaacc | tgccgcagtt | caaccgagga | acagctttca | cagcagagga | 180 |
| acgtgacctg | tttaatcttg | tggggaatct | tcccgctgcc | ctgcagactc | tgcagaatca | 240 |
| agtcgacaga | gcgtacgatc | agtattcctc | gatctcgacg | gctttgggga | agaataccct | 300 |
| tttgatgagt | ttaaaggtgc | aaaatgaggt | cctgtatttt | aagttgttgc | aggatcattt | 360 |
| gaaggagatg | tttagtataa | tttacacgcc | gactgaggta | ggatcaaatt | tagtttttgtt | 420 |
| ggtaagatat | tgctgaacga | tgagtagagt | gaagctattg | agcattattc | gagactgttt | 480 |
| agacgcccgg | agggctgctt | tctgaacatc | aaccaccctg | agtatatcga | acggtctctg | 540 |
| gcggcgtggg | gtacagagga | ggacattgac | tatatcatcg | ttagtgacgg | cgaggaggta | 600 |
| tgacatgatt | ttgttctaga | gttttcgaaa | tgcactcatg | ccggttatgc | agatcctcgg | 660 |
| aattggcgat | caaggagtcg | gagctatcgg | aatctcaagt | gcaaaagctg | tgcttatgac | 720 |
| tctatgcgcc | ggcgtccatc | catcgagatg | cattccagtc | gcgcttgatg | ttggcacgga | 780 |
| taacgagcag | ttgctcgagg | atgagctata | ccttggcaat | aggcacaaca | gagtccgcgg | 840 |
| cgggcgatat | ggtgagctga | tcgaatattc | taagctttcg | tgacgtgcta | atttattat | 900 |
| agataaattt | gtggacgatt | tgtgcaatg | tgtcaagaaa | ctgtatcctc | gtgcggttct | 960 |
| ccactttgag | gatttcggac | tacctaatgc | cagaagacta | ctcgacacct | acagaccacg | 1020 |
| actagcgtgc | tttaatgacg | atgttcaggg | tactggcgct | gtcactttgg | ccgcactctc | 1080 |
| atcagccgtc | cggtggcccg | gaattgactt | ccgagacctc | agaacggtga | tctttggagc | 1140 |
| gggaacagca | ggaactggca | tcgcggatca | gctgcgcgac | tttctcaaca | cacaagggat | 1200 |
| ttccaagcaa | caagttatcg | atcatatttg | gcttgttgac | aagccaggat | tgcttcttaa | 1260 |

-continued

```
atcaatgcat gataaactta catcagcgca acgtccgtac gctgcgtcgg acgatcgttg    1320
gaaagagatc gacaccaagt cattgtcaga atcgtgaag aaagtgaagc cgcatgtgtt     1380
gattgggtgc tccacgaagc caaaagcatt caacgaagca gttcttcgtg agatggccaa    1440
acacgttgaa cggccgattg tctttcccct gagcaatccc acgcgactac acgaagcgac    1500
gccggcggag attttaagt acacggacgg taaggcgctg gtggccaccg gttcgccgtt     1560
tgatcctgtc gatggcaagg aaattgccga gaacaataac tgtttcgtgt accctggtat    1620
tggcatgggg tcgatcttga gcagggccga tagagtcaca gagacgatga ttgcggcagt    1680
cgtgaaggag cttgcgtcgt tggcgccgtc ggagaaagat cctactggcg cactcttgcc    1740
tgatgtggca gatattagag atatttctgc gaagatcgcg actgcagtag tgttgcaagc    1800
gttagaggag ggaactgcga gagtggaaga gattgaaggt atcaaagttc acgagacag     1860 agatcactgc ctggaatggg tcaaagagca gatgtggaaa cctgagtata gaccattgag    1920
aaaggtgtga                                                           1930
```

<210> SEQ ID NO 34
<211> LENGTH: 572
<212> TYPE: PRT
<213> ORGANISM: Lipomyces starkeyi

<400> SEQUENCE: 34

```
Met Ala Pro Lys Ser Ser Thr Arg Val Pro Leu Ser Val Lys Gly Pro
1               5                   10                  15

Ile Asp Cys Pro Tyr Glu Gly Lys Glu Met Leu Asn Leu Pro Gln Phe
            20                  25                  30

Asn Arg Gly Thr Ala Phe Thr Ala Glu Glu Arg Asp Leu Phe Asn Leu
        35                  40                  45

Val Gly Asn Leu Pro Ala Ala Leu Gln Thr Leu Gln Asn Gln Val Asp
    50                  55                  60

Arg Ala Tyr Asp Gln Tyr Ser Ser Ile Ser Thr Ala Leu Gly Lys Asn
65                  70                  75                  80

Thr Phe Leu Met Ser Leu Lys Val Gln Asn Glu Val Leu Tyr Phe Lys
                85                  90                  95

Leu Leu Gln Asp His Leu Lys Glu Met Phe Ser Ile Ile Tyr Thr Pro
            100                 105                 110

Thr Glu Ser Glu Ala Ile Glu His Tyr Ser Arg Leu Phe Arg Arg Pro
        115                 120                 125

Glu Gly Cys Phe Leu Asn Ile Asn His Pro Glu Tyr Ile Glu Arg Ser
    130                 135                 140

Leu Ala Ala Trp Gly Thr Glu Glu Asp Ile Asp Tyr Ile Ile Val Ser
145                 150                 155                 160

Asp Gly Glu Glu Ile Leu Gly Ile Gly Asp Gln Gly Val Gly Ala Ile
                165                 170                 175

Gly Ile Ser Ser Ala Lys Ala Val Leu Met Thr Leu Cys Ala Gly Val
            180                 185                 190

His Pro Ser Arg Cys Ile Pro Val Ala Leu Asp Val Gly Thr Asp Asn
        195                 200                 205

Glu Gln Leu Leu Glu Asp Glu Leu Tyr Leu Gly Asn Arg His Asn Arg
    210                 215                 220

Val Arg Gly Gly Arg Tyr Asp Lys Phe Val Asp Phe Val Gln Cys
225                 230                 235                 240

Val Lys Lys Leu Tyr Pro Arg Ala Val Leu His Phe Glu Asp Phe Gly
                245                 250                 255
```

```
Leu Pro Asn Ala Arg Arg Leu Leu Asp Thr Tyr Arg Pro Arg Leu Ala
            260                 265                 270

Cys Phe Asn Asp Val Gln Gly Thr Gly Ala Val Thr Leu Ala Ala
            275                 280                 285

Leu Ser Ser Ala Val Arg Val Ala Gly Ile Asp Phe Arg Asp Leu Arg
            290                 295                 300

Thr Val Ile Phe Gly Ala Gly Thr Ala Gly Thr Gly Ile Ala Asp Gln
305                 310                 315                 320

Leu Arg Asp Phe Leu Asn Thr Gln Gly Ile Ser Lys Gln Gln Val Ile
                325                 330                 335

Asp His Ile Trp Leu Val Asp Lys Pro Gly Leu Leu Lys Ser Met
            340                 345                 350

His Asp Lys Leu Thr Ser Ala Gln Arg Pro Tyr Ala Ala Ser Asp Asp
            355                 360                 365

Arg Trp Lys Glu Ile Asp Thr Lys Ser Leu Ser Glu Ile Val Lys Lys
            370                 375                 380

Val Lys Pro His Val Leu Ile Gly Cys Ser Thr Lys Pro Lys Ala Phe
385                 390                 395                 400

Asn Glu Ala Val Leu Arg Glu Met Ala Lys His Val Glu Arg Pro Ile
                405                 410                 415

Val Phe Pro Leu Ser Asn Pro Thr Arg Leu His Glu Ala Thr Pro Ala
            420                 425                 430

Glu Ile Phe Lys Tyr Thr Asp Gly Lys Ala Leu Val Ala Thr Gly Ser
            435                 440                 445

Pro Phe Asp Pro Val Asp Gly Lys Glu Ile Ala Glu Asn Asn Asn Cys
            450                 455                 460

Phe Val Tyr Pro Gly Ile Gly Met Gly Ser Ile Leu Ser Arg Ala Asp
465                 470                 475                 480

Arg Val Thr Glu Thr Met Ile Ala Ala Val Lys Glu Leu Ala Ser
                485                 490                 495

Leu Ala Pro Ser Glu Lys Asp Pro Thr Gly Ala Leu Leu Pro Asp Val
            500                 505                 510

Ala Asp Ile Arg Asp Ile Ser Ala Lys Ile Ala Thr Ala Val Val Leu
            515                 520                 525

Gln Ala Leu Glu Glu Gly Thr Ala Arg Val Glu Glu Ile Glu Gly Ile
            530                 535                 540

Lys Val Pro Arg Asp Arg Asp His Cys Leu Glu Trp Val Lys Glu Gln
545                 550                 555                 560

Met Trp Lys Pro Glu Tyr Arg Pro Leu Arg Lys Val
                565                 570

<210> SEQ ID NO 35
<211> LENGTH: 1542
<212> TYPE: DNA
<213> ORGANISM: Marinobacter aquaeolei

<400> SEQUENCE: 35
atggcaatac agcaggtaca tcacgctgac acttcatcat caaaggtgct cggacagctc      60
cgtggcaagc gggttctgat caccggtacc actggctttc tgggcaaggt ggtcctcgaa     120
aggctgattc gggcggtgcc tgatatcggc gcaatttacc tgctgatccg ggcaataaaa     180
cggcatccgg atgctcgttc ccgtttcctg gaagaaattg ccacctcctc ggtgttgac      240 cgtcttcgcg aggccgattc agagggattt gacgcctttc tggaagagcg cattcactgc     300
```

-continued

```
gtgaccggtg aggtgaccga agcgggtttc gggatagggc aggaagacta tcgcaaactc    360
gccaccgaac tggatgcggt gatcaactcc gctgcaagcg tgaatttccg tgaagagctc    420
gacaaggcgc tggccatcaa caccctgtgc cttcggaata ttgccggcat ggtggatttg    480
aatccgaagc ttgcggtcct gcaggtctcc acctgctatg tcaatggcat gaactcgggg    540
caggtaaccg aatcggtgat caagccggca ggcgaggccg tgccgcgttc cccggacggc    600
ttctatgaga tagaagagct tgttcgcctg cttcaggata aaattgaaga cgttcaggcc    660
cgttattccg gcaaagtgct ggagaggaag ctggtggacc tggggattcg ggaagccaac    720
cgctatggct ggagcgatac ctacaccttt accaagtggc tggcgaaca  gttgctgatg    780 aaggcgttaa cgggcgcac  gctgaccatt ctgcgtcctt cgattatcga aagtgccctg    840
gaggaaccag cgcccggctg gattgagggg gtgaaggtgg cagatgccat catcctggct    900
tacgcacggg aaaaagtcac cctcttcccg ggcaaacgct ccgtatcat  cgatgtgatt    960 ccagtggacc tggtgccaa  ctccatcatc ctttccctgg cggaagctct tggagaaccc   1020
ggtcgacgtc gcatctatca atgttgcagc ggggcggca  atccaatctc cctgggtgag   1080
ttcatcgatc atctcatggc ggaatcaaaa gccaattacg ctgcctacga tcacctgttc   1140
taccggcagc cagcaagcc  gtttctggcg gttaaccggg cgctgtttga tttggtgatc   1200
agtggtgttc gcttaccgct ctccctgacg gaccgtgtgc tcaaattact gggaaattcc   1260
cgggacctga aaatgctcag gaatctggat accacccagt cgctggcaac cattttttggt   1320 ttctacaccg cgccggatta tatcttccgg aacgatgagc tgatggcgct ggcgaaccgg   1380
atgggtgagg tcgataaagg gctgttcccg gtggatgccc gcctgattga ctgggagctc   1440
tacctgcgca agattcacct ggccgggctc aatcgctatg ccctgaaaga acgaaaggtg   1500
tacagtctga aaaccgcgcg ccagcgcaaa aaagctgcct ga                      1542
```

<210> SEQ ID NO 36
<211> LENGTH: 513
<212> TYPE: PRT
<213> ORGANISM: Marinobacter aquaeolei

<400> SEQUENCE: 36

```
Met Ala Ile Gln Gln Val His His Ala Asp Thr Ser Ser Ser Lys Val
1               5                   10                  15

Leu Gly Gln Leu Arg Gly Lys Arg Val Leu Ile Thr Gly Thr Thr Gly
            20                  25                  30

Phe Leu Gly Lys Val Val Leu Glu Arg Leu Ile Arg Ala Val Pro Asp
        35                  40                  45

Ile Gly Ala Ile Tyr Leu Leu Ile Arg Gly Asn Lys Arg His Pro Asp
    50                  55                  60

Ala Arg Ser Arg Phe Leu Glu Glu Ile Ala Thr Ser Ser Val Phe Asp
65                  70                  75                  80

Arg Leu Arg Glu Ala Asp Ser Glu Gly Phe Asp Ala Phe Leu Glu Glu
                85                  90                  95

Arg Ile His Cys Val Thr Gly Glu Val Thr Glu Ala Gly Phe Gly Ile
            100                 105                 110

Gly Gln Glu Asp Tyr Arg Lys Leu Ala Thr Glu Leu Asp Ala Val Ile
        115                 120                 125

Asn Ser Ala Ala Ser Val Asn Phe Arg Glu Glu Leu Asp Lys Ala Leu
    130                 135                 140

Ala Ile Asn Thr Leu Cys Leu Arg Asn Ile Ala Gly Met Val Asp Leu
145                 150                 155                 160
```

Asn Pro Lys Leu Ala Val Leu Gln Val Ser Thr Cys Tyr Val Asn Gly
            165                 170                 175

Met Asn Ser Gly Gln Val Thr Glu Ser Val Ile Lys Pro Ala Gly Glu
        180                 185                 190

Ala Val Pro Arg Ser Pro Asp Gly Phe Tyr Glu Ile Glu Glu Leu Val
    195                 200                 205

Arg Leu Leu Gln Asp Lys Ile Glu Asp Val Gln Ala Arg Tyr Ser Gly
    210                 215                 220

Lys Val Leu Glu Arg Lys Leu Val Asp Leu Gly Ile Arg Glu Ala Asn
225                 230                 235                 240

Arg Tyr Gly Trp Ser Asp Thr Tyr Thr Phe Thr Lys Trp Leu Gly Glu
            245                 250                 255

Gln Leu Leu Met Lys Ala Leu Asn Gly Arg Thr Leu Thr Ile Leu Arg
            260                 265                 270

Pro Ser Ile Ile Glu Ser Ala Leu Glu Glu Pro Ala Pro Gly Trp Ile
            275                 280                 285

Glu Gly Val Lys Val Ala Asp Ala Ile Ile Leu Ala Tyr Ala Arg Glu
            290                 295                 300

Lys Val Thr Leu Phe Pro Gly Lys Arg Ser Gly Ile Ile Asp Val Ile
305                 310                 315                 320

Pro Val Asp Leu Val Ala Asn Ser Ile Ile Leu Ser Leu Ala Glu Ala
            325                 330                 335

Leu Gly Glu Pro Gly Arg Arg Arg Ile Tyr Gln Cys Cys Ser Gly Gly
            340                 345                 350

Gly Asn Pro Ile Ser Leu Gly Glu Phe Ile Asp His Leu Met Ala Glu
            355                 360                 365

Ser Lys Ala Asn Tyr Ala Ala Tyr Asp His Leu Phe Tyr Arg Gln Pro
            370                 375                 380

Ser Lys Pro Phe Leu Ala Val Asn Arg Ala Leu Phe Asp Leu Val Ile
385                 390                 395                 400

Ser Gly Val Arg Leu Pro Leu Ser Leu Thr Asp Arg Val Leu Lys Leu
            405                 410                 415

Leu Gly Asn Ser Arg Asp Leu Lys Met Leu Arg Asn Leu Asp Thr Thr
            420                 425                 430

Gln Ser Leu Ala Thr Ile Phe Gly Phe Tyr Thr Ala Pro Asp Tyr Ile
            435                 440                 445

Phe Arg Asn Asp Glu Leu Met Ala Leu Ala Asn Arg Met Gly Glu Val
450                 455                 460

Asp Lys Gly Leu Phe Pro Val Asp Ala Arg Leu Ile Asp Trp Glu Leu
465                 470                 475                 480

Tyr Leu Arg Lys Ile His Leu Ala Gly Leu Asn Arg Tyr Ala Leu Lys
            485                 490                 495

Glu Arg Lys Val Tyr Ser Leu Lys Thr Ala Arg Gln Arg Lys Lys Ala
            500                 505                 510

Ala

<210> SEQ ID NO 37
<211> LENGTH: 1514
<212> TYPE: DNA
<213> ORGANISM: Lipomyces starkeyi
<220> FEATURE:
<221> NAME/KEY: Intron
<222> LOCATION: (329)..(381)

<400> SEQUENCE: 37

```
atgactgcca gtgctgagac aacgtccgcg cagcctgtcg tcgagtcggc tcgcgcaagg    60
ccacccagat caagctcaac gtcgccttct cgttcggttg gtagtgctgc gtcgactgcg   120
aagcaagcgt ctcctacatt cgtccacatc tccgagcaac cgttcactct ccagaactgg   180
tacaagcaca tcagctggct caatgtcacg ctgatcatct tcatccctgt cattggctgc   240
actaccgcgg ttttcactcc tctgcaatct aagactgcca tccttgcctt tgtctactac   300
gccctgacgg gcctcggtat cactgcgggt atgtattgct attatactgc agtatatgat   360
tagagtgaac taattgatca ggttatcacc gcctctggtc gcaccgtgct acagtgccc    420
gtcttcctct ccgtattcta ctcgctgctt cggcggcgg tgctgttgag ggttccattc    480
gctggtggtc cgctggtcac cgtgtccatc acagattcac cgatactgag aaggacccttt   540
actctgtccg caagggtctg ctctattctc acatgggctg gatggtgttt ctccacaacc   600
ccaagaagtc cggccgggtc gatatcaccg acttgaacgc tgaccctgtc gtcagatggc   660
agcacaagaa ctacattctc gtccttctct ttatgggttt catcttcccc atggtagttg   720
ccggcctcgg atgggtgac tggaagggtg gtctcatctg ggctggcatt gtccgtttga    780
cagttgtcca ccatgccact ttttgtgtca actcgctcgc tcactggctc ggtgaccagc   840
ctttcgacga ccgccgctct ccgcgtgacc acttcttgac tgccatcgtt acgttcggcg   900
agggctatca caacttccac catgagttcc cctctgacta ccgtaacgcc ataagatggt   960
atcagtatga tcccactaag tggctcatct ggttcctcaa gaagatcggc tttgcttatg  1020
acctttaagac cttctctcac aatgccatcc agcaaggcct cgtccagcag aggcagaaaa  1080
agctcgacaa gtggcgcgca cgtcttaact ggggtgttcc tctcgagcag ctcccggtca  1140
tggaatttga agagtaccag gagcaggcca agacgcgtgc gctcgtcctc attgctggtg  1200
ttgtccacga tgtcaccaac tttattgagc agcatcctgg tggaaaggct ctgatccagt  1260
caggtattgg caaggatgcc accgctgtct tcaatggcgg tgtctacgac cactccaatg  1320
ctgcccacaa cctgctcggt accatgcgtg ttggtgtcat tcgcggcggc atggaagtcg  1380
aggtctggaa gatggctcag cgagagaata aggagtcaac gatcaagtcc gattcgaata  1440
atgccaatat cgtccgtgca ggttctcagg caacccggat acaagctccc atccagggcg  1500
ctggtgccgc ttag                                                     1514
```

<210> SEQ ID NO 38
<211> LENGTH: 486
<212> TYPE: PRT
<213> ORGANISM: Lipomyces starkeyi

<400> SEQUENCE: 38

```
Met Thr Ala Ser Ala Glu Thr Thr Ser Ala Gln Pro Val Val Glu Ser
1               5                   10                  15

Ala Arg Ala Arg Pro Pro Arg Ser Ser Ser Thr Ser Pro Ser Arg Ser
            20                  25                  30

Val Gly Ser Ala Ala Ser Thr Ala Lys Gln Ala Ser Pro Thr Phe Val
        35                  40                  45

His Ile Ser Glu Gln Pro Phe Thr Leu Gln Asn Trp Tyr Lys His Ile
    50                  55                  60

Ser Trp Leu Asn Val Thr Leu Ile Ile Phe Ile Pro Val Ile Gly Cys
65                  70                  75                  80

Thr Thr Ala Val Phe Thr Pro Leu Gln Ser Lys Thr Ala Ile Leu Ala
                85                  90                  95
```

```
Phe Val Tyr Tyr Ala Leu Thr Gly Leu Gly Ile Thr Ala Gly Tyr His
                100                 105                 110
Arg Leu Trp Ser His Arg Ala Tyr Ser Ala Arg Leu Pro Leu Arg Ile
            115                 120                 125
Leu Leu Ala Ala Phe Gly Gly Ala Val Glu Gly Ser Ile Arg Trp
    130                 135                 140
Trp Ser Ala Gly His Arg Val His Arg Phe Thr Asp Thr Glu Lys
145                 150                 155                 160
Asp Pro Tyr Ser Val Arg Lys Gly Leu Leu Tyr Ser His Met Gly Trp
                165                 170                 175
Met Val Phe Leu His Asn Pro Lys Lys Ser Gly Arg Val Asp Ile Thr
            180                 185                 190
Asp Leu Asn Ala Asp Pro Val Val Arg Trp Gln His Lys Asn Tyr Ile
        195                 200                 205
Leu Val Leu Leu Phe Met Gly Phe Ile Phe Pro Met Val Ala Gly
    210                 215                 220
Leu Gly Trp Gly Asp Trp Lys Gly Gly Leu Ile Trp Ala Gly Ile Val
225                 230                 235                 240
Arg Leu Thr Val Val His His Ala Thr Phe Cys Val Asn Ser Leu Ala
                245                 250                 255
His Trp Leu Gly Asp Gln Pro Phe Asp Asp Arg Arg Ser Pro Arg Asp
            260                 265                 270
His Phe Leu Thr Ala Ile Val Thr Phe Gly Glu Gly Tyr His Asn Phe
        275                 280                 285
His His Glu Phe Pro Ser Asp Tyr Arg Asn Ala Ile Arg Trp Tyr Gln
    290                 295                 300
Tyr Asp Pro Thr Lys Trp Leu Ile Trp Phe Leu Lys Lys Ile Gly Phe
305                 310                 315                 320
Ala Tyr Asp Leu Lys Thr Phe Ser His Asn Ala Ile Gln Gln Gly Leu
                325                 330                 335
Val Gln Gln Arg Gln Lys Lys Leu Asp Lys Trp Arg Ala Arg Leu Asn
            340                 345                 350
Trp Gly Val Pro Leu Glu Gln Leu Pro Val Met Glu Phe Glu Glu Tyr
        355                 360                 365
Gln Glu Gln Ala Lys Thr Arg Ala Leu Val Leu Ile Ala Gly Val Val
    370                 375                 380
His Asp Val Thr Asn Phe Ile Glu Gln His Pro Gly Gly Lys Ala Leu
385                 390                 395                 400
Ile Gln Ser Gly Ile Gly Lys Asp Ala Thr Ala Val Phe Asn Gly Gly
                405                 410                 415
Val Tyr Asp His Ser Asn Ala Ala His Asn Leu Leu Gly Thr Met Arg
            420                 425                 430
Val Gly Val Ile Arg Gly Gly Met Glu Val Glu Val Trp Lys Met Ala
        435                 440                 445
Gln Arg Glu Asn Lys Glu Ser Thr Ile Lys Ser Asp Ser Asn Asn Ala
    450                 455                 460
Asn Ile Val Arg Ala Gly Ser Gln Ala Thr Arg Ile Gln Ala Pro Ile
465                 470                 475                 480
Gln Gly Ala Gly Ala Ala
                485

<210> SEQ ID NO 39
<211> LENGTH: 1936
<212> TYPE: DNA
```

<213> ORGANISM: Lipomyces starkeyi
<220> FEATURE:
<221> NAME/KEY: Intron
<222> LOCATION: (164)..(224)
<220> FEATURE:
<221> NAME/KEY: Intron
<222> LOCATION: (326)..(382)

<400> SEQUENCE: 39

```
atggcttcct cagttcctca agctcccgtc acttccctac tctcggaggc tcgcggtaag      60
accgtacagc gtgataataa tgaattaccc ggtgctcgtt ccattgacac cgaggctacg     120
ttccagcatt ggatctacga catggttatc tggagtttat caggtgtgta caccgtatgc     180
tttaattagc aagccgatac tgccatatta acttgcgcat tcagtcgtgt tcgatctatt     240
tttccgtgaa atccgcccga ggggcgcata ccgaatcccg agacatggtc cgattatctt     300
tgttgccgct ccgcacgcca atcaggtgag tcttggccgc aatgatacca tcatacgacg     360
tatggagcta acacgaagac agtttattga ccccatcatg ctcatgcgtc aaattcgaat     420
tgaagcaggt cgcagaatat cgtttctggc ggccgaaagt tcaatgcacc gcaaattcgt     480
cggcactgtc gctcgatcag tttcttcaat tccggttgct agagctcagg acttggcgtc     540
tcacggaact ggtttgatct atattgaaga taaggagaag ccgttggtta tcaagggcca     600
gggaaccaag tttatgaagg aatgcagtca aggcgggttg ataatgttgg cgaagtcact     660
tggcagcgcc gagattgata gcatcgtgtc tgatgtcgag ttgattttgc gccggccttt     720
caaggaggag aaagccatcg agtatttatt ttccggtccg tccaagttta aaaaagcgcc     780
aaaggtcgac cagtcacaga tgtaccagaa ggtcttcgaa agactgaatg acggtggatg     840
tatcggtatc tttcccgaag gcggttcaca tgaccgacca gacttattac cactaaaagc     900
cggtgtcgcg gttatggctc ttggtgccct agagcagaac ccagagtgcg acatcagaat     960
tgtcccttgc ggtatgaact acttccaccc tcacaaattc cgatcacgag cagttattga    1020
gtttggtcct ccacttaacg ttcccaagga gcttgtcaag acgtacagtg aaggaaataa    1080
gagagattct ataccagcc tcttggaaat gattcatagc gcgttgttgg ctgttactgt    1140
tacctcgccg gattacgaca cattgatggt tattcaagcg gctcgacgac tatacaaacc    1200
cgcacacaag aaaatcccgc tatcgttggt tatcgagatg aatcggcggt tagtcatagg    1260
gtatacacat tacaaggacg atccacggat tattcatctt cgggaagccg ttgcgaacta    1320
taacaagcag ttgagacatt tgggaatcct ggatcatcag gttgagtacg caacattgcc    1380
aataccggag attgtcggaa aattagtcta ccggtcgctg aaactattta ttctggcatt    1440
gggcgctctg cccggagcta ttcttttcgc accggtattc atcgcgacca agatgatttc    1500
caagaagaag gcagccgaag cgttgaaggc gtcgaccgtg aagatcgctg ccagggatgt    1560
tgtcgcgaca tggaagattc tcgtagcgct gggtctcgcg ccgacgctat actggttcta    1620
cgcacttttg gcgacatggg cgacgtggaa gtacgatctt gttcctcaag tgcgaccggt    1680
gtggctcgtg actcttgcgg ctatgattat tttcccggcg atcacgtacg ctgcacttag    1740
aattggagag atcggaatgg atattttcaa gtcattaaag ccgcttgtga catgcttgaa    1800
cccgaataat ttgaacacga ttgcgaagtt gcggattacg agagaggaat tgtcgaagga    1860
agtcaccgag atgattaatt cattaggccc ggatgtcttt ccagagttcg actctcaccg    1920
gttaatgcag agttag                                                    1936
```

<210> SEQ ID NO 40
<211> LENGTH: 605

<212> TYPE: PRT
<213> ORGANISM: Lipomyces starkeyi

<400> SEQUENCE: 40

```
Met Ala Ser Ser Val Pro Gln Ala Pro Val Thr Ser Leu Leu Ser Glu
 1               5                  10                  15

Ala Arg Gly Lys Thr Val Gln Arg Asp Asn Asn Glu Leu Pro Gly Ala
                20                  25                  30

Arg Ser Ile Asp Thr Glu Ala Thr Phe Gln His Trp Ile Tyr Asp Met
            35                  40                  45

Val Ile Trp Ser Leu Ser Val Val Phe Asp Leu Phe Phe Arg Glu Ile
        50                  55                  60

Arg Pro Arg Gly Ala Tyr Arg Ile Pro Arg His Gly Pro Ile Ile Phe
 65                  70                  75                  80

Val Ala Ala Pro His Ala Asn Gln Phe Ile Asp Pro Ile Met Leu Met
                 85                  90                  95

Arg Gln Ile Arg Ile Glu Ala Gly Arg Arg Ile Ser Phe Leu Ala Ala
                100                 105                 110

Glu Ser Ser Met His Arg Lys Phe Val Gly Thr Val Ala Arg Ser Val
            115                 120                 125

Ser Ser Ile Pro Val Ala Arg Ala Gln Asp Leu Ala Ser His Gly Thr
        130                 135                 140

Gly Leu Ile Tyr Ile Glu Asp Lys Glu Lys Pro Leu Val Ile Lys Gly
145                 150                 155                 160

Gln Gly Thr Lys Phe Met Lys Glu Cys Ser Gln Gly Gly Leu Ile Met
                165                 170                 175

Leu Ala Lys Ser Leu Gly Ser Ala Glu Ile Asp Ser Ile Val Ser Asp
            180                 185                 190

Val Glu Leu Ile Leu Arg Arg Pro Phe Lys Glu Lys Ala Ile Glu
        195                 200                 205

Tyr Leu Phe Ser Gly Pro Ser Lys Phe Lys Lys Ala Pro Lys Val Asp
    210                 215                 220

Gln Ser Gln Met Tyr Gln Lys Val Phe Glu Arg Leu Asn Asp Gly Gly
225                 230                 235                 240

Cys Ile Gly Ile Phe Pro Glu Gly Gly Ser His Asp Arg Pro Asp Leu
                245                 250                 255

Leu Pro Leu Lys Ala Gly Val Ala Val Met Ala Leu Gly Ala Leu Glu
            260                 265                 270

Gln Asn Pro Glu Cys Asp Ile Arg Ile Val Pro Cys Gly Met Asn Tyr
        275                 280                 285

Phe His Pro His Lys Phe Arg Ser Arg Ala Val Ile Glu Phe Gly Pro
    290                 295                 300

Pro Leu Asn Val Pro Lys Glu Leu Val Lys Thr Tyr Ser Glu Gly Asn
305                 310                 315                 320

Lys Arg Asp Ser Ile His Gln Leu Leu Glu Met Ile His Ser Ala Leu
                325                 330                 335

Leu Ala Val Thr Val Thr Ser Pro Asp Tyr Asp Thr Leu Met Val Ile
            340                 345                 350

Gln Ala Ala Arg Arg Leu Tyr Lys Pro Ala His Lys Lys Ile Pro Leu
        355                 360                 365

Ser Leu Val Ile Glu Met Asn Arg Arg Leu Val Ile Gly Tyr Thr His
    370                 375                 380

Tyr Lys Asp Asp Pro Arg Ile Ile His Leu Arg Glu Ala Val Ala Asn
385                 390                 395                 400
```

```
Tyr Asn Lys Gln Leu Arg His Leu Gly Ile Leu Asp His Gln Val Glu
                405                 410                 415
Tyr Ala Thr Leu Pro Ile Pro Glu Ile Val Gly Lys Leu Val Tyr Arg
            420                 425                 430
Ser Leu Lys Leu Phe Ile Leu Ala Leu Gly Ala Leu Pro Gly Ala Ile
        435                 440                 445
Leu Phe Ala Pro Val Phe Ile Ala Thr Lys Met Ile Ser Lys Lys Lys
    450                 455                 460
Ala Ala Glu Ala Leu Lys Ala Ser Thr Val Lys Ile Ala Ala Arg Asp
465                 470                 475                 480
Val Val Ala Thr Trp Lys Ile Leu Val Ala Leu Gly Leu Ala Pro Thr
                485                 490                 495
Leu Tyr Trp Phe Tyr Ala Leu Leu Ala Thr Trp Ala Thr Trp Lys Tyr
            500                 505                 510
Asp Leu Val Pro Gln Val Arg Pro Val Trp Leu Val Thr Leu Ala Ala
        515                 520                 525
Met Ile Ile Phe Pro Ala Ile Thr Tyr Ala Ala Leu Arg Ile Gly Glu
    530                 535                 540
Ile Gly Met Asp Ile Phe Lys Ser Leu Lys Pro Leu Val Thr Cys Leu
545                 550                 555                 560
Asn Pro Asn Asn Leu Asn Thr Ile Ala Lys Leu Arg Ile Thr Arg Glu
                565                 570                 575
Glu Leu Ser Lys Glu Val Thr Glu Met Ile Asn Ser Leu Gly Pro Asp
            580                 585                 590
Val Phe Pro Glu Phe Asp Ser His Arg Leu Met Gln Ser
        595                 600                 605

<210> SEQ ID NO 41
<211> LENGTH: 1213
<212> TYPE: DNA
<213> ORGANISM: Lipomyces starkeyi
<220> FEATURE:
<221> NAME/KEY: Intron
<222> LOCATION: (355)..(406)
<220> FEATURE:
<221> NAME/KEY: Intron
<222> LOCATION: (477)..(525)
<220> FEATURE:
<221> NAME/KEY: Intron
<222> LOCATION: (642)..(694)

<400> SEQUENCE: 41
atggccgcca gtgacgtcgt cctctcaggt ctcggtatcg taatcgcatt cacgatgagt      60
ttgaacatcc tcggtctcat ctacaggcca ctacaattct atggcaagtt cctgctatgc     120
tttctgagca tgtgcacatg tgcctcgtat ggtttccttg cgtccatttt gttgtcgctg     180
attggcaaga aagggttgag tcagtggacg gccggaaggg cgtttagtac gctgacgtgc     240
cctctgattg gcctcaagat cgatatcaag aacgaagaga ttttgagaaa gacgagacca     300
gctattatta ttgcgaatca tcagagtgaa ttggatgttc tttattaggc cgggtatga      360 tgctagcgaa tatttatttt aacgttcgat gctgacacgt gtttagatat ttccaaaata     420
ctgcagtgtg actgcgaaga gtagtttgaa atatgtccca ttttgggat ggttcagtat      480 gttcttcggc tcgtttgcgt tagccatact aacatgagga tctagtgatg atcagcggca     540
ctgttttcat tgaccgccag aacagaggaa aggctatcaa ggctcttgat ggtgccatta     600
atgccatgaa gaagaataac caatgtgtct ttatcttccc tgtccgttat attccttctt     660
```

```
catttcaatg ttgctcatgc tgacttcatt acaggaaggc acaaggtcat atttcaccga    720
accagacatg ctgaagttca agcgtggagc gttccatctg gctatacagt caggcttccc    780
aattatcccc gtcgtgatct caaactactc gcatgtgttc aacttccgca aacgcattct    840
ccaagctgga acaatcgaca tccaagtcct cgatcctgtc acaactgaag gtatttcaaa    900
cgaagactta gacgacctcg tcgaaactac ccgcataaag atgcttaagg tgcttaagga    960
gatctcaccg aaagccgtaa aagagccgac tggtgatgtc gaagcggatg atactactct   1020
tttgtcagca tctggcaccg ctaatggatc tgacctcgtc ggcactattg acgatgacga   1080
tgtccttgaa ccgcgaataa cacgcgacac cgatgcttca gagatttcgg ccgcgttgtc   1140
cgagtctgcg accgaagaaa ctgatttgac accggatgtt tccaaagtta tcgagcttga   1200
cacccgaaac taa                                                      1213
```

<210> SEQ ID NO 42
<211> LENGTH: 352
<212> TYPE: PRT
<213> ORGANISM: Lipomyces starkeyi

<400> SEQUENCE: 42

```
Met Ala Ala Ser Asp Val Val Leu Ser Gly Leu Gly Ile Val Ile Ala
1               5                   10                  15

Phe Thr Met Ser Leu Asn Ile Leu Gly Leu Ile Tyr Arg Pro Leu Gln
            20                  25                  30

Phe Tyr Gly Lys Phe Ser Leu Cys Phe Ser Ser Met Cys Thr Cys Ala
        35                  40                  45

Ser Tyr Gly Phe Leu Ala Ser Ile Leu Leu Ser Ser Ile Gly Lys Lys
    50                  55                  60

Gly Leu Ser Gln Trp Thr Ala Gly Arg Ala Phe Ser Thr Ser Thr Cys
65                  70                  75                  80

Pro Ser Ile Gly Leu Lys Ile Asp Ile Lys Asn Glu Glu Ile Leu Arg
                85                  90                  95

Lys Thr Arg Pro Ala Ile Ile Ala Asn His Gln Ser Glu Leu Asp
            100                 105                 110

Val Leu Leu Leu Gly Arg Ile Phe Pro Lys Tyr Cys Ser Val Thr Ala
        115                 120                 125

Lys Ser Ser Leu Lys Tyr Val Pro Phe Leu Gly Trp Phe Met Met Ile
    130                 135                 140

Ser Gly Thr Val Phe Ile Asp Arg Gln Asn Arg Gly Lys Ala Ile Lys
145                 150                 155                 160

Ala Leu Asp Gly Ala Ile Asn Ala Met Lys Lys Asn Asn Gln Cys Val
                165                 170                 175

Phe Ile Phe Pro Glu Gly Thr Arg Ser Tyr Phe Thr Glu Pro Asp Met
            180                 185                 190

Ser Lys Phe Lys Arg Gly Ala Phe His Ser Ala Ile Gln Ser Gly Phe
        195                 200                 205

Pro Ile Ile Pro Val Val Ile Ser Asn Tyr Ser His Val Phe Asn Phe
    210                 215                 220

Arg Lys Arg Ile Leu Gln Ala Gly Thr Ile Asp Ile Gln Val Leu Asp
225                 230                 235                 240

Pro Val Thr Thr Glu Gly Ile Ser Asn Glu Asp Leu Asp Asp Leu Val
                245                 250                 255

Glu Thr Thr Arg Ile Lys Met Leu Lys Val Leu Lys Glu Ile Ser Pro
            260                 265                 270
```

-continued

Lys Ala Val Lys Glu Pro Thr Gly Asp Val Glu Ala Asp Asp Thr Thr
                275                 280                 285

Leu Leu Ser Ala Ser Gly Thr Ala Asn Gly Ser Asp Leu Val Gly Thr
            290                 295                 300

Ile Asp Asp Asp Val Leu Glu Pro Arg Ile Thr Arg Asp Thr Asp
305                 310                 315                 320

Ala Ser Glu Ile Ser Ala Ala Leu Ser Glu Ser Ala Thr Glu Glu Thr
                325                 330                 335

Asp Leu Thr Pro Asp Val Ser Lys Val Ile Glu Leu Asp Thr Arg Asn
            340                 345                 350

<210> SEQ ID NO 43
<211> LENGTH: 1832
<212> TYPE: DNA
<213> ORGANISM: Lipomyces starkeyi
<220> FEATURE:
<221> NAME/KEY: Intron
<222> LOCATION: (45)..(294)
<220> FEATURE:
<221> NAME/KEY: Intron
<222> LOCATION: (368)..(416)

<400> SEQUENCE: 43
atggctgata ctatcatctc ttccacgaag gcctccgaca ctgggtatgt gtgctctctc      60
ctaatcattc gcagccgcgc tctgccggcg cgagcagtcg acggccttc ctccgtctac      120 tcgataagcc cgagttgtta gctacagcac ctcaattcat tcgttgatga cttctgacta    180
ttcgaggatt atcacgaatg acttacgag cattgcgtgt gaattgattg tgttaatcgc     240
cgatggagat gtgaaggact tatctgtacg atcattttg ctaacaatgt ctagtgccgt    300
cccactacct ccgaactcga tcattgtggt cctgggagca tctggtgatc ttgcgaaaaa    360
gaagacagta cgttactatt atttggttgc ttatatgccg atagctgatc gaatagtacc    420
cggcgttgtt cggcttatat cgctatggat tgttgccaaa gaatgtcaag atcgtcggtt    480
atgcgcgcac aaagatggac gatgcagact acaagaagcg catatcgtca tatatgaaga    540
ctcctaccga gactatcgag acgcagttga aggagttcct ggcgatgacg tcgtacgtat    600
caggacagta cgaccaagac gaaggcttca ttagcttgac gaagcatata gaggaactcg    660
aaggcgatgt cgaggagcgt taccgtctat tttacatggc gctcccgcct aatgttttca    720
ttcctgtcgc ccagcacctt aagaagaact gctaccccaa gtctggcggt gcgagaatca    780
tcattgaaaa gccattcggt cacgatctgg ccagctcacg agagttgcag acagctcttc    840
agccgatttg gactgaagac gaaatttttcc gtatcgacca ctacctcggc aaggagatgg    900
ttaagaacat tttgattctg cggtttggca atgagttctt tggcgctgcc tggaacaaga    960
accatgtgtc gtcagtccag attactttca aggagccctt cggcaccgag ggtcgtggtg    1020
gttacttcga tcagtttggt attattcgag acgttatgca gaaccatttg ctccaggttc    1080
tcacgatgat cgccatggag cggcccgttt cattctctgc cgaggacatc cgtgacgaaa    1140
aagttcgtgt actacgggcc atgccaatca ttgatcccaa gaacgttgtc atcggccagt    1200
acgataagtc cctcgatggt accaagccga gctaccagga cgacgccacc gttcccaagg    1260
gctcgcgctg cccaacattc gctgcaattg tgatgtacat caagaacgac cgatgggacg    1320
gtgtcccgtt tattctcaag gccggcaagg cgctcgatgc cgccaaagtc gaggttcgtg    1380
ttcagttcaa ggacgtcacg tccggcatt tcaaggatat accccgaaac gagcttgtcc    1440
tgcgaattca gcctgacgag gccgtgtacg tcaaaatgaa caccaagctc cctggttaa    1500

-continued

```
ccatgaagac ttccgtcacc gagcttgacc tgacctacaa gcgccggttc tcggacctca    1560
agattcctga agcgtacgag gccctcatcc tcgatgcgat caatggtgac cactccaact    1620
ttgttcgaga cgatgagctc gacgcgtcct ggaagatttt cactccattt ctgcactacc    1680
tcgatgagaa caccgatatc gtaccggcca aatatcctta cggttcgcga gggccggctt    1740
tccttgatga ctttcttgcg tcgtacgggt acgcacgcga gcagcatggc atgtaccagt    1800
ggcctacaac caaggtcaat ggcaacttgt aa                                   1832
```

<210> SEQ ID NO 44
<211> LENGTH: 510
<212> TYPE: PRT
<213> ORGANISM: Lipomyces starkeyi

<400> SEQUENCE: 44

```
Met Ala Asp Thr Ile Ile Ser Ser Thr Lys Ala Ser Asp Thr Gly Ala
1               5                   10                  15

Val Pro Leu Pro Pro Asn Ser Ile Ile Val Ser Gly Ala Ser Gly
        20                  25                  30

Asp Leu Ala Lys Lys Lys Thr Tyr Pro Ala Leu Phe Gly Leu Tyr Arg
        35                  40                  45

Tyr Gly Leu Leu Pro Lys Asn Val Lys Ile Val Gly Tyr Ala Arg Thr
    50                  55                  60

Lys Met Asp Asp Ala Asp Tyr Lys Lys Arg Ile Ser Ser Tyr Met Lys
65                  70                  75                  80

Thr Pro Thr Glu Thr Ile Glu Thr Gln Leu Lys Glu Phe Ser Ala Met
                85                  90                  95

Thr Ser Tyr Val Ser Gly Gln Tyr Asp Gln Asp Glu Gly Phe Ile Ser
            100                 105                 110

Leu Thr Lys His Ile Glu Glu Leu Glu Gly Asp Val Glu Glu Arg Tyr
        115                 120                 125

Arg Leu Phe Tyr Met Ala Leu Pro Pro Asn Val Phe Ile Pro Val Ala
    130                 135                 140

Gln His Leu Lys Lys Asn Cys Tyr Pro Lys Ser Gly Gly Ala Arg Ile
145                 150                 155                 160

Ile Ile Glu Lys Pro Phe Gly His Asp Ser Ala Ser Ser Arg Glu Leu
                165                 170                 175

Gln Thr Ala Leu Gln Pro Ile Trp Thr Glu Asp Glu Ile Phe Arg Ile
            180                 185                 190

Asp His Tyr Leu Gly Lys Glu Met Val Lys Asn Ile Leu Ile Ser Arg
        195                 200                 205

Phe Gly Asn Glu Phe Phe Gly Ala Ala Trp Asn Lys Asn His Val Ser
    210                 215                 220

Ser Val Gln Ile Thr Phe Lys Glu Pro Phe Gly Thr Glu Gly Arg Gly
225                 230                 235                 240

Gly Tyr Phe Asp Gln Phe Gly Ile Ile Arg Asp Val Met Gln Asn His
                245                 250                 255

Leu Leu Gln Val Leu Thr Met Ile Ala Met Glu Arg Pro Val Ser Phe
            260                 265                 270

Ser Ala Glu Asp Ile Arg Asp Glu Lys Val Arg Val Leu Arg Ala Met
        275                 280                 285

Pro Ile Ile Asp Pro Lys Asn Val Val Ile Gly Gln Tyr Asp Lys Ser
    290                 295                 300

Leu Asp Gly Thr Lys Pro Ser Tyr Gln Asp Asp Ala Thr Val Pro Lys
305                 310                 315                 320
```

Gly Ser Arg Cys Pro Thr Phe Ala Ala Ile Val Met Tyr Ile Lys Asn
            325                 330                 335

Asp Arg Trp Asp Gly Val Pro Phe Ile Leu Lys Ala Gly Lys Ala Leu
            340                 345                 350

Asp Ala Ala Lys Val Glu Val Arg Val Gln Phe Lys Asp Val Thr Ser
            355                 360                 365

Gly Ile Phe Lys Asp Ile Pro Arg Asn Glu Leu Val Ser Arg Ile Gln
            370                 375                 380

Pro Asp Glu Ala Val Tyr Val Lys Met Asn Thr Lys Leu Pro Gly Leu
385                 390                 395                 400

Thr Met Lys Thr Ser Val Thr Glu Leu Asp Ser Thr Tyr Lys Arg Arg
            405                 410                 415

Phe Ser Asp Leu Lys Ile Pro Glu Ala Tyr Glu Ala Leu Ile Leu Asp
            420                 425                 430

Ala Ile Asn Gly Asp His Ser Asn Phe Val Arg Asp Glu Leu Asp
            435                 440                 445

Ala Ser Trp Lys Ile Phe Thr Pro Phe Ser His Tyr Leu Asp Glu Asn
    450                 455                 460

Thr Asp Ile Val Pro Ala Lys Tyr Pro Tyr Gly Ser Arg Gly Pro Ala
465                 470                 475                 480

Phe Leu Asp Asp Phe Leu Ala Ser Tyr Gly Tyr Ala Arg Glu Gln His
            485                 490                 495

Gly Met Tyr Gln Trp Pro Thr Thr Lys Val Asn Gly Asn Leu
            500                 505                 510

<210> SEQ ID NO 45
<211> LENGTH: 2781
<212> TYPE: DNA
<213> ORGANISM: Lipomyces starkeyi
<220> FEATURE:
<221> NAME/KEY: Intron
<222> LOCATION: (71)..(122)
<220> FEATURE:
<221> NAME/KEY: Intron
<222> LOCATION: (730)..(779)
<220> FEATURE:
<221> NAME/KEY: Intron
<222> LOCATION: (1096)..(1143)
<220> FEATURE:
<221> NAME/KEY: Intron
<222> LOCATION: (1861)..(1912)
<220> FEATURE:
<221> NAME/KEY: Intron
<222> LOCATION: (2147)..(2201)
<220> FEATURE:
<221> NAME/KEY: 3'UTR
<222> LOCATION: (2754)..(2781)

<400> SEQUENCE: 45
atggctgacc ttgacatcga atatgtgctt tcgcagctat ctcttgacga gaaagtctcg      60
ctgacaggag gttagtatca atctattcgc cattggcact tcattgacgc gtatggtgac     120
aggtcgagac atgtggcaca caactcctat tccccgtctg ggaataccgt cactgcggct     180
ctcagatggt ccgaacgggg tacgtgggac caagttcttt gacagtactc cagcggcctg     240
ccttccgtgt ggaaccggcc tgggtgcaac gtggacgta cagttattga gaaagtgggg     300
caactttctt ggattggagg caaaagccaa aggcgcgcat gtgcttctag cccaacagt      360 taacgtgcag cggagcccac tgggtggacg aggatttgag tcgttttccg aagacccgt      420 actttcagga tttcttgcag cagcatattg taatggcgta caggaccaga acattatacc     480

-continued

```
gtcgataaag cactttgtgt gcaacgatca ggaagacaaa cgcatgtcgg tcaatattac      540
agttggcgat agagctctgc gagagatcta tctcctccct ttcatgcttg ccgttcgcga      600
tgcgagtcct ggttcgttta tgacagcgta caacaaatta aatgggacac actgcagcga      660
gaacaaaaaa cttttgcatg atgtccttcg tagcgaatgg ggctgaaatg gactgcttgt      720
aagcgattgg taaactctgg ctcatattca ccattgcgtg cagaagctaa atttactagg      780
tatgggactt acagcaccac tgaggcgatt gaagcaggac tggatttgga gatgcctggt      840
ccaacgagat ggagaacaat cactctgtca catgcagtga gctcgggaa ggtggaagag       900 aagctacttg acgtacgggt ccggaatgtt ttgagtgccg tcaaggaggc tcacaaaagt      960
ggcattcccg caggatgcag ggagacgacg cgaaacacac cagaagatag aattttactc     1020
cggcgcgctg ccgcaaattc cattgtattg ctcaagaacg aagaccatgt actgcctttg     1080
aagagcgatc gaacggtaca ttgacaacta ttgagcccta aatgcaaaat actgactcta     1140
cagactgcga tcataggttc aaacgccaaa attgctacat tctgcggagg aggcagcgca     1200
tcacttaatc catactactc cacgtccgtc cttgattccg tacgtgccaa atgcggagat     1260
gtaagcttcg ctgagggtcc ttttttctcat ctcgaatttt ccttgctcga tggattgatc    1320
gtagatacaa atggccgtcc tggcttcact tttcggtcat atctcgaacc gccagaagtc    1380
aaagggcgag aatgtataga caagatgttt gtgaagacca ctaagttctt tttgaccgac    1440
tattctcctc cgaacttgaa atcttcactc ttttggactg aaatggaggc atatttgacc    1500
ccggatagga gcggtttgtg ggactttggg ctctgtaccc aaggtactgc aaggctttat    1560
attgatggtc ctgaagttgt tgataacgca acccggcaag agccgggcaa tgcattccta    1620
ggagcaggaa cgaaggaagt tataggaaca atcgatcttg tagcggggag aaagtacaag    1680
cttcttatca gtttcggtag cgcaccaact tcaaagctcg tcaagaaggg cgtagttaca    1740
ttccgcaaag gtggtgtgcg tctccgtggt ggaccaaaaa ttgatgtgga gaaagcaatt    1800
gaagaggcaa ctgaggtagc aaagaagact cagcaagttg tgattgttgt cggtctgaat    1860
gtaaggcaca tagtctgtat tattttttacc aagggcttac tcataatttc aggggggactg  1920 ggaggtagag ggtcaagatc gctcagatat gagtcttccg cctcacacag acgaacttat    1980
aactagggtt ttgggagtca ggcccgacgc agtagttgtc aatcaaagtg gtgcgcctgt    2040
tgcaatgcca tggcagatc aagcgaaggc tatagtgcaa atgtggtacg gaggcaacga     2100
gggaggaaac ggtctcgcag acgtgctctt cggagatgtt aatccggtca gtgctattgc    2160
atgtatgttt cgtttattgc acatgttgat tgatctcaca gggcggcaag ctgccattga    2220
cattcccgaa gcgtatttct gattgtccgg catatctcca ttccaagtcc aacaagggtc    2280
gcatgatata tggcgaaggc atattcgtgg gctatcgcta ctacgagaca attgatttgt    2340
ccgtgcggtt cccattcggg catggacttt catacacaac cttctcgcaa agcgcgcttc    2400
gggttcaaac tgacgacagg aagctcatcg tgcaacttaa gctcgagaat tctgggact    2460 ttgacggctc ggaggtgatc caggtttata tttctcaccc caaatcgtcc gtgtcacgtc    2520
ctgtgaaaga actgaaaggt ttctcaaaag tgatgcttaa atcaaaagag agcattgatg    2580
taaaaattga tattcccatt aagtatgcaa cttccttctg ggacgagagt gagaacgcgt    2640
ggacctcgga agcgggcgtt tacgaagtgt tcgtcggaaa tagtagtcag tcagagcgtt    2700
ttttatgcag cacatttgag acgagcaaga catttcttg gaatgggctt tgagatatgt     2760
tgtaatagag gaaatcactt a                                              2781
```

<210> SEQ ID NO 46
<211> LENGTH: 831
<212> TYPE: PRT
<213> ORGANISM: Lipomyces starkeyi

<400> SEQUENCE: 46

```
Met Ala Asp Leu Asp Ile Glu Tyr Val Leu Ser Gln Leu Ser Leu Asp
1               5                   10                  15

Glu Lys Val Ser Leu Thr Gly Gly Arg Asp Met Trp His Thr Thr Pro
            20                  25                  30

Ile Pro Arg Leu Gly Ile Pro Ser Leu Arg Leu Ser Asp Gly Pro Asn
        35                  40                  45

Gly Val Arg Gly Thr Lys Phe Phe Asp Ser Thr Pro Ala Ala Cys Leu
    50                  55                  60

Pro Cys Gly Thr Gly Leu Gly Ala Thr Trp Asp Val Gln Leu Leu Arg
65                  70                  75                  80

Glu Val Gly Asn Phe Leu Gly Leu Glu Ala Lys Ala Lys Gly Ala His
                85                  90                  95

Val Leu Leu Gly Pro Thr Val Asn Val Gln Arg Ser Pro Leu Gly Gly
            100                 105                 110

Arg Gly Phe Glu Ser Phe Ser Glu Asp Pro Val Leu Ser Gly Phe Leu
        115                 120                 125

Ala Ala Ala Tyr Cys Asn Gly Val Gln Asp Gln Asn Ile Ile Pro Ser
    130                 135                 140

Ile Lys His Phe Val Cys Asn Asp Gln Glu Asp Lys Arg Met Ser Val
145                 150                 155                 160

Asn Ile Thr Val Gly Asp Arg Ala Leu Arg Glu Ile Tyr Leu Leu Pro
                165                 170                 175

Phe Met Leu Ala Val Arg Asp Ala Ser Pro Gly Ser Phe Met Thr Ala
            180                 185                 190

Tyr Asn Lys Leu Asn Gly Thr His Cys Ser Glu Asn Lys Lys Leu Leu
        195                 200                 205

His Asp Val Leu Arg Ser Glu Trp Gly Trp Asn Gly Leu Leu Val Ser
    210                 215                 220

Asp Trp Tyr Gly Thr Tyr Ser Thr Thr Glu Ala Ile Glu Ala Gly Leu
225                 230                 235                 240

Asp Leu Glu Met Pro Gly Pro Thr Arg Trp Arg Thr Ile Thr Leu Ser
                245                 250                 255

His Ala Val Ser Ser Gly Lys Val Glu Glu Lys Leu Leu Asp Val Arg
            260                 265                 270

Val Arg Asn Val Leu Ser Ala Val Lys Glu Ala His Lys Ser Gly Ile
        275                 280                 285

Pro Ala Gly Cys Arg Glu Thr Thr Arg Asn Thr Pro Glu Asp Arg Ile
    290                 295                 300

Leu Leu Arg Arg Ala Ala Ala Asn Ser Ile Val Leu Leu Lys Asn Glu
305                 310                 315                 320

Asp His Val Leu Pro Leu Lys Ser Asp Arg Thr Thr Ala Ile Ile Gly
                325                 330                 335

Ser Asn Ala Lys Ile Ala Thr Phe Cys Gly Gly Gly Ser Ala Ser Leu
            340                 345                 350

Asn Pro Tyr Tyr Ser Thr Ser Val Leu Asp Ser Val Arg Ala Lys Cys
        355                 360                 365

Gly Asp Val Ser Phe Ala Glu Gly Pro Phe Ser His Leu Glu Phe Ser
    370                 375                 380
```

```
Leu Leu Asp Gly Leu Ile Val Asp Thr Asn Gly Arg Pro Gly Phe Thr
385                 390                 395                 400

Phe Arg Ser Tyr Leu Glu Pro Pro Glu Val Lys Gly Arg Glu Cys Ile
            405                 410                 415

Asp Lys Met Phe Val Lys Thr Thr Lys Phe Phe Leu Thr Asp Tyr Ser
        420                 425                 430

Pro Pro Asn Leu Lys Ser Ser Leu Phe Trp Thr Glu Met Glu Ala Tyr
    435                 440                 445

Leu Thr Pro Asp Arg Ser Gly Leu Trp Asp Phe Gly Leu Cys Thr Gln
    450                 455                 460

Gly Thr Ala Arg Leu Tyr Ile Asp Gly Ala Glu Val Val Asp Asn Ala
465                 470                 475                 480

Thr Arg Gln Glu Pro Gly Asn Ala Phe Leu Gly Ala Gly Thr Lys Glu
            485                 490                 495

Val Ile Gly Thr Ile Asp Leu Val Ala Gly Arg Lys Tyr Lys Leu Leu
        500                 505                 510

Ile Ser Phe Gly Ser Ala Pro Thr Ser Lys Leu Val Lys Lys Gly Val
    515                 520                 525

Val Thr Phe Arg Lys Gly Gly Val Arg Leu Arg Gly Gly Pro Lys Ile
    530                 535                 540

Asp Val Glu Lys Ala Ile Glu Ala Thr Glu Val Ala Lys Lys Thr
545                 550                 555                 560

Gln Gln Val Val Ile Val Val Gly Leu Asn Gly Asp Trp Glu Val Glu
            565                 570                 575

Gly Gln Asp Arg Ser Asp Met Ser Leu Pro Pro His Thr Asp Glu Leu
        580                 585                 590

Ile Thr Arg Val Leu Gly Val Arg Pro Asp Ala Val Val Val Asn Gln
    595                 600                 605

Ser Gly Ala Pro Val Ala Met Pro Trp Ala Asp Gln Ala Lys Ala Ile
    610                 615                 620

Val Gln Met Trp Tyr Gly Gly Asn Glu Gly Gly Asn Gly Leu Ala Asp
625                 630                 635                 640

Val Leu Phe Gly Asp Val Asn Pro Gly Gly Lys Leu Pro Leu Thr Phe
            645                 650                 655

Pro Lys Arg Ile Ser Asp Cys Pro Ala Tyr Leu His Ser Lys Ser Asn
        660                 665                 670

Lys Gly Arg Met Ile Tyr Gly Glu Gly Ile Phe Val Gly Tyr Arg Tyr
    675                 680                 685

Tyr Glu Thr Ile Asp Leu Ser Val Arg Phe Pro Phe Gly His Gly Leu
    690                 695                 700

Ser Tyr Thr Thr Phe Ser Gln Ser Ala Leu Arg Val Gln Thr Asp Asp
705                 710                 715                 720

Arg Lys Leu Ile Val Gln Leu Lys Leu Glu Asn Ser Gly Asp Phe Asp
            725                 730                 735

Gly Ser Glu Val Ile Gln Val Tyr Ile Ser His Pro Lys Ser Ser Val
        740                 745                 750

Ser Arg Pro Val Lys Glu Leu Lys Gly Phe Ser Lys Val Met Leu Lys
    755                 760                 765

Ser Lys Glu Ser Ile Asp Val Lys Ile Asp Ile Pro Ile Lys Tyr Ala
    770                 775                 780

Thr Ser Phe Trp Asp Glu Ser Glu Asn Ala Trp Thr Ser Glu Ala Gly
785                 790                 795                 800

Val Tyr Glu Val Phe Val Gly Asn Ser Ser Gln Ser Glu Arg Phe Leu
```

805                 810                 815
Cys Ser Thr Phe Glu Thr Ser Lys Thr Phe Ser Trp Asn Gly Leu
                820                 825                 830

<210> SEQ ID NO 47
<211> LENGTH: 2237
<212> TYPE: DNA
<213> ORGANISM: Lipomyces starkeyi
<220> FEATURE:
<221> NAME/KEY: 5'UTR
<222> LOCATION: (1)..(253)
<220> FEATURE:
<221> NAME/KEY: Intron
<222> LOCATION: (320)..(377)
<220> FEATURE:
<221> NAME/KEY: Intron
<222> LOCATION: (484)..(540)
<220> FEATURE:
<221> NAME/KEY: Intron
<222> LOCATION: (903)..(956)
<220> FEATURE:
<221> NAME/KEY: Intron
<222> LOCATION: (1103)..(1153)
<220> FEATURE:
<221> NAME/KEY: 3'UTR
<222> LOCATION: (2064)..(2237)

<400> SEQUENCE: 47

| | | | | |
|---|---|---|---|---|
| tttgaccccg | catccttaga | atttattgct | ttttcttcac | ttagtaaaag atatgggccc | 60 |
| gtgacgagcg | acatgctgtc | acttctaact | tatatcttct | tggccatagg ccttgttagt | 120 |
| ctaccagtgc | cccacaatat | ctgagcacca | tataagttcc | ccatctcctc tctttagaat | 180 |
| cccacattca | ggcaaagttc | tttatttaag | acatataact | gaatagaaat ttaccgctta | 240 |
| attcattgtc | atcatgggaa | tactgaagac | gtcaaacgaa | gggagcgcgg aggcagctct | 300 |
| tggaaaggaa | atcctagaag | tgggtacatc | ttcaaccatc | tctttcacga ggatccaact | 360 |
| aacagagtat | actcaaggtg | ttgccgatac | atcatcagcc | ttggtacaag acaaagcatc | 420 |
| tcgtgcatct | caacttgatc | ctcctggtcc | ctctattctc | ctccgctacg attggctttg | 480 |
| atggtaggca | aatcagtttt | tactcttcaa | aaatattctc | atagcataac cataatccag | 540 |
| gcggaatgat | gaacggtctt | cagaccctca | ctcagtggag | aacatatttc tctcatccca | 600 |
| atagctccac | tctgggagcg | atcaatgccc | tttatcccat | cgggaagctg cttggtcttt | 660 |
| ttccgtccac | ctggctctct | gatcggttcg | gtcgaaagag | gcccatgctt gttggcttta | 720 |
| ttttattgtt | catcgggacg | gttcttcaag | gtgcttctca | ggacatagct atgttgatcg | 780 |
| tctctcgttt | tgtgatgggg | ttcggaacgg | ctttccttgc | tcagccgtca cctatcttga | 840 |
| tcacagaact | tgcttacccg | acacagcgtg | gtaaaatcac | aagcttatat aacaccttct | 900 |
| acgtatgcac | atattgcatt | gcttcaatcg | tttatatatg | cttacctatt tgatagtatg | 960 |
| taggtgctgt | tctagcggct | tggtcgacct | atggcacctt | ccggttagcc tctaactgga | 1020 |
| gctggaggat | cccttcaatc | atgcagggcg | catttcctct | catacaattt tgcttttttct | 1080 |
| tcttaattcc | agaatctcca | aggtattcac | tttgtgtttt | attctcctaa ttcactactg | 1140 |
| accgagcaac | cagatggctt | gtggcccagg | gtcgagttga | agacgcacgg aaagtcctcg | 1200 |
| tcaaatatca | cgctggaggt | gatgaagcct | caccactagt | cgactacgaa atccgtgaaa | 1260 |
| tggaagagag | tattcagctc | gagaagctta | ttaactctca | atcctcctac atagacctaa | 1320 |
| ttcgcactcc | cgcgaatcgc | aagcgtacat | tcatcgccgc | catcttaggc ttcttcaccc | 1380 |
| aatggagcgg | caactcagtt | atctcctact | atctgactct | cgtacttgat acaattggta | 1440 |

-continued

```
tcacttccgt tccctcgcaa gcactcatca acggcctcct tcagaccttc aactggttcg    1500
cagctgttct agcgggtgca ttgatggtgg accgtatcgg gcgccgcaaa ctcttcctca    1560
tctccactgg cggaatgctt gcgtcatata ttatctggac cgtcttaagc agtgttttca    1620
caacgacgct aaatcagaaa gtaggtaata ccgtagtggc ctttatcttt atctattact    1680
tcttctacga cattgccttc acacctctga tgcccgctta tgttgttgaa atataccaat    1740
acacactgcg cggtcgtgga gtcactgcag catatacggt cgactattgt ggacttatcc    1800
ttggtaactt tgtcaatccg gtggcgatga aaaagattgg ctggcactac tatattttat    1860
tttgtgttct ccttacattc tcgtttactc ttatctggtt cttctttccc gaaaccaaag    1920
gacacaccct cgaggagata gcagaagtct tgatgggcc ccgaggaaat ggtcaggacg     1980
ttgaagttaa cgacgatcac gagaaaatcg agagcaacaa aaccagtcat atcgaggtcc    2040
ctcgtatggc agaggtcgca taaggttgga agtaatctgc aggaaagggt tcaaaaggtc    2100
actgttcaag attcaaatac taccatatgt gttgtttagc agttagttgt agcagtagct    2160
ctgtggcatc gtcgagatgt tggcgttcat catcatctcg ccagggtatt tgagccacat    2220
gatatggaat tttattc                                                   2237
```

<210> SEQ ID NO 48
<211> LENGTH: 529
<212> TYPE: PRT
<213> ORGANISM: Lipomyces starkeyi

<400> SEQUENCE: 48

```
Met Gly Ile Ser Lys Thr Ser Asn Glu Gly Ser Ala Glu Ala Ala Leu
1               5                   10                  15

Gly Lys Glu Ile Leu Glu Val Leu Pro Ile His His Gln Pro Trp Tyr
            20                  25                  30

Lys Thr Lys His Leu Val His Leu Asn Leu Ile Leu Ser Val Pro Leu
        35                  40                  45

Phe Ser Ser Ala Thr Ile Gly Phe Asp Gly Gly Met Met Asn Gly Leu
    50                  55                  60

Gln Thr Leu Thr Gln Trp Arg Thr Tyr Phe Ser His Pro Asn Ser Ser
65                  70                  75                  80

Thr Ser Gly Ala Ile Asn Ala Leu Tyr Pro Ile Gly Lys Ser Leu Gly
                85                  90                  95

Leu Phe Pro Ser Thr Trp Leu Ser Asp Arg Phe Gly Arg Lys Arg Pro
            100                 105                 110

Met Leu Val Gly Phe Ile Leu Leu Phe Ile Gly Thr Val Leu Gln Gly
        115                 120                 125

Ala Ser Gln Asp Ile Ala Met Leu Ile Val Ser Arg Phe Val Met Gly
    130                 135                 140

Phe Gly Thr Ala Phe Leu Ala Gln Pro Ser Pro Ile Leu Ile Thr Glu
145                 150                 155                 160

Leu Ala Tyr Pro Thr Gln Arg Gly Lys Ile Thr Ser Leu Tyr Asn Thr
                165                 170                 175

Phe Tyr Tyr Val Gly Ala Val Leu Ala Ala Trp Ser Thr Tyr Gly Thr
            180                 185                 190

Phe Arg Leu Ala Ser Asn Trp Ser Trp Arg Ile Pro Ser Ile Met Gln
        195                 200                 205

Gly Ala Phe Pro Leu Ile Gln Phe Cys Phe Phe Leu Ile Pro Glu
    210                 215                 220

Ser Pro Arg Trp Leu Val Ala Gln Gly Arg Val Glu Asp Ala Arg Lys
```

```
                225                 230                 235                 240
        Val Leu Val Lys Tyr His Ala Gly Gly Asp Glu Ala Ser Pro Leu Val
                        245                 250                 255

Asp Tyr Glu Ile Arg Glu Met Glu Glu Ser Ile Gln Leu Glu Lys Leu
                        260                 265                 270

Ile Asn Ser Gln Ser Ser Tyr Ile Asp Leu Ile Arg Thr Pro Ala Asn
                        275                 280                 285

Arg Lys Arg Thr Phe Ile Ala Ala Ile Leu Gly Phe Phe Thr Gln Trp
                        290                 295                 300

Ser Gly Asn Ser Val Ile Ser Tyr Tyr Ser Thr Leu Val Leu Asp Thr
        305                 310                 315                 320

Ile Gly Ile Thr Ser Val Ser Ser Gln Ala Leu Ile Asn Gly Leu Leu
                        325                 330                 335

Gln Thr Phe Asn Trp Phe Ala Ala Val Leu Ala Gly Ala Leu Met Val
                        340                 345                 350

Asp Arg Ile Gly Arg Arg Lys Leu Phe Leu Ile Ser Thr Gly Gly Met
                        355                 360                 365

Leu Ala Ser Tyr Ile Ile Trp Thr Val Leu Ser Ser Val Phe Thr Thr
                        370                 375                 380

Thr Leu Asn Gln Lys Val Gly Asn Thr Val Val Ala Phe Ile Phe Ile
        385                 390                 395                 400

Tyr Tyr Phe Phe Tyr Asp Ile Ala Phe Thr Pro Ser Met Pro Ala Tyr
                        405                 410                 415

Val Val Glu Ile Tyr Gln Tyr Thr Ser Arg Gly Arg Gly Val Thr Ala
                        420                 425                 430

Ala Tyr Thr Val Asp Tyr Cys Gly Leu Ile Leu Gly Asn Phe Val Asn
                        435                 440                 445

Pro Val Ala Met Lys Lys Ile Gly Trp His Tyr Tyr Ile Leu Phe Cys
                        450                 455                 460

Val Leu Leu Thr Phe Ser Phe Thr Leu Ile Trp Phe Phe Pro Glu
        465                 470                 475                 480

Thr Lys Gly His Thr Leu Glu Glu Ile Ala Glu Val Phe Asp Gly Pro
                        485                 490                 495

Arg Gly Asn Gly Gln Asp Val Glu Val Asn Asp Asp His Glu Lys Ile
                        500                 505                 510

Glu Ser Asn Lys Thr Ser His Ile Glu Val Pro Arg Met Ala Glu Val
                        515                 520                 525

Ala

<210> SEQ ID NO 49
<211> LENGTH: 2136
<212> TYPE: DNA
<213> ORGANISM: Lipomyces starkeyi
<220> FEATURE:
<221> NAME/KEY: 5'UTR
<222> LOCATION: (1)..(40)
<220> FEATURE:
<221> NAME/KEY: Intron
<222> LOCATION: (119)..(171)
<220> FEATURE:
<221> NAME/KEY: Intron
<222> LOCATION: (461)..(509)
<220> FEATURE:
<221> NAME/KEY: Intron
<222> LOCATION: (1015)..(1073)
<220> FEATURE:
<221> NAME/KEY: 3'UTR
<222> LOCATION: (1736)..(2136)
```

<400> SEQUENCE: 49

```
tggcagcatt gcaatttcgc tactccacac gcgactaaag atggctaccg gcattctacg      60
cgtcgcagat ggagccaaaa tcgttgatgc caatggcgat caagtggtcc ttcgcggggt     120
cagtcactga cggtgcagtt tacaactgtg tttactaaca atgtcactgt agacagcttt     180
aggtggccat atgatgatgg agaacttcat gaatggcttt ccgggcagag aaatgcaggt     240
gcgcaaggcg atcggaaagg ttcttggccc cgaaaagagt gacttctttt ttgacaagtt     300
cctcgagtac ttctttatgg acgaggatgc tgcattcttg aaatctcttg gcctaaactc     360
tctccgcgtg cctttttaact accaccacct cgaagacgac atgaatcccg cgtaatcgt     420
tcaggacggc ttcaaacata ttgaccgcgt tgttgaaata gtgagtctct tagctgccag     480
tggtattgga ttagcaactg ataatttagt gcgcccgcca tggcatctac accattctgg     540
accttcattc ggcgccgggc ggacagtctc aagattggca ctgcgataat ccgactggat     600
atgcggcgtt ctggaccag aaatccttc aagatcgagt cgttaaccta tggaaaacca     660
tcgcagccag gtacaggggg aatccctgga ttgcaggata caacccctg aacgagcctg     720
ccgacgagga gtggacccgc cttttggcgt tttacgaccg catcgagaag actattcgcg     780
aggttgaccc tgaccatatt ctctggctcg atgggaatac attcgcaatg gatttctctg     840
gattcacgaa agttttttcca aacactgtct atgccataca cgactactgc ggatatggat     900
ttccaaatcg aattggaagg taccagtgca acccgagca ggacaaatac attcgtgcga     960
tgtacgacag aaaggtcgag tttatgaaga cgcacaatgt gccaatctgg aatggtagtc    1020
aagttttaca tgctacgatt gcgagcccgg cacggtcact aacatatgaa caggtgagtt    1080
tggaccgatc tacgagcgcg aggaatacaa cccggattac aaagtgcaga acgaggagcg    1140
ttacaacatg ctggagaagc agctttcaat ctattccgct gagggcatcc attggtccat    1200
ctgggcgtac aaggatatca atgttatggg aatgcgctac gttgactctg attcggcctg    1260
gatcaaactc cttggtcctt tcatccacaa gaaacgcgaa cttgcggtcg attcatgggc    1320
ctacgacgac gcgcatcttc aggaaggatt gtttggtccc ttgcacaggt ggattgaaga    1380
gaacgtcccg gagaagtaca gcaaaaagta tccgtggcag tggcgcatgc atatgcacgt    1440
cttcagaggg atccgcggca ttactctggc tgagtatctc atcccagagt ttgccgacta    1500
ctttagcggc aagacgtttg aggagctaga tgagctcgca agcagctggt cttttgcgaa    1560
aactgttggc cgggatgaat taaatcgact gttgaaactt catgcgacga tgcagcctga    1620
cgatcctcac cttgtcaacg tcatcccgcc tgcaaacaag cggcagacta acgggtccag    1680
aggcgtattt gagctgtcgc ctttggagct gtcaatgcag aaggcacgtg attaagttac    1740
gatgaagtgc tcagcataat agccaatgtt attgcgggaa tagtaaccca attgtatttt    1800
gtgtttatga acagcaaata atattcatag taaccttgac aagatcaata actgcagcta    1860
atagcttcaa tgaacttgca agacaagtt atccagaact attcgttgac aaacttcgcg    1920
ctttgaatgg cctgtattgt cgtgctcgtt actgcatgtg gctgaggacg cacctaccgc    1980
acttaacgct gaattgtatc cttgaatgct tttcatagca atgtggaata tgaaatgtga    2040
aataagggac tgcgggaata ttaagcatac taatatgtct atacggccgt gtccaagaac    2100
acaagaagaa tttagaaaac aataaagact attttg                              2136
```

<210> SEQ ID NO 50
<211> LENGTH: 510
<212> TYPE: PRT
<213> ORGANISM: Lipomyces starkeyi

<400> SEQUENCE: 50

```
Met Ala Thr Gly Ile Leu Arg Val Ala Asp Gly Ala Lys Ile Val Asp
1               5                   10                  15

Ala Asn Gly Asp Gln Val Val Leu Arg Gly Thr Ala Leu Gly Gly His
            20                  25                  30

Met Met Met Glu Asn Phe Met Asn Gly Phe Pro Gly Arg Glu Met Gln
        35                  40                  45

Val Arg Lys Ala Ile Gly Lys Val Leu Gly Pro Glu Lys Ser Asp Phe
    50                  55                  60

Phe Phe Asp Lys Phe Leu Glu Tyr Phe Phe Met Asp Glu Asp Ala Ala
65                  70                  75                  80

Phe Leu Lys Ser Leu Gly Leu Asn Ser Leu Arg Val Pro Phe Asn Tyr
                85                  90                  95

His His Leu Glu Asp Asp Met Asn Pro Gly Val Ile Val Gln Asp Gly
            100                 105                 110

Phe Lys His Ile Asp Arg Val Val Glu Ile Cys Ala Arg His Gly Ile
        115                 120                 125

Tyr Thr Ile Ser Asp Leu His Ser Ala Pro Gly Gly Gln Ser Gln Asp
    130                 135                 140

Trp His Cys Asp Asn Pro Thr Gly Tyr Ala Ala Phe Trp Asp Gln Lys
145                 150                 155                 160

Ser Phe Gln Asp Arg Val Val Asn Leu Trp Lys Thr Ile Ala Ala Arg
                165                 170                 175

Tyr Arg Gly Asn Pro Trp Ile Ala Gly Tyr Asn Pro Ser Asn Glu Pro
            180                 185                 190

Ala Asp Glu Glu Trp Thr Arg Leu Leu Ala Phe Tyr Asp Arg Ile Glu
        195                 200                 205

Lys Thr Ile Arg Glu Val Asp Pro Asp His Ile Leu Trp Leu Asp Gly
    210                 215                 220

Asn Thr Phe Ala Met Asp Phe Ser Gly Phe Thr Lys Val Phe Pro Asn
225                 230                 235                 240

Thr Val Tyr Ala Ile His Asp Tyr Cys Gly Tyr Gly Phe Pro Asn Arg
                245                 250                 255

Ile Gly Arg Tyr Gln Cys Lys Pro Glu Gln Asp Lys Tyr Ile Arg Ala
            260                 265                 270

Met Tyr Asp Arg Lys Val Glu Phe Met Lys Thr His Asn Val Pro Ile
        275                 280                 285

Trp Asn Gly Glu Phe Gly Pro Ile Tyr Glu Arg Glu Tyr Asn Pro
290                 295                 300

Asp Tyr Lys Val Gln Asn Glu Glu Arg Tyr Asn Met Ser Glu Lys Gln
305                 310                 315                 320

Leu Ser Ile Tyr Ser Ala Glu Gly Ile His Trp Ser Ile Trp Ala Tyr
                325                 330                 335

Lys Asp Ile Asn Val Met Gly Met Arg Tyr Val Asp Ser Asp Ser Ala
            340                 345                 350

Trp Ile Lys Leu Leu Gly Pro Phe Ile His Lys Arg Glu Leu Ala
        355                 360                 365

Val Asp Ser Trp Ala Tyr Asp Asp Ala His Leu Gln Glu Gly Leu Phe
    370                 375                 380

Gly Pro Leu His Arg Trp Ile Glu Glu Asn Val Pro Glu Lys Tyr Ser
385                 390                 395                 400

Lys Lys Tyr Pro Trp Gln Trp Arg Met His Met His Val Phe Arg Gly
```

| | 405 | | | | 410 | | | | | 415 | |
|---|---|---|---|---|---|---|---|---|---|---|---|
Ile Arg Gly Ile Thr Ser Ala Glu Tyr Leu Ile Pro Glu Phe Ala Asp
            420                     425                     430

Tyr Phe Ser Gly Lys Thr Phe Glu Glu Leu Asp Glu Leu Ala Ser Ser
            435                     440                     445

Trp Ser Phe Ala Lys Thr Val Gly Arg Asp Glu Leu Asn Arg Ser Leu
    450                     455                     460

Lys Leu His Ala Thr Met Gln Pro Asp Pro His Leu Val Asn Val
465                     470                     475                     480

Ile Pro Pro Ala Asn Lys Arg Gln Thr Asn Gly Ser Arg Gly Val Phe
                485                     490                     495

Glu Ser Ser Pro Leu Glu Ser Ser Met Gln Lys Ala Arg Asp
        500                     505                     510

<210> SEQ ID NO 51
<211> LENGTH: 2288
<212> TYPE: DNA
<213> ORGANISM: Lipomyces starkeyi
<220> FEATURE:
<221> NAME/KEY: Intron
<222> LOCATION: (285)..(348)
<220> FEATURE:
<221> NAME/KEY: Intron
<222> LOCATION: (449)..(503)

<400> SEQUENCE: 51

```
atggcgttca aagtggagat tgactcgttc ggaaatttcc gcgataacga gaaccgagtc      60
attactctac gcggtatcaa tctcgccgcc gactctaagc tgccggctag tccgccaata     120
ccatcgcatg tttcggagaa cttttcgat ggcgataatg tatcgtttgt tggacgtccg     180
tttccttga acgagggtga tgtacatctt gcaaggataa agagctgggg gtttaacgtt     240
attcgctatg tttatacttg ggaggcacta gagcatgcgg gaccgtaagc tgtgttgtgg     300
acttctcgaa cttaggacgt atattaactc ctcgttctca ttatttagtg gaaaatatga     360
tgatgtgttt attcagaaca caattgcatt tttgagaaaa ataaaggact atggatttta     420
cgtgtttatg gatccccatc aggacgtggt atgctttgcc tgttacctaa acagtcatag     480
atagagacgc taactcggtt cagtggagcc gtttttctgg agggtccggt gcgcctatgt     540
ggactttgta tgctgcggga ttggatccaa aagcattcgc aaagaccgag gcggctgtcg     600
tccaaaatac ttggccagat cccgcaactt ttccacgaat gacctgggca actaattacg     660
acagacttgc gtgccttacg attttacaa tgttttgggc cggaaaggat tttgctccga     720
aatgtataat tgacggacaa atattcagg attatttgca gggtcacttc attgacgcta     780
ttaagcactt tgcacaacag gtgtatgaag atggtgattt gggcgacgac ttcattcttg     840
ggtgggagtc aatcaacgag cctttccgtg gttttctcgg caacagaaat ctcacagttt     900
atcccgagta ccagaaaactt cagaagtaca cctcccctac gccattccaa gccattttgt     960
taggcgccgg tcgaacgctt gatatcgcag tttacgattt cgggttactt ggagcttata    1020
aagttggcac tcaggtcgtt aatgctgacg atattcagc atggcttccc aaagattatg    1080
acgattcacg gtacgatgg aagcgcaatc ctgagtggaa gcttggcgag tgcgtctggg    1140
cgcagcacgg cgtgtgggat ccggagacgg ataatatctt acgtcctgat tactttctag    1200
atgctccaga cggcacgcga cttgacggcg aatcgtgggc agagacgtac ttcattgacc    1260
actggaataa atttgccgac actatccgat cgatccgttc ggagacaatg ttgttttgcc    1320
agactccggt tttggctgtg ccgccgaatt ttgtggaact tggtgccttg agatctcgca    1380
```

-continued

```
tggtgtttac gcctcatttt tacgacgggc tgacgcttat ccgcaagcac tggagtagat    1440
tctggaacgt tgatgtcatc ggcgtgttga gaggtaaata ctggagcccc gtgtttgcgc    1500
tcagatttgg cgagacctct atcaggaact gtcttcgtga ccagttgaaa actttgaaat    1560 atgaagggt cgaaagtttc ggtattggtg tcccctgcct gatgagcgag atcggcattc     1620
cttacgacat gaatgaaaag acagcctatg tcgacggtga ttacacggcc caaattcgag    1680
cactagatgc aaatatatat gctttggaag gcgcgaaact gcatcatact tactgggtgt    1740
acgcctcctg caactctcac aaatggggcg accattggaa cggtgaggat ctcagcctct    1800
ggagtccatc tgatgttaag cacaggatca gtggctcaca atattcgtac tcgctcgccc    1860
cgtccgattc tagtttaatg gcgggaaagc agtattcttt tacagacgaa tcgcagatca    1920
cagatacagt gggatcgcga gcgatagagg catttagccg tccgttcccg cttgttacgg    1980
tcggtgttcc tcaggaatac ggatttgata ttaataatgc catgttctct atggaactct    2040
atgcggatga ggaagtcgcg tccaaacttg taccctcgga gattcatgtt ccggattttc    2100
attacccgaa tggagaccttt caagtcgaag tctcgtcggg acgttgggag ctcgatagac    2160
ccaaccaaat tctccgatgg tggcatgatg gtggtaagca gacaatcaaa ataattggga    2220
ttagaggagg tcagacaatg aagccgggga agaattctta tgctgaattc tgtgccgtct    2280
gttcgtag                                                              2288
```

<210> SEQ ID NO 52
<211> LENGTH: 722
<212> TYPE: PRT
<213> ORGANISM: Lipomyces starkeyi

<400> SEQUENCE: 52

```
Met Ala Phe Lys Val Glu Ile Asp Ser Phe Gly Asn Phe Arg Asp Asn
1               5                   10                  15

Glu Asn Arg Val Ile Thr Leu Arg Gly Ile Asn Leu Ala Ala Asp Ser
            20                  25                  30

Lys Leu Pro Ala Ser Pro Pro Ile Pro Ser His Val Ser Glu Asn Phe
        35                  40                  45

Phe Asp Gly Asp Asn Val Ser Phe Val Gly Arg Pro Phe Pro Leu Asn
    50                  55                  60

Glu Gly Asp Val His Leu Ala Arg Ile Lys Ser Trp Gly Phe Asn Val
65                  70                  75                  80

Ile Arg Tyr Val Tyr Thr Trp Glu Ala Leu Glu His Ala Gly Pro Gly
                85                  90                  95

Lys Tyr Asp Asp Val Phe Ile Gln Asn Thr Ile Ala Phe Leu Arg Lys
            100                 105                 110

Ile Lys Asp Tyr Gly Phe Tyr Val Phe Met Asp Pro His Gln Asp Val
        115                 120                 125

Trp Ser Arg Phe Ser Gly Gly Ser Gly Ala Pro Met Trp Thr Leu Tyr
    130                 135                 140

Ala Ala Gly Leu Asp Pro Lys Ala Phe Ala Lys Thr Glu Ala Ala Val
145                 150                 155                 160

Val Gln Asn Thr Trp Pro Asp Pro Ala Thr Phe Pro Arg Met Thr Trp
                165                 170                 175

Ala Thr Asn Tyr Asp Arg Leu Ala Cys Leu Thr Ile Phe Thr Met Phe
            180                 185                 190

Trp Ala Gly Lys Asp Phe Ala Pro Lys Cys Ile Ile Asp Gly Gln Asn
        195                 200                 205
```

```
Ile Gln Asp Tyr Leu Gln Gly His Phe Ile Asp Ala Ile Lys His Phe
    210                 215                 220

Ala Gln Gln Val Tyr Glu Asp Gly Asp Leu Gly Asp Asp Phe Ile Leu
225                 230                 235                 240

Gly Trp Glu Ser Ile Asn Glu Pro Phe Arg Gly Phe Leu Gly Asn Arg
                245                 250                 255

Asn Leu Thr Val Tyr Pro Glu Tyr Gln Lys Leu Gln Lys Tyr Thr Ser
            260                 265                 270

Pro Thr Pro Phe Gln Ala Ile Leu Leu Gly Ala Gly Arg Thr Leu Asp
        275                 280                 285

Ile Ala Val Tyr Asp Phe Gly Leu Leu Gly Ala Tyr Lys Val Gly Thr
    290                 295                 300

Gln Val Val Asn Ala Asp Gly Tyr Ser Ala Trp Leu Pro Lys Asp Tyr
305                 310                 315                 320

Asp Asp Ser Arg Tyr Gly Trp Lys Arg Asn Pro Glu Trp Lys Leu Gly
                325                 330                 335

Glu Cys Val Trp Ala Gln His Gly Val Trp Asp Pro Glu Thr Asp Asn
            340                 345                 350

Ile Leu Arg Pro Asp Tyr Phe Leu Asp Ala Pro Asp Gly Thr Arg Leu
        355                 360                 365

Asp Gly Glu Ser Trp Ala Glu Thr Tyr Phe Ile Asp His Trp Asn Lys
    370                 375                 380

Phe Ala Asp Thr Ile Arg Ser Ile Arg Ser Glu Thr Met Leu Phe Cys
385                 390                 395                 400

Gln Thr Pro Val Leu Ala Val Pro Pro Asn Phe Val Glu Leu Gly Ala
                405                 410                 415

Leu Arg Ser Arg Met Val Phe Thr Pro His Phe Tyr Asp Gly Leu Thr
            420                 425                 430

Leu Ile Arg Lys His Trp Ser Arg Phe Trp Asn Val Asp Val Ile Gly
        435                 440                 445

Val Leu Arg Gly Lys Tyr Trp Ser Pro Val Phe Ala Leu Arg Phe Gly
    450                 455                 460

Glu Thr Ser Ile Arg Asn Cys Leu Arg Asp Gln Leu Lys Thr Leu Lys
465                 470                 475                 480

Tyr Glu Gly Val Glu Ser Phe Gly Ile Gly Val Pro Cys Leu Met Ser
                485                 490                 495

Glu Ile Gly Ile Pro Tyr Asp Met Asn Glu Lys Thr Ala Tyr Val Asp
            500                 505                 510

Gly Asp Tyr Thr Ala Gln Ile Arg Ala Leu Asp Ala Asn Ile Tyr Ala
        515                 520                 525

Leu Glu Gly Ala Lys Leu His His Thr Tyr Trp Val Tyr Ala Ser Cys
    530                 535                 540

Asn Ser His Lys Trp Gly Asp His Trp Asn Gly Glu Asp Leu Ser Leu
545                 550                 555                 560

Trp Ser Pro Ser Asp Val Lys His Arg Ile Ser Gly Ser Gln Tyr Ser
                565                 570                 575

Tyr Ser Leu Ala Pro Ser Asp Ser Ser Leu Met Ala Gly Lys Gln Tyr
            580                 585                 590

Ser Phe Thr Asp Glu Ser Gln Ile Thr Asp Thr Val Gly Ser Arg Ala
        595                 600                 605

Ile Glu Ala Phe Ser Arg Pro Phe Pro Leu Val Thr Val Gly Val Pro
    610                 615                 620
```

Gln Glu Tyr Gly Phe Asp Ile Asn Asn Ala Met Phe Ser Met Glu Leu
625                 630                 635                 640

Tyr Ala Asp Glu Glu Val Ala Ser Lys Leu Val Pro Ser Glu Ile His
            645                 650                 655

Val Pro Asp Phe His Tyr Pro Asn Gly Asp Leu Gln Val Glu Val Ser
        660                 665                 670

Ser Gly Arg Trp Glu Leu Asp Arg Pro Asn Gln Ile Leu Arg Trp Trp
    675                 680                 685

His Asp Gly Gly Lys Gln Thr Ile Lys Ile Ile Gly Ile Arg Gly Gly
    690                 695                 700

Gln Thr Met Lys Pro Gly Lys Asn Ser Tyr Ala Glu Phe Cys Ala Val
705                 710                 715                 720

Cys Ser

<210> SEQ ID NO 53
<211> LENGTH: 1263
<212> TYPE: DNA
<213> ORGANISM: Lipomyces starkeyi

<400> SEQUENCE: 53
atgacaacac tactcccatt catgctggtg ctcagcttac tcgtcacctc ggcggcagct      60
catggctata tcacaaactt ctggaatccg acgaagcaga cgtacggtaa gtgcatccgg     120
ccgtatgtgc tctaccatga aagaacccca atcacggacc ggtactcgga cgaaatgacg     180
tgcggccatc tgccaggcgg ggcaacgttc ccgagcagga cgtgcagcgt agcgaaagcg     240
ggtgacaagg tcgcgttgca gtggtccgtc atggatagga gtcatatcgg ccagtgttg      300 gtgtatatcg cgtcggcaga gagcaagggg gaaggcgaag cgtggtggaa gatctactac     360
gaaggatacg acgcagagac ggactattgg gcgacttcaa agctctggga caacggcggc     420
acgctctgga tctcgctgcc agactatctt ccggttggcg agtacatcat ccgcggcgaa     480
atcatcgcca tccataatgc gtcatatatt gatggcgctc aaatctatgt caattgcatt     540
cacatcaaca tcgaggccgc ggcggaatct aacacaatcg acattaacac tattccgaaa     600
gtcgcgtttc ccggctacta cacctatgac acgcccgggtc tgcatctcaa tgtctggtgg     660
ccgcctccta tcggctatcc ggaggtcggt ccgccaatat tcacgccgtc cactgcctca     720
ctagctgcca ctaacaccat cgcgtctttc gctgaccaaa cgggcgactc ctcagacggc     780
aatctcgtcg ttcagccatg cagcacgtca ataactatcg cgtatcaggc gacgagctcg     840
agggtgttct acgagcctgt gacggctaag gcccagctag tttcggttat cccgacgccg     900
tcgtccaagt tgcaatcgcg actcgggact gtcgccgctg tgttccccga cttgacctgc     960
tcatcaacat cgacgccgcc gacagcgaca atgccttctc tcatctccac cacttcgact    1020
gcatcatctg ccagacgtac cgcagtcttt ccagatctca cctgctcatc gtcgtccacg    1080
ttgtctttag ctgcaaccac attcctgact gcagtcacca tagagactgc gtcccagcat    1140
atacgtacac taacagtcac gctcgaccca gtgaccgtcc acgctatcgt caccgtctcc    1200
gtctacaaga ctgagtacgt gaccgacaca gtcactgtcg gggacatgaa tattgcttac    1260
tag                                                                 1263

<210> SEQ ID NO 54
<211> LENGTH: 420
<212> TYPE: PRT
<213> ORGANISM: Lipomyces starkeyi

<400> SEQUENCE: 54

-continued

```
Met Thr Thr Leu Leu Pro Phe Met Leu Val Leu Ser Leu Leu Val Thr
1               5                   10                  15

Ser Ala Ala Ala His Gly Tyr Ile Thr Asn Phe Trp Asn Pro Thr Lys
            20                  25                  30

Gln Thr Tyr Gly Lys Cys Ile Arg Pro Tyr Val Leu Tyr His Glu Lys
        35                  40                  45

Asn Pro Ile Thr Asp Arg Tyr Ser Asp Glu Met Thr Cys Gly His Leu
    50                  55                  60

Pro Gly Gly Ala Thr Phe Pro Ser Arg Thr Cys Ser Val Ala Lys Ala
65                  70                  75                  80

Gly Asp Lys Val Ala Leu Gln Trp Ser Val Met Asp Arg Ser His Ile
                85                  90                  95

Gly Pro Val Leu Val Tyr Ile Ala Ser Ala Glu Ser Lys Gly Glu Gly
            100                 105                 110

Glu Ala Trp Trp Lys Ile Tyr Tyr Glu Gly Tyr Asp Ala Glu Thr Asp
        115                 120                 125

Tyr Trp Ala Thr Ser Lys Leu Trp Asp Asn Gly Gly Thr Leu Trp Ile
    130                 135                 140

Ser Leu Pro Asp Tyr Leu Pro Val Gly Glu Tyr Ile Ile Arg Gly Glu
145                 150                 155                 160

Ile Ile Ala Ile His Asn Ala Ser Tyr Ile Asp Gly Ala Gln Ile Tyr
                165                 170                 175

Val Asn Cys Ile His Ile Asn Ile Glu Ala Ala Ala Glu Ser Asn Thr
            180                 185                 190

Ile Asp Ile Asn Thr Ile Pro Lys Val Ala Phe Pro Gly Tyr Tyr Thr
        195                 200                 205

Tyr Asp Thr Pro Gly Leu His Leu Asn Val Trp Trp Pro Pro Pro Ile
    210                 215                 220

Gly Tyr Pro Glu Val Gly Pro Pro Ile Phe Thr Pro Ser Thr Ala Ser
225                 230                 235                 240

Leu Ala Ala Thr Asn Thr Ile Ala Ser Phe Ala Asp Gln Thr Gly Asp
                245                 250                 255

Ser Ser Asp Gly Asn Leu Val Val Gln Pro Cys Ser Thr Ser Ile Thr
            260                 265                 270

Ile Ala Tyr Gln Ala Thr Ser Ser Arg Val Phe Tyr Glu Pro Val Thr
        275                 280                 285

Ala Lys Ala Gln Leu Val Ser Val Ile Pro Thr Pro Ser Ser Lys Leu
    290                 295                 300

Gln Ser Arg Leu Gly Thr Val Ala Ala Val Phe Pro Asp Leu Thr Cys
305                 310                 315                 320

Ser Ser Thr Ser Thr Pro Pro Thr Ala Thr Met Pro Ser Leu Ile Ser
                325                 330                 335

Thr Thr Ser Thr Ala Ser Ser Ala Arg Arg Thr Ala Val Phe Pro Asp
            340                 345                 350

Leu Thr Cys Ser Ser Ser Ser Thr Leu Ser Leu Ala Ala Thr Thr Phe
        355                 360                 365

Leu Thr Ala Val Thr Ile Glu Thr Ala Ser Gln His Ile Arg Thr Leu
    370                 375                 380

Thr Val Thr Leu Asp Pro Val Thr Val His Ala Ile Val Thr Val Ser
385                 390                 395                 400

Val Tyr Lys Thr Glu Tyr Val Asp Thr Val Thr Val Gly Asp Met
                405                 410                 415
```

Asn Ile Ala Tyr
            420

<210> SEQ ID NO 55
<211> LENGTH: 2057
<212> TYPE: DNA
<213> ORGANISM: Lipomyces starkeyi
<220> FEATURE:
<221> NAME/KEY: Intron
<222> LOCATION: (409)..(462)
<220> FEATURE:
<221> NAME/KEY: Intron
<222> LOCATION: (579)..(637)
<220> FEATURE:
<221> NAME/KEY: Intron
<222> LOCATION: (981)..(1028)

<400> SEQUENCE: 55

```
atgtcatttc gccaggcatt gttctcagct acccggactc atcgtgtgct gcttcgctcc    60
gttgccgcgg gcgggatcct gagcaccaca gcgttcttcc tctcgaacac agactcgttc   120
ggctcaatac accaccaggc tgagcaggac gtgccttga actatcctgt cccggccccc    180
tttgccttgc ccccgtcccg agaagaacag atcaagaagt tggaaaccga acagttcgac   240
ttgctgatca taggcggtgg agctaccggt gccggctgcg cattggatgc cgtcagcaga   300
ggattaaagg tcgcgttggt tgagcgtgat gactttgcat gtggtacaag tagtaggagt   360
acgaagcttg tacacggtgg tgtgagatac ttggagaaag cattctgggt aggtgacaat   420
cacagctatg gcatgacatg aacgctaaca gcgtgatttc agaacctcga ctatgagcag   480
tacaaattgg tcaaggaggc acttgctgag cgtgctactt tcttgaaaat tgcgcctcat   540
ttgagtttcc cgctcccaat catggtccct gtctacaagt atgtctatag ccatttga    600
tctataagct taatcaatct aataatgcat gcgtaggtg gtggcaagtc ccatattact    660
gggctggaac caagatgtac gatcttattg ctggaaagga gaacatggaa tcaagttact   720
tcatgggccg tggtaagacc ctcgagaact tcccaatgct taagcctcag aacttgaagg   780
gtgccattgt ctactacgac ggtagtcaca atgactcgcg aatgaacact gctatcgctc   840
tcactgctgc tcagaaaggt gccgttatcc tgaaccacat ggaggttaca gagttgtcca   900
aggacgcgtc tggtcgcgtc aatggtgctg ttgtccgcga caatgacggt actgctggga   960
agatccaggt tgatgctaag gtatgttgtg gagatacaat ttatatagtg cttgctgacc  1020
tgtttcaggg tgttattaac gcgaccggtc cgttcgcgga ccggatccgt cagctcgata  1080
ctcctgttgc gatcgacatc gtcgctccat catccggtgt gcatgtgatt cttcctgact  1140
actactgctc tcccagcatg ggtttgatcg acccagctac ttctgatgga cgagtagttt  1200
tctttcttcc atggcaaggc catactcttg ccggtacaac cgactctcct accacagtca  1260
cgaaggatcc tattccttcc gaggacgaga taagctggat cttgaacgaa attcaacact  1320
acgttgccga tgatattacc gttcgccggg aagatgttct tgccgcttgg agcggtatcc  1380
gtccattagt ccgcgaccca cgtgctaaga cacagagtc gctggtccgc aaccatttga  1440
tcacccttc cgacagtggt ctcttgactg tcgctggcgg caagtggact acctatcgag  1500
aaatggcaga agacactgtc aacacctctg tcaaagagtt cggtcttgag ccgaccgccc  1560
catgtggaac caaggatatc aagcttgtcg gggctgaggg atacagaaaa ctcatgttca  1620
ttcacttgat ccagacattt ggcattgaga ctggcatagc caagcatctt gctgacaact  1680
atggagatcg tgcgtacgac gtcgtcaggc tttcagccac tacgggcgag agatggccca  1740
caagaggtgt caagctgtcg ccagcttatc cgtacattga tggcgagatc cgttacgcag  1800
```

```
ttcagcacga gtatgctcga acggctgtcg acgtgctgtc gcgacgcatc cgtctcgcgt   1860
tcttgaactc caaggctgcg ttggagagct tgcccaaggt catcgatatc atggccgaag   1920
agttgaagtg ggacaaggcg cgtcaggaca aggagtggga tgacaccatc aggttcttgt   1980
acagcatggg tctccagaac gggaagtact tctcgagagc ggacgttgag agcggaaaaa   2040
caaaaatgtt gggttaa                                                  2057
```

<210> SEQ ID NO 56
<211> LENGTH: 631
<212> TYPE: PRT
<213> ORGANISM: Lipomyces starkeyi

<400> SEQUENCE: 56

```
Met Ser Phe Arg Gln Ala Leu Phe Ser Ala Thr Arg Thr His Arg Val
1               5                   10                  15

Leu Leu Arg Ser Val Ala Ala Gly Gly Ile Leu Ser Thr Thr Ala Phe
            20                  25                  30

Phe Leu Ser Asn Thr Asp Ser Phe Gly Ser Ile His His Gln Ala Glu
        35                  40                  45

Gln Asp Val Pro Leu Asn Tyr Pro Val Pro Ala Pro Phe Ala Leu Pro
    50                  55                  60

Pro Ser Arg Glu Glu Gln Ile Lys Lys Leu Glu Thr Glu Gln Phe Asp
65                  70                  75                  80

Leu Leu Ile Ile Gly Gly Gly Ala Thr Gly Ala Gly Cys Ala Leu Asp
                85                  90                  95

Ala Val Ser Arg Gly Leu Lys Val Ala Leu Val Glu Arg Asp Asp Phe
            100                 105                 110

Ala Cys Gly Thr Ser Ser Arg Ser Thr Lys Leu Val His Gly Gly Val
        115                 120                 125

Arg Tyr Leu Glu Lys Ala Phe Trp Asn Leu Asp Tyr Glu Gln Tyr Lys
    130                 135                 140

Leu Val Lys Glu Ala Leu Ala Glu Arg Ala Thr Phe Leu Lys Ile Ala
145                 150                 155                 160

Pro His Leu Ser Phe Pro Leu Pro Ile Met Val Pro Val Tyr Lys Trp
                165                 170                 175

Trp Gln Val Pro Tyr Tyr Trp Ala Gly Thr Lys Met Tyr Asp Leu Ile
            180                 185                 190

Ala Gly Lys Glu Asn Met Glu Ser Ser Tyr Phe Met Gly Arg Gly Lys
        195                 200                 205

Thr Leu Glu Asn Phe Pro Met Leu Lys Pro Gln Asn Leu Lys Gly Ala
    210                 215                 220

Ile Val Tyr Tyr Asp Gly Ser His Asn Asp Ser Arg Met Asn Thr Ala
225                 230                 235                 240

Ile Ala Leu Thr Ala Ala Gln Lys Gly Ala Val Ile Leu Asn His Met
                245                 250                 255

Glu Val Thr Glu Leu Ser Lys Asp Ala Ser Gly Arg Val Asn Gly Ala
            260                 265                 270

Val Val Arg Asp Asn Asp Gly Thr Ala Gly Lys Ile Gln Val Asp Ala
        275                 280                 285

Lys Gly Val Ile Asn Ala Thr Gly Pro Phe Ala Asp Arg Ile Arg Gln
    290                 295                 300

Leu Asp Thr Pro Val Ala Ile Asp Ile Val Ala Pro Ser Ser Gly Val
305                 310                 315                 320
```

-continued

His Val Ile Leu Pro Asp Tyr Tyr Cys Ser Pro Met Gly Leu Ile
            325                 330                 335

Asp Pro Ala Thr Ser Asp Gly Arg Val Val Phe Phe Leu Pro Trp Gln
        340                 345                 350

Gly His Thr Leu Ala Gly Thr Thr Asp Ser Pro Thr Thr Val Thr Lys
            355                 360                 365

Asp Pro Ile Pro Ser Glu Asp Glu Ile Ser Trp Ile Leu Asn Glu Ile
        370                 375                 380

Gln His Tyr Val Ala Asp Ile Thr Val Arg Arg Glu Asp Val Leu
385                 390                 395                 400

Ala Ala Trp Ser Gly Ile Arg Pro Leu Val Arg Asp Pro Arg Ala Lys
            405                 410                 415

Asn Thr Glu Ser Leu Val Arg Asn His Leu Ile Thr Leu Ser Asp Ser
        420                 425                 430

Gly Leu Leu Thr Val Ala Gly Gly Lys Trp Thr Thr Tyr Arg Glu Met
            435                 440                 445

Ala Glu Asp Thr Val Asn Thr Ser Val Lys Glu Phe Gly Leu Glu Pro
        450                 455                 460

Thr Ala Pro Cys Gly Thr Lys Asp Ile Lys Leu Val Gly Ala Glu Gly
465                 470                 475                 480

Tyr Arg Lys Leu Met Phe Ile His Leu Ile Gln Thr Phe Gly Ile Glu
            485                 490                 495

Thr Gly Ile Ala Lys His Leu Ala Asp Asn Tyr Gly Asp Arg Ala Tyr
        500                 505                 510

Asp Val Val Arg Leu Ser Ala Thr Thr Gly Glu Arg Trp Pro Thr Arg
515                 520                 525

Gly Val Lys Leu Ser Pro Ala Tyr Pro Tyr Ile Asp Gly Glu Ile Arg
            530                 535                 540

Tyr Ala Val Gln His Glu Tyr Ala Arg Thr Ala Val Asp Val Leu Ser
545                 550                 555                 560

Arg Arg Ile Arg Leu Ala Phe Leu Asn Ser Lys Ala Ala Leu Glu Ser
            565                 570                 575

Leu Pro Lys Val Ile Asp Ile Met Ala Glu Glu Leu Lys Trp Asp Lys
        580                 585                 590

Ala Arg Gln Asp Lys Glu Trp Asp Asp Thr Ile Arg Phe Leu Tyr Ser
            595                 600                 605

Met Gly Leu Gln Asn Gly Lys Tyr Phe Ser Arg Ala Asp Val Glu Ser
        610                 615                 620

Gly Lys Thr Lys Met Leu Gly
625                 630

<210> SEQ ID NO 57
<211> LENGTH: 1879
<212> TYPE: DNA
<213> ORGANISM: Lipomyces starkeyi
<220> FEATURE:
<221> NAME/KEY: Intron
<222> LOCATION: (439)..(493)
<220> FEATURE:
<221> NAME/KEY: Intron
<222> LOCATION: (861)..(911)
<220> FEATURE:
<221> NAME/KEY: Intron
<222> LOCATION: (1301)..(1349)
<220> FEATURE:
<221> NAME/KEY: Intron
<222> LOCATION: (1625)..(1675)

<400> SEQUENCE: 57

```
atgtcgaccg ctgcacaatc tgatacagac aacgaggata tatcgactgt cgatttggtt      60
gactctcgtg cagatactca cacatcttca aatgttatgt tgcaacagca aaaatcgcgt     120
cggagactaa tcgggaaaga cgccgagcca agaacacagc atccgtctgg aggcaaatcg     180
gagaaggagg agttgacgaa gccggatgac tcaaagggac ccataaaatt aagtcacata     240
tacccgatac atgccgttag ccgaggcagt attctgtcac gagagtcgac aactcctaca     300
ccgagttttg ttgggtttcg aaacttagcc atgatagtgc tagggaagtt acagtattca     360
ttattctttt ggtgcgatcg ggctaacatt ccgacagccg tcagcaatct tcgattggtg     420
attgaaaatt actcaaaggt atgcctgctc gacagaaata attgtggctg tatgacgagc     480
tgactttgaa cagtacggcg ttctgatccg attcgcccga ctcggtattt cacaaaagga     540
cattctgtat tgcatattct tgaccgctac catcccgctg cacctattta ttgctattgt     600
cattgaaaga ctagttgcga ttccgacggt aaactacgtc gcttcgctca gcgagagcga     660
ggataaaaaa cgctccaacc ccaaaatggg acggaagggg ggcagtatat cgattttgcg     720
tcctaagcca aaatatatgt ggcgcctgat cgtcctattg cattcaataa acgcaatggc     780
ttgcttgtgg gttacgactg ttgttgttta caattctatt tatcatcccc ttattgggac     840
agcttgtgaa tttcatgcag gtgagctata ctctaatttg tggtacgcat tgtaccgcta     900
acaagttgac agtgattgtg tgtcttaagg tcgcatcgtt tgcgcttacc aatcgcgatc     960
ttcgggagtc gatgctgaac tctcaacctg tgccagccat atacaacttg gcccctatc    1020
caaaaaactt aaccctcaag aacttgtcat acttttggtg ggcgccgact cttgtttatc    1080
aacctgtcta tccgcgatcg ccttcattcc ggcctttgtt ttttgtcaag cggattctgg    1140
agatggtggg cctatcattt taatatggt tcttgtcagc tcaatatgct gtgccgacgc    1200
tagaaaatag tttggtgcat tttcacagtt tgcaattcat gggaattatg gagcgactca    1260
tgaagcttgc tagcattagc atggctattt ggcttgctgg gtatgttcgg atagcaactt    1320
tggtctcgtg atgataaact aatttcgtta gttttttctg cattttttcag tctggactca    1380
atgcgcttgc ggaggtaatg cggtttggtg acagagcctt ttacgacgac tggtggaaca    1440
gcaaatctgt gggagagtat tggcgtctgt ggaataagcc ggttacgaat tacttccggc    1500
gtcatattta cgtaccgctt gtgcgccgcg ggtggaattc tgcgacagcc agtgtcatgg    1560
tattttcgt cagcgcggtg ttgcatgagc tagttgttgg agttccgacg cataacgtaa    1620
ttgggtacga ttgcctttat atagtatgaa aattgctgtt aactgagtta ataacagagt    1680
tgcattctcg tcgatgattc tacaaatccc actcatacaa gtaaccgcgc tctctggagaa   1740
gatgcatgga cctacatctg gaataatagg gaactgtatc ttttggttta gcttcttcat    1800
cggtcagcct ctgggcgtgc tactttacta ttttgcgtgg aacgttagta tgagcaaagt    1860
aaagatggtc gagagctag                                                 1879
```

<210> SEQ ID NO 58  
<211> LENGTH: 555  
<212> TYPE: PRT  
<213> ORGANISM: Lipomyces starkeyi

<400> SEQUENCE: 58

Met Ser Thr Ala Ala Gln Ser Asp Thr Asp Asn Glu Asp Ile Ser Thr  
1               5                   10                  15

Val Asp Leu Val Asp Ser Arg Ala Asp Thr His Thr Ser Ser Asn Val  
            20                  25                  30

```
Met Leu Gln Gln Gln Lys Ser Arg Arg Leu Ile Gly Lys Asp Ala
         35                  40                  45
Glu Pro Arg Thr Gln His Pro Ser Gly Gly Lys Ser Glu Lys Glu Glu
 50                  55                  60
Leu Thr Lys Pro Asp Asp Ser Lys Gly Pro Ile Lys Leu Ser His Ile
 65                  70                  75                  80
Tyr Pro Ile His Ala Val Ser Arg Gly Ser Ile Leu Ser Arg Glu Ser
                 85                  90                  95
Thr Thr Pro Thr Pro Ser Phe Val Gly Phe Arg Asn Leu Ala Met Ile
                100                 105                 110
Val Leu Gly Lys Leu Gln Tyr Ser Leu Phe Phe Trp Cys Asp Arg Ala
                115                 120                 125
Asn Ile Pro Thr Ala Val Ser Asn Leu Arg Leu Val Ile Glu Asn Tyr
                130                 135                 140
Ser Lys Tyr Gly Val Leu Ile Arg Phe Ala Arg Leu Gly Ile Ser Gln
145                 150                 155                 160
Lys Asp Ile Leu Tyr Cys Ile Phe Leu Thr Ala Thr Ile Pro Leu His
                165                 170                 175
Leu Phe Ile Ala Ile Val Ile Glu Arg Leu Val Ala Ile Pro Thr Val
                180                 185                 190
Asn Tyr Val Ala Ser Leu Ser Glu Ser Glu Asp Lys Lys Arg Ser Asn
                195                 200                 205
Pro Lys Met Gly Arg Lys Gly Gly Ser Ile Ser Ile Leu Arg Pro Lys
                210                 215                 220
Pro Lys Tyr Met Trp Arg Leu Ile Val Leu Leu His Ser Ile Asn Ala
225                 230                 235                 240
Met Ala Cys Leu Trp Val Thr Thr Val Val Tyr Asn Ser Ile Tyr
                245                 250                 255
His Pro Leu Ile Gly Thr Ala Cys Glu Phe His Ala Val Ile Val Cys
                260                 265                 270
Leu Lys Val Ala Ser Phe Ala Leu Thr Asn Arg Asp Leu Arg Glu Ser
                275                 280                 285
Met Leu Asn Ser Gln Pro Val Pro Ala Ile Tyr Asn Leu Ala Pro Tyr
                290                 295                 300
Pro Lys Asn Leu Thr Leu Lys Asn Leu Ser Tyr Phe Trp Trp Ala Pro
305                 310                 315                 320
Thr Leu Val Tyr Gln Pro Val Tyr Pro Arg Ser Pro Ser Phe Arg Pro
                325                 330                 335
Leu Phe Phe Val Lys Arg Ile Leu Glu Met Val Gly Leu Ser Phe Leu
                340                 345                 350
Ile Trp Phe Leu Ser Ala Gln Tyr Ala Val Pro Thr Leu Glu Asn Ser
                355                 360                 365
Leu Val His Phe His Ser Leu Gln Phe Met Gly Ile Met Glu Arg Leu
                370                 375                 380
Met Lys Leu Ala Ser Ile Ser Met Ala Ile Trp Leu Ala Gly Phe Phe
385                 390                 395                 400
Cys Ile Phe Gln Ser Gly Leu Asn Ala Leu Ala Glu Val Met Arg Phe
                405                 410                 415
Gly Asp Arg Ala Phe Tyr Asp Asp Trp Trp Asn Ser Lys Ser Val Gly
                420                 425                 430
Glu Tyr Trp Arg Leu Trp Asn Lys Pro Val Thr Asn Tyr Phe Arg Arg
                435                 440                 445
His Ile Tyr Val Pro Leu Val Arg Arg Gly Trp Asn Ser Ala Thr Ala
```

```
                450             455             460
Ser Val Met Val Phe Phe Val Ser Ala Val Leu His Glu Leu Val Val
465                 470                 475                 480

Gly Val Pro Thr His Asn Val Ile Gly Val Ala Phe Ser Ser Met Ile
                    485                 490                 495

Leu Gln Ile Pro Leu Ile Gln Val Thr Ala Pro Leu Glu Lys Met His
                500                 505                 510

Gly Pro Thr Ser Gly Ile Ile Gly Asn Cys Ile Phe Trp Phe Ser Phe
            515                 520                 525

Phe Ile Gly Gln Pro Leu Gly Val Leu Leu Tyr Tyr Phe Ala Trp Asn
        530                 535                 540

Val Ser Met Ser Lys Val Lys Met Val Glu Ser
545                 550                 555

<210> SEQ ID NO 59
<211> LENGTH: 2382
<212> TYPE: DNA
<213> ORGANISM: Lipomyces starkeyi
<220> FEATURE:
<221> NAME/KEY: Intron
<222> LOCATION: (166)..(295)
<220> FEATURE:
<221> NAME/KEY: Intron
<222> LOCATION: (366)..(420)

<400> SEQUENCE: 59
atggcaagta aatcagtatc agccgcagct ggatcgcggc agtcatctgt ttcatcgacc      60
ggatccattg atccattctc tgtcgcccag gtctactatg gccctgagac tgatttcact     120
acccacaaga tgagcaatct tattcgcacg aggactctgt cgacggtatg ttgtatattg     180
cttactttaa taatgcatgg atcgggaaga aatccactgg cgttccacag atcctattca     240
aagcgtggcg acctatagtg aaacgatttt cagacgctaa ttgtgtgtcg attaggtaca     300
aacgcgaagc agtaacaata cgcctgacta tctgaaatca gttcctcgca gaagagcatc     360
tcaaggtttg tcatgcggtg gaaattgtcg caaggttgcc gcaactgatt tgtggttata     420
gacgctgagt ccctgacgcc gcgcaagttc tcgtcgacg tgaacttgac tcttcaggcg     480
ctgcttgaaa gcgaagacac tgacggaaac atgcaaataa cgattgagga tctgggtccg     540
aaagtattgc agctcggtac cgcgaactcg aacgggttca acaagttcga cattcgcggc     600
acttacatgt tgtcgaacct tttgcaagag ctcactcttg ccaaggagta cggccgaaag     660
tcgattatcc tggacgaaca gcgtctgaac gagaatccag tcagcaggtt gtcccgattg     720
atccgtacac agttctggga ctcgctaacc cgtcggatcg acgcttctct gttggaaatt     780
atcgctgtcg atcccaagaa ccgttcaaag gatcagagcc ctcgaatcta cgttccgcca     840
acggagaagg agcaatatga atactatgtc aaggaagctt ctaaacgccc tcatctgaat     900
ctccaggtgg agtatcttcc tgccactatc acggcggaat gggtcaagtc agtcaatgag     960
aaagcgggat tacttgcact ggcgatggac catgtggtcg atgaattcac tgacaatcg    1020 acattgcgag ggaaaccttt tgttgtgcct ggtggacgat caacgagct ctatgggtgg    1080 gactcgtata tgattgcctt aggtctattg gtggatggaa gagtcgatct tgctaagggt    1140
atcctcgaaa acttcatctt cgaaatcaac aattacggga agatcttgaa tgccaatcgt    1200
tcttactatc tttgcaggtc gcagccacca tttttgacag acttggcttt gaaggtgtat    1260
gaaaaaacga tattcgaacc aggagcattg gagttactga agaatcgtt caaggctgca    1320 atcgtggagt ataagcaagt ttggacgtcc cctccacgat tggatcaaga gtcgggattg    1380
```

-continued

```
tcgtgctacc atccggatgg cattggtata ccgcctgaga ctgaggctag tcattttgag   1440
cacctcttga tgccttatgc ggaaaagcat aagctctcct tggaggattt ccagagacaa   1500
tacaatgatg aatagtcaa ggagcctgct ctcgacgagt atttcgttca cgatcgagct    1560
gtccgagaat ctggtcatga cactacttac cgactcgaga aacgttgtgc caatctggca   1620
acaatcgatt tgaacagctt gttgtacaag tacgaagtcg atatcgctca tactatccga   1680
acaatgtttg gtgataagct ggtgctccat gacggaagtg tagaaaccag tgcgtcttgg   1740
gatcgtcgtg cacgacgacg aaagaatttg attgatcaat atttgtggga tgaggaaaag   1800
ggcatgtatt ttgattacga cattgtgcag aaaaagaagt ctgattatga gtctgctacg   1860
acattctggg cgatgtgggc tggttgcgcg tctcccaagc aagccgccag actagtttcg   1920
gacgcgctac caaagttcga agagtttggc ggtctggttt ctgggactga gaggtctcgc   1980
ggggtcatag gacttgatcg accgaacaga cagtgggact acccttacgg atgggcgccg   2040
caacagattc ttgcctgggt tggcttgatc agatatggat atgaagaaga tgctgagcga   2100
ctagtctatc gatggctgta catgattacc aaagcctttg tggattataa cggtattgtt   2160
gtcgagaaat atgatgtcac gcgaccagtg gatccacacc gcgtcgacgc cgagtatggt   2220
aaccaggggt cagatttcaa gggagttgcc aaggaaggat ttggctgggt aaatgcgtcc   2280 tatactttg ggctgacgtt gattaccagt cacgcgcgac gtgctctcgg ggcatgcact    2340
ccaccaggtc ttttctatgc gagccagtac tcttacgttt aa                     2382
```

<210> SEQ ID NO 60
<211> LENGTH: 731
<212> TYPE: PRT
<213> ORGANISM: Lipomyces starkeyi

<400> SEQUENCE: 60

```
Met Ala Ser Lys Ser Val Ser Ala Ala Gly Ser Arg Gln Ser Ser
1               5                   10                  15

Val Ser Ser Thr Gly Ser Ile Asp Pro Phe Ser Val Ala Gln Val Tyr
            20                  25                  30

Tyr Gly Pro Glu Thr Asp Phe Thr Thr His Lys Met Ser Asn Leu Ile
        35                  40                  45

Arg Thr Arg Thr Leu Ser Thr Val Gln Thr Arg Ser Ser Asn Asn Thr
    50                  55                  60

Pro Asp Tyr Leu Lys Ser Val Pro Arg Arg Ala Ser Gln Asp Ala
65                  70                  75                  80

Glu Ser Leu Thr Pro Arg Lys Phe Leu Val Asp Val Asn Leu Thr Leu
                85                  90                  95

Gln Ala Leu Leu Glu Ser Glu Asp Thr Asp Gly Asn Met Gln Ile Thr
            100                 105                 110

Ile Glu Asp Leu Gly Pro Lys Val Leu Gln Leu Gly Thr Ala Asn Ser
        115                 120                 125

Asn Gly Phe Asn Lys Phe Asp Ile Arg Gly Thr Tyr Met Leu Ser Asn
    130                 135                 140

Leu Leu Gln Glu Leu Thr Leu Ala Lys Glu Tyr Gly Arg Lys Ser Ile
145                 150                 155                 160

Ile Leu Asp Glu Gln Arg Leu Asn Glu Asn Pro Val Ser Arg Leu Ser
                165                 170                 175

Arg Leu Ile Arg Thr Gln Phe Trp Asp Ser Leu Thr Arg Ile Asp
            180                 185                 190
```

```
Ala Ser Leu Leu Glu Ile Ile Ala Val Asp Pro Lys Asn Arg Ser Lys
        195                 200                 205

Asp Gln Ser Pro Arg Ile Tyr Val Pro Pro Thr Glu Lys Glu Gln Tyr
    210                 215                 220

Glu Tyr Tyr Val Lys Glu Ala Ser Lys Arg Pro His Leu Asn Leu Gln
225                 230                 235                 240

Val Glu Tyr Leu Pro Ala Thr Ile Thr Ala Glu Trp Val Lys Ser Val
                245                 250                 255

Asn Glu Lys Ala Gly Leu Leu Ala Leu Ala Met Asp His Val Val Asp
            260                 265                 270

Glu Phe Thr Gly Gln Ser Thr Leu Arg Gly Lys Pro Phe Val Val Pro
        275                 280                 285

Gly Gly Arg Phe Asn Glu Leu Tyr Gly Trp Asp Ser Tyr Met Ile Ala
290                 295                 300

Leu Gly Leu Leu Val Asp Gly Arg Val Asp Leu Ala Lys Gly Ile Leu
305                 310                 315                 320

Glu Asn Phe Ile Phe Glu Ile Asn Asn Tyr Gly Lys Ile Leu Asn Ala
                325                 330                 335

Asn Arg Ser Tyr Tyr Leu Cys Arg Ser Gln Pro Pro Phe Leu Thr Asp
            340                 345                 350

Leu Ala Leu Lys Val Tyr Glu Lys Thr Ile Phe Glu Pro Gly Ala Leu
        355                 360                 365

Glu Leu Leu Lys Glu Ser Phe Lys Ala Ala Ile Val Glu Tyr Lys Gln
        370                 375                 380

Val Trp Thr Ser Pro Pro Arg Leu Asp Gln Glu Ser Gly Leu Ser Cys
385                 390                 395                 400

Tyr His Pro Asp Gly Ile Gly Ile Pro Pro Glu Thr Glu Ala Ser His
                405                 410                 415

Phe Glu His Leu Leu Met Pro Tyr Ala Glu Lys His Lys Leu Ser Leu
            420                 425                 430

Glu Asp Phe Gln Arg Gln Tyr Asn Asp Gly Ile Val Lys Glu Pro Ala
        435                 440                 445

Leu Asp Glu Tyr Phe Val His Asp Arg Ala Val Arg Glu Ser Gly His
450                 455                 460

Asp Thr Thr Tyr Arg Leu Glu Lys Arg Cys Ala Asn Leu Ala Thr Ile
465                 470                 475                 480

Asp Leu Asn Ser Leu Leu Tyr Lys Tyr Glu Val Asp Ile Ala His Thr
                485                 490                 495

Ile Arg Thr Met Phe Gly Asp Lys Leu Val Leu His Asp Gly Ser Val
            500                 505                 510

Glu Thr Ser Ala Ser Trp Asp Arg Arg Ala Arg Arg Lys Asn Leu
        515                 520                 525

Ile Asp Gln Tyr Leu Trp Asp Glu Lys Gly Met Tyr Phe Asp Tyr
        530                 535                 540

Asp Ile Val Gln Lys Lys Ser Asp Tyr Glu Ser Ala Thr Thr Phe
545                 550                 555                 560

Trp Ala Met Trp Ala Gly Cys Ala Ser Pro Lys Gln Ala Ala Arg Leu
                565                 570                 575

Val Ser Asp Ala Leu Pro Lys Phe Glu Glu Phe Gly Gly Leu Val Ser
            580                 585                 590

Gly Thr Glu Arg Ser Arg Gly Val Ile Gly Leu Asp Arg Pro Asn Arg
        595                 600                 605

Gln Trp Asp Tyr Pro Tyr Gly Trp Ala Pro Gln Gln Ile Leu Ala Trp
```

-continued

```
                    610                 615                 620
Val Gly Leu Ile Arg Tyr Gly Tyr Glu Glu Asp Ala Glu Arg Leu Val
625                 630                 635                 640

Tyr Arg Trp Leu Tyr Met Ile Thr Lys Ala Phe Val Asp Tyr Asn Gly
                645                 650                 655

Ile Val Val Glu Lys Tyr Asp Val Thr Arg Pro Val Asp Pro His Arg
            660                 665                 670

Val Asp Ala Glu Tyr Gly Asn Gln Gly Ser Asp Phe Lys Gly Val Ala
        675                 680                 685

Lys Glu Gly Phe Gly Trp Val Asn Ala Ser Tyr Thr Phe Gly Leu Thr
    690                 695                 700

Leu Ile Thr Ser His Ala Arg Arg Ala Leu Gly Ala Cys Thr Pro Pro
705                 710                 715                 720

Gly Leu Phe Tyr Ala Ser Gln Tyr Ser Tyr Val
                725                 730

<210> SEQ ID NO 61
<211> LENGTH: 3176
<212> TYPE: DNA
<213> ORGANISM: Lipomyces starkeyi
<220> FEATURE:
<221> NAME/KEY: Intron
<222> LOCATION: (1276)..(1328)
<220> FEATURE:
<221> NAME/KEY: Intron
<222> LOCATION: (2040)..(2090)

<400> SEQUENCE: 61
atgagattaa atgttttact ttctggctgt gttgctctat cgcatctcgc gctcgccagt      60
gtttcactta agttaaggca gcagctgtcc aaagaggctg tcacgaacga tccgattctt    120
gacggcgtcg agtacaatga tggcacctgg acgttaacaa accgtctgct cactacgaac    180
aggttccaac ttcagccata tgtttctaac ggatatattg gtgcccgtct gccgttggaa    240
ggtaccggct acgtccaaga cacttttgag agcgaggacg cggcagtgt caatggcgcc     300 gagccgacga tggttggcc cctgttttcg cctcggttca cgggagcgta catcgcgggc    360
ttttgggact tgcagccaaa caccacagcc acaaatttcc cagagttatt gacgagaggc    420
ggcgagagtg taatttcgac cgtgcccgta tggtctacac tgttagtcac tgctcacgga    480
gataccttca acgtcaattg tcctctagga aatgtgcaca actatacgca gtcgctttcc    540
atgaaggacg gtatcgtcag gaccaaacta gaatggtacc gaatgggaa tgcgtcgcag     600 gcgatttctc tcgcgtacga ggtcttggcc cacagagtga ttccgacgct ggcaatggtt    660
aagctggaag tactggccgc cgaagatacc aatatcaagc tctccgacat tctcgacggc    720
gcgggttcgt tccggacgat atttttggag aagaactact catcgcatga cgctaccggc    780
atgtggactg gcgttcgtcc ttatggtttg accagtgttc aggcttacga atactcgcac    840
ctcgagtttt cggattcggc tgtggtcaac ataagcagtc ggcaaaagtc tcctattgcg    900
aacaagagcc cggcaacgat atcgcaagag tttgaagtgt cactcgaagc tggcaagccg    960
ttcttggtct acaagttcgt cggtatcgcc tcgtcggatg cgtataagga cccgaagcgc   1020
gtagctgcat acacggcgcg tattgctgcg tcaattggat ataggctggc aaaggcggat   1080
cacaagcttg cgtggcataa gctttgggaa tctggcgaca ttgtctttcc tggggacaag   1140
gagcttcaga tttctatccg agcttcgctc ttccacttgt tgagtgctct ccggtcgggg   1200
gacgagcctt ctggtcgagg tgacaattcg atcgcagttt ctggactcag ttcggactcc   1260
```

| | |
|---|---|
| tatggaggcc tggtggtaag tattgaaatt gcggaacggg ctgcatgaga gttgctgatc | 1320 |
| aatataagtt ctgggacgcc gacacgtgga tgtatcctgc gatgtctgtg cttcatccca | 1380 |
| agtatgcggc gaatgtcaac aacttccggc aacgaattca taaccagtcg attgagaacg | 1440 |
| cgcggtcata taacctcagt ggtgccatct actcgtggac gtctggtcgt ttcggcaact | 1500 |
| gcactggcac cggtccttgc gttgactacg agtatcatat caacgtcgat attgcccaag | 1560 |
| ctcactggaa tcaatttctg ttgtcgaatg atacggactg gttggaggcg aaaggatggc | 1620 |
| cgatcattcg tgatgcggcg gagatgtttt cgtcgtatgt cgtgaagaac gcgtcgacgg | 1680 |
| gaccatacta ctacacgtac aatatgaccg accctgacga gtatgccaat tttgtcgaca | 1740 |
| acggcgcgtt cacgaacgca ggcatttcca agcttatggg atgggcgcga cgagccgctg | 1800 |
| agattgttgg acaggactca atccggagt gggcagatat tgaggagaat atttacattc | 1860 |
| cggtcaactc ggacgtgaat ctggtgttgg aattctcgaa tatgaatggg tcagtagaga | 1920 |
| tcaagcaggc ggacgtggtt ttgcttgact atcctctcga atatcaccgt tcgtggcagc | 1980 |
| agagtttgaa caatctggat ttttacgcca tggctcagag tgcagatggt ccagctatgg | 2040 |
| tacgcggtga ttgttatgca attgagagtc gttttaaccg aaactttag acatgggcga | 2100 |
| ttttcgcaat cagctctgcg gaactgagtc ctgtcggctg cgcatcgtac acgtacctcc | 2160 |
| tgtacgcgtc gcagccgtac ctgcgggcgc cgttttacca gttttcggag cagatggacg | 2220 |
| acaacgcgac gacgaacggc ggtacgaggc ccgcgttccc gttcttgacg ggccacggcg | 2280 |
| ggtttctgca ggttctgacg cacggattca cgggcttccg acctcgcgag gacgtgtttt | 2340 |
| acctcgatcc ttcgctgccg ccgcagattg agcgcgggta cacggttaac gggatgaaat | 2400 |
| ggcgggacag cgttttcgac gtgacgatta gcttgacga gacagttata caccgtcgta | 2460 |
| ccaaagcgac gtcgagatcg cggactggga atgcggatct ggtggagtat ctttcggcgc | 2520 |
| actacgacaa gcggcggcac gacgacgagg gctcgagtat tcaaaagggc ggcacgccag | 2580 |
| ttaccgtccg tatcggcgcc ggcgacggaa aaggcgatta cacgctgtac gaaggtggtc | 2640 |
| ggctcgttgt gcctacccgc cgggctgatc tcaatggcac gttagtggcg ggcaatgtcg | 2700 |
| cgcaatgcca gcccgccatc tcgaacgtga cctgggcgag cggacatttc ccgatctcgg | 2760 |
| ccgtcgacgg gtcgaattcg acgtcctggc agccatctac gcgcgaccca tccgcgctgc | 2820 |
| tggtcgattt ggggaaagcc acgactgtcg ctggcgtgag cctaaactgg gggcgcacgc | 2880 |
| ctccgctggc attttcggtc gggtacgcag ccacggtcgt cgacgatggt ccgacgttcg | 2940 |
| gcagcgtgga tttcgcgtgg cctatcgtgc ggcagaacgt gtcgatttct gacgaataca | 3000 |
| acgccgcgac ggcgctcgag gtcaggttgt cggtcggcaa cgtcacgacc gcaggcctgg | 3060 |
| ccgaaaccgt gcgtacgcgg tggataatgt tggtcgtgga agggtcgtac gacacggggt | 3120 |
| tgcggtacgg cgacgtcggt gccactgttg ccgagtttgc ggtcattgag gggtga | 3176 |

<210> SEQ ID NO 62
<211> LENGTH: 1023
<212> TYPE: PRT
<213> ORGANISM: Lipomyces starkeyi

<400> SEQUENCE: 62

Met Arg Leu Asn Val Leu Leu Ser Gly Cys Val Ala Leu Ser His Leu
1               5                   10                  15

Ala Leu Ala Ser Val Ser Leu Lys Leu Arg Gln Gln Leu Ser Lys Glu
            20                  25                  30

Ala Val Thr Asn Asp Pro Ile Leu Asp Gly Val Glu Tyr Asn Asp Gly

-continued

```
                35                  40                  45
Thr Trp Thr Leu Thr Asn Arg Leu Leu Thr Thr Asn Arg Phe Gln Leu
 50                  55                  60
Gln Pro Tyr Val Ser Asn Gly Tyr Ile Gly Ala Arg Leu Pro Leu Glu
 65                  70                  75                  80
Gly Thr Gly Tyr Val Gln Asp Thr Phe Glu Ser Asp Gly Gly Ser
                     85                  90                  95
Val Asn Gly Ala Glu Pro Thr Asn Gly Trp Pro Leu Phe Ser Pro Arg
                100                 105                 110
Phe Thr Gly Ala Tyr Ile Ala Gly Phe Trp Asp Leu Gln Pro Asn Thr
                115                 120                 125
Thr Ala Thr Asn Phe Pro Glu Leu Leu Thr Arg Gly Gly Glu Ser Val
                130                 135                 140
Ile Ser Thr Val Pro Val Trp Ser Thr Leu Leu Val Thr Ala His Gly
145                 150                 155                 160
Asp Thr Phe Asn Val Asn Cys Pro Leu Gly Asn Val His Asn Tyr Thr
                165                 170                 175
Gln Ser Leu Ser Met Lys Asp Gly Ile Val Arg Thr Lys Leu Glu Trp
                180                 185                 190
Tyr Pro Asn Gly Asn Ala Ser Gln Ala Ile Ser Leu Ala Tyr Glu Val
                195                 200                 205
Leu Ala His Arg Val Ile Pro Thr Leu Ala Met Val Lys Leu Glu Val
210                 215                 220
Leu Ala Ala Glu Asp Thr Asn Ile Lys Leu Ser Asp Ile Leu Asp Gly
225                 230                 235                 240
Ala Gly Ser Phe Arg Thr Ile Phe Leu Glu Lys Asn Tyr Ser Ser His
                245                 250                 255
Asp Ala Thr Gly Met Trp Thr Gly Val Arg Pro Tyr Gly Leu Thr Ser
                260                 265                 270
Val Gln Ala Tyr Glu Tyr Ser His Leu Glu Phe Ser Asp Ser Ala Val
                275                 280                 285
Val Asn Ile Ser Ser Arg Gln Lys Ser Pro Ile Ala Asn Lys Ser Pro
290                 295                 300
Ala Thr Ile Ser Gln Glu Phe Glu Val Ser Leu Glu Ala Gly Lys Pro
305                 310                 315                 320
Phe Leu Val Tyr Lys Phe Val Gly Ile Ala Ser Ser Asp Ala Tyr Lys
                325                 330                 335
Asp Pro Lys Arg Val Ala Ala Tyr Thr Ala Arg Ile Ala Ala Ser Ile
                340                 345                 350
Gly Tyr Arg Leu Ala Lys Ala Asp His Lys Leu Ala Trp His Lys Leu
                355                 360                 365
Trp Glu Ser Gly Asp Ile Val Phe Pro Gly Asp Lys Glu Leu Gln Ile
                370                 375                 380
Ser Ile Arg Ala Ser Leu Phe His Leu Leu Ser Ala Leu Arg Ser Gly
385                 390                 395                 400
Asp Glu Pro Ser Gly Arg Gly Asp Asn Ser Ile Ala Val Ser Gly Leu
                405                 410                 415
Ser Ser Asp Ser Tyr Gly Gly Leu Val Phe Trp Asp Ala Asp Thr Trp
                420                 425                 430
Met Tyr Pro Ala Met Ser Val Leu His Pro Lys Tyr Ala Ala Asn Val
                435                 440                 445
Asn Asn Phe Arg Gln Arg Ile His Asn Gln Ser Ile Glu Asn Ala Arg
450                 455                 460
```

Ser Tyr Asn Leu Ser Gly Ala Ile Tyr Ser Trp Thr Ser Arg Phe
465                 470                 475                 480

Gly Asn Cys Thr Gly Thr Gly Pro Cys Val Asp Tyr Glu Tyr His Ile
                485                 490                 495

Asn Val Asp Ile Ala Gln Ala His Trp Asn Gln Phe Leu Leu Ser Asn
            500                 505                 510

Asp Thr Asp Trp Leu Glu Ala Lys Gly Trp Pro Ile Ile Arg Asp Ala
            515                 520                 525

Ala Glu Met Phe Ser Ser Tyr Val Lys Asn Ala Ser Thr Gly Pro
530                 535                 540

Tyr Tyr Tyr Thr Tyr Asn Met Thr Asp Pro Asp Glu Tyr Ala Asn Phe
545                 550                 555                 560

Val Asp Asn Gly Ala Phe Thr Asn Ala Gly Ile Ser Lys Leu Met Gly
                565                 570                 575

Trp Ala Arg Arg Ala Ala Glu Ile Val Gly Gln Asp Ser Asn Pro Glu
            580                 585                 590

Trp Ala Asp Ile Glu Glu Asn Ile Tyr Ile Pro Val Asn Ser Asp Val
            595                 600                 605

Asn Leu Val Leu Glu Phe Ser Asn Met Asn Gly Ser Val Glu Ile Lys
610                 615                 620

Gln Ala Asp Val Val Leu Leu Asp Tyr Pro Leu Glu Tyr His Arg Ser
625                 630                 635                 640

Trp Gln Gln Ser Leu Asn Asn Leu Asp Phe Tyr Ala Met Ala Gln Ser
                645                 650                 655

Ala Asp Gly Pro Ala Met Thr Trp Ala Ile Phe Ala Ile Ser Ser Ala
            660                 665                 670

Glu Leu Ser Pro Val Gly Cys Ala Ser Tyr Thr Tyr Leu Leu Tyr Ala
            675                 680                 685

Ser Gln Pro Tyr Leu Arg Ala Pro Phe Tyr Gln Phe Ser Glu Gln Met
690                 695                 700

Asp Asp Asn Ala Thr Thr Asn Gly Gly Thr Arg Pro Ala Phe Pro Phe
705                 710                 715                 720

Leu Thr Gly His Gly Gly Phe Leu Gln Val Leu Thr His Gly Phe Thr
                725                 730                 735

Gly Phe Arg Pro Arg Glu Asp Val Phe Tyr Leu Asp Pro Ser Leu Pro
            740                 745                 750

Pro Gln Ile Glu Arg Gly Tyr Thr Val Asn Gly Met Lys Trp Arg Asp
            755                 760                 765

Ser Val Phe Asp Val Thr Ile Lys Leu Asp Glu Thr Val Ile His Arg
            770                 775                 780

Arg Thr Lys Ala Thr Ser Arg Ser Arg Thr Gly Asn Ala Asp Leu Val
785                 790                 795                 800

Glu Tyr Leu Ser Ala His Tyr Asp Lys Arg His Asp Asp Glu Gly
                805                 810                 815

Ser Ser Ile Gln Lys Gly Gly Thr Pro Val Thr Val Arg Ile Gly Ala
            820                 825                 830

Gly Asp Gly Lys Gly Asp Tyr Thr Leu Tyr Glu Gly Gly Arg Leu Val
            835                 840                 845

Val Pro Thr Arg Arg Ala Asp Leu Asn Gly Thr Leu Val Ala Gly Asn
            850                 855                 860

Val Ala Gln Cys Gln Pro Ala Ile Ser Asn Val Thr Trp Ala Ser Gly
865                 870                 875                 880

```
His Phe Pro Ile Ser Ala Val Asp Gly Ser Asn Ser Thr Ser Trp Gln
            885                 890                 895

Pro Ser Thr Arg Asp Pro Ser Ala Leu Leu Val Asp Leu Gly Lys Ala
        900                 905                 910

Thr Thr Val Ala Gly Val Ser Leu Asn Trp Gly Arg Thr Pro Pro Leu
        915                 920                 925

Ala Phe Ser Val Gly Tyr Ala Ala Thr Val Val Asp Asp Gly Pro Thr
        930                 935                 940

Phe Gly Ser Val Asp Phe Ala Trp Pro Ile Val Arg Gln Asn Val Ser
945                 950                 955                 960

Ile Ser Asp Glu Tyr Asn Ala Ala Thr Ala Leu Glu Val Arg Leu Ser
            965                 970                 975

Val Gly Asn Val Thr Thr Ala Gly Leu Ala Glu Thr Val Arg Thr Arg
            980                 985                 990

Trp Ile Met Leu Val Glu Gly Ser Tyr Asp Thr Gly Leu Arg Tyr
            995                1000                1005

Gly Asp Val Gly Ala Thr Val Ala Glu Phe Ala Val Ile Glu Gly
    1010                1015                 1020
```

<210> SEQ ID NO 63
<211> LENGTH: 1385
<212> TYPE: DNA
<213> ORGANISM: Lipomyces starkeyi
<220> FEATURE:
<221> NAME/KEY: Intron
<222> LOCATION: (204)..(254)

<400> SEQUENCE: 63

```
atgaccatcg gcactgccat tcagtgctcc tcgttctcac ttgctcagtt catcatcggc     60
cgcattgtca ctggctgcgg aaacggattt attacagcga cggtgccgat gtggcagtct    120
gagtgtgcta agcggaggc acgtggccag ttagttatga ttcagggtgc gctgattact    180
ggcggtattg cctatctta ctggtaattc tgctttgact caattggctt aatatttgat    240
aatgacatgg ttttaggatt gactttgcat tctacttcgt ccccggccaa gctgattggc    300
gtttccctat cgcttttccaa gccgtgtttg caatcatcct catgtgcaca gtcctggaac    360
tccctgagtc ccctcgatgg ctcttaaaaa agggtcacga gaaagaagca gcccttgtct    420
ttgcctcgct tgctgatttg cctgaggaca gcccagttat cgccgaacaa gtcgaagagg    480
tcaagtcgac cctcacctct gagccccgct cgtcgttccg agaaatattc acctttacac    540
atgagaaaca ctttcatcgg actatgctcg cttttttggaa ccaggtcatg cagcaaattt    600
ctggtatcaa ccttatcaca tactacgccg gaaccatcta cgagaattcc ataggtctca    660
caccgatgaa agcaaagatc cttgccgctt gcaacggtac cgagtacttc atggcggcgt    720
gggtcgcgtt ctacgcgatc gagcgtctcg gccgccgcaa gttgatgctc ataggtgctg    780
ttggccaagc gatcaccatg gcgattctca ccggcaccgc gcacgcggct gacaatgcaa    840
acagcaaagg gggtatcgca gccgccgtct tcctcttcgt ctttaacacg ttcttcggga    900
ttggctggct tggtatgact tggttgtatc ctgctgagat cgtgtcgctc caagtccgcg    960
cgcctgcaaa tggtctttcg accgccggca actggatcgc caatttctta gtcgtcatga   1020
ttaccccat cgcctttaat aatattggcg cctacactta cctcgtcttc gcagtcatca   1080
atgcagtgat ggtgcccacc gtctacttct tctacccgga gacatcgggt cgctcgctcg   1140
aggaaatcga cgtatcttc gcacagagca actcatggac cccgtgggat gtcgttggaa   1200
tcgcgaaccg catgccaaag catcacaccg atgttaacga aatcggagtt gaggagaacg   1260
```

```
gcaaggcata tttaaagcat aggacgagca gccagggcga cgaacacgac gagaaggtgg    1320
gtcgtttcga gactggaagt ggtagcgaga gttcaccagg cgtcgcagga gaaatcaatg    1380
attag                                                                 1385
```

<210> SEQ ID NO 64
<211> LENGTH: 443
<212> TYPE: PRT
<213> ORGANISM: Lipomyces starkeyi

<400> SEQUENCE: 64

```
Met Thr Ile Gly Thr Ala Ile Gln Cys Ser Ser Phe Ser Leu Ala Gln
1               5                   10                  15

Phe Ile Ile Gly Arg Ile Val Thr Gly Cys Gly Asn Gly Phe Ile Thr
                20                  25                  30

Ala Thr Val Pro Met Trp Gln Ser Glu Cys Ala Lys Ala Glu Ala Arg
            35                  40                  45

Gly Gln Leu Val Met Ile Gln Gly Ala Leu Ile Thr Gly Gly Ile Ala
        50                  55                  60

Leu Ser Tyr Arg Ile Asp Phe Ala Phe Tyr Phe Val Pro Gly Gln Ala
65                  70                  75                  80

Asp Trp Arg Phe Pro Ile Ala Phe Gln Ala Val Phe Ala Ile Ile Leu
                85                  90                  95

Met Cys Thr Val Leu Glu Leu Pro Glu Ser Pro Arg Trp Leu Leu Lys
            100                 105                 110

Lys Gly His Glu Lys Glu Ala Ala Leu Val Phe Ala Ser Leu Ala Asp
        115                 120                 125

Leu Pro Glu Asp Ser Pro Val Ile Ala Glu Gln Val Glu Glu Val Lys
130                 135                 140

Ser Thr Leu Thr Ser Glu Pro Arg Ser Ser Phe Arg Glu Ile Phe Thr
145                 150                 155                 160

Phe Thr His Glu Lys His Phe His Arg Thr Met Leu Ala Phe Trp Asn
                165                 170                 175

Gln Val Met Gln Gln Ile Ser Gly Ile Asn Leu Ile Thr Tyr Tyr Ala
            180                 185                 190

Gly Thr Ile Tyr Glu Asn Ser Ile Gly Leu Thr Pro Met Lys Ala Lys
        195                 200                 205

Ile Leu Ala Ala Cys Asn Gly Thr Glu Tyr Phe Met Ala Ala Trp Val
210                 215                 220

Ala Phe Tyr Thr Ile Glu Arg Leu Gly Arg Arg Lys Leu Met Leu Ile
225                 230                 235                 240

Gly Ala Val Gly Gln Ala Ile Thr Met Ala Ile Leu Thr Gly Thr Ala
                245                 250                 255

His Ala Ala Asp Asn Ala Asn Ser Lys Gly Gly Ile Ala Ala Ala Val
            260                 265                 270

Phe Leu Phe Val Phe Asn Thr Phe Phe Gly Ile Gly Trp Leu Gly Met
        275                 280                 285

Thr Trp Leu Tyr Pro Ala Glu Ile Val Ser Leu Gln Val Arg Ala Pro
290                 295                 300

Ala Asn Gly Leu Ser Thr Ala Gly Asn Trp Ile Ala Asn Phe Leu Val
305                 310                 315                 320

Val Met Ile Thr Pro Ile Ala Phe Asn Asn Ile Gly Ala Tyr Thr Tyr
                325                 330                 335

Leu Val Phe Ala Val Ile Asn Ala Val Met Val Pro Thr Val Tyr Phe
```

|  | 340 |  |  | 345 |  |  | 350 |  |  |  |
| --- | --- | --- | --- | --- | --- | --- | --- | --- | --- | --- |

Phe Tyr Pro Glu Thr Ser Gly Arg Ser Leu Glu Glu Ile Asp Asp Ile
355 360 365

Phe Ala Gln Ser Asn Ser Trp Thr Pro Trp Asp Val Val Gly Ile Ala
370 375 380

Asn Arg Met Pro Lys His His Thr Asp Val Asn Glu Ile Gly Val Glu
385 390 395 400

Glu Asn Gly Lys Ala Tyr Leu Lys His Arg Thr Ser Ser Gln Gly Asp
405 410 415

Glu His Asp Glu Lys Val Gly Arg Phe Glu Thr Gly Ser Gly Ser Glu
420 425 430

Ser Ser Pro Gly Val Ala Gly Glu Ile Asn Asp
435 440

<210> SEQ ID NO 65
<211> LENGTH: 1712
<212> TYPE: DNA
<213> ORGANISM: Lipomyces starkeyi
<220> FEATURE:
<221> NAME/KEY: Intron
<222> LOCATION: (86)..(136)
<220> FEATURE:
<221> NAME/KEY: Intron
<222> LOCATION: (576)..(626)

<400> SEQUENCE: 65

```
atgtcaaagc gataccacgg actacggggc catatgctca acaaagccat cgccaccatt      60
gctggtatcg gtttcctact gtttggttac tatccccgtt tgatccctag atatgcattg     120
cagctaacaa tttccaggat acgatcaggg cgtaatgggg agcttgctca cgctcaagac     180
attcaccggg accttcccgt ccttggatac cagtaatggt cttccggcat cggttcgttc     240
gcacaattcc actattcagg gaactgcagt cgctctctac gaaatcggat gcatgatggg     300
cgcattgaca accatgtggc ttggcgacaa gcttggtaga cggaagatta tctttatcgg     360
cgcctttgtt atgattgtgg aactgcgat tcagtgttcc tcctttaccc tggcgcagtt     420
tattgtcggg agaattatta ctggatacg taatggctac atcactgcca ctgttccaat     480
gtggcagtcc gagtgcgcaa aagcagaatc ccgaggaaaa ttggtcatgg tccagggtgc     540
attgattacc ggtggtatcg ccatttccta ctggtctgtc ccgttttcc cctcgatat      600
gcattatagc taacaatttt tgtaggattg actttggctt ctactttgtt gataacgaag     660
tcaattggcg attcccaatc gcgtttcaag ctatttttgc gatcattcta ctatgcactg     720
tccttcaatt gccggaatct ccgcgatggt tgattcgtca cggtaatgag caggaggcaa     780
aatatgtctt ttctgccctc gcggatgttg acatcaccca tccccttatc gatgagcaag     840
taaacgagat taaggcgacc atcacagcgg agcaccaggg cagaatccgg gaaatattca     900
cgttcactaa gaagaagcac ttccatcgca ctatgcttgc tttttggaat caggccatgc     960
agcaagtgac tggtattaat ctcattacat actacgccgc gacgatttac gagaactcaa    1020
ttgggttgtc accactgaat tcgaaaatct tagctgcagc aaatggaaca gagtatttca    1080
ttgtatcatg gatcgcgttc ttcactatcg aacgaattgg ccgtcgcaaa ctgatgttgt    1140
tcggcgcaat gggacaagct gctactatgg ctatgcttac cggcactgcg catgcagctg    1200
acagaggaaa cagccaagcc ggtattgctg ctgctgcctt tctcttcgtg tttaatacgt    1260
tcttcgcaat cggatggctg gaatgacat ggctttatcc cgctgaaatc gtatcgctgc    1320
aggtccgtgc accggcgaac ggcctttcga ccgcagcgaa ttggattttc aactttatgg    1380
```

```
ttgtcatgat cacaccggtc gcgttcaaca gcattggagc gtacacgtac ttggtattcg   1440
ctgtcatcaa tgcgataatg gtaccctgtg tctacctatt ctatccggag accgccggcc   1500
gttcgctcga agagattgac gagatcttcg agaaaagcaa tccctggacg ccctgggacg   1560
tcgtcggcat cgcaagtaaa ttaccacgcc atcatattga tgttcttgaa atcgtagatg   1620
agcaacacga tatagaggcc ggcgtcaaga gaagacatcc acacggtgca gcagatcaag   1680
agaagccggt tgtattgcat tctgaagtat aa                                 1712
```

<210> SEQ ID NO 66
<211> LENGTH: 535
<212> TYPE: PRT
<213> ORGANISM: Lipomyces starkeyi

<400> SEQUENCE: 66

```
Met Ser Lys Arg Tyr His Gly Leu Arg Gly His Met Leu Asn Lys Ala
1               5                   10                  15

Ile Ala Thr Ile Ala Gly Ile Gly Phe Leu Leu Phe Gly Tyr Asp Gln
            20                  25                  30

Gly Val Met Gly Ser Leu Leu Thr Leu Lys Thr Phe Thr Gly Thr Phe
        35                  40                  45

Pro Ser Leu Asp Thr Ser Asn Gly Leu Ser Ala Ser Val Arg Ser His
    50                  55                  60

Asn Ser Thr Ile Gln Gly Thr Ala Val Ala Leu Tyr Glu Ile Gly Cys
65                  70                  75                  80

Met Met Gly Ala Leu Thr Thr Met Trp Leu Gly Asp Lys Leu Gly Arg
                85                  90                  95

Arg Lys Ile Ile Phe Ile Gly Ala Phe Val Met Ile Val Gly Thr Ala
            100                 105                 110

Ile Gln Cys Ser Ser Phe Thr Leu Ala Gln Phe Ile Val Gly Arg Ile
        115                 120                 125

Ile Thr Gly Tyr Gly Asn Gly Tyr Ile Thr Ala Thr Val Pro Met Trp
    130                 135                 140

Gln Ser Glu Cys Ala Lys Ala Glu Ser Arg Gly Lys Leu Val Met Val
145                 150                 155                 160

Gln Gly Ala Leu Ile Thr Gly Gly Ile Ala Ile Ser Tyr Trp Ile Asp
                165                 170                 175

Phe Gly Phe Tyr Phe Val Asp Asn Glu Val Asn Trp Arg Phe Pro Ile
            180                 185                 190

Ala Phe Gln Ala Ile Phe Ala Ile Ile Leu Leu Cys Thr Val Leu Gln
        195                 200                 205

Leu Pro Glu Ser Pro Arg Trp Leu Ile Arg His Gly Asn Glu Gln Glu
    210                 215                 220

Ala Lys Tyr Val Phe Ser Ala Leu Ala Asp Val Asp Ile Thr His Pro
225                 230                 235                 240

Leu Ile Asp Glu Gln Val Asn Glu Ile Lys Ala Thr Ile Thr Ala Glu
                245                 250                 255

His Gln Gly Arg Ile Arg Glu Ile Phe Thr Phe Thr Lys Lys Lys His
            260                 265                 270

Phe His Arg Thr Met Leu Ala Phe Trp Asn Gln Ala Met Gln Gln Val
        275                 280                 285

Thr Gly Ile Asn Leu Ile Thr Tyr Tyr Ala Ala Thr Ile Tyr Glu Asn
    290                 295                 300

Ser Ile Gly Leu Ser Pro Leu Asn Ser Lys Ile Leu Ala Ala Ala Asn
```

```
            305                 310                 315                 320
Gly Thr Glu Tyr Phe Ile Val Ser Trp Ile Ala Phe Phe Thr Ile Glu
                325                 330                 335

Arg Ile Gly Arg Arg Lys Leu Met Leu Phe Gly Ala Met Gly Gln Ala
                340                 345                 350

Ala Thr Met Ala Met Leu Thr Gly Thr Ala His Ala Ala Asp Arg Gly
                355                 360                 365

Asn Ser Gln Ala Gly Ile Ala Ala Ala Ala Phe Leu Phe Val Phe Asn
            370                 375                 380

Thr Phe Phe Ala Ile Gly Trp Leu Gly Met Thr Trp Leu Tyr Pro Ala
385                 390                 395                 400

Glu Ile Val Ser Leu Gln Val Arg Ala Pro Ala Asn Gly Leu Ser Thr
                405                 410                 415

Ala Ala Asn Trp Ile Phe Asn Phe Met Val Val Met Ile Thr Pro Val
                420                 425                 430

Ala Phe Asn Ser Ile Gly Ala Tyr Thr Tyr Leu Val Phe Ala Val Ile
                435                 440                 445

Asn Ala Ile Met Val Pro Cys Val Tyr Leu Phe Tyr Pro Glu Thr Ala
            450                 455                 460

Gly Arg Ser Leu Glu Glu Ile Asp Glu Ile Phe Glu Lys Ser Asn Pro
465                 470                 475                 480

Trp Thr Pro Trp Asp Val Val Gly Ile Ala Ser Lys Leu Pro Arg His
                485                 490                 495

His Ile Asp Val Leu Glu Ile Val Asp Glu Gln His Asp Ile Glu Ala
                500                 505                 510

Gly Val Lys Arg Arg His Pro His Gly Ala Ala Asp Gln Glu Lys Pro
            515                 520                 525

Val Val Leu His Ser Glu Val
            530                 535

<210> SEQ ID NO 67
<211> LENGTH: 1134
<212> TYPE: DNA
<213> ORGANISM: Lipomyces starkeyi

<400> SEQUENCE: 67
atggaaaagg cgagtgctag ccatggactt gcgagaacgg gcatgtctag taccgaagac      60
agtaactgct cgtctactcc agcatctgac ttctcctcga aggggccgta taagcatgat     120
caatcacctg ctcgcatggt ggaccatgaa gacttcctta ctcgtcctga tattcgcggc     180
gatgacgagg aagaaataga agctgaggag agacgccgcc gcgtcaaggt gtcactgtac     240
aagcagtttc gtcgagatat tcgagagccg ctttctgaga tgcttggtag tgctcttctt     300
atcattatcg gagatggtgc tgtggctcag gcattgttgt cgaattatca gatgggtaac     360
gaggtcacta tcaacctgtg cttcggcttt ggtcttacta tgggctatct tacagcaatc     420
actggcggag cagcaggaca tctgaaccca gctattacac tgacgaactg tattttccga     480
ggatttccgt ggtggaaact gccaatttat gttttggcgc aggtagtggg atgtggcgtc     540
ggcgctgctt tgtgtcttcg catttatagg aatgcgatta ctgcctacga tggaggccaa     600
cgacaggtga ctggtccttt gaggacagct ggtatttact gcacatatcc ggttagcttt     660
cttgacttgc ccgtcgtgc aatgcaggag ttcttcgcga ctattgtttt ggtgttcttc     720
gtaaatgcta tcgcatgcca gtcctccccg catttgcctt acaagcttcc tgtggaatgg     780
aatctggtcc gtgcgctggt gcttggactt tcattgtatg gtatcggagc ctcccttggt     840
```

-continued

```
tggcagactg gatatgctat caatcctgct cgtgattttg gacctcgatt agtttcatac    900
atggctggat atggacgcga agttttcaca acagctggtc attacttctg gattcctata    960
gtgatgccct gtgtgggtgc cattacggga caattacttt tcgatttcat ggtgtatgaa   1020
ggcgaacacg ataatttcgt cacgaatccc gaggtggcag tcaaaagatt aaaggagaat   1080
gtggtaggaa gtaagaaaag gtcggaggcc gatattgaga tgaggggata ttga         1134

<210> SEQ ID NO 68
<211> LENGTH: 377
<212> TYPE: PRT
<213> ORGANISM: Lipomyces starkeyi

<400> SEQUENCE: 68
```

Met Glu Lys Ala Ser Ala Ser His Gly Leu Ala Arg Thr Gly Met Ser
1               5                   10                  15

Ser Thr Glu Asp Ser Asn Cys Ser Ser Thr Pro Ala Ser Asp Phe Ser
            20                  25                  30

Ser Lys Gly Pro Tyr Lys His Asp Gln Ser Pro Ala Arg Met Val Asp
        35                  40                  45

His Glu Asp Phe Leu Thr Arg Pro Asp Ile Arg Gly Asp Glu Glu
    50                  55                  60

Glu Ile Glu Ala Glu Arg Arg Arg Val Lys Val Ser Leu Tyr
65                  70                  75                  80

Lys Gln Phe Arg Arg Asp Ile Arg Glu Pro Leu Ser Glu Met Leu Gly
                85                  90                  95

Ser Ala Leu Leu Ile Ile Ile Gly Asp Gly Ala Val Ala Gln Ala Leu
            100                 105                 110

Leu Ser Asn Tyr Gln Met Gly Asn Glu Val Thr Ile Asn Leu Cys Phe
        115                 120                 125

Gly Phe Gly Leu Thr Met Gly Tyr Leu Thr Ala Ile Thr Gly Gly Ala
    130                 135                 140

Ala Gly His Leu Asn Pro Ala Ile Thr Leu Thr Asn Cys Ile Phe Arg
145                 150                 155                 160

Gly Phe Pro Trp Trp Lys Leu Pro Ile Tyr Val Leu Ala Gln Val Val
                165                 170                 175

Gly Cys Gly Val Gly Ala Ala Cys Val Phe Gly Ile Tyr Arg Asn Ala
            180                 185                 190

Ile Thr Ala Tyr Asp Gly Gly Gln Arg Gln Val Thr Gly Pro Leu Arg
        195                 200                 205

Thr Ala Gly Ile Tyr Cys Thr Tyr Pro Val Ser Phe Leu Asp Leu Pro
    210                 215                 220

Gly Arg Ala Met Gln Glu Phe Phe Ala Thr Ile Val Leu Val Phe Phe
225                 230                 235                 240

Val Asn Ala Ile Ala Cys Gln Ser Ser Pro His Leu Pro Tyr Lys Leu
                245                 250                 255

Pro Val Glu Trp Asn Leu Val Arg Ala Leu Val Leu Gly Leu Ser Leu
            260                 265                 270

Tyr Gly Ile Gly Ala Ser Leu Gly Trp Gln Thr Gly Tyr Ala Ile Asn
        275                 280                 285

Pro Ala Arg Asp Phe Gly Pro Arg Leu Val Ser Tyr Met Ala Gly Tyr
    290                 295                 300

Gly Arg Glu Val Phe Thr Thr Ala Gly His Tyr Phe Trp Ile Pro Ile
305                 310                 315                 320

```
Val Met Pro Cys Val Gly Ala Ile Thr Gly Gln Leu Leu Phe Asp Phe
            325                 330                 335

Met Val Tyr Glu Gly Glu His Asp Asn Phe Val Thr Asn Pro Glu Val
        340                 345                 350

Ala Val Lys Arg Leu Lys Glu Asn Val Val Gly Ser Lys Lys Arg Ser
        355                 360                 365

Glu Ala Asp Ile Glu Met Arg Gly Tyr
        370                 375

<210> SEQ ID NO 69
<211> LENGTH: 2199
<212> TYPE: DNA
<213> ORGANISM: Lipomyces starkeyi
<220> FEATURE:
<221> NAME/KEY: Intron
<222> LOCATION: (408)..(459)

<400> SEQUENCE: 69
tggactcgaa agtgtccgcg cgcgcggcag cacttgccgg ccatctctcc atgagaaatt      60
cgtcggccga gagcaaggat acgtctatcc ttggacttgg aaatccaatg gcatctatgg     120
ccgtggaacg cacaaaggcg tcattcccga ttcgtgagct cacctatttt ctcgatggcg     180
gcaaggagat gaccgcagta aaggagcgaa tgatgactga gctggaacgt gatccggtct     240
tccaaaacgt ggactttat gatcttacaa aggaacaatt acgcgagcgt actatgtcta      300
aaattgccag gttgatccat tatatcacgt ctgagcggga ggaaatttca cacttgcggt     360
tttcgctcgt tggcctcatc gatatggggtt tgctcaccag aacagggtaa gtaagtatct    420
ccttattatt gcattgacgg gtgctaatga aggtgtagtg tccactacgc tttgttcttc     480
ggctctctgc gaggctcggc atcgccgaaa cagttttcgt actggatctc acaaggagcc     540
gccgagatga agggcatggt tggctgcttt tgcatgaccg agctggcgca cggcagcaac     600
gtcgccggtc tcgagactac cgccacattt gacgagcgaa cggacgagtt tatcatccat     660
actccacata tcggcgcaac caagtggtgg ataggtggtg ccgctcatac agcaacacac     720
acggtctgct ttgctagatt gatagtgaag ggtaaagatt acggagtcaa gtcatttgtc     780
gttccactcc gtgatccgaa gacatacgac cttaaaccag gcgtcagcat cggcgacatc     840
ggcaagaaga tgggtcgtga cggcattgat aatggctggg ttcagttctc gtatgtgcga     900
attccacgac agttcatgtt gatgaaacac agcaaagttg accgtcacgg aaatgtcact     960
cagcccccac ttgagcagct tgcgtatggt gcgttggttg ttggccgcgt ctcaatggtc    1020
gccgactcgg ctcagatgag caagcgtttt gtgacgattg ctcttagata cgctgccgtc    1080
agacggcaat ttacgtcgaa gaagggtgaa gttgagacga agattttgga ttacgcatta    1140
catcagcggc gactgctacc gctacttgct cagactttcg cgatgcagtt cagttcggat    1200
gaaatgtcgg ccatgcaccg ggcattgatg cggaagattg attcaactga tcctagtgac    1260
ctgaaggcta tggcggttgt gattgaagag ttgaaggaag tattcaccac tagtgccggt    1320
ttgaaggctt tcactacctg gcttgtgct gagacgattg atcagacgcg tcaggcatgc     1380
ggtgggcatg gatactctgc atatagtggt ttcggacaag catacaatga ctgggttgtg    1440
caatgtacct gggagggaga caataacatt ctcgcgcttt ctgccggccg cggtcttgtt    1500
cagcgctatc tggacgtcca gagaggttcc aaagcccctc cacaaacgga atatctcaac    1560
aagctcgcca gactcaagtt cgcacaggca gggtcgcgcc agattgactc tgccgcggtt    1620
ctttccgaag cttgggaggc tgttgcggct gctgttgtat cgaaggctgg cgaatcattc    1680
```

```
atcgcgctaa gaaagaaagg tctttctgcc gacgaggcat tgaggagac  atcacagcag   1740 cgcttccttg ctgctagaat ccataccaaa tgcttttggg tcttgaagtt ttttgaccgc   1800
atttcctcct ccggaccgga gatcaaaccg gttttgactg atctctctta tctgtatgcg   1860
atgtggtcca tcgagaatga cgccggacta tttctccaag ccgaattctt cacatccgag   1920
caaattgacg acattcgtga actgtgcaac ttatactgcc gcaaagtccg cgagcaggct   1980
gtcccaatta ctgatgcgtt caacttgagt gatttcttca tcaactctgc tatcggcaga   2040
tatgatggca atgtctacga gaattatttt acgcaggtta agaggcagaa tccatcaaag   2100
ccacaagctc catatttcga gaaagtgata aagccgtttg tgcacagggt tgctgaagta   2160
gaagttgatg ctgaggagtt agatgaggat gaggcgtag                          2199
```

<210> SEQ ID NO 70
<211> LENGTH: 715
<212> TYPE: PRT
<213> ORGANISM: Lipomyces starkeyi

<400> SEQUENCE: 70

```
Met Asp Ser Lys Val Ser Ala Arg Ala Ala Leu Ala Gly His Leu
1               5                   10                  15

Ser Met Arg Asn Ser Ser Ala Glu Ser Lys Asp Thr Ser Ile Leu Gly
            20                  25                  30

Leu Gly Asn Pro Met Ala Ser Met Ala Val Glu Arg Thr Lys Ala Ser
        35                  40                  45

Phe Pro Ile Arg Glu Leu Thr Tyr Phe Leu Asp Gly Gly Lys Glu Met
    50                  55                  60

Thr Ala Val Lys Glu Arg Met Met Thr Glu Leu Glu Arg Asp Pro Val
65                  70                  75                  80

Phe Gln Asn Val Asp Phe Tyr Asp Leu Thr Lys Glu Gln Leu Arg Glu
                85                  90                  95

Arg Thr Met Ser Lys Ile Ala Arg Leu Ile His Tyr Ile Thr Ser Glu
            100                 105                 110

Arg Glu Glu Ile Ser His Leu Arg Phe Ser Leu Val Gly Leu Ile Asp
        115                 120                 125

Met Gly Leu Leu Thr Arg Thr Gly Val His Tyr Ala Leu Phe Phe Gly
    130                 135                 140

Ser Leu Arg Gly Ser Ala Ser Pro Lys Gln Phe Ser Tyr Trp Ile Ser
145                 150                 155                 160

Gln Gly Ala Ala Glu Met Lys Gly Met Val Gly Cys Phe Cys Met Thr
                165                 170                 175

Glu Leu Ala His Gly Ser Asn Val Ala Gly Leu Glu Thr Thr Ala Thr
            180                 185                 190

Phe Asp Glu Arg Thr Asp Glu Phe Ile Ile His Thr Pro His Ile Gly
        195                 200                 205

Ala Thr Lys Trp Trp Ile Gly Gly Ala Ala His Thr Ala Thr His Thr
    210                 215                 220

Val Cys Phe Ala Arg Leu Ile Val Lys Gly Lys Asp Tyr Gly Val Lys
225                 230                 235                 240

Ser Phe Val Val Pro Leu Arg Asp Pro Lys Thr Tyr Asp Leu Lys Pro
                245                 250                 255

Gly Val Ser Ile Gly Asp Ile Gly Lys Lys Met Gly Arg Asp Gly Ile
            260                 265                 270

Asp Asn Gly Trp Val Gln Phe Ser Tyr Val Arg Ile Pro Arg Gln Phe
        275                 280                 285
```

```
Met Leu Met Lys His Ser Lys Val Asp Arg His Gly Asn Val Thr Gln
    290                 295                 300
Pro Pro Leu Glu Gln Leu Ala Tyr Gly Ala Leu Val Val Gly Arg Val
305                 310                 315                 320
Ser Met Val Ala Asp Ser Ala Gln Met Ser Lys Arg Phe Val Thr Ile
                325                 330                 335
Ala Leu Arg Tyr Ala Ala Val Arg Arg Gln Phe Thr Ser Lys Lys Gly
            340                 345                 350
Glu Val Glu Thr Lys Ile Leu Asp Tyr Ala Leu His Gln Arg Arg Leu
        355                 360                 365
Leu Pro Leu Leu Ala Gln Thr Phe Ala Met Gln Phe Ser Ser Asp Glu
    370                 375                 380
Met Ser Ala Met His Arg Ala Leu Met Arg Lys Ile Asp Ser Thr Asp
385                 390                 395                 400
Pro Ser Asp Leu Lys Ala Met Ala Val Val Ile Glu Glu Leu Lys Glu
                405                 410                 415
Val Phe Thr Thr Ser Ala Gly Leu Lys Ala Phe Thr Thr Trp Ala Cys
            420                 425                 430
Ala Glu Thr Ile Asp Gln Thr Arg Gln Ala Cys Gly Gly His Gly Tyr
        435                 440                 445
Ser Ala Tyr Ser Gly Phe Gly Gln Ala Tyr Asn Asp Trp Val Val Gln
    450                 455                 460
Cys Thr Trp Glu Gly Asp Asn Asn Ile Leu Ala Leu Ser Ala Gly Arg
465                 470                 475                 480
Gly Leu Val Gln Arg Tyr Leu Asp Val Gln Arg Gly Ser Lys Ala Pro
                485                 490                 495
Pro Gln Thr Glu Tyr Leu Asn Lys Leu Ala Arg Leu Lys Phe Ala Gln
            500                 505                 510
Ala Gly Ser Arg Gln Ile Asp Ser Ala Ala Val Leu Ser Glu Ala Trp
        515                 520                 525
Glu Ala Val Ala Ala Ala Val Val Ser Lys Ala Gly Glu Ser Phe Ile
    530                 535                 540
Ala Leu Arg Lys Lys Gly Leu Ser Ala Asp Glu Ala Phe Glu Glu Thr
545                 550                 555                 560
Ser Gln Gln Arg Phe Leu Ala Ala Arg Ile His Thr Lys Cys Phe Leu
                565                 570                 575
Val Leu Lys Phe Phe Asp Arg Ile Ser Ser Ser Gly Pro Glu Ile Lys
            580                 585                 590
Pro Val Leu Thr Asp Leu Ser Tyr Leu Tyr Ala Met Trp Ser Ile Glu
        595                 600                 605
Asn Asp Ala Gly Leu Phe Leu Gln Ala Glu Phe Phe Thr Ser Glu Gln
    610                 615                 620
Ile Asp Asp Ile Arg Glu Leu Cys Asn Leu Tyr Cys Arg Lys Val Arg
625                 630                 635                 640
Glu Gln Ala Val Pro Ile Thr Asp Ala Phe Asn Leu Ser Asp Phe Phe
                645                 650                 655
Ile Asn Ser Ala Ile Gly Arg Tyr Asp Gly Asn Val Tyr Glu Asn Tyr
            660                 665                 670
Phe Thr Gln Val Lys Arg Gln Asn Pro Ser Lys Pro Gln Ala Pro Tyr
        675                 680                 685
Phe Glu Lys Val Ile Lys Pro Phe Val His Arg Val Ala Glu Val Glu
    690                 695                 700
```

Val Asp Ala Glu Glu Leu Asp Glu Asp Glu Ala
705                 710                 715

<210> SEQ ID NO 71
<211> LENGTH: 2787
<212> TYPE: DNA
<213> ORGANISM: Lipomyces starkeyi
<220> FEATURE:
<221> NAME/KEY: Intron
<222> LOCATION: (182)..(228)
<220> FEATURE:
<221> NAME/KEY: Intron
<222> LOCATION: (2091)..(2142)

<400> SEQUENCE: 71

| | | | | |
|---|---|---|---|---|
| atgccgcacg | aactacgatt | tgacggtcaa | accgttgtca | ttacaggtgc cggcggcggt | 60 |
| ctagggaggg | catacgcttt | atttttcgga | tcccgcggcg | ctaatgttgt cgttaacgat | 120 |
| ttgggctcta | gttccaaggg | cgaaggccac | tcgacaaagg | cagctgacgt tgtagtggaa | 180 |
| ggtgagcttg | cattactgtc | aatgttgtgt | ggaacaattc | taatgtagaa atagaaatta | 240 |
| agaaggctgg | aggaaacgct | gttccgaatt | acgattcggt | cgaattcggt gacagaattg | 300 |
| ttgagaccgc | gattaaagca | ttcggcagcg | tgcatgtgct | aatcaacaat gccggcatac | 360 |
| tgcgtgatat | ctcgttcaag | aacatgaaag | acgcagattg | ggacttgatc caacttgtac | 420 |
| atctcaaggg | cgcgtacaaa | accacgaaag | ccgcctggcc | agtattccgc aaacaaaagt | 480 |
| tcggccgaat | tatcaacact | gcttctgcgg | cgggcttgta | cggaagtttc gggcaggcca | 540 |
| attattcggc | tgcgaaactc | ggattggttg | gattcacaga | gactttggcc aaggaagggg | 600 |
| ccaaatacgg | cattttttgct | aacgtgatag | cgcctatggc | ggccagcaga atgacacaga | 660 |
| cggtcatgcc | cgaggatctg | ttgagcatgc | tgaagcccga | atgggttgtt cctctcgttt | 720 |
| cgtaccttac | acacaaggac | acggacgata | ccggcggaat | ctacgaggtt ggcgcagggt | 780 |
| tcgtttcaaa | gcttcgctgg | gagcgatcaa | atggcgctct | tttcaagact gatgacagtt | 840 |
| tcacacccgc | atcgatcctt | gcgcgatggt | ctgagattca | ggacttcgag tccaaaacac | 900 |
| cacagtaccc | gactggccca | aatgacttca | tgacgcttct | cgagtcggca cgtgaactgc | 960 |
| catccaacaa | acaaggcgac | gtccccgttg | acgtgaagga | caaagtcgtc attgtcaccg | 1020 |
| gctccggcgg | cggtcttggt | cgcgcatacg | ctctttttatt | cgctaagctc ggtgctaagc | 1080 |
| ttgttatcaa | cgatgtcggc | gacccaaatg | gtacggttaa | tgaaattaac aagctctatg | 1140 |
| gcgaaggcac | tgcaatatct | gatcgtcatt | ccgtcgagga | aggagacgca gtcgtcaaga | 1200 |
| cagcagttga | ccactttgga | accgtgcatg | tagtcgtcaa | caatgccgga atcttgcgtg | 1260 |
| acaagtcctt | cgctagtatg | actgacgacc | tgtgggatca | agtcatagcc gtccacttgc | 1320 |
| gcggtacata | taagattacc | aaggcagctt | ggccatactc | cttgaagcaa aaattcggac | 1380 |
| gaatcgtcaa | cactacttcg | acgtctggta | tatacggcaa | ttttggtcag ctaactacg | 1440 |
| ctactgccaa | atgcgcaata | attggcttca | caaaaacaat | tgcattggaa ggaaagaaat | 1500 |
| acaacatttt | cgcgaatgcg | attgccccca | atgctggtac | caatatgact cgtactattt | 1560 |
| tgcctgagga | gattgtgcag | gctttcaagc | cggactatgt | agcgcctctt gccgtcctct | 1620 |
| tgtcctctga | cagggcccct | gttactggcg | aaatctttga | accggctct ggttggatcg | 1680 |
| gaaatacaag | atggcagcgg | accggcggcg | ttggattccc | tgtcgacaag ccgcttacac | 1740 |
| ctgaggccat | ccaggagaat | tgggcgaaga | tcactgactt | tagtgacggc cgtgcgactt | 1800 |
| acccgaagac | cacacaagag | agcatggggtg | cgattctcga | gaatatgtcg aacaaaacct | 1860 |

```
cagtatcatc gtcatcggct tcggagcaga caggccccga ttttcatttc agttatgaaa    1920
ctagagatct aatcctatat aacctcggag ttggtgcgaa ggcgtccgaa ttgaagtacg    1980
tgtttgaagg tgcggatgat ttcacagtct tgcctaccta cggtgttgtt ccatactttg    2040
gcgcatctgg ttcattagac ttcagcgagc ttgttcccaa ctttaacccg gtatggtttt    2100
acccattctc ttcacgacga ttttgatact aactttacta agatgatgct tctccatggc    2160
gagcaatatc tggaaatcaa atcctggcca cttcccacgt cgggtgggag gctcgttttcc   2220
aaagcccgtc taattgaagt tcttgacaag ggcaaggctg cctgcgttat cactggtact    2280
gagacaaatg acgccgagac aggaaagcca gttttctaca atgagtcgac catcgtcctt    2340
cgcggttccg gtggttttgg cggacctagc aagggcaagg accgaggtgc tgctacagct    2400
gccaacactc cgcccaagcg tgcgcccgat ttcgttgctg tagtcaagac tactgaagac    2460
caagcagcca tctatcgatt gtccggcgat tataacccac ttcacattga ccctgagttc    2520
gcggcagtcg gtaagttccc gaaaccaatc ctacacggtc tttgcacgtt tggtattgct    2580
ggaaaacaga tatatgacaa gttcggaatg ttcaagaaca ttaaggttcg tttcgctggt    2640
cacgttttcc cgggcgagac attaaaggtt gagatgtgga agcttggcgg tggcaagatt    2700
attttccaga caactgttat tgaacgaaat acagttgcta tatcgtcggc tgctgtggag    2760
ttaataactg atacatcgaa gttgtag                                        2787
```

<210> SEQ ID NO 72
<211> LENGTH: 870
<212> TYPE: PRT
<213> ORGANISM: Lipomyces starkeyi

<400> SEQUENCE: 72

```
Met Pro His Glu Leu Arg Phe Asp Gly Gln Thr Val Val Ile Thr Gly
 1               5                  10                  15
Ala Gly Gly Leu Gly Arg Ala Tyr Ala Leu Phe Phe Gly Ser Arg
            20                  25                  30
Gly Ala Asn Val Val Asn Asp Leu Gly Ser Ser Lys Gly Glu
        35                  40                  45
Gly His Ser Thr Lys Ala Ala Asp Val Val Glu Glu Ile Glu Ile
    50                  55                  60
Lys Lys Ala Gly Gly Asn Ala Val Pro Asn Tyr Asp Ser Val Glu Phe
65                  70                  75                  80
Gly Asp Arg Ile Val Glu Thr Ala Ile Lys Ala Phe Gly Ser Val His
                85                  90                  95
Val Leu Ile Asn Asn Ala Gly Ile Ser Arg Asp Ile Ser Phe Lys Asn
            100                 105                 110
Met Lys Asp Ala Asp Trp Asp Leu Ile Gln Leu Val His Leu Lys Gly
        115                 120                 125
Ala Tyr Lys Thr Thr Lys Ala Ala Trp Pro Val Phe Arg Lys Gln Lys
    130                 135                 140
Phe Gly Arg Ile Ile Asn Thr Ala Ser Ala Ala Gly Leu Tyr Gly Ser
145                 150                 155                 160
Phe Gly Gln Ala Asn Tyr Ser Ala Ala Lys Leu Gly Leu Val Gly Phe
                165                 170                 175
Thr Glu Thr Leu Ala Lys Glu Gly Ala Lys Tyr Gly Ile Phe Ala Asn
            180                 185                 190
Val Ile Ala Pro Met Ala Ala Ser Arg Met Thr Gln Thr Val Met Pro
        195                 200                 205
```

```
Glu Asp Ser Leu Ser Met Ser Lys Pro Glu Trp Val Pro Leu Val
210                 215                 220

Ser Tyr Leu Thr His Lys Asp Thr Asp Thr Gly Ile Tyr Glu
225                 230                 235                 240

Val Gly Ala Gly Phe Val Ser Lys Leu Arg Trp Glu Arg Ser Asn Gly
            245                 250                 255

Ala Leu Phe Lys Thr Asp Asp Ser Phe Thr Pro Ala Ser Ile Leu Ala
            260                 265                 270

Arg Trp Ser Glu Ile Gln Asp Phe Glu Ser Lys Thr Pro Gln Tyr Pro
        275                 280                 285

Thr Gly Pro Asn Asp Phe Met Thr Leu Leu Glu Ser Ala Arg Glu Ser
290                 295                 300

Pro Ser Asn Lys Gln Gly Asp Val Pro Val Asp Val Lys Asp Lys Val
305                 310                 315                 320

Val Ile Val Thr Gly Ser Gly Gly Leu Gly Arg Ala Tyr Ala Leu
                325                 330                 335

Leu Phe Ala Lys Leu Gly Ala Lys Leu Val Ile Asn Asp Val Gly Asp
            340                 345                 350

Pro Asn Gly Thr Val Asn Glu Ile Asn Lys Leu Tyr Gly Glu Gly Thr
            355                 360                 365

Ala Ile Ser Asp Arg His Ser Val Glu Glu Gly Asp Ala Val Val Lys
370                 375                 380

Thr Ala Val Asp His Phe Gly Thr Val His Val Val Asn Asn Ala
385                 390                 395                 400

Gly Ile Leu Arg Asp Lys Ser Phe Ala Ser Met Thr Asp Asp Ser Trp
            405                 410                 415

Asp Gln Val Ile Ala Val His Leu Arg Gly Thr Tyr Lys Ile Thr Lys
            420                 425                 430

Ala Ala Trp Pro Tyr Phe Leu Lys Gln Lys Phe Gly Arg Ile Val Asn
            435                 440                 445

Thr Thr Ser Thr Ser Gly Ile Tyr Gly Asn Phe Gly Gln Ala Asn Tyr
            450                 455                 460

Ala Thr Ala Lys Cys Ala Ile Ile Gly Phe Thr Lys Thr Ile Ala Leu
465                 470                 475                 480

Glu Gly Lys Lys Tyr Asn Ile Phe Ala Asn Ala Ile Ala Pro Asn Ala
            485                 490                 495

Gly Thr Asn Met Thr Arg Thr Ile Leu Pro Glu Glu Ile Val Gln Ala
            500                 505                 510

Phe Lys Pro Asp Tyr Val Ala Pro Leu Ala Val Leu Leu Ser Ser Asp
            515                 520                 525

Arg Ala Pro Val Thr Gly Glu Ile Phe Glu Thr Gly Ser Gly Trp Ile
530                 535                 540

Gly Asn Thr Arg Trp Gln Arg Thr Gly Gly Val Gly Phe Pro Val Asp
545                 550                 555                 560

Lys Pro Leu Thr Pro Glu Ala Ile Gln Glu Asn Trp Ala Lys Ile Thr
            565                 570                 575

Asp Phe Ser Asp Gly Arg Ala Thr Tyr Pro Lys Thr Thr Gln Glu Ser
            580                 585                 590

Met Gly Ala Ile Leu Glu Asn Met Ser Asn Lys Thr Ser Val Ser Ser
            595                 600                 605

Ser Ser Ala Ser Glu Gln Thr Gly Pro Asp Phe His Phe Ser Tyr Glu
610                 615                 620

Thr Arg Asp Leu Ile Leu Tyr Asn Leu Gly Val Gly Ala Lys Ala Ser
```

|     |     |     |     |     |     |     |     |     |     |     |     |
| --- | --- | --- | --- | --- | --- | --- | --- | --- | --- | --- | --- |
| 625 |     |     |     | 630 |     |     |     | 635 |     |     | 640 |
| Glu | Leu | Lys | Tyr | Val | Phe | Glu | Gly | Ala | Asp | Asp | Phe | Thr | Val | Leu | Pro |
|     |     |     |     | 645 |     |     |     |     |     | 650 |     |     |     | 655 |     |
| Thr | Tyr | Gly | Val | Val | Pro | Tyr | Phe | Gly | Ala | Ser | Gly | Ser | Leu | Asp | Phe |
|     |     |     |     | 660 |     |     |     |     |     | 665 |     |     |     | 670 |     |
| Ser | Glu | Leu | Val | Pro | Asn | Phe | Asn | Pro | Met | Met | Leu | Leu | His | Gly | Glu |
|     |     |     |     | 675 |     |     |     |     |     | 680 |     |     |     | 685 |     |
| Gln | Tyr | Ser | Glu | Ile | Lys | Ser | Trp | Pro | Leu | Pro | Thr | Ser | Gly | Gly | Arg |
|     |     |     |     | 690 |     |     |     |     |     | 695 |     |     |     | 700 |     |
| Leu | Val | Ser | Lys | Ala | Arg | Leu | Ile | Glu | Val | Leu | Asp | Lys | Gly | Lys | Ala |
| 705 |     |     |     |     |     | 710 |     |     |     |     |     | 715 |     |     | 720 |
| Ala | Cys | Val | Ile | Thr | Gly | Thr | Glu | Thr | Asn | Asp | Ala | Glu | Thr | Gly | Lys |
|     |     |     |     |     |     | 725 |     |     |     |     |     | 730 |     |     | 735 |
| Pro | Val | Phe | Tyr | Asn | Glu | Ser | Thr | Ile | Val | Leu | Arg | Gly | Ser | Gly | Gly |
|     |     |     |     | 740 |     |     |     |     |     | 745 |     |     |     | 750 |     |
| Phe | Gly | Gly | Pro | Ser | Lys | Gly | Lys | Asp | Arg | Gly | Ala | Ala | Thr | Ala | Ala |
|     |     |     |     | 755 |     |     |     |     |     | 760 |     |     |     | 765 |     |
| Asn | Thr | Pro | Pro | Lys | Arg | Ala | Pro | Asp | Phe | Val | Ala | Val | Val | Lys | Thr |
|     |     |     |     | 770 |     |     |     |     |     | 775 |     |     |     | 780 |     |
| Thr | Glu | Asp | Gln | Ala | Ala | Ile | Tyr | Arg | Leu | Ser | Gly | Asp | Tyr | Asn | Pro |
| 785 |     |     |     |     |     | 790 |     |     |     |     |     | 795 |     |     | 800 |
| Leu | His | Ile | Asp | Pro | Glu | Phe | Ala | Ala | Val | Gly | Lys | Phe | Pro | Lys | Pro |
|     |     |     |     |     |     | 805 |     |     |     |     |     | 810 |     |     | 815 |
| Ile | Leu | His | Gly | Leu | Cys | Thr | Phe | Gly | Ile | Ala | Gly | Lys | Gln | Ile | Tyr |
|     |     |     |     |     |     | 820 |     |     |     |     |     | 825 |     |     | 830 |
| Asp | Lys | Phe | Gly | Met | Phe | Lys | Asn | Ile | Lys | Val | Arg | Phe | Ala | Gly | His |
|     |     |     |     |     |     | 835 |     |     |     |     |     | 840 |     |     | 845 |
| Val | Phe | Pro | Gly | Glu | Thr | Leu | Lys | Val | Glu | Met | Trp | Lys | Leu | Gly | Gly |
|     |     |     |     | 850 |     |     |     |     |     | 855 |     |     |     | 860 |     |
| Gly | Lys | Ile | Ile | Phe | Gln |
| 865 |     |     |     |     | 870 |

<210> SEQ ID NO 73
<211> LENGTH: 3759
<212> TYPE: DNA
<213> ORGANISM: Lipomyces starkeyi

<400> SEQUENCE: 73

```
atggatgact cgatggatga ctcgattgaa caagatccat gggtcgagga cgagacattg      60
ttatctcgac cacagaatac cgggccatcg ccgccatttc acacaattat aactggtctt     120
attaatccgg tattgaaggc gtcaaataag aagactggat tcacggagg acctgcgacg      180
aatgtgcgca taacaagatt caaggttcta agtaattata ttcaaagatg gaagcaggaa     240
gttgggaacg atatctaccc gtgctttcgg ctaagtgagt tgctatcaac tctcgttctt     300
gtggggttaa ttgctaattg tattttagtt ctgccatatg tgagtattcg aagatcattg     360
caatggactt gctactaatt ctgagatcaa atcagaaaga caaagagcga caaatgcatg     420
tgatttagct taatctgaag gtctcgccca atattaacga tagataggta cggcttaaaa     480
gaaaaagcaa ttgcgcggtt acttattaag gttattctcg actttacttc tgctagtgtc     540
gggactggat atgttgacct gtcatagatc ctcggcatct cacctgaatc agaagatgcg     600
aactcaatgg tcaactacaa gcttccaggt caatatagag gtgccggcga ctttgcagag     660
cgatgctacg aggtcatcaa gcaacgtcag attagaacag agtatggatc aatgaccatc     720
```

-continued

```
gaagacgtca acggtctatt ggacgaactc agtaagcaca gcaaatcgta tgcctgtagt     780
tgttctgata gcaactatat gtgatgctga tgacgagata gtgatgacca acttccaata     840
ctatctaagt tttatcactt gatgaatgcc gaggagatga agtggttaat ccgagttatt     900
ttacgacgtg agtttgacaa ttaaggaacc ttggctgaat ctaacttgca cagaaatgca     960
cataggtgtt tctgaacgga cattattctc agcatggcat ccaaatgcaa acgaactcta    1020
taatatttcc agcagtctta aacgcgtatg ctgggaactg ttcgatagca attacagact    1080
gtcggacgat gtaagatatc aagcttctga ttacctctac gacgctaata tcaataggcg    1140
aaagatgtga atctgatgag ttgtttccaa ccacagctag cagcttttcc caaagcctcg    1200
tacgatcaag tcataaggag catgaacaaa gagacattct tcatcgaaga gaaactagat    1260
ggagagagaa tccaagtgca catgtctgac tacggaaaag tgttcaagtt ttacagccgt    1320
cgagcaaaag attatacata tctctatggc agctctctag acgataagaa cggtgctctg    1380
acgaagcatc ttcgaggggt gtttgaagaa accgtggaaa agtatgtaaa tggttgagta    1440
ttgaacgggc tttactgacg ttgtatagct gcatattgga tggagaaatg gtgtcctggg    1500
atcccgttga tgaaaagatt gaacccttg gctacttaaa aactgccgcg aatgccgaga    1560 aagaagacg gggcgagtca tatccattat gtgagtatcc ggccttaatc attatcagca    1620
tttactaact gattctaaga ccgcgtattt gacatattgt atgccaacaa caaatcggta    1680
gtgaactact ctttggtaca acgacagttg ctgttacaac gagttgttaa ccccgctcct    1740
acacatttcg aaattcatcc gcatgaagaa gggtcaacga aggaagatat tgaacgacgc    1800
ctgcggcaag tcatagcaga gtcgtacgtg atcatgagta cgcatggtat ttcaaacgct    1860
tatttcatgc aggtctgagg gactggtcat caaattgcct accgcgccat atgttgtgaa    1920
tggcagggag gattcatgga ttaaggtcaa acccgagtac atgctagaat ttggcgaaaa    1980
tttggattgt ctcgttattg gtacgagctt cattgcacat ctgaacccat cgaagactaa    2040
cgcttagtag ggggatatta cgggcaaggc aaacgaggtg agatcctcgc cagtttcctc    2100
tgcggtcttc gagtagaaga cgagcaagat cccgatgcac cacccaaatt ctggtctttc    2160
tgccgagtag gaggtggttt cacagctgca gaatatggaa caattcggca tttaactgac    2220
ggacagtggc aaaaatggga ttcccggcga ccgccactgc agtacatgga gctcgcaggt    2280
gacaagaacg agaaggaaat gccggacgtg tggattctgc ccgagaaatc cgttgtgctg    2340
gagattaagg ctgcgagtgt cgtacccgag tctgaacagt accggacgaa tgttacgctg    2400
aggtttccgc ggttcagacg aatacgacaa gataagaatt atcttactgc gttgtcgttg    2460
aaggaattta tgactttgaa ggagcaagct gagactgagt ctcaagagcg gcaattgtat    2520
attctgttga tatgcactat ttggaccggt actgataata tcctagggaa ttggaggagc    2580
acagacgaac ttccaaacgg cccaagaagg tagactatta tatatatcta tatggagcaa    2640
ctagaattga ctgagagcag caactaagaa ttttaggagg caacgagacg gtggttctgg    2700
aaggcgctcc tacgagtcaa attttgatg gccatatctt ctgtacgtat aacaatgtgc    2760
taatgatcga catttgccaa tctgggatgt ataggtgtgt tgttgattc taaacgaaaa    2820 accgagctgc agaagatcat catcagtcac ggcgggacca caattcaaga tgtacccgcc    2880
ggacctcaga atatgacaca cgttatagcc gacaaagatc ttgtcaaaat cgcgagtctt    2940
aagaggcagg ggaagtggaa tattatcaga ccgacgtgga ttcaggactg tgttttcaat    3000
cagaggattg ttccatacga gccgaggtca gctttaggtt ttcatgaata ggttgctagg    3060
tgtgcttgtg ctgacgagat ggtaggcatg tatattttgc cacggaaggt ttgcttgaag    3120
```

```
cagttcgacg acacgtggat ccgtacggag atagttacac tcggtcaatg gaagatatca    3180
aagaattgcg agatatgctc aaccttatgc ccgatccaag tatcgacgct atcgcaaaag    3240
aatatgacat tttactcagc gaatctgact cgtcgtttta taacattccg agcttgatat    3300
tctacaatac tgtgatgtat ctcgacgagc cagatcttcc atcgagcgag aatctaccgc    3360
ggcattcgca cgattcatct gcaactttca ggtatttctc ttcacaccaa tacaaaaaaa    3420
attatgtaaa tgctgatatc tctcaaagac tgcaaattgc ggcaaactac gcaaccttcg    3480
gcggcgcaag actatcggac gacatcaaca gccgagaaat aacacacatt gtcaccatgt    3540
gtgacgcgcc caagaatcga atcacggcta tccgaagtga aatttctttg tgcgtatatt    3600
tttgctgaca gtgggggttg tggaaagagc ctaattgata ttttagtcg cctgagagtg     3660 cctcgcgtgg tatctgtcga atggattgag cagtcttgga agaaactac aaggttgagc     3720 gaagaaggta tgaatataat ctcaaccgta cgtgcctaa                            3759
```

<210> SEQ ID NO 74
<211> LENGTH: 956
<212> TYPE: PRT
<213> ORGANISM: Lipomyces starkeyi

<400> SEQUENCE: 74

```
Met Asp Asp Ser Met Asp Asp Ser Ile Glu Gln Asp Pro Trp Val Glu
1               5                   10                  15

Asp Glu Thr Leu Leu Ser Arg Pro Gln Asn Thr Gly Pro Ser Pro Pro
            20                  25                  30

Phe His Thr Ile Ile Thr Gly Leu Ile Asn Pro Val Leu Lys Ala Ser
        35                  40                  45

Asn Lys Lys Thr Gly Phe His Gly Gly Pro Ala Thr Asn Val Arg Ile
    50                  55                  60

Thr Arg Phe Lys Val Leu Ser Asn Tyr Ile Gln Arg Trp Lys Gln Glu
65                  70                  75                  80

Val Gly Asn Asp Ile Tyr Pro Cys Phe Arg Leu Ile Leu Pro Tyr Thr
                85                  90                  95

Lys Ser Asp Lys Cys Met Tyr Gly Leu Lys Glu Lys Ala Ile Ala Arg
            100                 105                 110

Leu Leu Ile Lys Ile Leu Gly Ile Ser Pro Glu Ser Glu Asp Ala Asn
        115                 120                 125

Ser Met Val Asn Tyr Lys Leu Pro Gly Gln Tyr Arg Gly Ala Gly Asp
    130                 135                 140

Phe Ala Glu Arg Cys Tyr Glu Val Ile Lys Gln Arg Gln Ile Arg Thr
145                 150                 155                 160

Glu Tyr Gly Ser Met Thr Ile Glu Asp Val Asn Gly Leu Leu Asp Glu
                165                 170                 175

Leu Ser Lys His Ser Lys Ser Asp Asp Gln Leu Pro Ile Leu Ser Lys
            180                 185                 190

Phe Tyr His Leu Met Asn Ala Glu Glu Met Lys Trp Leu Ile Arg Val
        195                 200                 205

Ile Leu Arg Gln Met His Ile Gly Val Ser Glu Arg Thr Leu Phe Ser
    210                 215                 220

Ala Trp His Pro Asn Ala Asn Glu Leu Tyr Asn Ile Ser Ser Ser Leu
225                 230                 235                 240

Lys Arg Val Cys Trp Glu Leu Phe Asp Ser Asn Tyr Arg Leu Ser Asp
                245                 250                 255
```

```
Asp Ala Lys Asp Val Asn Leu Met Ser Cys Phe Gln Pro Gln Leu Ala
            260                 265                 270

Ala Phe Pro Lys Ala Ser Tyr Asp Gln Val Ile Arg Ser Met Asn Lys
            275                 280                 285

Glu Thr Phe Phe Ile Glu Glu Lys Leu Asp Gly Glu Arg Ile Gln Val
            290                 295                 300

His Met Ser Asp Tyr Gly Lys Val Phe Lys Phe Tyr Ser Arg Arg Ala
305                 310                 315                 320

Lys Asp Tyr Thr Tyr Leu Tyr Gly Ser Ser Leu Asp Asp Lys Asn Gly
                325                 330                 335

Ala Leu Thr Lys His Leu Arg Gly Val Phe Glu Glu Thr Val Glu Asn
            340                 345                 350

Cys Ile Leu Asp Gly Glu Met Val Ser Trp Asp Pro Val Asp Glu Lys
            355                 360                 365

Ile Glu Pro Phe Gly Tyr Leu Lys Thr Ala Ala Asn Ala Glu Lys Glu
            370                 375                 380

Asp Ala Gly Glu Ser Tyr Pro Leu Tyr Arg Val Phe Asp Ile Leu Tyr
385                 390                 395                 400

Ala Asn Asn Lys Ser Val Val Asn Tyr Ser Leu Val Gln Arg Gln Leu
            405                 410                 415

Leu Leu Gln Arg Val Val Asn Pro Ala Pro Thr His Phe Glu Ile His
            420                 425                 430

Pro His Glu Glu Gly Ser Thr Lys Glu Asp Ile Glu Arg Arg Leu Arg
            435                 440                 445

Gln Val Ile Ala Glu Ser Ser Glu Gly Leu Val Ile Lys Leu Pro Thr
            450                 455                 460

Ala Pro Tyr Val Val Asn Gly Arg Glu Asp Ser Trp Ile Lys Val Lys
465                 470                 475                 480

Pro Glu Tyr Met Leu Glu Phe Gly Glu Asn Leu Asp Cys Leu Val Ile
            485                 490                 495

Gly Gly Tyr Tyr Gly Gln Gly Lys Arg Gly Glu Ile Leu Ala Ser Phe
            500                 505                 510

Leu Cys Gly Leu Arg Val Glu Asp Glu Gln Asp Pro Asp Ala Pro Pro
            515                 520                 525

Lys Phe Trp Ser Phe Cys Arg Val Gly Gly Phe Thr Ala Ala Glu
            530                 535                 540

Tyr Gly Thr Ile Arg His Leu Thr Asp Gly Gln Trp Gln Lys Trp Asp
545                 550                 555                 560

Ser Arg Arg Pro Pro Leu Gln Tyr Met Glu Leu Ala Gly Asp Lys Asn
                565                 570                 575

Glu Lys Glu Met Pro Asp Val Trp Ile Leu Pro Glu Lys Ser Val Val
            580                 585                 590

Leu Glu Ile Lys Ala Ala Ser Val Pro Glu Ser Glu Gln Tyr Arg
            595                 600                 605

Thr Asn Val Thr Leu Arg Phe Pro Arg Phe Arg Ile Arg Gln Asp
            610                 615                 620

Lys Asn Tyr Leu Thr Ala Leu Ser Leu Lys Glu Phe Met Thr Leu Lys
625                 630                 635                 640

Glu Gln Ala Glu Thr Glu Ser Gln Glu Arg Gln Leu Glu Leu Glu Glu
                645                 650                 655

His Arg Arg Thr Ser Lys Arg Pro Lys Lys Gln Leu Arg Ile Leu Gly
                660                 665                 670

Gly Asn Glu Thr Val Val Leu Glu Gly Ala Pro Thr Ser Gln Ile Phe
```

```
                675                 680                 685
Asp Gly His Ile Phe Cys Val Phe Val Asp Ser Lys Arg Lys Thr Glu
            690                 695                 700

Leu Gln Lys Ile Ile Ile Ser His Gly Gly Thr Thr Ile Gln Asp Val
705                 710                 715                 720

Pro Ala Gly Pro Gln Asn Met Thr His Val Ile Ala Asp Lys Asp Leu
                725                 730                 735

Val Lys Ile Ala Ser Leu Lys Arg Gln Gly Lys Trp Asn Ile Ile Arg
            740                 745                 750

Pro Thr Trp Ile Gln Asp Cys Val Phe Asn Gln Arg Ile Val Pro Tyr
                755                 760                 765

Glu Pro Arg His Val Tyr Phe Ala Thr Glu Gly Leu Leu Glu Ala Val
770                 775                 780

Arg Arg His Val Asp Pro Tyr Gly Asp Ser Tyr Thr Arg Ser Met Glu
785                 790                 795                 800

Asp Ile Lys Glu Leu Arg Asp Met Leu Asn Leu Met Pro Asp Pro Ser
                805                 810                 815

Ile Asp Ala Ile Ala Lys Glu Tyr Asp Ile Leu Leu Ser Glu Ser Asp
            820                 825                 830

Ser Ser Phe Tyr Asn Ile Pro Ser Leu Ile Phe Tyr Asn Thr Val Met
            835                 840                 845

Tyr Leu Asp Glu Pro Asp Leu Pro Ser Ser Gly Asn Leu Pro Arg His
850                 855                 860

Ser His Asp Ser Ser Ala Thr Phe Arg Leu Gln Ile Ala Ala Asn Tyr
865                 870                 875                 880

Ala Thr Phe Gly Gly Ala Arg Leu Ser Asp Asp Ile Asn Ser Arg Glu
                885                 890                 895

Ile Thr His Ile Val Thr Met Cys Asp Ala Pro Lys Asn Arg Ile Thr
            900                 905                 910

Ala Ile Arg Ser Glu Ile Ser Phe Arg Leu Arg Val Pro Arg Val Val
            915                 920                 925

Ser Val Glu Trp Ile Glu Gln Ser Trp Lys Gly Thr Thr Arg Leu Ser
        930                 935                 940

Glu Glu Gly Met Asn Ile Ile Ser Thr Val Arg Ala
945                 950                 955
```

<210> SEQ ID NO 75
<211> LENGTH: 1000
<212> TYPE: DNA
<213> ORGANISM: Lipomyces starkeyi

<400> SEQUENCE: 75

```
tcaaaaccta gacagcggct ctacggtcaa atcaaaacac atcactctgt agtgtccaac      60
gtcagtcgga taactaggca gctgagcaag tgaatgggct gtatgtctct gagataatgt     120
cggccagctt agctagcagt agcagccagt agagtgtttg tgcgttgcat ggaggcaaat     180
ctcgcaccag actaggacta cagagctgag aaggatgaag tcggcaatca gaggattagc     240
tctatcgcat ctcaatcaaa tgcaacagca gacggacgcc acacggggcc aagaccgcaa     300
aggctaggaa actgtcgaaa attgtgcccg cgaaggcttc tgccggggta gccgagagcg     360
tatgtaatat gatactactg agaggaagtt ccagtcgctc caaatgggtt gggtcggtgc     420
ggcggtcggc gaaagcggca atcgccaccg gttgctctag acggcaacaa agatgccagt     480
ctgagcgacc gtgccgagag tttcttccgc agtgatagtc ggcgcgtaga cgtgggcacg     540
```

```
cgctatcgcc cgcattttcg tgtgcttgcc ctataacgcc tgccgccacg caaaaaaaca      600
agccgcggta cccggccgtt gtttgtttat gtgctggcca ggaccgggtt aggtcgctcc      660
cccgggccgc ccaatcgcag cgaacagcag tcggcgccga ctcgttcccc tccagtagca      720
ccgtagcaga ctctgtcccc ggctcggccg cgccgccaac gctcgtatat attcccgcga      780
ctcgcccggc ccactcttgt ttctttcttc tcttactctc cctccgtccc ttcccgtccg      840
tcggttttgt tcatttcgtt cgcgcttgcc attccgcgat cgtttccctt tcgtttttg      900 tttgtctgtg attttccgt agctacgcgc gcaggagggt gccgtgtttg cttcctaata      960
ccgcaacaat agtcttaatc tgttaattac caccacaaca                          1000
```

<210> SEQ ID NO 76
<211> LENGTH: 1000
<212> TYPE: DNA
<213> ORGANISM: Lipomyces starkeyi

<400> SEQUENCE: 76

```
cacacttcag tgggcagacg acatggctag tacggctcgg cgccggacac ggaagagcag       60
gccgaaacgc gtgacctggg aaagtcggcg cccacggatg gtgctgctgc gactccggcg      120
gaatcgttcg tgtcgcgctg aatcaagctc agcacagaca cggggtgctg gcagtctggg      180
taagaagaat atttctcttt tgagtctccc ttaacagcag cgcacacaat acaaaaacag      240
tcgacatcta acgccgcggc ccttaaagcg gtgcctctct cgagactgtg tcgagcttat      300
gtcgaccatg tccgtgttgc gatcacgacc agtaggtacc gcaggcagcg tatcgaccaa      360
gttctgtctg gccacgagga atcccgtctc gcatgctacg cgctgtctgt cgagcgtgtc      420
gtaatattac tgtcccgtgt gttgtgcggg gggtggggga ggaactttcc tgtcgtttgt      480
gtgcacgaca cagagtgcct ttacagatct gtgggtattg gcgtgtcggc atcgcttccg      540
gacttctcat tggatccccc aacggttctg ccttacccgg ccggctcaat ccgacactca      600
gcaaataaga gccgtcctct ctttgcttct tcatttccgc tgctcctcgt tgcgtcttct      660
cgtcttccta cacatatccc tctccccatc ctcttttcgt cgtactacct cgtctacaaa      720
tatgcctgct ccttcgcgaa ttgctacgtc tttcgtccgc gcctcccagc gccctttggc      780
tgcgtcctat ctcagggccg cgcgcctcta ctccacggcg aaggaacctg tacgttgctc      840
tcactataaa ttttattcta gacaattgat ccacgccgct tctgtgtttg gcatcatgca      900
tgctcttctc gtcacagcaa tccgtcgaga tcaaattgct cttgttttgc ctccattcg     960 gccgattacc acttctgtac taacacatca ctcgttctag                         1000
```

<210> SEQ ID NO 77
<211> LENGTH: 678
<212> TYPE: DNA
<213> ORGANISM: Lipomyces starkeyi

<400> SEQUENCE: 77

```
atttatgtta ccggtggttt tttatttaaa ttttgtgtag tattaataac ggttggcaca       60
ataagcttgt gccactatta taattattat tgttaaattg ttattgttat taaattgtta      120
ttattattac atcatggacg gagttaaaag atattctgct cagtgggctc ggaggaacgg      180
ggggtcggtt gccctccagg cggacctaac cagtcatgag ccaactaact tccttgttag      240
aaggccatta gcggagccgc agtgtcggca atggctatat ttttgggcaa cggcactaga      300
cggtaggcta gagctgttga gcacgtgaat gaatggtcga gggcagggtg gatccggcaa      360
ttgtccagca agccatgttt ccgatgaggc tcttgcccgg ggaattcgga ttacttaaat      420
```

| | |
|---|---|
| tgtatttcaa ggaacttatg gggtgtggcc ttcccatgtc actctaattt ttttgtgcga | 480 |
| cctaaaggtt gctggggttc gaagctcccg cttgtcgccg caaaccttaa acgcacttcc | 540 |
| gcttcgctca tacatacaaa tacaatagag tggcccctcc tccctcggcc acgttcccat | 600 |
| cttgctgatt ttatctcgct gcctcattga tcccatccac tctattttca cggttttcgt | 660 |
| cgtctcacta cattgatc | 678 |

<210> SEQ ID NO 78
<211> LENGTH: 1000
<212> TYPE: DNA
<213> ORGANISM: Lipomyces starkeyi

<400> SEQUENCE: 78

| | |
|---|---|
| catcaagaat atgcgtaatt tgcaagtcct gtgcacaaag gaagagtagg agcgggctaa | 60 |
| tcgaaggtgc gaaacgttat cagcggtgac gaatagctgt tatcggtcga tagagcgcat | 120 |
| gccggggtcc tcgctcggtc tggcctctct tttcactatt atattagctc tccactagtg | 180 |
| cggagtactg acggttgaca gcttctggtg tcttccatcg tatagacttg aacttgcggg | 240 |
| ctctgtctgc taaatctgtt cttcacattg tatgtcaact acacatactc tttcgataac | 300 |
| ggcttcattc ccgccgacac aagtgtggct ctgcgtgtaa tatacggcga atccgtcgtg | 360 |
| ctccactggc tctgcgcact gacacaagac gagcccttcg tcggtgttgc ggccacgccg | 420 |
| ctgacgcgta tacgccagaa cccgcacaac gtcgattcgt gtaccccga agttaaggtt | 480 |
| tcagtggcgt cgcagacccg aacgaccaga cccgaaataa tgtctgttgc gcagttgtgc | 540 |
| cgtaagtcgc ctcaaactag ttgcgcctcg ccattgatta tctgctcccg atcagcgagg | 600 |
| acggtagttt ctcgaaattg cactgcaacg gagactcagt ctgactccgt atcacgaccg | 660 |
| ccgcaggggc gaaagtttcc ttaccttgtc ctgttctaat atgttcaaag cacagtactg | 720 |
| acaacacgac cttgacactg ttccggacgt cgggtcagcc acagaacgcc actagcgtcg | 780 |
| aggttagccc caatatggtc tagcgccatt cactctgctg ggtctccttg cgctccgtga | 840 |
| ctccctgatt ccgggtcagc tttcagacac ttccgacccg gctaccagta ccgcctactt | 900 |
| tctcaccggt gcctccttct gctacttaat ctctttctcg cccgtcgacg ttttctcct | 960 |
| ctccacagac tacctacgca acctatccac atctttcaca | 1000 |

<210> SEQ ID NO 79
<211> LENGTH: 998
<212> TYPE: DNA
<213> ORGANISM: Lipomyces starkeyi

<400> SEQUENCE: 79

| | |
|---|---|
| ttaatttgct gaagcggttt gcctctggta cgtaagatta cggagctgtc cctttccgcg | 60 |
| ctatcagcca ataccacaca accagcctga atttgtactg catccagcat ttatctcgcg | 120 |
| tgttagtgtg ctatgcccga gaactggcag acagatttca ccacgtaaaa tgtgcagata | 180 |
| ggtgaaaggt ccaaatcaac cgtctgaccg gtagatccgg ctcggtcggg aacgaacgat | 240 |
| gatgacgata gtgttgcgga tgctgaataa ttattgtctg cggcatatgt ggccactggc | 300 |
| aaaaccgccg ccccatcatg agtccttgca ctgcggaatg ctcatcattt taatccgcgg | 360 |
| agcaaatttt tctctggtgg tcaggctgcg tagtaattag ctggggtgct ctgtgcgtca | 420 |
| tagcaaggct ggctgcgggc caatcatatt cccgtatgct ggggcgcgcc agacgaacgt | 480 |
| cacccgtggc tggcggtgtg gcgctggcgg cgcatagacg tggcggtgcg tagtttatca | 540 |

```
ccttgctggg taccgtcagc ttgtctacct gctggacctc gggtaatcat ggcctgaaga    600
tagggcaaca gtatagtcgg acggaagcta ctgcgtgcgt gcatcacgac tagaaacaga    660
attaaagaaa atggtgacgt ctgggaatag ctgctattgg gaagtgaacg gcggaggctt    720
gtttgggcaa tgatgctatg tacgcagtac gctggaagcg gtgagaataa taatggcttg    780
gtctgtggtt ctcgatgctg ccatccgtac cacacagtac actccagcac gccctcccta    840
cccaccaact cacttctcct ccgtcgctct gcagcttata ataatccgaa ctgccgcccc    900
gacccttcct cttttctccc ttcgcctcag gcattttaat tccatactcc gcccttccca    960
gataaaagtt atctatctta ctctaatcca cattcgca                            998

<210> SEQ ID NO 80
<211> LENGTH: 584
<212> TYPE: DNA
<213> ORGANISM: Lipomyces starkeyi

<400> SEQUENCE: 80
tacatagatg tacaatagat tgtaaataga cgatattcgt agtgagtacg cgacacatct     60
gtttgtaaac aaaccctctc gcaaccgcta ttgttgtcct attattgggc gtgcgatcgt    120
tgggatagtg gctaacgggg ctgtcagctg gtcgcccatt ggcgggacca cttattctgg    180
agagtctgcc ggataatcga tggacatttg ggcgaatcgc gactcaacag ttactgcaca    240
ttgcagactg gccgcacatg tgagcacggc accagtgctg ctcagttgca tggtataata    300
gtcgacagca attggattga catatacaaa aaattacatg acctttttac attgagtttg    360
aaatggaaag catatcaaat aaaagtctag gaaaatgttg agctgccgcg tgttctgccc    420
gtgatgcctg tgcacacgcg gctaacaccg attgcagcgt atgtgtcgtt gcttcggcgt    480
ggtagcaata aatcttgcgc tcgcctctga gtgcctttct attctctcca tctctctact    540
ctcccctcct tcaaccactc tgcgtccgta tcactacagc caac                     584

<210> SEQ ID NO 81
<211> LENGTH: 1000
<212> TYPE: DNA
<213> ORGANISM: Lipomyces starkeyi

<400> SEQUENCE: 81
accattaaga ttcactgtcc ttgatcaccg gcgagatatc gggccatcag ggatgagtgg     60
atataatata ttaatagtgt gaattaggaa tagagcagag gagatgttgt tctcacagca    120
tcactaatgc atagcacaag aatgcggaga atcgcctgt ccgcctgggg caaggggaag    180
cctccgatag tatcattgac cagctgagcc gaccctgagt cgatagagtt ttggcgtgtg    240
gtcaatattc aggtggggcc gagcccttcg ctaagcctca tctattaact ttccttattc    300
ggtcagggct tgagcactgc cagctaaacc ctacatatta catcctaacc ctgggcaata    360
aacagtcaca gcccatatgt gtggctgtgc gagtgcggaa cgtgtcagct cgtgaagcac    420
atggagtgcg aacaggagtt agacgacacc gcacatggaa attagggctg tatcgacact    480
ttattgccac cgccacgacg gcaaattgtg gtcgctgtat ccgcaaaggg gaggccggcc    540
ttgtcagtgg tcagcaatgt agaatagacg tagctggtgg tggacaggct aaccatgggg    600
acagtcgatc tgcattagtg gtccactgag gcaccgggaa gacaaagaca aaaaaatgcg    660
gacgaaaaac attgacgtca gccaaatccg agcgatgttt acgacttccc ttgtcgggca    720
ccggctagtt aatgcaaagt gctggcataa gtgcgcaaac gcaagcgcgg tacgtgcgct    780
gagcgtagag taaaaaaaat tttcttagcc gcgagcctag caacggcgcc aggccgtatc    840
```
tttctataaa gctctgcttc acccgccaca atttccattc cttttcttct ttttttcttt        900
gtctactcac acccgaaatc atagcatttc catctgagta tctttaatct taatcacatc        960
catccactta tcttttatac atcctcttta atctttcaaa                              1000

<210> SEQ ID NO 82
<211> LENGTH: 672
<212> TYPE: DNA
<213> ORGANISM: Lipomyces starkeyi

<400> SEQUENCE: 82
cgcgcataga tcatgactga tgcggggtac cagatcgtgc gttggtccga gctacggacg         60
caaagagaaa caccggtgca tatgcaaatt catgttatag atcatatgtt ggctttggga        120
ttatgaagtg tatcatgtca attgggaact aaggagattg ggtcgcatta tcttttaatt        180
ggtgtatcaa tctaatattt agagagatta tttgagtaca agcatttctt ccgacgctgg        240
ctcatactgg ccgaaggccc gactgagaca tgcattgggg attatcgtct ccagaccact        300
ctcgaggttg actcagaaga agcttccttg gtgtggtgga actcactcgg aaggtgtcgc        360
gctgggtcga gacagtggat atgttgccgg gtggtcgata gcagcgtgtc aaattgtatc        420
cgctgattta ggcaatattc tcgtattgct aataatcgag cttaagtctc cacttctcctc       480 aacaaacagc tcagctttta tatggggtta gggtagtatc ccacggccat ccggccgcac       540
tgacggatgc ctgttccttt ccgtgtgccg cataccccccc gattttttc gttcccaatt       600 ggattcacac tattgcagac gaatacattc gtacactttc ttctaaattt gcatatatta       660
taactattta at                                                           672

<210> SEQ ID NO 83
<211> LENGTH: 399
<212> TYPE: DNA
<213> ORGANISM: Lipomyces starkeyi

<400> SEQUENCE: 83
tgtattcgtt gatagatggg cgttgagtgc acgagaagaa tcgcgagtga acttgttagg         60
cctactctcg aggcggagtg gcgctatgct gaccggcgcc gcatgtgggt gacagcaagg        120
gcatgctgag acgtacgtac ttcgttctca caattactta tagacccaac ggaatgcgcc        180
ttctgcgtca ctgttttctt tcggctgtcc aaccaccacg cagcagagca gccgacgccc        240
cgtgcccaca tctgccgtca tcaggcaacg ttttttcatat ttttaagtcg atccctgctc      300
ttccttcgtc ttccgttccg ccctcgtctc tagagagaat aaaattctata taaacacctt      360 tacgttctgt cgcctcgatt ctcgtcttcg tctagtaca                              399

<210> SEQ ID NO 84
<211> LENGTH: 878
<212> TYPE: DNA
<213> ORGANISM: Lipomyces starkeyi

<400> SEQUENCE: 84
gaggtcagat gggacgagat gagattgtac aataggttaa tattgccgta gctcatggtg         60
attgcatagg ttggttgggt ttgtgctggg ttgacaagtg tattatggaa ttaaatgtat        120
atgatggttt tgtttcgaat tccaaggcgg ctgtgtcact cggggacgat ctcgtcacta        180 aggagaaacat ggcacacgtta cgaggtctga taatttcagg agacgcggga tggcaaccgg      240
tctgataatt atcagattgt ctcgaacaaa gagacagacg catttggtca tcgtatatgg       300

```
ccgatacagt cggcagcgca gttgtcttgt agatctgtcc agactcagga actcgctttt    360
cgctgagttc gatgaattgt gtacgatcgt aatgttaatt tattatgatt tgatatgata    420
gagtgatatg tgacatctca ttcgcgggag caattgccag gcttcaaaat actgggtcgg    480
ctagagtagt ataatcaaaa tcagataaga aagtgtcact ggggagccct ggcttagttt    540
acactttgca caattagcta ctctgtggtt ggccggttaa cttgcttata ataattgctc    600
ttaatatgat tggctggaat tttttcaaca gcgcttcagc caatggatgt gctggcaata    660
gtaagcattt taccgtcagc caccgccgca agggcgagca ctatcaggcg atctctcggc    720
gccgcatgac tcacgggtag gtagactctc tataaagcag tctgttcctc gatcttcagc    780
tagtcatacc aaaaatccta tcatttaata tctcgacttg gctcttaccc tacacaatat    840
actacaacct tcgcttcatt gcttctacta taattaca                            878
```

<210> SEQ ID NO 85
<211> LENGTH: 750
<212> TYPE: DNA
<213> ORGANISM: Lipomyces starkeyi

<400> SEQUENCE: 85

```
acgtttttt  gtgttattgc gcgcttgttt tggaacggca tttgtatgtg acatagtggg     60
ttcattctag cagaaaagct gttttgaaag attatagagg gtgttgacac tttggcggct    120
ggaggaatta tgcgagatag agatgatttc gaatgggagt aatttgggaa aagagttata    180
gtttgatttt cgcttttat ccatataccg gacggacgga attggaaagt attatatgag     240
tatgatacat gtgttaatta ataagtaata tataccgttg tgtttatta  tatgtacttg    300 tcgtttttcc ggttactctt tcgtcgcgtc atctctttat ctcgtacatt cttatgctac    360
ttctcttttg ctacatttac tcgttgtttc gtttattatc cgtcgctcat ttggacattt    420
ctcttgttct cgacttgttt tccgatggaa tgttatcgca ttacgtcccg tgcaagagtc    480
attgattgtt gtactttatc cacacatttt gttacattac acgatctttt cttttcagtt    540
tttgtgtttt ttacataatg taatagactt tctttgcca  tcatgatatc taaaagttac    600
agttatgttg actgaatttt gcccttgagt gcgtgagttt tgtcagtcgt tttaagacat    660
gccattaatg gcggatttac ccagtcgggg gagcctcaca tggccaagag aggaagaaac    720 cttttccacca atgcgggcaa tgtgattggt                                    750
```

<210> SEQ ID NO 86
<211> LENGTH: 300
<212> TYPE: DNA
<213> ORGANISM: Lipomyces starkeyi

<400> SEQUENCE: 86

```
tggaatccat ctaaaatcgt gggaaccgcc agagagaaca gtttctttgt tcgttcaact     60
gcatgtttat gcattttaat caacttcagt tactaagaat aatttttgtgt gtttccttc    120 gctcgttcgt tgctcattac gtgcggtcgg tcgtaatatc gtgtatgtca cttggtccaa    180
atgatccaaa aagattacga attatcgtat aaaacagata gatacatctt taatactaca    240 cccctttgcag ccaattagcg aaaactcgtc aggtccggcg cacgatgacg tcttgccttc    300
```

<210> SEQ ID NO 87
<211> LENGTH: 205
<212> TYPE: DNA
<213> ORGANISM: Lipomyces starkeyi

<400> SEQUENCE: 87

```
atttcttcat ttcttgtatg tgatattagg tgaatgcgtt ggttaagttt ttggtaatgt    60
cacttttgac gtgtttctat aatacataat gttgcgcttg tctttatttc gtgcctagat   120
tgtgagtgct tcatagttgt tcagctccat tgcgttgaga cgtttagtgc ctactttga    180 gcagattttt taagtgtgcg tgtgt                                         205

<210> SEQ ID NO 88
<211> LENGTH: 512
<212> TYPE: DNA
<213> ORGANISM: Lipomyces starkeyi

<400> SEQUENCE: 88
gtgtgcggtt gatggtcttc tatcttccca catttcctca caacatgtat agccgtattc    60
tataataccg aattagacaa aagaatgaat ttgtcttata ttataaacaa agaaattaag   120
tttatgttta tgtcgctagt tatttgggat gttacttgcg gattcagctt gctttgatag   180
tattgcctgg gacgcagatc taatgaaaat tttgtaacac agtataacta ggtgtaatca   240
caaattgccg tttaccgcaa tatatttaaa ttatgactcc aattcatgag gattatggcc   300
cgaatttagt tggtcctagt tatttggtta tcgtaatttt attgaataat gttgaaaacc   360
tggctcgagt gctcgaagtt agttcttcag acagggggctt gggtgtcggg tccgacgcgt   420
cgccggtgga ctagccaccc gccgccgcat cgcgcatcac tacatatcga gatcttaaaa   480
acaactttgt tccaccatca ccacccgcta ca                                 512

<210> SEQ ID NO 89
<211> LENGTH: 1500
<212> TYPE: DNA
<213> ORGANISM: Lipomyces starkeyi

<400> SEQUENCE: 89
acggtcaatg cggtgcaaga tagctctgca attgggtcca gtcggtaaat catatatagt    60
gtcgatcgcg aggatggccg gttgtgcccg attgttgatg tgtttatgtg cttatagact   120
ttgttgttgt ttatgatatg tgtacagcga tttcttatcg cgtgacgttt gtattcgcag   180
gattttgtgc ccttgcttgg atattgcgtg aatcgagcta tgcacggcac tactggtagt   240
gcgaggtgtt tcatggacga tttaaacata caattatttc tcgttgagcc ttgtagatgc   300
aaactaagat tactcacaac gctacgtgcc gggcgacctt atttcctcca tactcttgta   360
agtagtagta tttttggaaga tgtcgctgac ggtaatcgaa tggagttcga ccccaatgac   420
ctgcgttagg ctttcgcaaa gatgctaact tatacaaaaa tatgacaccg agcagcccat   480
gacggtctat ttcacaacta aagaagagtt ggaggcatgg atccaggagc accgtctgta   540
ttgtaagctg cgctagattt attgcgagac agttcttcta ttcaaatgga actttattgg   600
cagcacaatc gacatgaacc agaattaccc agctgtcaaa aaaatggact gatgccaggg   660
tttctcaata ctataacacg cattcctcta aggagctttt gaggttgcgt gaatcagacc   720
ggcaacggta tgcggcggtt aaagttactc tcatatgatg atgattaacg agatggtcta   780
gatgcaggat aaggatagcg atgtgatctt tgcttccctg cgcgttactt ttgtctggag   840
tccatttcat agtaaatcag aatccctgat tataatgggt agctgtgcca agttgtgca    900 tgaaaacgtt gccatgacag gtgttttttgg gcttttgccg atttcattcg cgactgtcat   960
ttggcttaca atcgctgtac catcacaccg aatttgctca ggtgccccat ctttacgtcg  1020
ctgcataaca gggtgttaac aacatcaccg agtagcaaag cataacaggt tcaccccgcc  1080
```

```
aggttgctat cgcttagcaa gctcaacaaa catttcagtg acttcaagga ttcaaaatat    1140
tgaatcaagc tcttaatatc tagtaggcta gttgaagata ctttcagcct tggcagaatt    1200
gtgcggaacg ctgttagttt ctatattggg tacacgtttg cagaagtctg caccaatatt    1260
tgccagaaaa ttagagaggt ttcgcaacca tttttacgcc gcaaatttac aggaaataac    1320
ccttacccac ggttttcaag taaatttggt ctcgtaaatt tacacgattt cgtccatcat    1380
gcgtaaaacc ttaatgccaa atttacgcca attttaaggt tagcgttagc ctgaagaggc    1440
aagcgctaaa ccttcttcta aatatcgagc acattagaat ttacgcgtct tccctaggt     1500

<210> SEQ ID NO 90
<211> LENGTH: 300
<212> TYPE: DNA
<213> ORGANISM: Lipomyces starkeyi

<400> SEQUENCE: 90
aggggcgggt cgattttgtg aaccactgtt ttggacaatg acgagttctc tagagtagtc      60 ccttttgtt aatatagtgt aaagtgtgca tgtttgccag tgcgctattg ccagcaccaa     120
ttgtataacc actccttccg tttcactata tacaacaaag gcaataaatc gatgcaagtt     180
cactagatat aaatacaggt gtatatatta cacgatcaag acgtcgatga taaagtgtaa     240 tatgccccc ccctcttcct ctatggctta atttccactg agaccatatt ttcggcattc     300

<210> SEQ ID NO 91
<211> LENGTH: 4869
<212> TYPE: DNA
<213> ORGANISM: Artificial Sequence
<220> FEATURE:
<223> OTHER INFORMATION: pXC301 Base Vector
<220> FEATURE:
<221> NAME/KEY: Kanamycin-r (rev)
<222> LOCATION: (1)..(810)
<220> FEATURE:
<221> NAME/KEY: KanR Primer II
<222> LOCATION: (237)..(257)
<220> FEATURE:
<221> NAME/KEY: KanR Primer I (rev)
<222> LOCATION: (722)..(743)
<220> FEATURE:
<221> NAME/KEY: P_Amp (rev)
<222> LOCATION: (821)..(938)
<220> FEATURE:
<221> NAME/KEY: Vector Sequencing Primer Reverse
<222> LOCATION: (1064)..(1080)
<220> FEATURE:
<221> NAME/KEY: loxRE
<222> LOCATION: (1215)..(1248)
<220> FEATURE:
<221> NAME/KEY: Forward Primer to Clone Ls TDH3 Pro Term
<222> LOCATION: (1235)..(1274)
<220> FEATURE:
<221> NAME/KEY: LsTDH3 Promoter Primer
<222> LOCATION: (1255)..(1275)
<220> FEATURE:
<221> NAME/KEY: LsTDH3 Promoter
<222> LOCATION: (1255)..(2252)
<220> FEATURE:
<221> NAME/KEY: NAT1 ORF
<222> LOCATION: (2253)..(2822)
<220> FEATURE:
<221> NAME/KEY: NAT1 PCR Primer Forward
<222> LOCATION: (2260)..(2289)
<220> FEATURE:
<221> NAME/KEY: NAT1 Sequencing Primer 5' Reverse (rev)
<222> LOCATION: (2260)..(2289)
<220> FEATURE:
<221> NAME/KEY: NAT1 PCR Primer Reverse  (rev)
<222> LOCATION: (2736)..(2765)
<220> FEATURE:
```

```
<221> NAME/KEY: NAT1 Primer Reverse  (rev)
<222> LOCATION: (2802)..(2822)
<220> FEATURE:
<221> NAME/KEY: LsTDH3 Terminator
<222> LOCATION: (2823)..(3335)
<220> FEATURE:
<221> NAME/KEY: Reverse Primer to Clone Ls TDH3 Pro Term (rev)
<222> LOCATION: (3316)..(3355)
<220> FEATURE:
<221> NAME/KEY: loxLE
<222> LOCATION: (3349)..(3382)
<220> FEATURE:
<221> NAME/KEY: Term_bla (rev)
<222> LOCATION: (3435)..(3735)
<220> FEATURE:
<221> NAME/KEY: Vector Sequencing Primer Forward (rev)
<222> LOCATION: (3526)..(3551)
<220> FEATURE:
<221> NAME/KEY: Term_rpoC (rev)
<222> LOCATION: (3736)..(3855)
<220> FEATURE:
<221> NAME/KEY: Ori_pUC (rev)
<222> LOCATION: (4100)..(4772)

<400> SEQUENCE: 91
ttagaaaaac tcatcgagca tcaaatgaaa ctgcaattta ttcatatcag gattatcaat     60
accatatttt tgaaaaagcc gtttctgtaa tgaaggagaa aactcaccga ggcagttcca    120
taggatggca agatcctggt atcggtctgc gattccgact cgtccaacat caatacaacc    180
tattaatttc ccctcgtcaa aaataaggtt atcaagtgag aaatcaccat gagtgacgac    240
tgaatccggt gagaatggca aaagtttatg catttctttc cagacttgtt caacaggcca    300
gccattacgc tcgtcatcaa aatcactcgc atcaaccaaa ccgttattca ttcgtgattg    360
cgcctgagcg aggcgaaata cgcgatcgct gttaaaagga caattacaaa caggaatcga    420
gtgcaaccgg cgcaggaaca ctgccagcgc atcaacaata ttttcacctg aatcaggata    480
ttcttctaat acctggaacg ctgttttttcc ggggatcgca gtggtgagta accatgcatc    540
atcaggagta cggataaaat gcttgatggt cggaagtggc ataaattccg tcagccagtt    600
tagtctgacc atctcatctg taacatcatt ggcaacgcta cctttgccat gtttcagaaa    660
caactctggc gcatcgggct tcccatacaa gcgatagatt gtcgcacctg attgcccgac    720
attatcgcga gcccatttat acccatataa atcagcatcc atgttggaat ttaatcgcgg    780
cctcgacgtt tcccgttgaa tatggctcat attcttcctt tttcaatatt attgaagcat    840
ttatcagggt tattgtctca tgagcggata catatttgaa tgtatttaga aaaataaaca    900
aataggggtc agtgttacaa ccaattaacc aattctgaac attatcgcga gcccatttat    960
acctgaatat ggctcataac accccttgtt tgcctggcgg cagtagcgcg gtggtcccac   1020
ctgaccccat gccgaactca gaagtgaaac gccgtagcgc cgatggtagt gtggggactc   1080
cccatgcgag agtagggaac tgccaggcat caaataaaac gaaaggctca gtcgaaagac   1140
tgggcctttc gccgggcta attaggggg gtcgcccttc gctgaagcga tcgcggcgcg   1200
cctgcaggcc ggcctaccgt tcgtataatg tatgctatac gaagttatgg atccttaatt   1260
tgctgaagcg gtttgcctct ggtacgtaag attacggagc tgtcccttc cgcgctatca   1320 gccaatacca cacaaccagc ctgaatttgt actgcatcca gcatttatct cgcgtgttag   1380
tgtgctatgc ccgagaactg gcagacagat ttcaccacgt aaaatgtgca gataggtgaa   1440
aggtccaaat caaccgtctg accggtagat ccggctcggt cgggaacgaa cgatgatgac   1500
gatagtgttg cggatgctga ataattattg tctgcgcat atgtggccac tggcaaaacc   1560 gccgcccat catgagtctt gcacctgcgg aatgctcatc attttaatcc gcggagcaaa   1620
```

```
tttttctctg gtggtcaggc tgcgtagtaa ttagctgggg tgctctgtgc gtcatagcaa    1680
ggctggctgc gggccaatca tattcccgta tgctggggcg cgccagacga acgtcacccg    1740
tggctggcgg tgtggcgctg gcggcgcata gacgtggcgg tgcgtagttt atcaccttgc    1800
tgggtaccgt cagcttgtct acctgctgga cctcgggtaa tcatggcctg aagatagggc    1860
aacagtatag tcggacggaa gctactgcgt gcgtgcatca cgactagaaa cagaattaaa    1920
gaaaatggtg acgtctggga atagctgcta ttgggaagtg aacggcggag gcttgtttgg    1980
gcaatgatgc tatgtacgca gtacgctgga agcggtgaga ataataatgg cttggtctgt    2040
ggttctcgat gctgccatcc gtaccacaca gtacactcca gcacgccctc cctacccacc    2100
aactcacttc tcctccgtcg ctctgcagct tataataatc cgaactgccg ccccgaccct    2160 ttctctttt  tcccttcgcc tcaggcattt taattccata ctccgccctt cccagataaa    2220
agttatctat cttactctaa tccacattcg caatgactac tttggatgac actgcataca    2280
gatataggac ttctgtccct ggtgacgctg aagctataga ggcattagat ggctcattca    2340
caacagatac agttttcgt  gtaactgcta ctggtgacgg attcacattg agagaagtcc    2400
cagtcgatcc tccattgacc aaagtgttcc cagatgacga atcagacgat gaatctgatg    2460
ctggtgagga tggagatcca gactcaagaa cattcgttgc atacggagat gatggagatt    2520
tagctggatt tgtcgttgtc agttacagtg gttggaacag gcgtttaacc gtggaagata    2580
ttgaagttgc acccgaacat aggggacacg tgttggtcg  tgccttaatg ggcttagcca    2640
ccgaatttgc aagagaaagg ggagctggtc atttgtggtt agaagttact aatgttaatg    2700
cccctgcaat tcatgcctac aggaggatgg gattcacatt atgcggcttg gatactgcct    2760
tgtatgacgg tacagcttcc gacggcgagc aagctttata catgtccatg ccatgtccat    2820
aagtgtgcgg ttgatggtct tctatcttcc cacatttcct cacaacatgt atagccgtat    2880
tctataatac cgaattagac aaaagaatga atttgtctta tattataaac aaagaaatta    2940
agtttatgtt tatgtcgcta gttatttggg atgttacttg cggattcagc ttgctttgat    3000
agtattgcct gggacgcaga tctaatgaaa attttgtaac acagtataac taggtgtaat    3060
cacaaattgc cgtttaccgc aatatattta aattatgact ccaattcatg aggattatgg    3120
cccgaattta gttggtccta gttatttggt tatcgtaatt ttattgaata atgttgaaaa    3180
cctggctcga gtgctcgaag ttagttcttc agacaggggc ttgggtgtcg ggtccgacgc    3240
gtcgccggtg gactagccac ccgccgccgc atcgcgcatc actacatatc gagatcttaa    3300
aaacaacttt gttccaccat caccacccgc tacatgtcga caccggtgat aacttcgtat    3360
aatgtatgct atacgaacgg tacggaccgc ggcggccgcc taggcgatcg ccgtcaaaag    3420
ggcgacacaa aatttattct aaatgcataa taaatactga taacatctta tagtttgtat    3480
tatattttgt attatcgttg acatgtataa ttttgatatc aaaaactgat tttcccttta    3540
ttattttcga gatttatttt cttaattctc tttaacaaac tagaaatatt gtatatacaa    3600
aaaatcataa ataatagatg aatagtttaa ttataggtgt tcatcaatcg aaaaagcaac    3660
gtatcttatt taaagtgcgt tgcttttttc tcatttataa ggttaaataa ttctcatata    3720
tcaagcaaag tgacaggcgc ccttaaatat tctgacaaat gctctttccc taaactcccc    3780
ccataaaaaa acccgccgaa gcgggttttt acgttatttg cggattaacg attactcgtt    3840 atcgaaccg  cccaggggc  ccgagcttaa gactggccgt cgttttacaa cacagaaaga    3900
gtttgtagaa acgcaaaaag gccatccgtc aggggccttc tgcttagttt gatgcctggc    3960
```

```
agttccctac tctcgccttc cgcttcctcg ctcactgact cgctgcgctc ggtcgttcgg    4020
ctgcggcgag cggtatcagc tcactcaaag gcggtaatac ggttatccac agaatcaggg    4080
gataacgcag gaaagaacat gtgagcaaaa ggccagcaaa aggccaggaa ccgtaaaaag    4140
gccgcgttgc tggcgttttt ccataggctc cgcccccctg acgagcatca caaaaatcga    4200
cgctcaagtc agaggtggcg aaacccgaca ggactataaa gataccaggc gtttccccct    4260
ggaagctccc tcgtgcgctc tcctgttccg accctgccgc ttaccggata cctgtccgcc    4320
tttctcccct cgggaagcgt ggcgctttct catagctcac gctgtaggta tctcagttcg    4380
gtgtaggtcg ttcgctccaa gctgggctgt gtgcacgaac cccccgttca gcccgaccgc    4440
tgcgccttat ccggtaacta tcgtcttgag tccaacccgg taagacacga cttatcgcca    4500
ctggcagcag ccactggtaa caggattagc agagcgaggt atgtaggcgg tgctacagag    4560
ttcttgaagt ggtgggctaa ctacggctac actagaagaa cagtatttgg tatctgcgct    4620
ctgctgaagc cagttacctt cggaaaaaga gttggtagct cttgatccgg caaacaaacc    4680
accgctggta gcggtggttt ttttgtttgc aagcagcaga ttacgcgcag aaaaaaagga    4740
tctcaagaag atcctttgat cttttctacg gggtctgacg ctcagtggaa cgacgcgcgc    4800
gtaactcacg ttaagggatt ttggtcatga gcttgcgccg tcccgtcaag tcagcgtaat    4860
gctctgctt                                                           4869
```

COMPOSITIONS AND METHODS FOR PRODUCING LIPIDS AND OTHER BIOMATERIALS FROM GRAIN ETHANOL STILLAGE AND STILLAGE DERIVATIVES

SEQUENCE LISTING

The instant application contains a Sequence Listing which has been submitted in ASCII format via EFS-Web and is hereby incporated by reference in its entirety. The ASCII copy, created on Aug. 11, 2017, is name USPTO—170817—Nonprovisional_Patent_Application—SEQUENCE_LISTING_ST25.txt and is 401,461 bytes in size.

STATEMENT REGARDING FEDERALLY SPONSERED RESEARCH

This invention was made with Government support under IIP 1520485 and IIP 1632255 awarded by the National Science Foundation. The Government has certain rights in this invention.

FIELD OF THE INVENTION

The invention is directed to engineered yeasts and methods for converting stillage organics into lipids and other biomaterials.

BACKGROUND

Renewable fuels are environmentally desirable, especially fuels with higher energy density such as biodiesel. U.S. biodiesel production capacity however, is underused. From January of 2014 to July 2016, annual production of biodiesel did not exceeded 60% of plant capacity. This was due in part to a lack of inexpensive feedstock supply, which the industry greatly needs as an alternative source of seed oils (Anon 2016).

Plant triglycerides from soybeans, canola, rapeseed and palm oil can be converted into methyl or ethyl esters for use as biodiesel. Biodiesel produced in the U.S. is mainly derived from waste cooking oils, the edible oils of soybean and rapeseed (canola) (Hammond et al. 2005), from the inedible corn oil recovered following fermentation and distillation of grain to ethanol, and with lesser amounts generated from animal fats.

If the U.S. were to use all of its domestic soybeans to make biodiesel, it would result in about 5.1 billion gallons of biofuel. This approach, however, is not realistic because these oilseeds are also key components of the food chain and are used for the production of many household and industrial products. Thus, increasing the production of biodiesel from foodstuffs would lead to higher prices of commodities derived from them, and economic hardship for the consumer.

Biodiesel can be made from the triglycerides generated by oleaginous (lipogenic) yeast or algae. In fact, 2 to 3 times more lipid/g dry weight is generated by these microbial sources than from seed oils. Certain algae can accumulate lipids when cultivated on sunlight and $CO_2$, but fixation of $CO_2$ by photosynthesis requires a great deal of metabolic energy, so cell growth and lipid accumulation is relatively slow. Some algae can grow heterotrophically on simple organic compounds dissolved in water, which greatly increases their rates of lipid accumulation. Algae, however, do not generally assimilate more complex organic materials such as starch, cellulosic or hemicellulosic oligomers. Ascomyceteous and basidiomyceteous lipogenic yeasts and filamentous fungi will, however, readily assimilate these compounds. Moreover, because these yeasts and fungi are heterotrophic, their growth rates on simple or complex dissolved organic materials are much faster than algae cultivated under heterotrophic conditions.

If it were possible to produce biodiesel from cellulosic residues or other waste organic materials in yields similar to what could be achieved with ethanol production, domestic biodiesel production could satisfy a significant fraction of the national transport energy demand without affecting the food supply. Furthermore, this increased domestic production would also decrease dependency on foreign oil.

Agricultural residue (e.g. corn stover) is a potential source of renewable biomass that could be converted into liquid transportation fuels such as biodiesel if recalcitrance of the biomass to hydrolysis, the presence of inhibitors mixed with the hydrolyzed sugars, and the difficulty in obtaining microbial catalysts that will convert the sugars to lipids in high yield can be overcome. The potential for biodiesel production from agricultural residues is significant. If the residues from U.S. soybean production alone were collected and converted by a microbial process with a mass yield of 35% based on the starting sugar, it would be possible to produce about 10 million metric tons of lipid annually or about 15% more oil than the total of what is presently recovered from the processing of soybeans itself.

Cellulosic biodiesel produced by a lipogenic yeast cultivated on agricultural hydrolysate would generate an animal feed byproduct similar to that obtained from processing oil from soybeans or palm oil. Based on comparisons with existing prices for wholesale yeast protein from brewing, biodiesel production by lipogenic yeast would yield residual yeast protein with the same or slightly higher market value as soy protein.

While several technologies exist to pretreat and enzymatically saccharify agricultural residues for hydrolysis to create fermentable sugars, new microbial biocatalysts are needed to convert the resulting mixed sugars into lipids and other higher value materials.

Grain ethanol plants are a potential source of unused, soluble and insoluble organic materials suitable for biodiesel production. In wet and dry-mill ethanol operations, corn-starch is enzymatically converted into sugar then fermented to ethanol. The process leaves behind significant amounts of corn fiber and generates soluble organics as byproducts of ethanol production.

Grain ethanol plants are becoming less economical to operate due to lack of demand for ethanol and to low profit margins when grain prices are high and petroleum prices are low. Ethanol derived from grain is also criticized for having poor compatibility with fuel distribution systems, reducing the food supply, contributing to soil erosion, and releasing net $CO_2$ emissions that are only marginally better than gasoline. Reduced operating costs, increased process efficiency, better fuel compatibility, and higher product value and diversity could significantly improve the economics and environmental acceptability of this process.

In a conventional dry mill process, whole grain is hammer milled, then steam treated in a jet cooker as it is sent to the fermentation tank for liquefaction with a thermostable alpha-amylase. Following cooling and saccharification, the mash is inoculated for fermentation. Variations on this basic process can involve separation of corn hulls (fiber), starch and germ gluten (protein) prior to saccharification, use of less steam for cooking, use of raw starch, recovery of edible corn oil from the germ and other changes. Following fermentation, ethanol is recovered by distillation, and the bulk of the fiber and protein, along with yeast cells and corn oil, are separated from the dissolved organics by centrifugation. This yields wet cake or distiller's wet grain (DWG) solids and thin stillage (TS) solubles. In a conventional process, the distiller's wet grain is dried to make distiller's dried grain (DDG) and the thin stillage containing the solubles (S) is evaporated to make a syrup, which is sprayed back onto the distiller's dried grain to make DDGS. Evaporation of the thin stillage separates a fraction of the inedible corn oil, which can be recovered for biodiesel production (FIG. 1).

Stillages (vinasse) following distillation of ethanol from industrial ethanol fermentations of grain include corn gluten and yeast protein, residual corn fiber, yeast cells, corn oil, and dissolved organics. Thin stillage contains significant quantities of glycerol (14 to 20 g/l), glucose disaccharides (e.g., cellobiose, trehalose, etc.) (6 to 10 g/l), xylose, lactic acid, corn oil and various oligosaccharides derived from residual undigested starch, dextrins, cellulose and hemicellulose. The total dissolved and suspended organic content of thin stillage is about 10% w/v. Table 1 presents a published summary of stillage components (Kim et al. 2008).

TABLE 1

Exemplary Stillage Composition

| Stillage Component | g/l |
| --- | --- |
| Glucose | 0.9 |
| Glucan (oligosaccharide) | 12.4 |
| Xylose | 0.7 |
| Xylan (oligosaccharide) | 3.7 |
| Arabinose | 0.4 |
| Arabinan (oligosaccharide) | 0.5 |
| Lactic acid | 16.8 |
| Glycerol | 14.4 |
| Acetic acid | 0.3 |
| Butanediol | 1.9 |
| Ethanol | 0.6 |

The glycerol and oligosaccharide contents of thin stillage retain water during evaporation and prevent drying. This makes thin stillage evaporation energy-inefficient. Removing glycerol and oligosaccharides prior to evaporation is therefore desirable. Stillages from other ethanol distillation processes also present disposal problems. Stillage is difficult and non-economical to treat in a waste water system because of its high biological oxygen demand (BOD), its high organic content and low pH. Stillage can also have relatively high nitrogen and phosphorous contents, about 2 g/l and 130 mg/l respectively (Yen et al. 2012). The massive volumes of thin stillage resulting from fuel ethanol production are particularly difficult to handle. A significant fraction of the thin stillage is therefore recycled or "backset" into the liquefaction stage, which increases the level of dissolved organics in the fermentation and whole stillage.

Methods and tools for converting on-site low value soluble organic stillage byproducts from ethanol production into biodiesel are needed to increase fuel production without harvesting more grain. Such methods and tools would reduce the organic load in the backset while creating higher value products such as yeast oil, enzymes, and animal feed from underutilized organic byproducts.

SUMMARY OF THE INVENTION

The invention addresses the aforementioned needs by providing engineered yeasts and methods for converting stillage organics into lipids and other biomaterials.

An exemplary method of the invention for converting stillage organics into yeast oil, cell protein, and enzymes is shown in FIG. 2. This method is similar to standard dry mill operations up through the centrifugation of whole stillage to separate thin stillage (TS) and distiller's wet grain (DWG). Instead of sending thin stillage directly to evaporation, however, oil (e.g., corn oil) is first removed. Second stage thin film evaporators then remove 50 to 80% of the water, and residual protein is separated. The clarified, concentrated thin stillage (CTS) is used as a medium to cultivate native or bioengineered lipogenic yeasts that produce enzymes that will accelerate liquefaction of starch, rapidly consume glycerol, cellobiose, trehalose xylose, lactic acid and residual oligosaccharides while accumulating yeast lipids and biomass. An advantage of microbial bioconversion is that a glycerol byproduct generated during conversion of triglycerides to biodiesel can be fed back into the bioreactor to increase both the rate and yield of lipid production.

An amylolytic, lipogenic yeast specifically bioengineered for rapid lipid and enzyme production from dissolved organics in the clarified thin stillage and other stillage forms is preferred for use in this process. The yeasts are modified to express, constitutively express, or overexpress an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme, or any combination thereof. The yeasts are in some cases also modified to reduce or ablate activity of other enzymes. The bioengineered yeasts of the invention produce enzymes that accelerate liquefaction of starch, rapidly consume glycerol, cellobiose, trehalose, xylose, lactic acid and residual oligosaccharides while accumulating yeast lipids.

The technology described herein can increase profit margins for grain ethanol producers by making higher value and more diverse byproducts. The technology also has the added benefits of decreasing thin stillage viscosity, increasing protein production, reducing organic load from wastewaters, reducing natural gas-based processing expenses, and, in some cases, releasing a larger fraction of corn oil from the dried grain solids. Hence, the technologies would be of interest to several industries by providing a means to diversify products and increase the supply of high energy density renewable fuels while at the same time reducing environmental pressures.

The objects and advantages of the invention will appear more fully from the following detailed description of the preferred embodiment of the invention made in conjunction with the accompanying drawings.

citrate lyase; ACC, acetyl-CoA carboxylase; ICDH, isocitrate dehydrogenase; FAS, fatty acid synthase; DGA, diacylglycerol acyltransferase. a, b, c and d are transporters.

Figure 4:
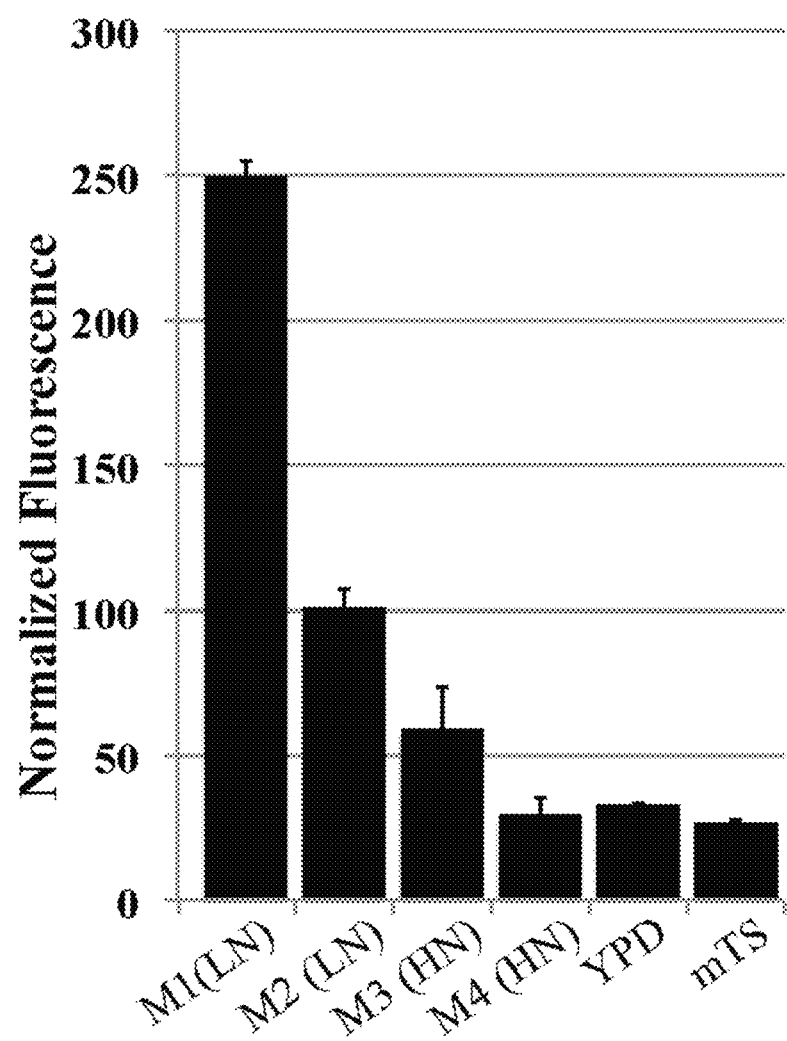

FIG. 4 shows a graph of the effects of different culture media on basal lipid content of Lipomyces starkeyi type strain NRRL Y-11557. The effects of six types of culture media on L. starkeyi basal lipid production were evaluated. YPD is yeast peptone dextrose media. M1 (LN) is a minimally defined, low nitrogen media containing yeast nitrogen base and supplemented with urea, M2 (LN) is a low nitrogen media having the same components as YPD but containing only 3.64% and 1.82% of the yeast extract and peptone contained in YPD. M3 (HN) and M4 (HN) are the high nitrogen containing versions of M1, with M4 HN containing peptone. mTS is modified thin stillage, prepared by clarifying and concentrating ethanol thin stillage. Results are shown as normalized fluorescence to OD630.

Figure 5:
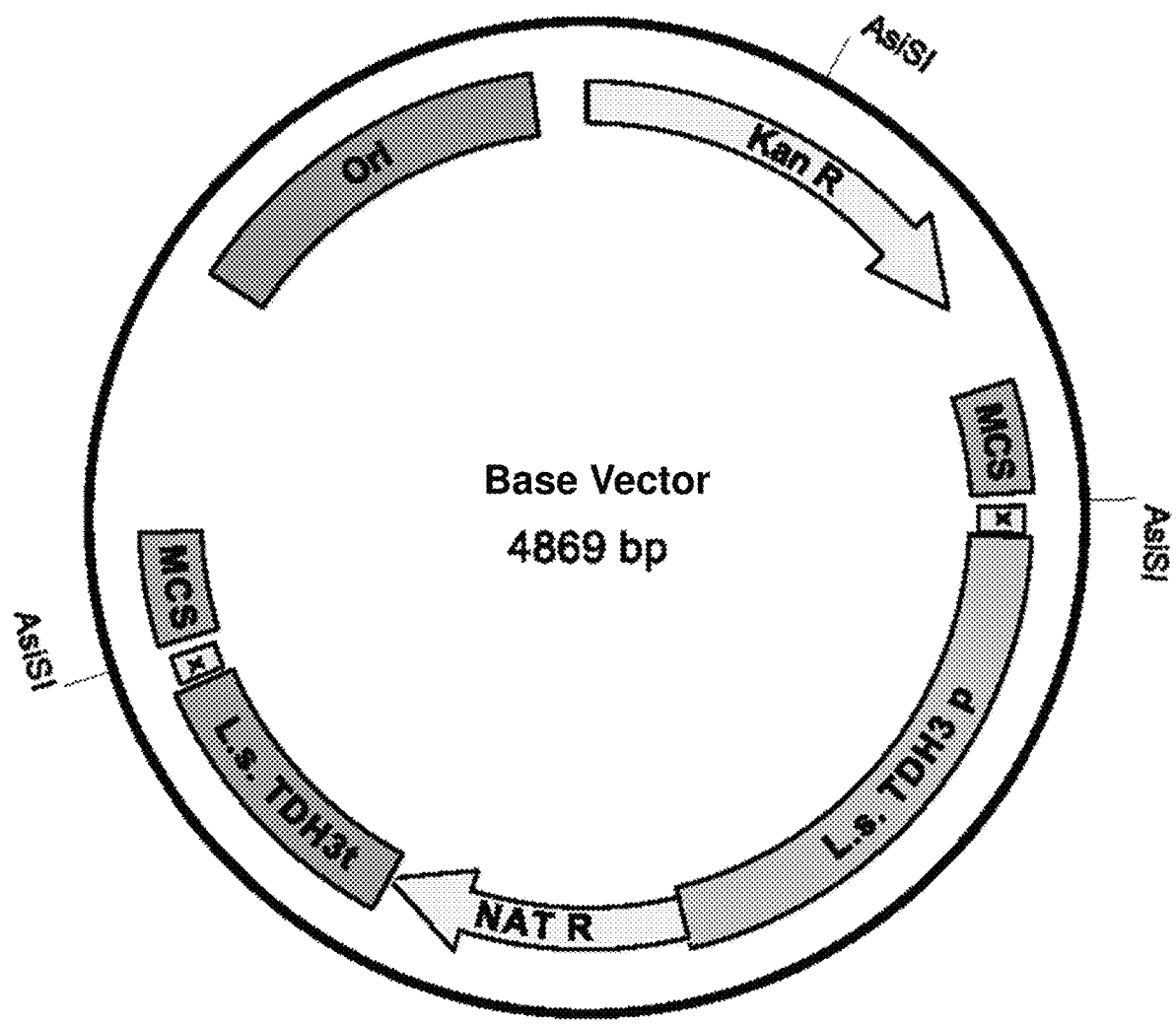

FIG. 5 is a diagram of a base vector used for creating genomic integrating cassettes. The origin of replication (Ori) and kanamycin resistance gene (Kan R) permit propagation and maintenance in E. coli. Two multiple cloning sites (MCSs) enable insertion of gene target cassettes adjacent to loxP sites (Xs), which flank an expression cassette for nourseothricin resistance (NAT R) driven by the constitutive TDH3 promoter (TDH3p) and terminator (TDH3t). Digestion of the vector with AsiSI enables linearization and integration into the yeast genome. The sequence of the base vector is represented by SEQ ID NO:91.

Figure 6:
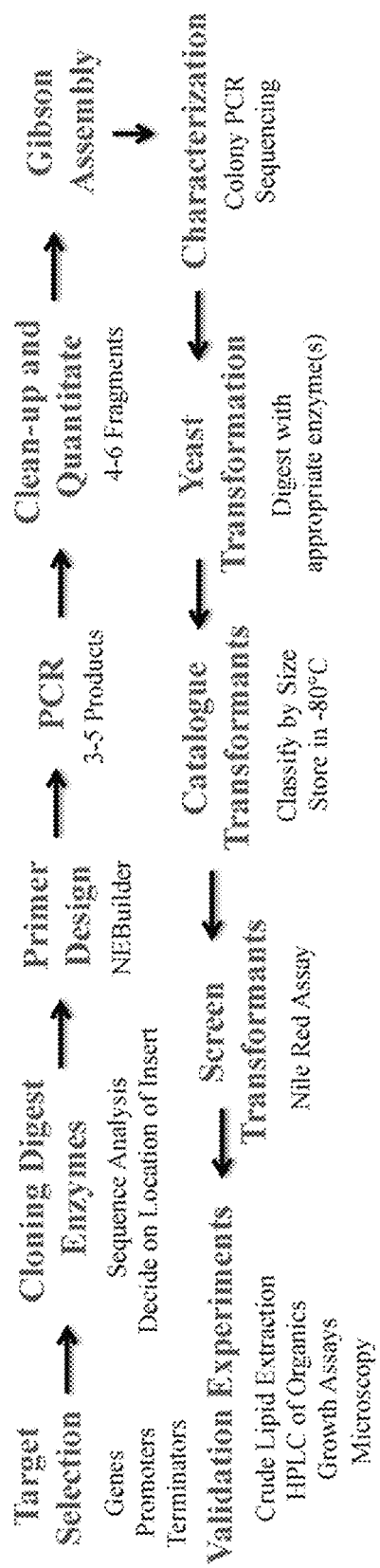

FIG. 6 shows a schema of a screening pipeline used for generating metabolically engineered yeast.

Figure 7:
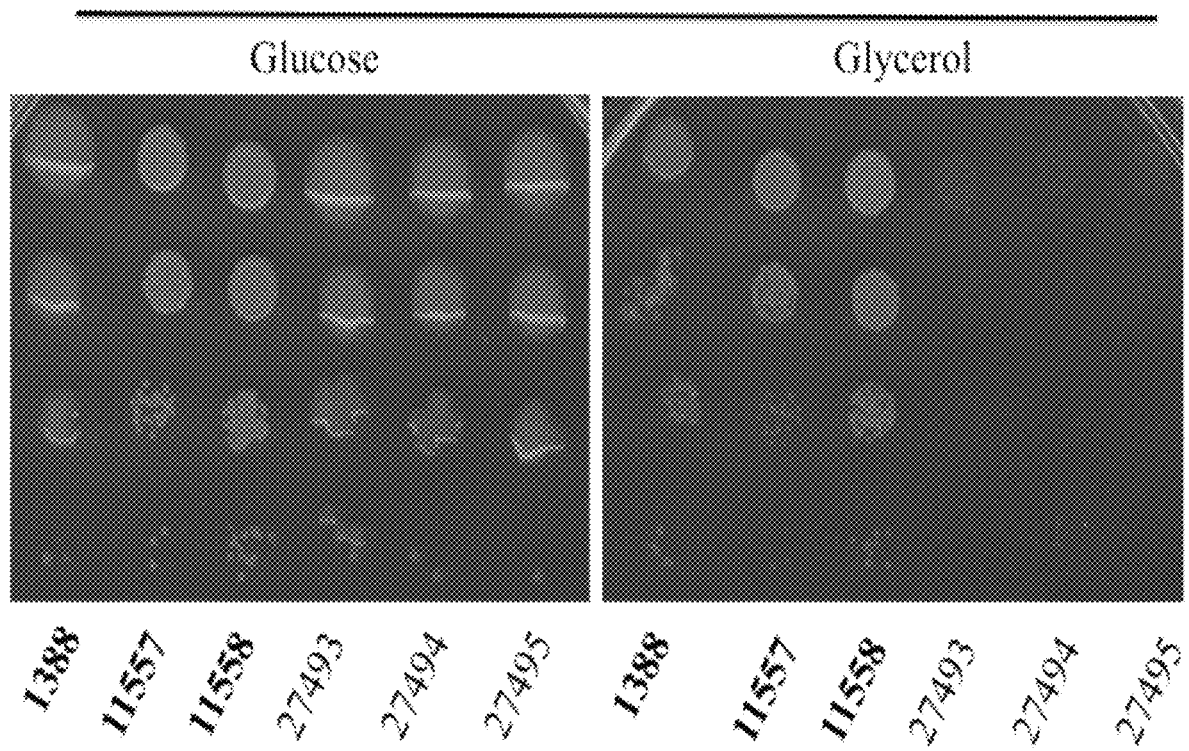

FIG. 7 shows growth of various strains of L. starkeyi on glucose as the sole carbon source (left panel) or glycerol as the sole carbon source (right panel).

Figure 8A:
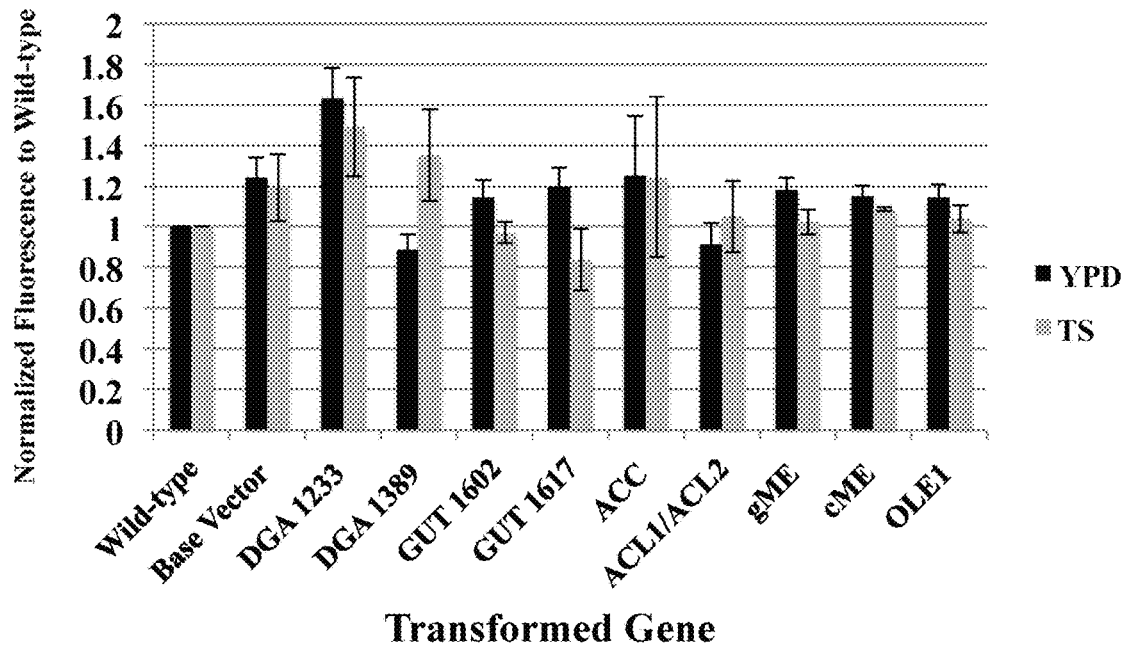
Figure 8B:
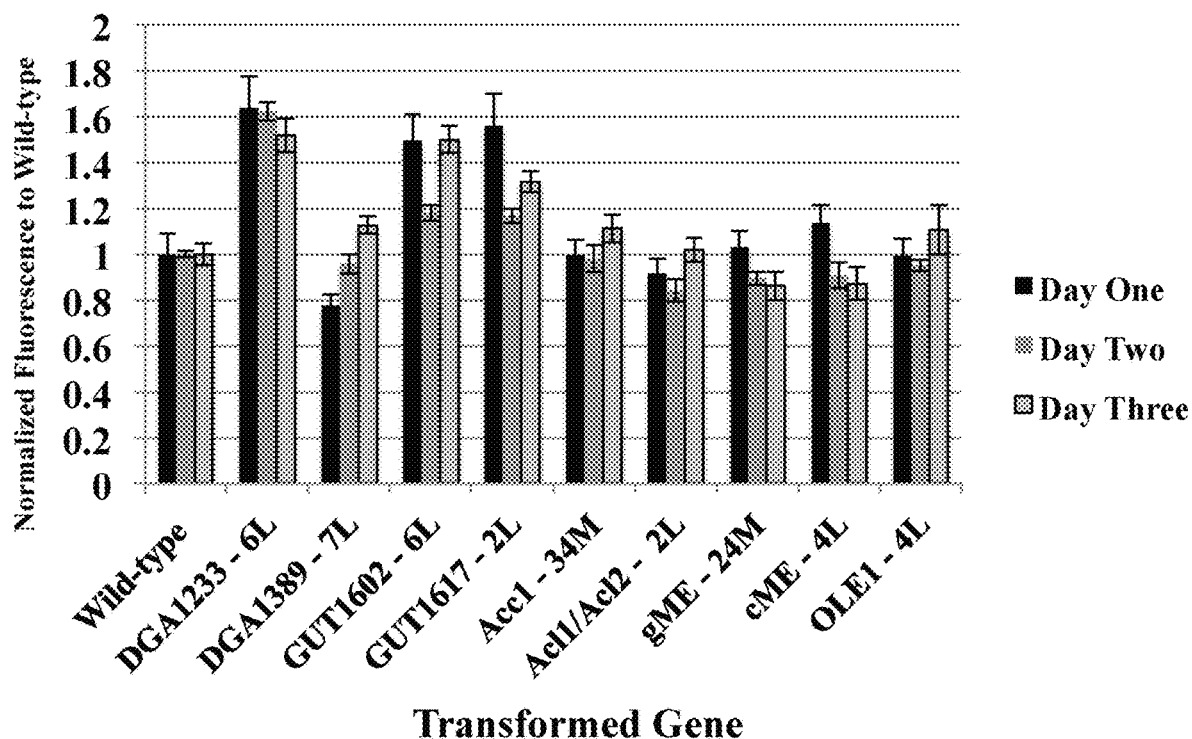

FIGS. 8A and B show Nile Red screening of yeast transformants in YPD or mTS. Results are shown normalized to the wild-type and OD600 after two (YPD) or three (mTS) days of growth. FIG. 8A shows averages of the top 50% of transformants with each gene in preliminary screening. Of 234 transformants cultivated, preliminary screening revealed three strains transformed with three genes (cDGA1-1233, cDGA1-1389, and cACC1) that showed large standard deviations or higher means than the base vector transformed strains. Data is shown for the end of the growth phase in each media (YPD=2 days, mTS=3 days). FIG. 8B shows results of a validation screen of the prime performers of each gene in mTS evaluated in triplicate, revealing that the transformants DGA1-1233 6L, GUT1-1602 6L, and GUT1-1617 2L show superior lipid accumulation over the WT as deemed by Nile Red fluorescence.

Figure 9:
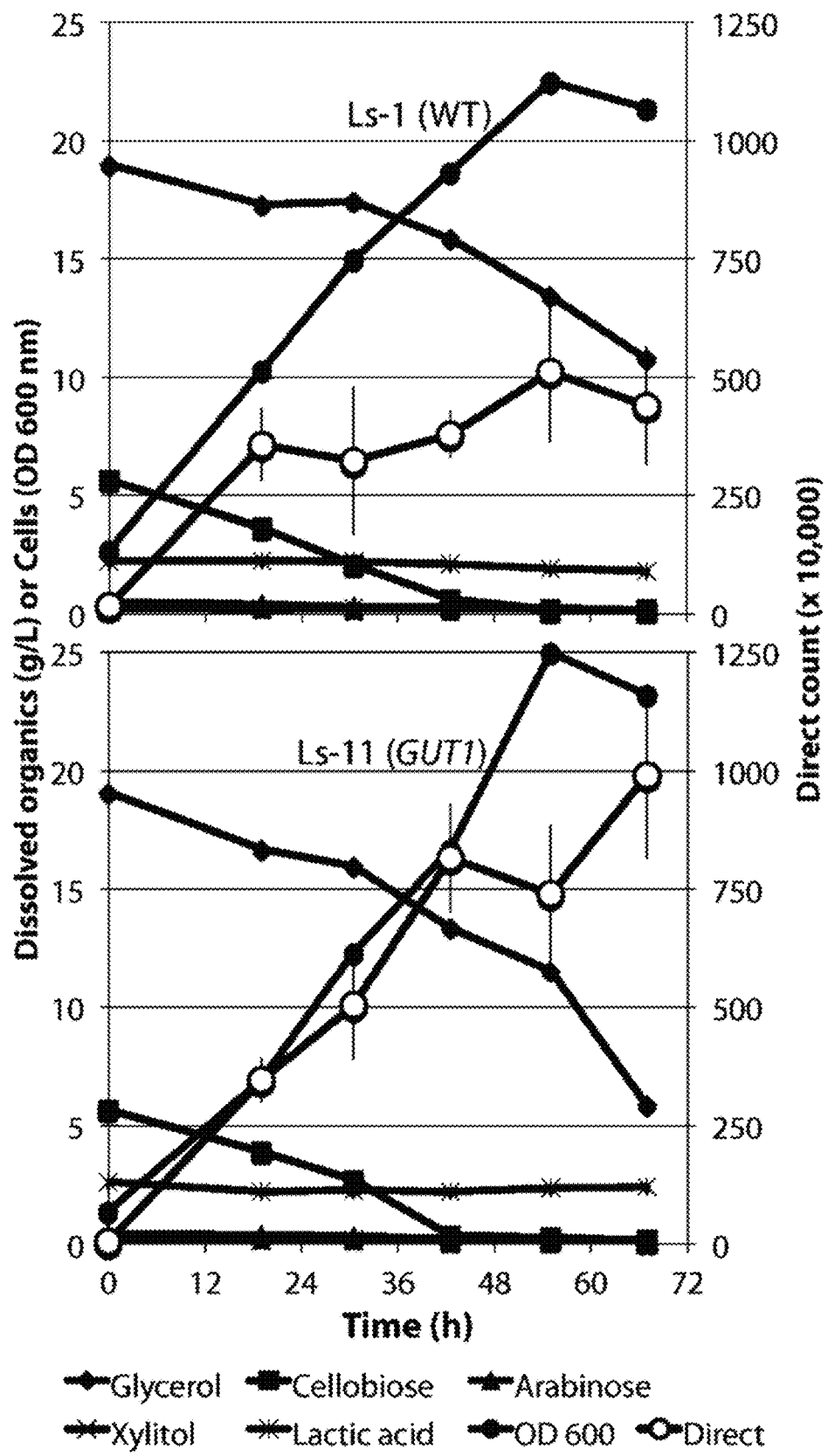

FIG. 9 shows consumption of organics and cell density of wild-type L. starkeyi (Ls-1) and a GUT1 engineered strain (Ls-11). The presence of glycerol, xylitol, cellobiose, lactic acid, and arabinose in 200 mL of mTS solution in shake flasks were monitored by HPLC analysis during cultivation of wild-type L. starkeyi (Ls-1) and a strain with an engineered version of the glycerol kinase gene (GUT1 Ls-11). Cell density (OD600) and direct cell counts were also determined. In this experiment, the Ls-11 engineered strain achieved higher cell density and consumed more glycerol than the wild-type strain.

Figures 10A, 10B:
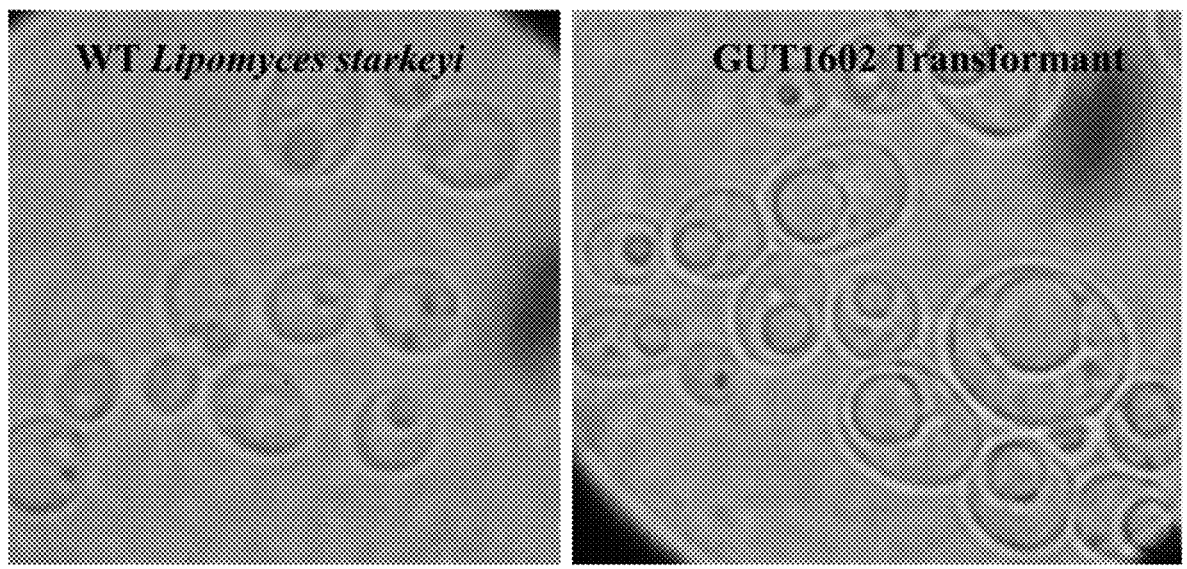

FIGS. 10A and 10B show a difference in the cellular morphologies of wild-type L. starkeyi (FIG. 10A) and a strain overexpressing GUT1 (FIG. 10B) when cultured on mTS. Besides generating larger liposomes in some cells, the strain overexpressing GUT1 also formed cellular assemblies similar to pseudomycelium. Photos were taken after two days of growth in mTS.

FIGS. 11A-11C show a comparison of wild-type L. starkeyi with engineered strain DGA1-1233 6L comprising the DGA1-1233 gene. FIG. 11A shows growth rates and carbon utilization of wild-type (solid shapes) and DGA1-1233 6L (open shapes) of glycerol and cellobiose. Cultures were grown in triplicate on mTS media, error bars denote the standard deviation. FIGS. 11B and 11C show cellular morphologies for wild-type (FIG. 11B) and DGA1-1233 6L (FIG. 11C), showing significantly more liposomes in DGA1-1233 6L.

FIGS. 12A and 12B show Nile Red fluorescence and percent lipid analysis of wild-type L. starkeyi and the engineered strain designated DGA1-1233 6L cultured in mTS using bioreactors. FIG. 12A shows relative Nile Red fluorescence of the wild-type strain and the DGA1-1233 transformant measured at different time points. Spent media was drawn off and the bioreactors refilled with thin stillage after 48 hours of growth. FIG. 12B shows percent lipid content of cell dry weight of wild-type L. starkeyi and the DGA1-1233 transformant. The engineered DGA1-1233 6L strain had more than double the Nile Red fluorescence and percent lipid content.

Figure 13:
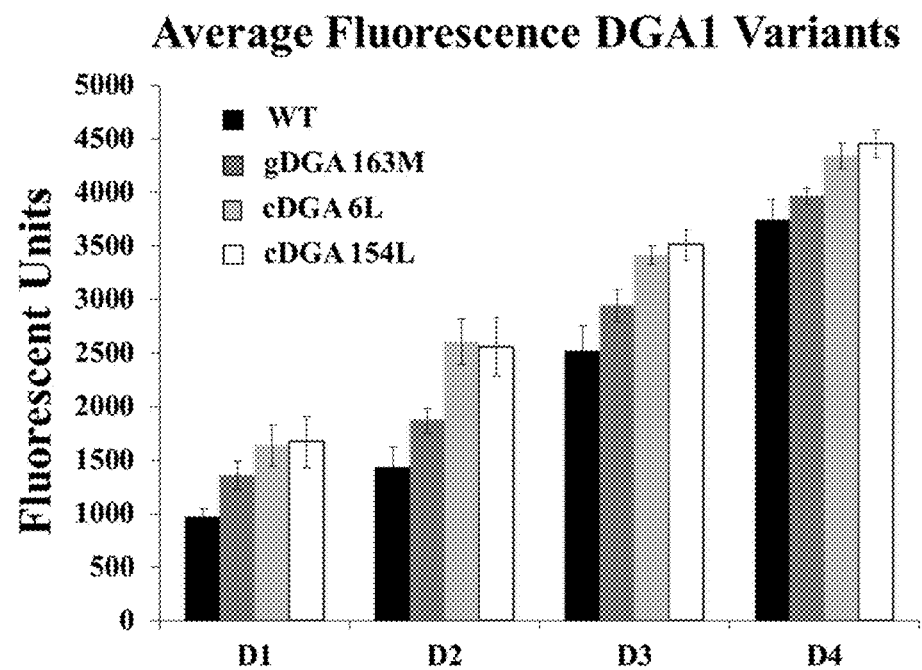

FIG. 13 shows a comparison of strains overexpressing DGA1 variants in synthetic thin stillage medium (sTS) by Bodipy fluorescence. A) Bodipy fluorescence of the wild-type Ls-1 (black), gDGA1 163M (dark gray), cDGA-1233 6L (light gray), and cDGA 154L (white) L. starkeyi transformants as monitored over the course of 4 days (denoted as D1, D2, D3, and D4). The cDGA 154L strain was chosen as the platform strain for further improvement due to its similar performance to cDGA 6L and Hygromycin B resistance marker.

Figure 14:
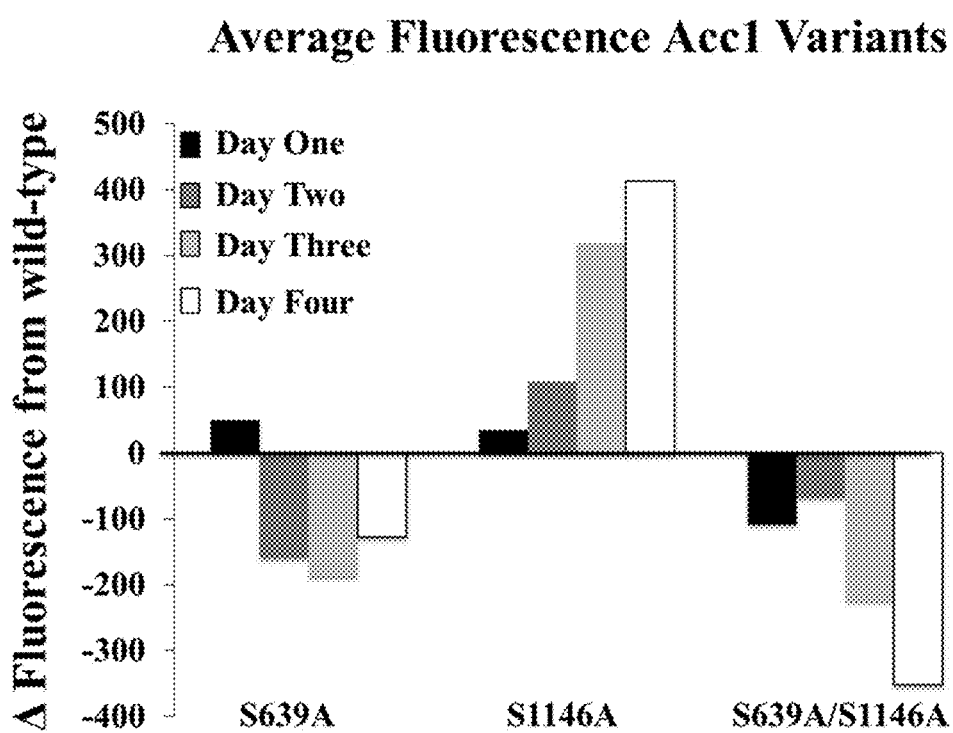

FIG. 14 shows dilution-corrected Bodipy fluorescence in mutant and wild-type Acc1-transformed L. starkeyi. The S1146 point mutation increases fluorescence values relative to the wild-type strain, whereas S639A and the double mutation leads to slightly inferior performance. Data is plotted as the average difference in fluorescence from the untransformed wild-type strain over the course of four days from 63-188 transformants in each pool.

Figure 15:
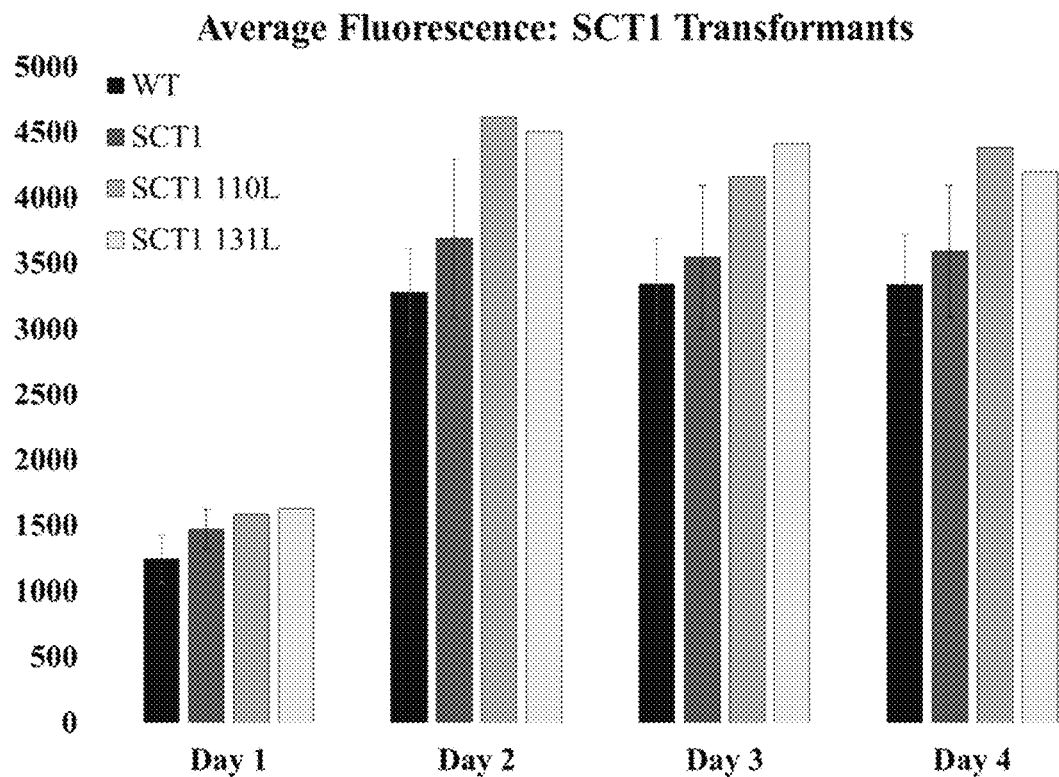

FIG. 15 shows dilution-corrected Bodipy fluorescence in wild-type and SCT1-transformed L. starkeyi. Average wild-type fluorescence, average transformant fluorescence, SCT1 110L fluorescence, and transformant SCT1 131L fluorescence are shown. In FIG. 15, as well as in FIGS. 16, 24, 25, and 27, there are no error bars included with the data for the single transformants because each data point represents fluorescence from one culture of each transformant.

Figure 16:
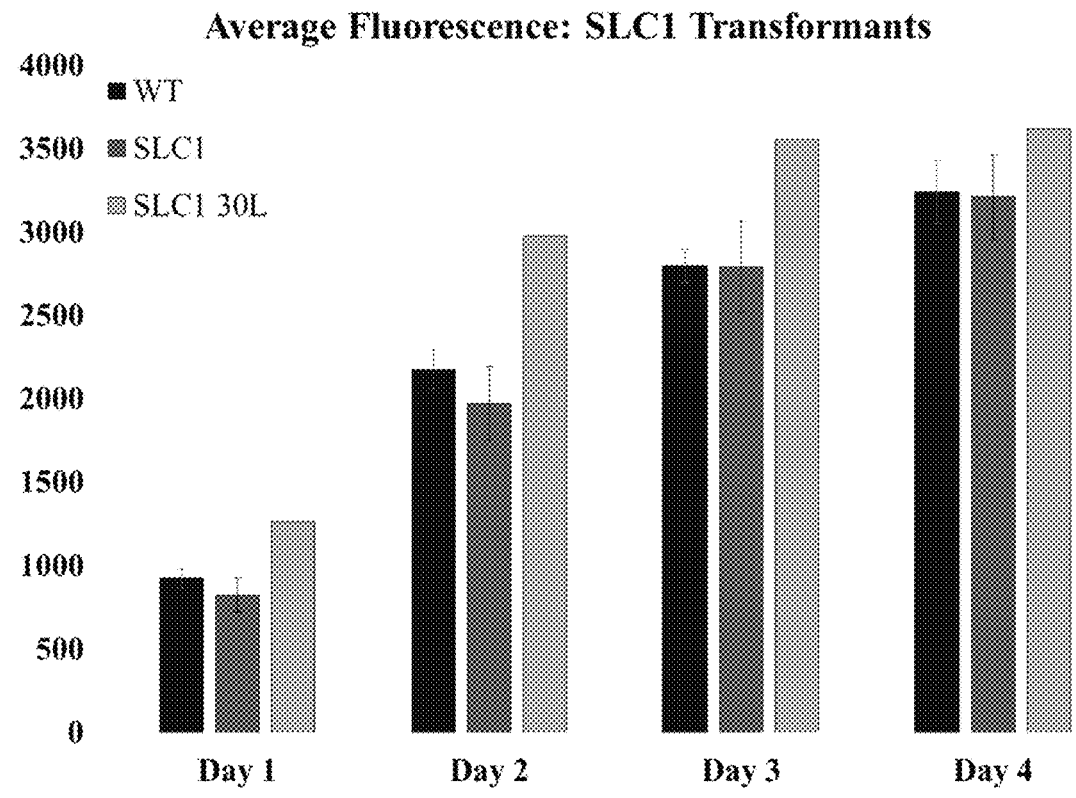

FIG. 16 shows dilution-corrected Bodipy fluorescence in wild-type and SLC1-transformed L. starkeyi. Average wild-type fluorescence, average transformant fluorescence, and SCT1 30L transformant fluorescence are shown.

Figure 17:
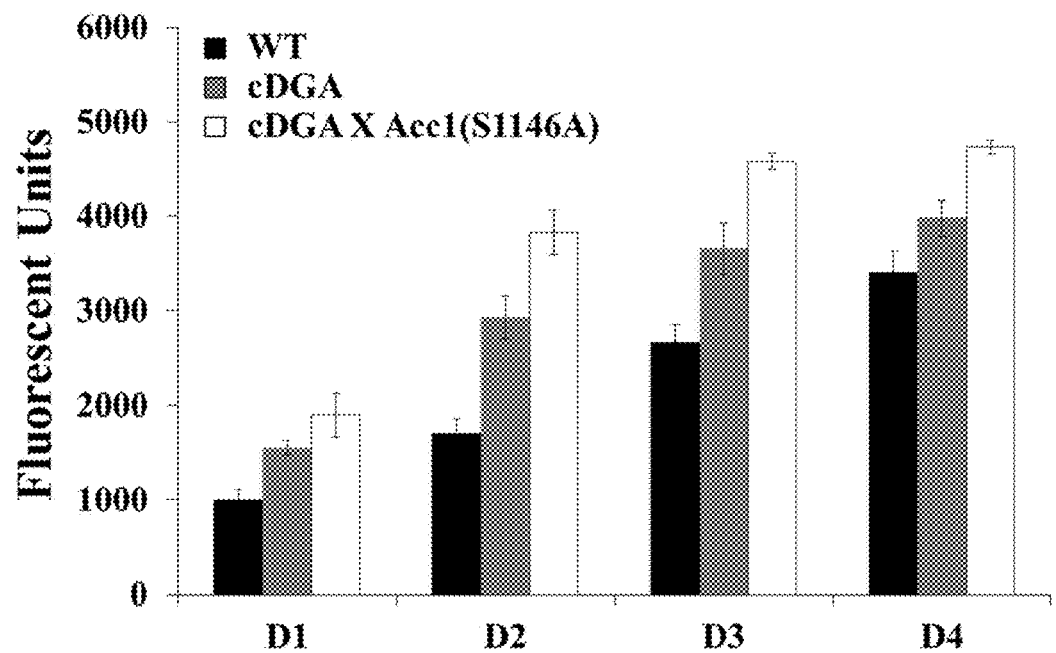

FIG. 17 shows dilution-corrected Bodipy fluorescence with dual overexpression of DGA1 and the gene for the deregulated protein Acc1(S1146A) in L. starkeyi. Dilution corrected Bodipy fluorescence of wild-type strain (black), the strain overexpressing cDGA1 (dark gray), and the strain in which overexpressed cDGA1 was crossed with Acc1 (S1146A) overexpressing strains was monitored over the course of 4 days (D1, D2, D3, and D4). The mated strain was obtained by crossing the top performers from each cDGA1 and Acc1(S1146A) transformant pool. Overexpression of both the DGA1 gene and the gene for the mutated protein Acc1(S1146A) synergistically enhanced lipid accumulation compared to overexpression of each gene alone.

Figure 18:
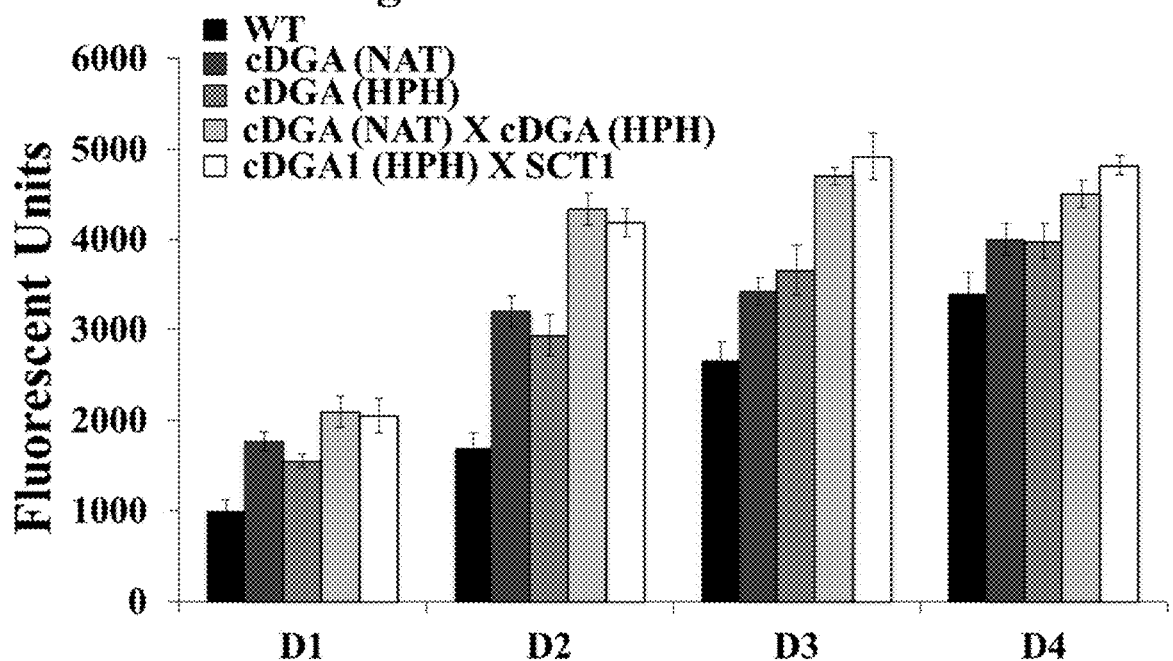

FIG. 18 shows dilution-corrected Bodipy fluorescence of L. starkeyi strains with combinatorial expression of lipogenic cassettes. The strains are shown in the following order (from left (black) to right (white): wild-type, cDGA-NAT (the top cDGA1-1233 strain), cDGA-HPH (a new platform strain), and cDGA-HPH crossed with either cDGA-NAT or a strain transformed with engineered SCT1. Fluorescence was monitored over the course of 4 days (D1, D2, D3, and D4). The top strains (lightest gray and white) exhibited improvement in lipid production through dual overexpression of lipogenic cassettes.

Figure 19:
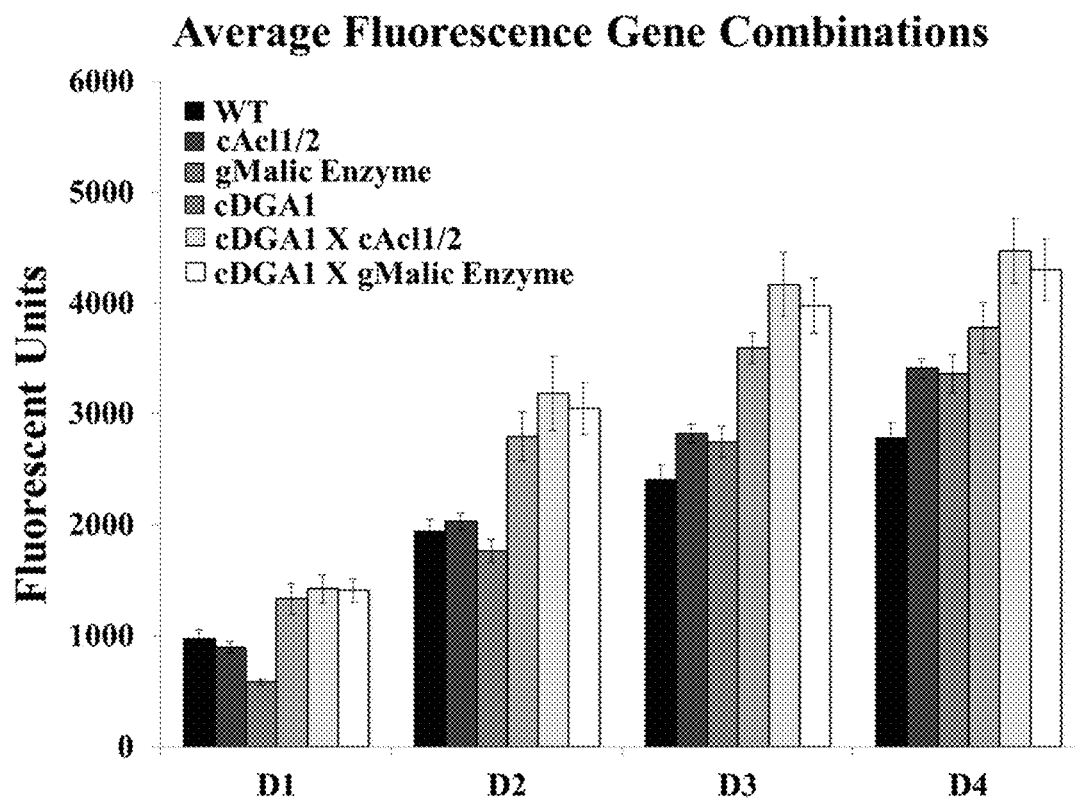

FIG. 19 shows dilution-corrected Bodipy fluorescence of L. starkeyi strains with combinatorial expression of lipogenic and auxiliary cassettes. The strains are shown in the following order (from left (black) to right (white): wild-type, ATP citrate lyase α and β subunit overexpressing strain (designated as cAcl1/2), malic enzyme cloned from gDNA overexpressing strain (designated as gMalic Enzyme), diacylglycerol transferase (designated as cDGA1-1233) cloned from cDNA overexpressing strain (cDGA1), combinatorial cDGA1-1233 and Acl1/2 overexpressing strain (cDGA1× cAcl1/2), and combinatorial cDGA1-1233 and genomic malic enzyme overexpressing strain (cDGA1×gMalic Enzyme). Combinatorial expression of lipogenic and auxiliary cassettes improved lipid production.

Figure 20:
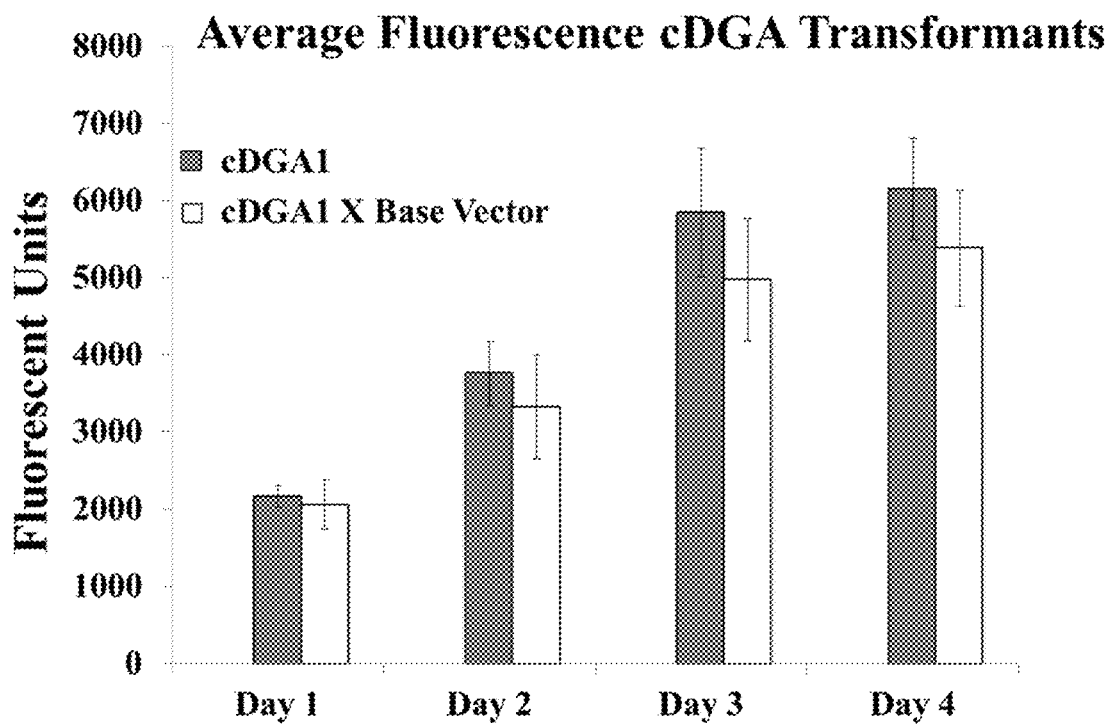

FIG. 20 shows Bodipy analysis in sTS of a lipogenic diacylglycerol transferase overexpressing strain (cDGA) and the same strain transformed with a second base vector. The introduction of expressing a second resistance marker does not increase lipid accumulation on its own, and may even decrease lipid levels.

Figure 21:
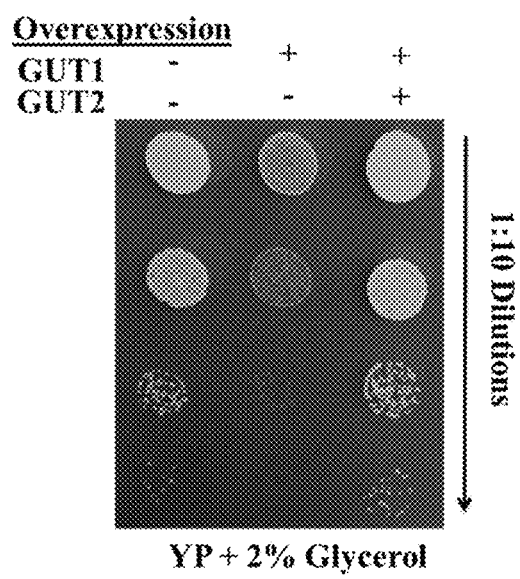

FIG. 21 shows wild-type L. starkeyi (first column), or transformed cells overexpressing the gene for glycerol kinase (GUT1, second column) or GUT1 and an FAD-dependent glycerol-3-phosphate dehydrogenase (GUT1/GUT2, third column) plated onto YP solid media containing 2% glycerol and incubated for 4-5 days at 30° C. The growth defect of the GUT1 single transformant was rescued by overexpression of GUT2.

Figure 22:
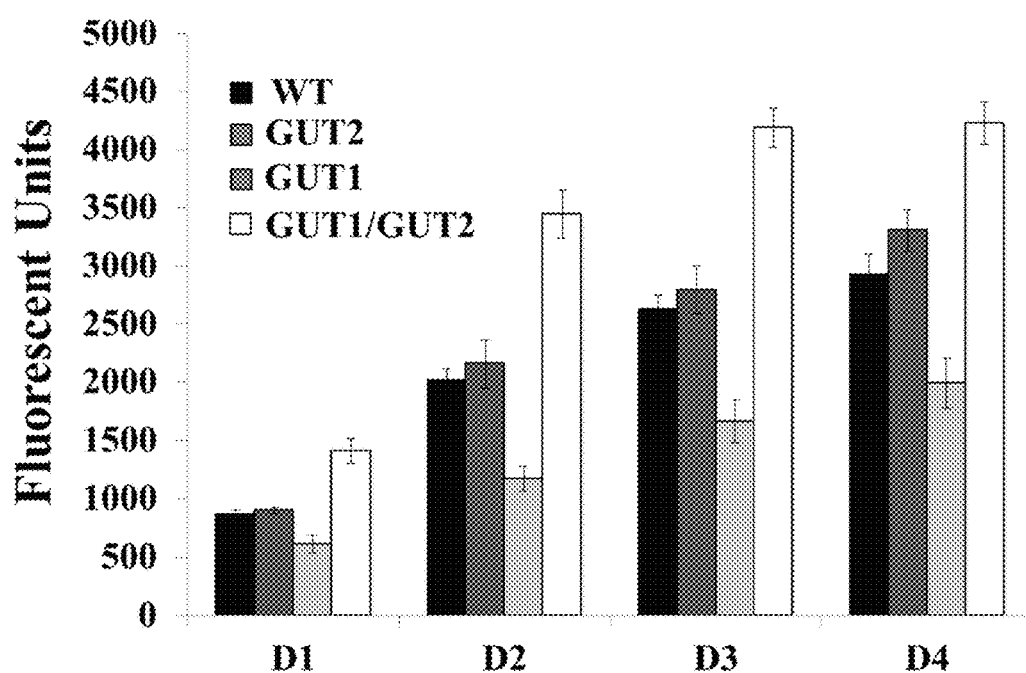

FIG. 22 shows average dilution-corrected Bodipy fluorescence in a parental wild-type L. starkeyi strain (black), a strain overexpressing GUT2 (dark gray), a strain overexpressing GUT1 (light gray), and a GUT1/GUT2 double transformant (white). The GUT1/GUT2 double transformant accumulates more lipid than parental wild-type or GUT1 overexpressing strains. Overexpression of GUT2 alone has little effect on lipid accumulation.

Figure 23A:
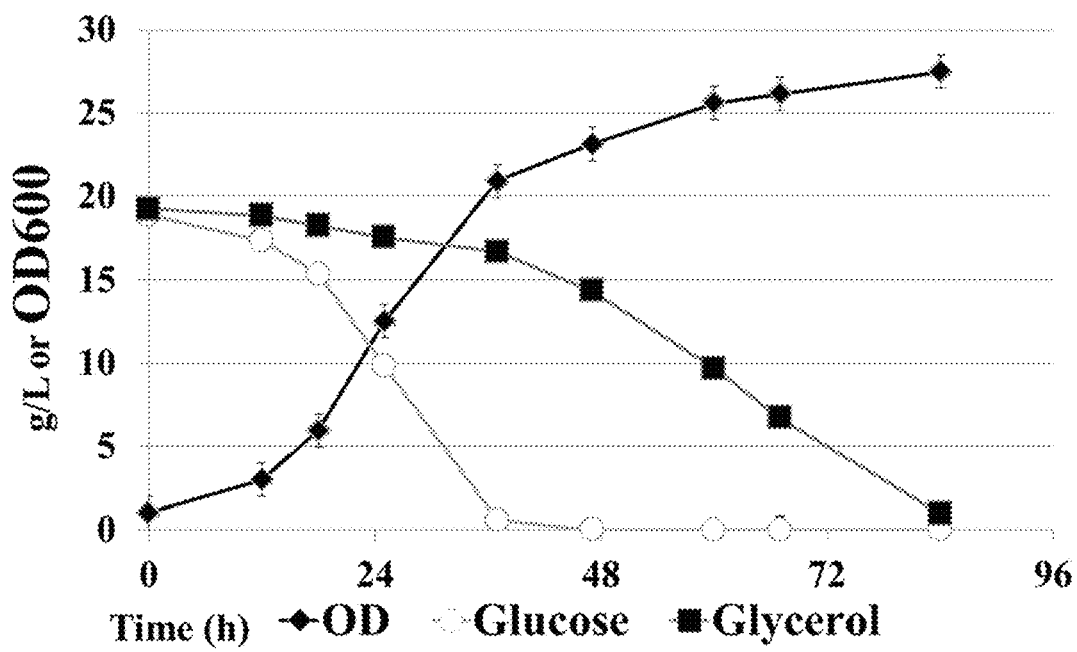
Figure 23B:
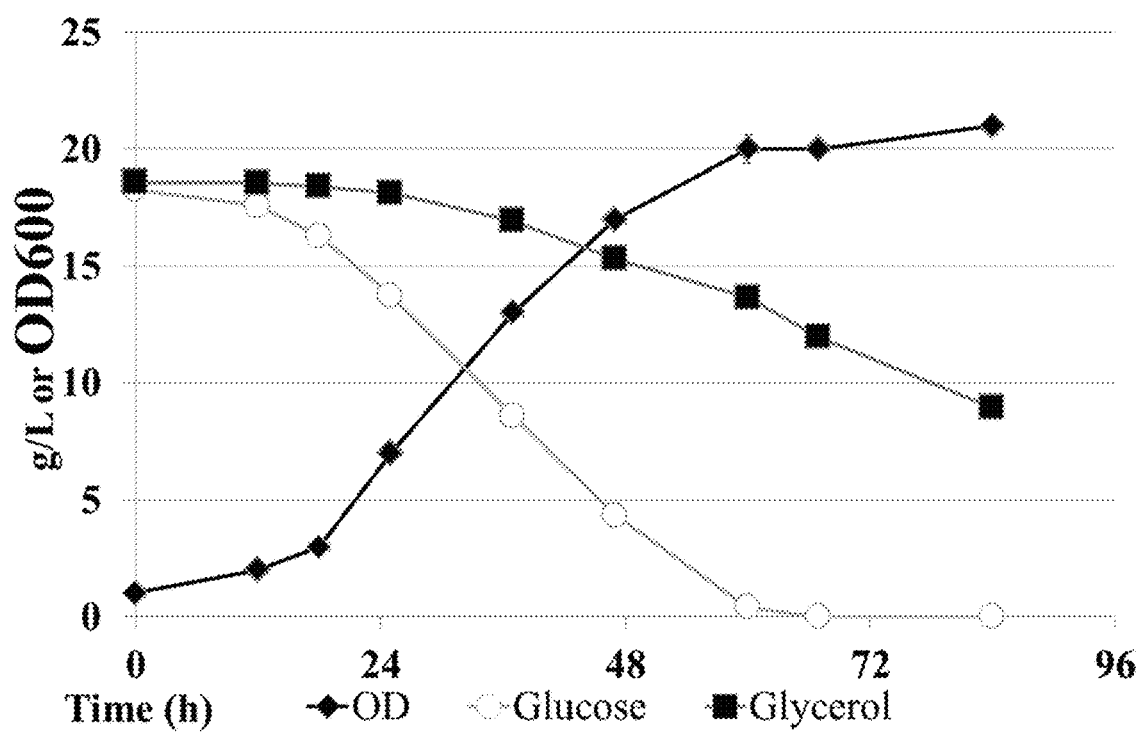
Figure 23C:
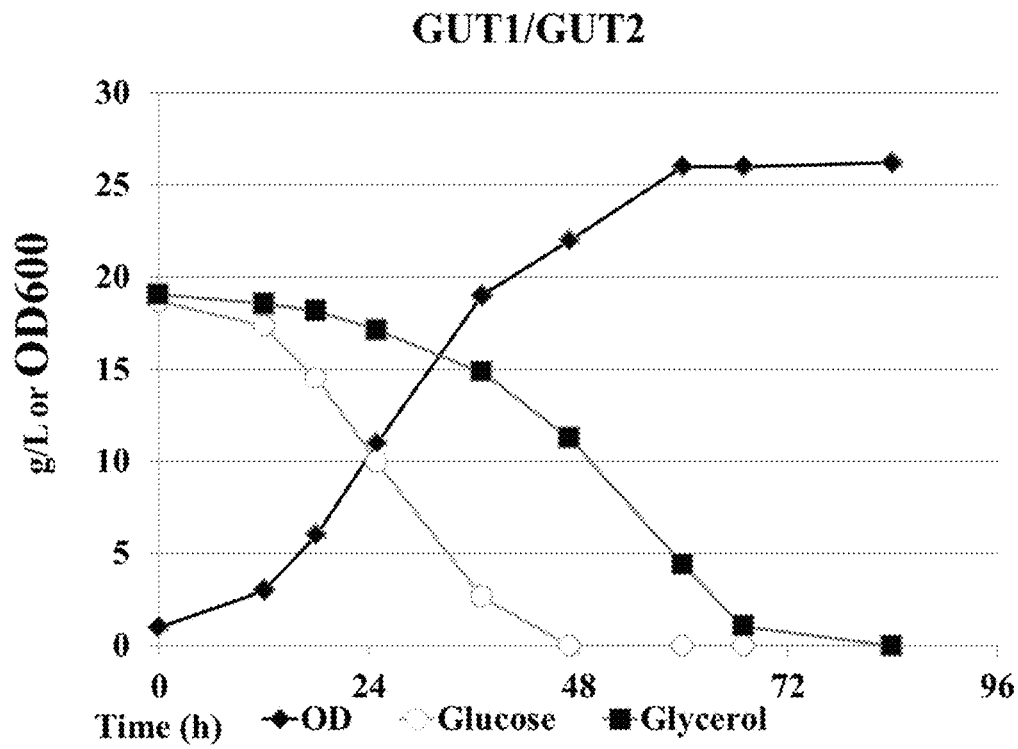
Figure 23D:
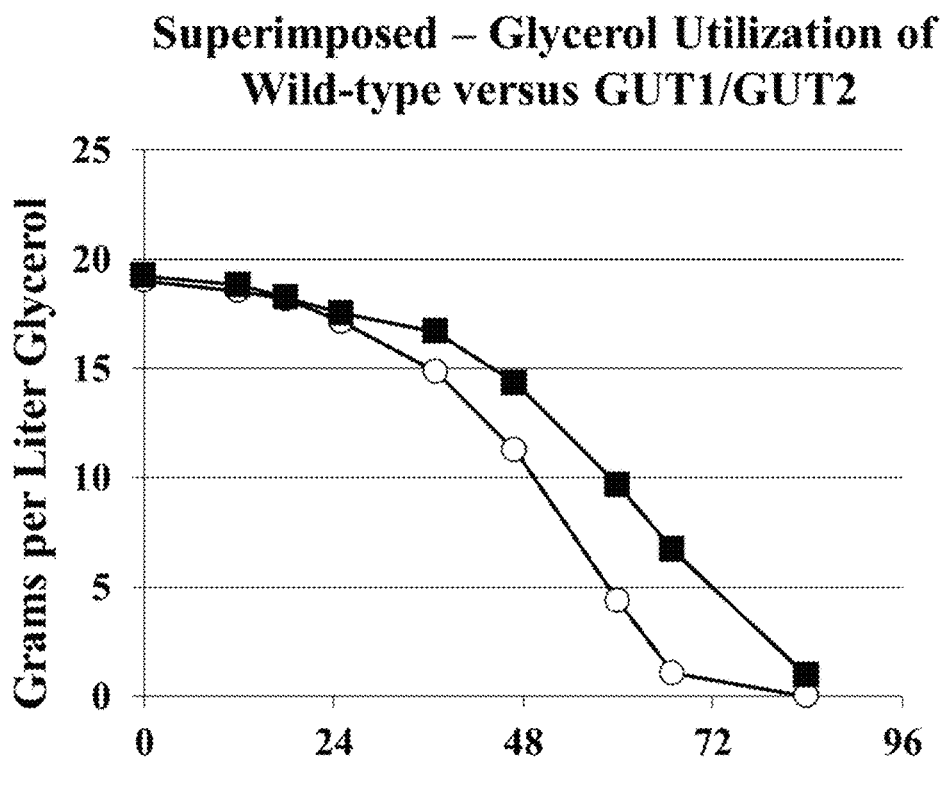

FIGS. 23A-23C show cell density (OD), glucose consumption, and glycerol consumption in a parental wild-type L. starkeyi strain (FIG. 23A), a GUT1 single transformant (FIG. 23B), and a GUT1/GUT2 double transformant (FIG. 23C). FIG. 23D shows superimposed curves of glycerol utilization in the wild-type strain and the GUT1/GUT2 double transformant. Glycerol was depleted in just 67 hours in the GUT1/GUT2 double transformant versus 84 hours in the wild-type strain.

Figure 24:
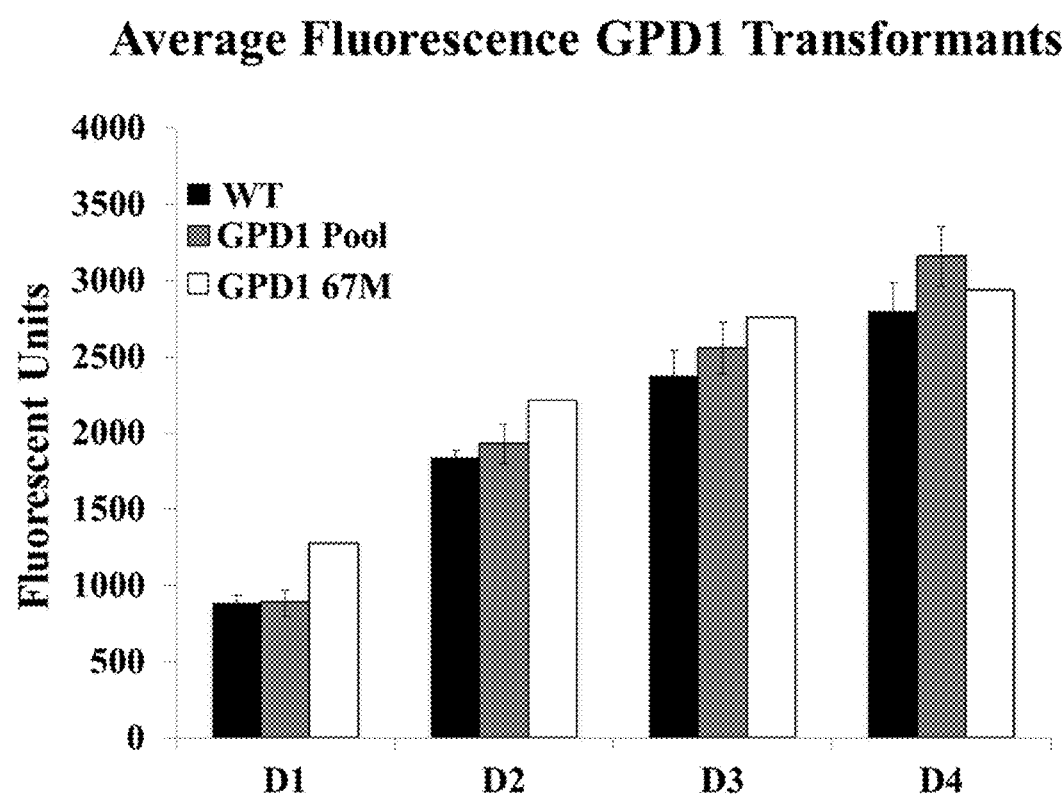

FIG. 24 shows dilution-corrected Bodipy fluorescence of wild-type L. starkeyi (black) and a pool of GPD1 transformants (gray). Bodipy fluorescence was monitored in synthetic thin stillage over the course of 4 days. Overall, the transformants exhibited moderately higher fluorescence over the wild-type, with almost 13% improvement on the fourth day. The top transformant GPD1 67M (white) is also shown. The data indicate that overexpression of glycerol-3-phosphate in L. starkeyi increases lipid production.

Figure 25:
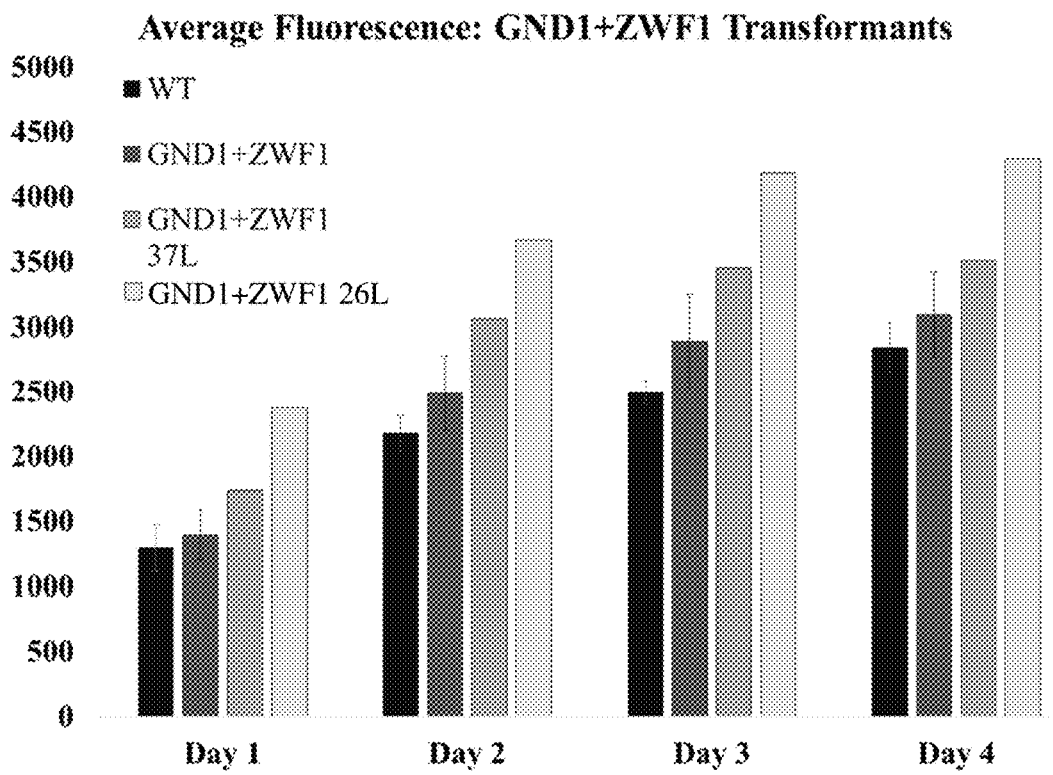

FIG. 25 shows dilution-corrected Bodipy fluorescence in wild-type L. starkeyi and GND1/ZWF1 transformants. Average wild-type fluorescence, average transformant fluorescence, transformant GND1+ZWF1 37L fluorescence, and transformant GND1+ZWF1 26L fluorescence are shown.

Figure 26:
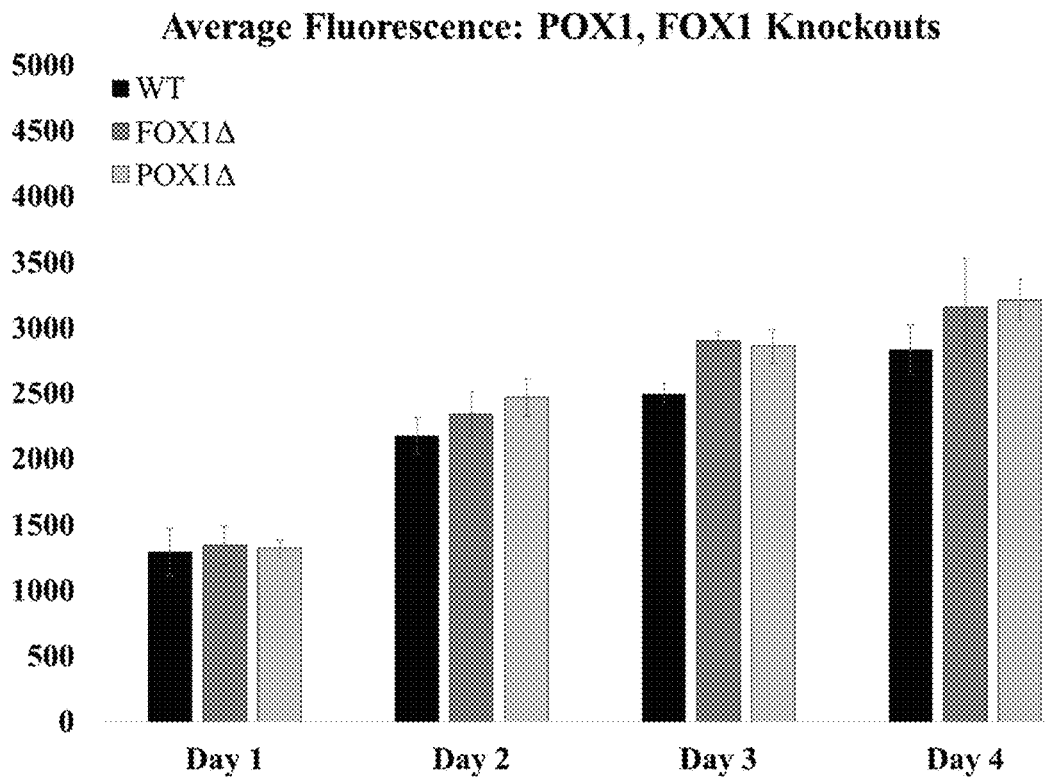

FIG. 26 shows dilution-corrected Bodipy fluorescence in wild-type L. starkeyi and FOX1 and POX1 knockouts.

Figure 27:
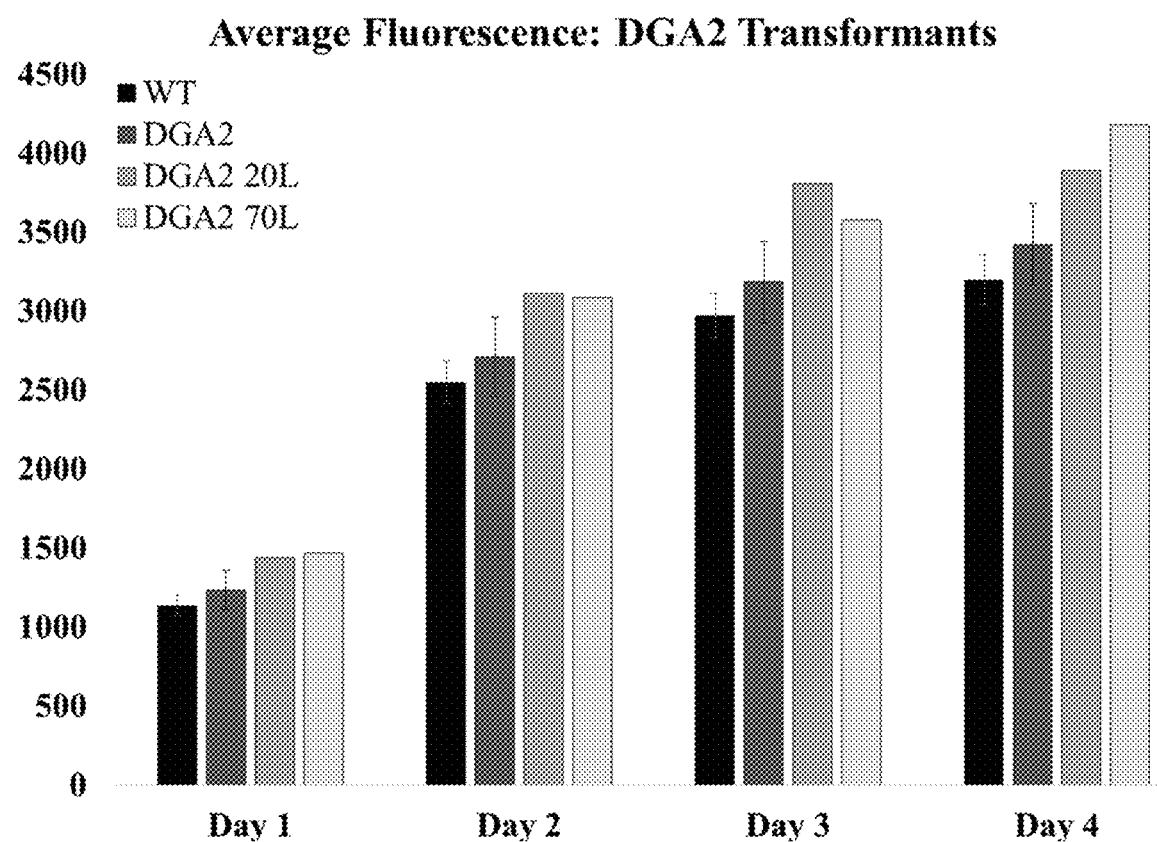

FIG. 27 shows dilution-corrected Bodipy fluorescence in wild-type L. starkeyi and DGA2 transformants. Average wild-type fluorescence, average transformant fluorescence, transformant DGA2 20L fluorescence, and transformant DGA2 70L fluorescence are shown.

Figure 28:
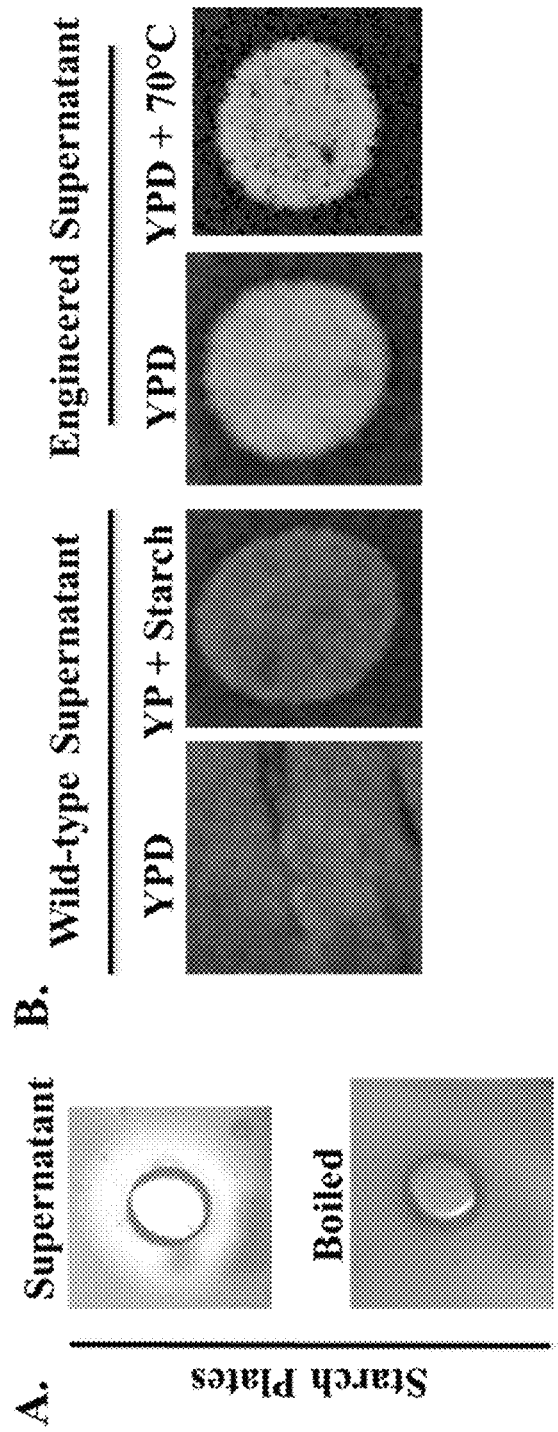

FIG. 28 shows an engineered yeast constitutively secreting a glucoamylase that retains activity following incubation for 1 hour at 70° C. A) Supernatant of a wild-type L. starkeyi culture conditioned to secrete enzyme incubated on 1% corn starch plates prior to (top) or after (bottom) boiling. The presence of a clearing zone indicates starch hydrolytic activity, which is lost after boiling. B) Supernatant of wild-type cells display glucoamylase activity when cultured in starch containing media, but not YPD (left two boxes). In this case, starch hydrolysis is indicated by a zone impervious to iodine staining on a 2% starch plate. The supernatant of the engineered strain exhibits activity when cultured on both YPD and starch containing media, and is retained following incubation for one hour at 70° C. (right two boxes).

DETAILED DESCRIPTION OF THE INVENTION

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

All protein identification (PID) numbers provided herein refer to proteins in the database of the Joint Genome Institute (JGI) of the United States Department of Energy. See, e.g., Jeffries 2013.

It is understood that the invention is not confined to the particular construction and arrangement of parts herein illustrated and described, but embraces such modified forms thereof as come within the scope of the claims.

Lipogenic (Oleaginous) Yeasts

An aspect of the invention encompasses bioengineered yeasts. The bioengineered yeasts are preferably derived from lipogenic yeasts. The methods of the invention are preferably performed with either native, non-bioengineered lipogenic yeasts or bioengineered lipogenic yeasts.

Lipogenic yeasts (also known as oleaginous yeasts) have been recognized for more than 50 years. They are defined as those that accumulate lipids in intracellular oil bodies to greater than 20% of their dry mass. In some yeasts, lipids have been reported to account for up to 71% of the cell's total biomass (Holdsworth et al. 1988). Out of the 1200 to 1500 known yeast species, only a fraction qualifies as lipogenic. *Lipomyces starkeyi* was among the earliest lipogenic yeasts studied (Lodder et al. 1952). Other known lipogenic yeasts include *Yarrowia lipolytica* (Papanikolaou et al. 2001), and species in the genera of *Rhodotorula, Cryptococcus* (Ratledge 2002), *Candida, Trichosporon* (Holdsworth et al. 1988), *Rhodosporidium, Sporidiobolus, Sporodobolomyces*, and various other ascomyceteous and basidiomycete genera amounting for a total of about 100 species (Garay et al. 2016).

Lipogenic yeasts belong to the larger taxonomic groups of filamentous ascomyceteous and basidiomycetous fungi. Exemplary lipogenic yeasts include yeasts from the genus *Lipomyces*, such as *L. starkeyi, L. anomalus, L. arxii, L. chichibuensis, L. doorenjongii, L. japonicus, L. kockii, L. kononenkoae, L. lipofer, L. mesembrius, L. oligophaga, L. orientalis, L. smithiae, L. spencermartinsiae, L. suomiensis, L. tetrasporus, L. yamadae, L. yarrowii*, and *L.* Sp.; yeasts from the genus *Yarrowia*, such as *Y. lipolytica, Y. bubula, Y. deformans, Y. divulgata, Y. keelungensis, Y. porcina, Y. yakushimensis*, and *Y.* Sp.; yeasts from the genus *Candida*, such as *C.* Sp.; yeasts from the genus *Hansenula*, such as *H. polymorpha*; yeasts from the genus *Cunninghamella*, such as *S. bigelovii* sp nov CGMCC 8094, *S. echinulate, S. blakesleeana* JSK2, and *S.* Sp. *Salicorn* 5; yeasts from the genus *Mortierella*, such as *M. alpina, M. isabellina*, and *M.* Sp.; yeasts from the genus *Rhodosporidium*, such as *R. toruloides, R. babjevae, R. diobovatum, R. fluviale, R. krato-chvilovae, R. paludigenum, R. sphaerocarpum, R. araucariae, R. colostri, R. dairenensis, R. graminis, R. lusitaniae*, and *R. mucilaginosa*; yeasts from the genus *Sporidiobolus*, such as *S. johnsonii, S. pararoseus, S. ruineniae, S. ruineniae*, and *S. salmonicolor*; yeasts from the genus *Sporobolomyces*, such as *S. bannaensis, S. beijingensis, S. carnicolor, S. metaroseus, S. odoratus, S. poonsookiae, S. singularis*, and *S. inositophilus*; yeasts from the genus *Occultifur*, such as *O. externus*; yeasts from the genus *Rhodotorula*, such as *R. bogoriensis, R. hylophila, R. glutinis*, and *R. rhodochrous*; yeasts from the genus *Trichosporon*, such as *T. fermentans, T. oleaginosus* ATCC 20509, and *T. cutaneum*; and yeasts from the genus *Cryptococcus*, such as *C. curvatus* and *C.* Sp.

Certain filamentous fungi and unicellular algae can also be lipogenic. These include filamentous fungi from the genus *Aspergillus*, such as *A. nidulans*, and from the genus *Mucor*, such as *M. circinelloides* and *M. rouxii*. Lipogenic algae include species from the genus *Scenedesmus*, such as *S. quadricauda*.

Nontraditional lipogenic yeasts have an innate ability to convert poorly metabolized wastes from ethanol fermentation into lipids, protein, and enzymes. Some lipogenic yeasts naturally make large amounts of lipids from a wide variety of carbon sources, and this prodigious capacity renders them amenable to many bioprocessing applications.

*Lipomyces starkeyi* is a particularly preferred lipogenic yeast in this regard. *L. starkeyi* can utilize many different substrates, including the oligosaccharides and sugars found in both agricultural waste products and the hydrolysates of lignocellulosic material (Calvey et al. 2014, Gong et al. 2012, Zhao et al. 2008).

Figure 1:
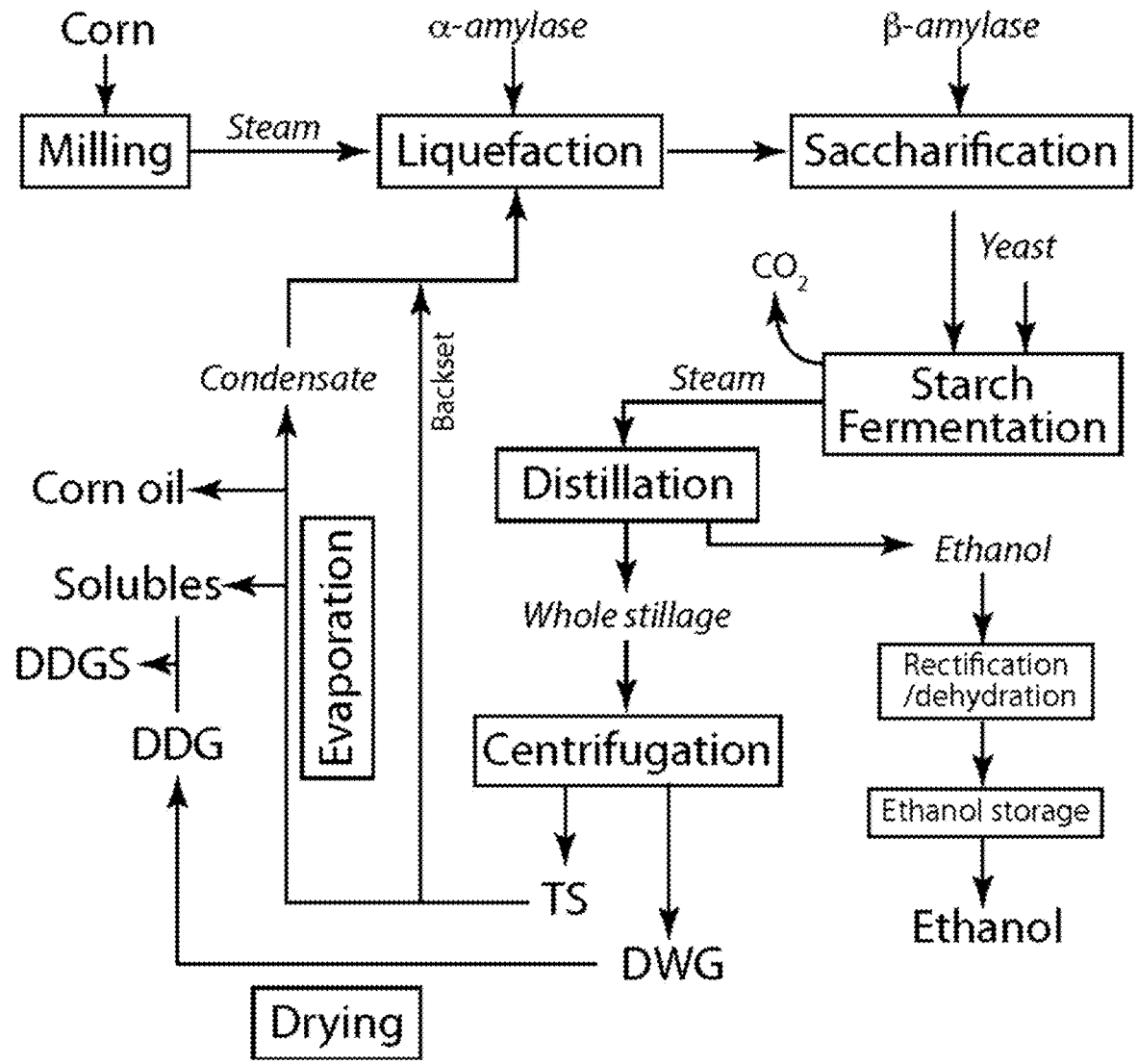
FIG. 1 shows a schema of a conventional dry mill ethanol process.
Figure 2:
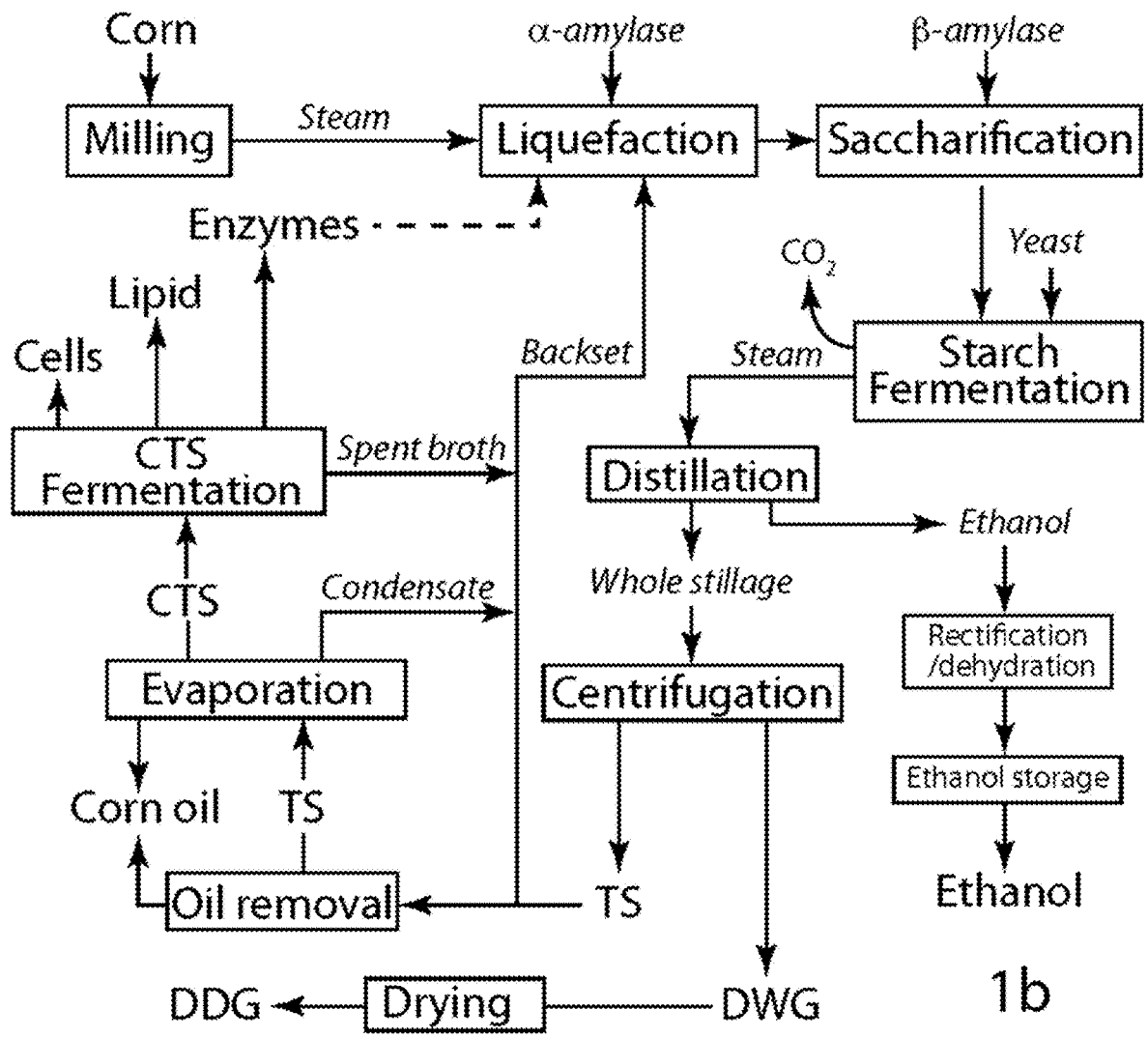
FIG. 2 shows a schema of a process of the present invention for converting stillage organics into yeast oil, protein, and enzymes.

*L. starkeyi* genes of notable importance include 24 glycoside hydrolases, three alpha-amylases, a highly versatile dextranase to metabolize the lateral starch side chains, and 15 copies of maltase that convert oligosaccharides into glucose (Riley et al. 2016, Kang et al. 2005). Overproduction and secretion of the thermostable alpha-amylase and dextranase found in *L. starkeyi* are particularly useful for starch saccharification in the integrated process described here (FIG. 2).

The *L. starkeyi* genome also encodes at least two secreted $\beta$-1,4-glucosidases and four non-secreted $\beta$-1,4-glucosidases, all of which have cellulosic carbohydrate binding domains, and at least two endo-1,4-$\beta$-D-glucanases (cellulases) (Chen et al. 2008). These enzymatic activities are useful for hydrolyzing corn fiber or other agricultural residues for additional ethanol or biodiesel production.

An ensemble of lipogenic genes are found in the genome of *L. starkeyi*, along with the metabolic machinery to supply the acetyl-CoA and NADPH needed to support high levels of lipid biosynthesis. For example, *L. starkeyi* has two complete genes for pyruvate carboxylase (LsPYC1, LsPYC2). This enzyme combines $CO_2$ with pyruvate to make oxaloacetate, which in turn citrate synthase (LsCIT1, LsCIT2, LsCIT3) combines with acetyl-CoA to make citrate. Genes coding for the alpha and beta subunits of ATP:citrate lyase (LsACL1, LsACL2) are found in a tandem bidirectional operon. Likewise, the genome of *L. starkeyi* codes for two complete fatty acid synthase complexes (LsFAS1.1, LsFAS1.2; LsFAS2.1, LsFAS2.2) with each organized into tandem bidirectional operons. Most yeasts and fungi have only a single FAS complex with the alpha and beta-subunits occurring in different parts of the genome. Mitochondrial NAD-dependent malate dehydrogenase (MDm, LsMDH2; PID_5229), and cytosolic NAD-dependent malate dehydrogenase (MDc, LSMDH1; PID_3988) exist as single copies in wild type *L. starkeyi*. Tandem bidirectional operons or clusters of metabolically associated genes indicate close interdependence and coordinated regulation of genes comprising a metabolic trait (Jeffries 2013).

*L. starkeyi* yeast maintains a basal lipid content that increases throughout fermentation, which already meets or exceeds that of any other native lipogenic yeast or alga. The lipid profile produced by *L. starkeyi* is remarkably similar to that of palm oil, one of the most common biodiesel feedstocks, which indicates that a biodiesel produced from this species naturally has desirable fuel properties (Calvey et al. 2016).

*L. starkeyi* is generally regarded as safe (GRAS) and is easily propagated, rendering residual cells and cell proteins useful for fortifying livestock or other animal feeds (Collett et al. 2014). Lastly, its genome has been sequenced, which enables the use of rational metabolic engineering methodologies to target specific genes for overexpression or deletion. By simply altering the expression or regulation of genes already present in the genome it is possible to improve lipid production and accumulation on poorly utilized substrates or under conditions when lipogenesis would not normally occur.

*Lipomyces starkeyi* is among the yeasts that can metabolize glucose, xylose and cellobiose, which are the main sugars released from the hydrolysis of lignocellulosic materials (Pan et al. 2009). With *L. starkeyi*, optimal lipid production is attained when growing on a 2:1 mixture of glucose and xylose, the same ratio found in enzymatic hydrolysates. Some strains of *L. starkeyi* also produce lipid from glycerol.

The lipid profile of *Lipomyces* is similar to that of palm oil (Calvey et al. 2016), which is important for both food and fuel production. By developing technology that uses *Lipomyces* to produce biofuels from the hydrolysates of agricultural cellulosic residues as an alternative to seed-based oils, the present invention provides for generating fuel from a renewable, environmentally benign resource that does not compete with food production. Furthermore, biodiesel derived from non-food sources such as lignocellulosic hydrolysate is advantageous because it meets the criteria delineated under Renewable Fuel Standard 2 (RFS2), which mandates the increased use of advanced cellulosic biofuels.

In addition to yeasts, a large number of eukaryotic algae also accumulate lipids, particularly when cultivated under heterotrophic conditions (U.S. Pat. No. 8,110,670). These eukaryotic algae can also be used in the methods of the present invention. One advantage to using lipogenic yeasts over algae, however, is that they can be grown readily in bioreactors and, unlike heterotrophically cultivated lipogenic algae, lipogenic yeasts can be cultivated on a wide range of organic substrates.

Lipid accumulation typically occurs when a readily assimilated carbon source is present in excess and nitrogen is limiting (Wei et al. 2009, Zhu et al. 2012). For example, when *L. starkeyi* transitions into a nitrogen-limited environment the biosynthetic pathways dependent on abundant nitrogen shut down and lipogenesis becomes the dominant metabolic feature of the cell. The cells continue to assimilate carbon, and in the absence of new cell growth, they store it as triacylglycerols. The most readily assimilated lipogenic carbon source is typically glucose (Ratledge 2002), and xylose has been reported to increase lipid accumulation even more (Gong et al. 2012, Zhao et al. 2008). Other substrates include cellobiose, glycerol, oligosaccharides, various industrial organic byproducts and hydrolysate from non-edible cellulosic feedstocks (Vicente et al. 2010). The yeasts engineered herein are capable of producing lipid when glucose is limited and carbon organics and nitrogen are in abundance.

Any or all of the genes described above can be driven by promoters that may be regulated or constitutive, strong, moderately strong or weak in *L. starkeyi* to modulate their activity therein. Alternately these genes may be deleted or inactivated. Likewise genes for metabolic pathways competing with the desired product of the genes described above may be modulated, deleted, or inactivated in order to improve the desired product or its formation rate.

Any or all of the genes described above in *L. starkeyi* can be incorporated in any other lipogenic yeast to confer similar benefits therein.

Biochemistry of Lipid Synthesis by Yeasts

Figure 3:
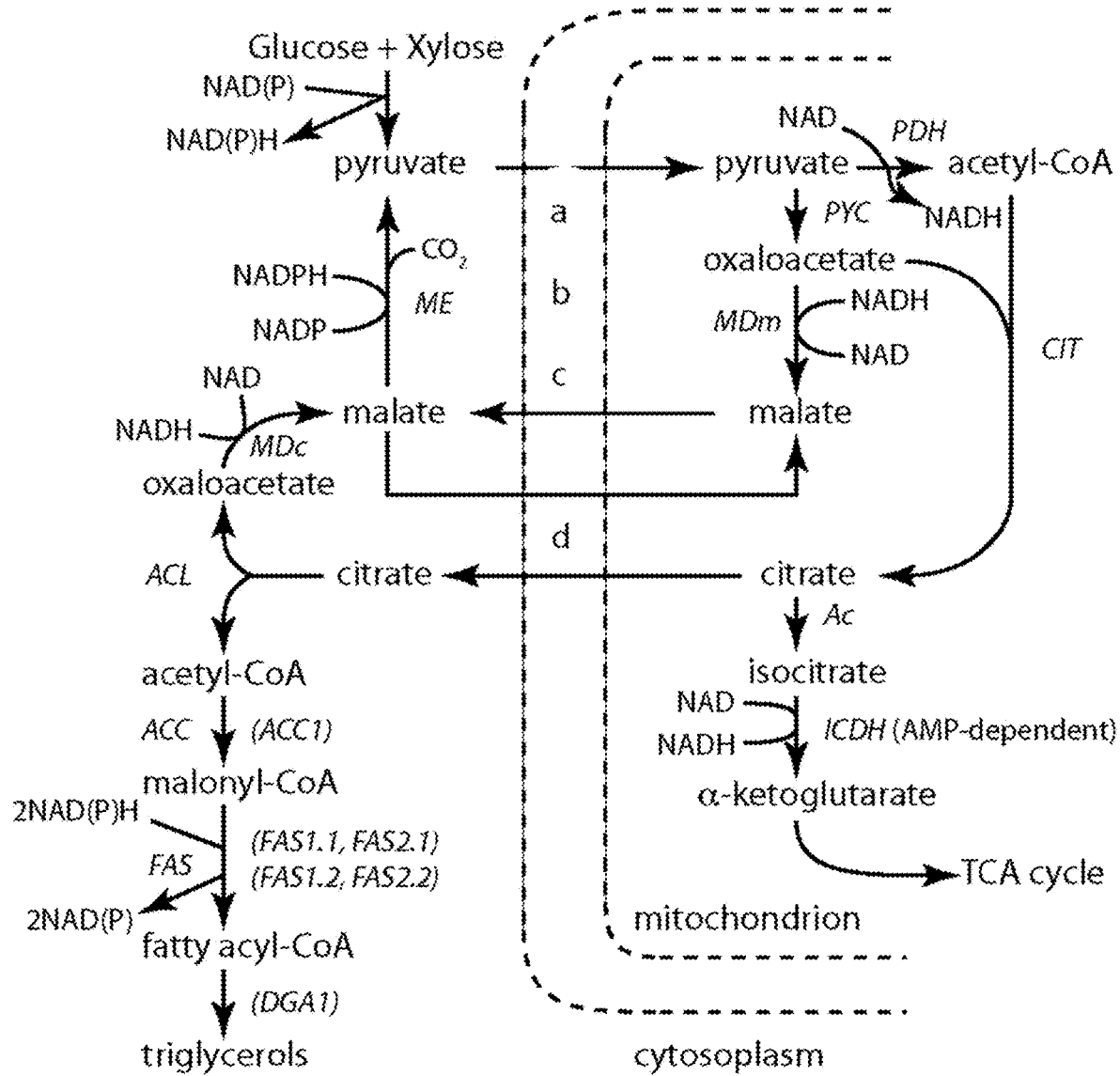
FIG. 3 shows a schema of intermediary metabolism linked to fatty acid biosynthesis in yeast. PDH, pyruvate dehydrogenase; PYC Pyruvate carboxylase; Ac, aconitase; ME malic enzyme; MDc malate decarboxylase, cytosolic; MDm malate dehydrogenase, mitochondrial; ACL ATP.

The biochemistry of lipid synthesis by yeasts is outlined in FIG. 3. Pyruvate is transported from the cytosol into the mitochondrion where pyruvate carboxylase (PYC) combines $CO_2$ with pyruvate to make oxaloacetate, and pyruvate dehydrogenase (PDH) oxidizes pyruvate to acetyl-CoA and NADH. Citrate synthase (CIT) combines with acetyl-CoA to make citrate while mitochondrial malate dehydrogenase (MDm) reduces oxaloacetate to malate.

The first step in response to nitrogen limitation is the activation of AMP deaminase, which cleaves adenosine monophosphate (AMP) into inosine monophosphate (IMP) and ammonia ($NH_4$). This activation lowers the intracellular concentrations of AMP, which inhibits the TCA cycle at the level of isocitrate dehydrogenase (ICDH), whose function is uniquely dependent on AMP in lipogenic yeasts (Ratledge 2004).

Significant evidence exists to support this mechanism. Intracellular AMP concentrations fall 11-fold within 24 hours after a transition to nitrogen limitation (Boulton et al. 1983). Also, assays of the *Lipomyces* ICDH1/2 enzyme show that its activity decreases about 5-fold when cells are transferred to a nitrogen-limiting medium (Tang et al. 2009). Activation of AMP deaminase and decreases in ICDH activity result in the accumulation of isocitrate and citrate (Boulton et al. 1983, Tang et al. 2009). Furthermore, lipid-accumulating *Lipomyces* cells display higher ACL enzymatic activity than proliferating cells (Naganuma et al. 1987).

When ICDH is no longer active, but the flux of glycolysis to pyruvate continues, isocitrate accumulates in the mitochondria and then equilibrates with citrate via isomerization. Citrate is exported into the cytosol via the citrate efflux system, which transports citrate out of the mitochondria in exchange for malate. The reduction in NADH formation by ICDH also results in less need for oxygen uptake and a lower rate of ATP synthesis.

Next, ATP:citrate lyase (ACL) catalyzes the cleavage of citrate into oxaloacetate and acetyl-CoA. This reaction is thought to be the primary source of the acetyl-CoA used for lipid synthesis and has been recognized as a key to efficient lipid production in lipogenic yeasts. ACL occurs in all lipogenic yeasts, but not in non-oleaginous species, which suggests a central role in lipid accumulation (Ratledge 2002, Evans et al. 1985). In the presence of CoA and ATP this enzyme cleaves citrate to acetyl-CoA and oxaloacetate, and supplies acetyl-CoA for lipid synthesis (Ratledge 1987). ACL is a dimeric protein with alpha and beta-subunits coded for by ACL1 and ACL2, which occur in a tandem bidirectional operon in the *Lipomyces starkeyi* genome (Jeffries 2013). The holoenzyme has a high affinity for citrate and ATP and is inhibited by ADP, glucose 6-phosphate, palmitoyl-CoA, and oleoyl-CoA. These allosteric inhibitors indicate that low ATP levels, high glycolytic flux, and the accumulation of fatty acid end products limit activity. The oxaloacetate formed by ACL can be converted to malate by a cytosolic malate dehydrogenase (MDc) and thus facilitate the export of more citrate from the mitochondrion.

Malate can also undergo conversion by malic enzyme (ME) into pyruvate and $CO_2$, while regenerating NADPH in the cytosol. The NADPH produced by the action of malic enzyme is thought to be the primary provider of reducing power for both fatty acid biosynthesis and desaturation reactions (Wynn et al. 1999). Lipid production may, however, draw on sources of NADPH in the cell such as the oxidative pentose phosphate pathway (Ratledge 2014). Specifically, two molecules of NADPH are required for each acetyl-CoA added to the growing fatty acyl chain during the standard fatty acid elongation cycle on the fatty acid synthase (FAS) complex (Ratledge 2004).

Malic enzyme (ME) has a high affinity for malate, and is only weakly inhibited by citrate, pyruvate, oxaloacetate, and ATP. ME is found in all lipogenic yeasts and its activity disappears following the period of active lipid accumulation. In contrast, acetyl-CoA carboxylase (ACC), fatty acid synthase (FAS), diacyglycerol acyltransferase (DGA), ATP:citrate lyase (ACL) and the NADPH-generating enzymes glucose-6-phosphate dehydrogenase, 6-phosphogluconate dehydrogenase and NADP(+):isocitrate dehydrogenase, do not demonstrate any changes in activities correlating with the accumulation of storage lipid (Wynn et al. 1999). ME therefore appears to be a source of NADPH for lipogenesis and a target for modification.

Metabolic pathways are often regulated at the first committing step. In this case, synthesis of malonyl-CoA, which is catalyzed by acetyl-CoA carboxylase (ACC), is a limiting step in attaining high titers of fatty acids and polyketides. Some versions of acetyl-CoA carboxylase are deactivated by a serine/threonine protein kinase, which is in turn activated by AMP. This relationship causes the acetyl-CoA carboxylase to be inactivated when glucose is depleted. To prevent this deactivation, a site-directed mutation is introduced in the serine residues of acetyl-CoA carboxylase that are phosphorylated by the AMP-activated protein kinase (AMPK). By converting these serines in Acct into an alanine or other non-serine and non-threonine residue, phosphorylation and inactivation is avoided. When the mutated gene is introduced into a host, acetyl-CoA carboxylase activity and total lipid accumulation increase.

Overexpression of the L. starkeyi ACC1 and GPD1 genes increase lipid production. Overexpression of ACC1, GUT2, and GUT1 also increases lipid production. In the case of GUT2 and GUT1 overexpression, higher levels of the coded proteins should increase the uptake of glycerol from thin stillage. In the case of ACC1 (acetyl-CoA carboxylase) overexpression and modification, altering the regulation should increase the formation of malonyl-CoA as a precursor for lipid synthesis and thereby increase the flux of malonyl-CoA into malonyl transferase which is an enzymatic activity of fatty acid synthase (FAS1).

Enzymes Involved in Substrate Assimilation

Lipomyces species and other lipogenic yeasts produce active amylases and other enzymes that degrade polysaccharides, and so are able to produce lipids from starch. L. starkeyi and other lipogenic yeasts also use a wide range of other polysaccharides (Gallagher et al. 1991, Punpeng et al. 1992, Steyn et al. 1995, Bignell et al. 2000, Ryu et al. 2000, Wilkie et al. 2000, Lee et al. 2003).

The genome of Lipomyces starkeyi contains numerous starch degrading alpha-amylase glycoside hydrolases (CAZY family GH13). Genes for several of these enzymes occur in clusters along with sugar transporters (e.g. Lipomyces starkeyi [PID_5034, PID_5035, PID_5036, PID_29016]; [PID_73677, PID_5097]; [PID_5097, PID_73677]; [PID_205534, PID_205437]; [PID_32360, PID_71673, PID_3625]). At least one of the alpha-amylases encoded in the L. starkeyi genome is thermostable (TAM1, PID_272826). Thermostable alpha-amylases are rarely found in yeasts. A gene for an amylo-alpha-1,6-glycosidase (dextranase) is also present (PID_5189) (Jeffries 2013). These features make L. starkeyi particularly suitable for lipid production when cultivated on starch (Gallagher et al. 1991, Punpeng et al. 1992).

Different strains of Lipomyces starkeyi show variable capacities for the assimilation of glycerol. The first step in glycerol metabolism is phosphorylation of glycerol by glycerol kinase (GUT1, PID_332345) to form glycerol-3-phosphate. This is followed by oxidation of glycerol-3-phosphate to dihydroxyacetone phosphate by an FAD-dependent glycerol-3-phosphate dehydrogenase (GUT2, PID_3942). Genes for both of these enzymes are present in Lipomyces starkeyi NRRL Y-11557 (Jeffries 2013).

Beta-1,4-endo-glucanase (BGL; GH5) depolymerizes glucan oligosaccharides. The genome of L. starkeyi encodes at least two GH5 cellulases, EGC1 and EGC2 (PID_72543 and PID_5513). The gene EGC1 is adjacent to a HXT2 sugar transporter (PID_4247) in the Lipomyces starkeyi genome. The HXT2 imports cellobiose (or cellulooligosaccharides). Beta-glucosidase (BGL; EC 3.2.1.21; GH3) is involved in the bioconversion of cellobiose to glucose. The genome of Lipomyces starkeyi encodes six putative enzymes in this family. At least one appears to be highly expressed (PID_69491) and at least two appear to be secreted (PID_147 and PID_5081). Several of the genes for GH3 proteins are proximally associated with genes coding for HXT2 sugar transporters (PID_3714, PID_334883, PID_7343).

Such proximal clustering of genes having associated physiological functions indicates that L. starkeyi has evolved for efficient use of beta- and alpha-linked glucans such as cellulose and starch.

The genome of L. starkeyi also contains a putative "glycoside hydrolase Family 61" auxiliary redox enzyme for cellulose hydrolysis (PID_61479) (Jeffries 2013). This protein includes a secretion signal and occurs rarely in ascomyceteous yeasts (Riley et al. 2016). This enzyme family is now known to not belong to the glycoside hydrolases, but rather is a "lytic polysaccharide mono-oxygenase" (LPMO). Enzymes belonging to this class are important components of commercial cellulase preparations (Cannella et al. 2014).

Glycerol kinase (GUT1) and glycerol-3-phosphate dehydrogenase (GUT2) are the first two genes involved in the assimilation of glycerol. Both of these genes are present in the genome of L. starkeyi NRRL-11557 (Jeffries 2013).

Any or all of the genes described above in L. starkeyi can be constitutively or overexpressed in L. starkeyi to enhance their activity therein.

Any or all of the genes described above in L. starkeyi can be incorporated in any other lipogenic yeast to confer similar benefits therein.

Genetic Targets for Metabolic Engineering

Various versions of the invention are directed to yeasts genetically modified to comprise one or more recombinant nucleic acids configured to express one or more proteins. The one or more recombinant nucleic acids are preferably configured to constitutively express or to overexpress the one or more proteins. The one or more recombinant nucleic acids preferably comprise one or more recombinant genes configured to constitutively express or to overexpress the one or more proteins. The expressed proteins include enzymes and other types of proteins such as transporters. If a cell endogenously expresses a particular protein, the nucleic acid expressing that protein may be modified to exchange or optimize promoters, exchange or optimize enhancers, or exchange or optimize any other genetic element that results in increased or constitutive expression of the proteins. Alternatively or additionally, one or more additional copies of a gene or coding sequence thereof may be introduced to the cell for enhanced expression of the proteins. If a cell does not endogenously express a particular protein, one or more copies of a recombinant nucleic acid configured to express that protein may be introduced to the cell for expression of the protein. The recombinant nucleic acid may be incorporated into the genome of the cell or may be contained on an extra-chromosomal plasmid. Techniques for genetic manipulation are described in further detail below. The genetically modified yeasts of the invention are also referred to herein as "recombinant," "engineered," or "bioengineered" yeasts, or other designations.

The recombinant yeasts of the invention may comprise one or more recombinant nucleic acids configured to express any one or more of the following proteins in any combination: an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme. The one or more recombinant nucleic acids preferably comprise one or more recombinant genes configured to express the above-referenced proteins.

For example, the recombinant yeasts of the invention may comprise one or more recombinant genes configured to express an acetyl-CoA carboxylase alone or with any one or more of an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination. The recombinant yeasts of the invention may comprise one or more recombinant genes configured to express an alpha-amylase alone or with any one or more of an acetyl-CoA carboxylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express an ATP citrate lyase alone or with any one or more of an acetyl-CoA carboxylase, an alpha-amylase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a diacylglycerol acyltransferase alone or with any one or more of an acetyl-CoA carboxylase, an alpha-amylase, an ATP citrate lyase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a fatty acid synthase alone or with any one or more of an acetyl-CoA carboxylase, an alpha-amylase, an ATP citrate lyase, a diacylglycerol acyltransferase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a glycerol kinase alone or with any one or more of an acetyl-CoA carboxylase, an alpha-amylase, an ATP citrate lyase, a diacylglycerol acyltransferase, a fatty acid synthase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a 6-phosphogluconate dehydrogenase alone or with any one or more of an acetyl-CoA carboxylase, an alpha-amylase, an ATP citrate lyase, a diacylglycerol acyltransferase, a fatty acid synthase, a glycerol kinase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a glycerol-3-phosphate dehydrogenase alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination. The recombinant yeasts of the invention may comprise one or more recombinant genes configured to express a malic enzyme alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a fatty acyl-CoA reductase alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a delta-9 acyl-CoA desaturase alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a glycerol-3-phosphate acyltransferase alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a lysophosphatidate acyltransferase alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a glucose-6-phosphate dehydrogenase alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a beta-glucosidase alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a hexose transporter, a glycerol transporter, a glycoside hydrolase enzyme, and an auxiliary activity family 9 enzyme in any combination.

The recombinant yeasts of the invention may comprise one or more recombinant genes configured to express a hexose transporter alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a glycerol transporter, a glycoside hydrolase enzyme, and an auxiliary activity family 9 enzyme in any combination.

The recombinant yeasts of the invention may comprise one or more recombinant genes configured to express a glycerol transporter alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycoside hydrolase enzyme, and an auxiliary activity family 9 enzyme in any combination.

The recombinant yeasts of the invention may comprise one or more recombinant genes configured to express a glycoside hydrolase enzyme alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, and an auxiliary activity family 9 enzyme in any combination.

The recombinant yeasts of the invention may comprise one or more recombinant genes configured to express an auxiliary activity family 9 enzyme alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, and a glycoside hydrolase enzyme in any combination.

Acetyl-CoA carboxylases include enzymes falling under Enzyme Commission (EC) number 6.4.1.2. An exemplary acetyl-CoA carboxylase that may be expressed includes Acc1 (SEQ ID NO:2) encoded by Acc1 (SEQ ID NO:1) from *L. starkeyi* (PID_72701) Other exemplary acetyl-coA carboxylases include Acc1 mutants that comprise a residue other than serine at a position corresponding to position 1146 of SEQ ID NO:2. The residue at position 1146 is preferably a residue other than serine and threonine. The residue at position 1146 may be any amino acid other than serine or, more preferably any amino acid other than serine and threonine. The residue at position 1146 may be alanine.

Other exemplary acetyl-coA carboxylases include Acc1 mutants that comprise serine at a position corresponding to position 639 of SEQ ID NO:2 and a residue other than serine and threonine at a position corresponding to position 1146 of SEQ ID NO:2.

Alpha-amylases include enzymes falling under EC number 3.2.1.1. Exemplary alpha-amylases that may be expressed include the secreted alpha-amylase designated by PID_3772 (SEQ ID NO:4) encoded by the corresponding nucleic acid (SEQ ID NO:3) from *Lipomyces starkeyi*, the thermostable α-amylase designated by PID_272826 (SEQ ID NO:6) encoded by the corresponding nucleic acid (SEQ ID NO:5) from *L. starkeyi*, and a chimera of the secreted alpha-amylase and the thermostable α-amylase (SEQ ID NO:8) encoded by the corresponding nucleic acid (SEQ ID NO:7).

ATP citrate lyases include enzymes falling under EC number 2.3.3.8. An exemplary ATP citrate lyase that may be expressed includes the alpha subunit Acl1 (SEQ ID NO:10) encoded by Acl1 (SEQ ID NO:9) and the beta subunit Acl2 (SEQ ID NO:12) encoded by Acl2 (SEQ ID NO:11) from *L. starkeyi*. The alpha and beta subunits are preferably expressed as a pair.

Diacylglycerol acyltransferases (DGAs) include enzymes falling under EC number 2.3.1.20. Exemplary diacylglycerol acyltransferases that may be expressed include a 1233 variant of DGA1 (SEQ ID NO:14) encoded by DGA1-1233 (SEQ ID NO:13), a 1389 variant of DGA1 (SEQ ID NO:16) encoded by DGA1-1389 (SEQ ID NO:15), and DGA2 (SEQ ID NO:58) encoded by DGA2 (SEQ ID NO:57), all derived from *L. starkeyi*. The 1233 variant of DGA1 is identical to the 1389 variant except that it lacks the first 52 residues of the 1389 variant. The 1233 variant unexpectedly confers enhanced lipogenic properties compared to the 1389 variant. Accordingly, preferred diacylglycerol acyltransferases of the invention lack a sequence corresponding to positions 1-52 of SEQ ID NO:16.

Fatty acid synthases (FASs) include enzymes falling under EC number 2.3.1.85. Exemplary fatty acid synthases that may be expressed include any combination of alpha and beta fatty acid synthase subunits from *L. starkeyi*. Alpha fatty acid synthase subunits from *L. starkeyi* include FAS2.1 (SEQ ID NO:18) encoded by FAS2.1 (SEQ ID NO:17) and FAS2.2 (SEQ ID NO:22) encoded by FAS2.2 (SEQ ID NO:21). Beta fatty acid synthase subunits from *L. starkeyi* include FAS1.1 (SEQ ID NO:20) encoded by FAS1.1 (SEQ ID NO:19) and FAS1.2 (SEQ ID NO:24) encoded by FAS1.2 (SEQ ID NO:23). FAS2.1 is preferably expressed with FAS1.1, and FAS2.2 is preferably expressed with FAS1.2. However, FAS2.1 may be expressed with FAS1.2, and FAS2.2 may be expressed with FAS1.1.

Glycerol kinases include enzymes falling under EC number 2.7.1.30. Exemplary glycerol kinases that may be expressed include a 1602 variant of GUT1 (SEQ ID NO:26) encoded by GUT1-1602 (SEQ ID NO:25) and a 1617 variant of GUT1 (SEQ ID NO:28) encoded by GUT1-1617 (SEQ ID NO:27), both derived from *L. starkeyi*. The 1602 variant of DGA1 is identical to the 1617 variant except that it lacks the first 5 residues of the 1617 variant. Accordingly, some glycerol kinases of the invention lack a sequence corresponding to positions 1-5 of SEQ ID NO:28.

6-Phosphogluconate dehydrogenases include enzymes falling under EC number 1.1.1.44. An exemplary 6-phosphogluconate dehydrogenase that may be expressed includes GND1 (SEQ ID NO:30) encoded by GND1 (SEQ ID NO:29) from *L. starkeyi*.

Glycerol-3-phosphate dehydrogenases include enzymes falling under EC number 1.1.1.8. Exemplary glycerol-3-phosphate dehydrogenases that may be expressed include GPD1 (SEQ ID NO:32) encoded by GPD1 (SEQ ID NO:31) and the FAD-dependent glycerol-3-phosphate dehydrogenase GUT2 (SEQ ID NO:56) encoded by GUT2 (SEQ ID NO:55), both from *L. starkeyi*.

Malic enzymes include enzymes falling under EC numbers 1.1.1.38, 1.1.1.39, 1.1.1.40, and 83. An exemplary malic enzyme that may be expressed includes ME (SEQ ID NO:34) encoded by ME (SEQ ID NO:33) from *L. starkeyi*.

Fatty acyl-CoA reductases include enzymes falling under EC numbers 1.2.1, such as 1.2.1.84 and others. These enzymes include the preferred alcohol-forming fatty acyl-CoA reductases (EC 1.2.1.84). An exemplary fatty acyl-CoA reductase that may be expressed includes FALDR (SEQ ID NO:36) encoded by FALDR (SEQ ID NO:35) from *Marinobacter aquaeolei*.

Delta-9 acyl-CoA desaturases include enzymes falling under EC number 1.14.19.1. An exemplary delta-9 acyl-CoA desaturase that may be expressed includes OLE1 (SEQ ID NO:38) encoded by OLE1 (SEQ ID NO:37) from *L. starkeyi*. In addition to or instead of expressing a delta-9 acyl-CoA desaturase, other fatty acid desaturases may be expressed, such as acyl-CoA (8-3)-desaturases (delta-5 desaturases) (EC 1.14.19.44) and acyl-CoA 6-desaturases (delta-6 desaturases) (EC 1.14.19.3).

Glycerol-3-phosphate acyltransferases include enzymes falling under EC number 2.3.1.15. An exemplary glycerol-3-phosphate acyltransferase that may be expressed includes SCT1 (SEQ ID NO:40) encoded by SCT1 (SEQ ID NO:39) from *L. starkeyi*.

Lysophosphatidate acyltransferases include enzymes falling under EC number 2.3.1.51. An exemplary lysophosphatidate acyltransferase that may be expressed includes SLC1 (SEQ ID NO:42) encoded by SLC1 (SEQ ID NO:41) from *L. starkeyi*.

Glucose-6-phosphate dehydrogenases include enzymes falling under EC number 1.1.1.49. An exemplary glucose-6-phosphate dehydrogenase that may be expressed includes ZWF1 (SEQ ID NO:44) encoded by ZWF1 (SEQ ID NO:43) from *L. starkeyi*.

Beta-glucosidases include enzymes falling under EC number 3.2.1.21. An exemplary beta-glucosidase that may be expressed includes BGL1.1 (SEQ ID NO:46) encoded by BGL1.1 (SEQ ID NO:45) from *L. starkeyi*.

Hexose transporters include proteins falling under the Hxt family (e.g., Hxt1, Hxt2, Hxt3, Hxt4, Hxt5, Hxt6, Hxt7, Hxt8, Hxt9, Hxt11, etc.). An exemplary hexose transporter that may be expressed includes Hxt2.2 (SEQ ID NO:48) encoded by Hxt2.2 (SEQ ID NO:47) from *L. starkeyi*.

Glycerol transporters that may be expressed include the glycerol/H+ symporters STL1 (SEQ ID NO:64) encoded by STL1 (SEQ ID NO:63) and STL2 (SEQ ID NO:66) encoded by STL2 (SEQ ID NO:65) from *L. starkeyi*. Glycerol transporters that may be expressed also include the glycerol facilitator FPS1 (SEQ ID NO:68) encoded by FPS1 (SEQ ID NO:67) from *L. starkeyi*.

Glycoside hydrolases include a number of families. Preferred glycoside hydrolases that may be expressed include glycoside hydrolase family 5 enzymes. Glycoside hydrolase family 5 enzymes include endoglucanases (EC 3.2.1.4), beta-mannanases (EC 3.2.1.78), exo-1,3-glucanases (EC 3.2.1.58), endo-1,6-glucanases (EC 3.2.1.75), xylanases (EC 3.2.1.8), endoglycoceramidases (EC 3.2.1.123), and trehalases (EC 3.2.1.28). Preferred glucosidase hydrolase family 5 enzymes that may be expressed include endoglucanases. Exemplary endoglucanases that may be expressed include EGC1 (SEQ ID NO:50) encoded by EGC1 (SEQ ID NO:49) from *L. starkeyi* and EGC2 (SEQ ID NO:52) encoded by EGC2 (SEQ ID NO:51) from *L. starkeyi*. Exemplary trehalases that may be expressed include the "neutral" trehalase NTH1 (SEQ ID NO:60) encoded by NTH1 (SEQ ID NO:59) and the "acidic" trehalase ATH1 (SEQ ID NO:62) encoded by ATH1 (SEQ ID NO:61), both from *L. starkeyi*.

Auxiliary activity family 9 enzymes are copper-dependent lytic polysaccharide monooxygenases (LPMOs). These enzymes are involved in the cleavage of cellulose chains with oxidation of various carbons (C-1, C-4 and C-6). Auxiliary activity family 9 enzymes were originally classified as glycoside hydrolases under glycoside hydrolase family 61 (GH61). An exemplary auxiliary activity family 9 enzyme that may be expressed includes AAC9 (SEQ ID NO:54) encoded by AAC9 (SEQ ID NO:53) from *L. starkeyi*.

Other suitable proteins that may be expressed include those comprising polypeptide sequences at least about 80%, at least about 85%, at least about 90%, at least about 95%, at least about 97%, or at least about 99% identical to the sequences listed above. Other suitable proteins that may be expressed include orthologs and paralogs of the proteins listed above. Other suitable proteins that may be expressed include those comprising polypeptide sequences at least about 80%, at least about 85%, at least about 90%, at least about 95%, at least about 97%, or at least about 99% identical to orthologs and paralogs of the proteins listed above. The orthologs are preferably from lipogenic yeasts, such as any of the lipogenic yeasts described herein. The recombinant gene encoding the proteins may include introns or be devoid of introns or any or all other non-coding regions in the native gene. Any nucleotide sequences capable of expressing the polypeptide sequences encompassed herein are acceptable. Tremendous variation from the exemplary nucleotide sequences described herein is possible due to the redundancy in the genetic code and codon optimization.

Coding sequences of the above-mentioned proteins are preferably operably linked to a promoter. The promoter may be a constitutive promoter or an inducible promoter. Exemplary promoters that may be operably linked to the coding sequences of the above-mentioned proteins include the *L. starkeyi* ATPase 3900 promoter (SEQ ID NO:75), the *L. starkeyi* citrate synthase (CIT1) promoter (SEQ ID NO:76), the *L. starkeyi* fructose bisphosphate aldolase (FBA1) promoter (SEQ ID NO:77), the *L. starkeyi* glutamine synthetase (GLN1) promoter (SEQ ID NO:78), the *L. starkeyi* glyceraldehyde 3-phosphate dehydrogenase (TDH3) promoter (SEQ ID NO:79), the *L. starkeyi* pyruvate kinase (PYK1) promoter (SEQ ID NO:80), the *L. starkeyi* translation elongation factor (TEF1) promoter (SEQ ID NO:81), the *L. starkeyi* triosephosphate isomerase (TPI) promoter (SEQ ID NO:82), the *L. starkeyi* enolase (ENO1) promoter (SEQ ID NO:83), the copper inducible (CUP1) promoter (SEQ ID NO:84), or sequence variants at least about at least about 80%, at least about 85%, at least about 90%, at least about 95%, at least about 97%, or at least about 99% identical thereto.

Coding sequences of the above-mentioned proteins are preferably operably linked to a terminator. Exemplary terminators that may be operably linked to the coding sequences of the above-mentioned proteins include the *L. starkeyi* ATPase 3900 terminator (SEQ ID NO:85), the *L. starkeyi* fructose bisphosphate aldolase (FBA1) terminator (SEQ ID NO:86), the *L. starkeyi* glutamine synthetase (GLN1) terminator (SEQ ID NO:87), the *L. starkeyi* glyceraldehyde 3-phosphate dehydrogenase (TDH3) terminator (SEQ ID NO:88), the *L. starkeyi* pyruvate kinase (PYK1) terminator (SEQ ID NO:89), the *L. starkeyi* triosephosphate isomerase (TPI) terminator (SEQ ID NO:90), or sequence variants at least about at least about 80%, at least about 85%, at least about 90%, at least about 95%, at least about 97%, or at least about 99% identical thereto.

In addition to expressing any one or more of the proteins listed above, the recombinant yeasts of the invention may be modified to reduce or ablate the activity of one or more native or non-native proteins. The recombinant yeasts, for example, may comprise a modification that reduces or ablates the activity of one or more of the following native proteins: a delta-9 acyl-CoA desaturase, a glycerol-3-phosphate dehydrogenase, an acyl-CoA oxidase, a 3-hydroxyacyl-CoA dehydrogenase, and an enoyl-CoA hydratase.

Delta-9 acyl-CoA desaturases include enzymes falling under EC number 1.14.19.1. An exemplary delta-9 acyl-CoA desaturase whose activity may be reduced or ablated includes OLE1 (SEQ ID NO:38) encoded by OLE1 (SEQ ID NO:37) from *L. starkeyi*. In addition to or instead of reducing or ablating the activity of a delta-9 acyl-CoA desaturase, the activity of other fatty acid desaturases may be reduced or ablated, such as acyl-CoA (8-3)-desaturases (delta-5 desaturases) (EC 1.14.19.44) and acyl-CoA 6-desaturases (delta-6 desaturases) (EC 1.14.19.3).

Glycerol-3-phosphate dehydrogenases include enzymes falling under EC number 1.1.1.8. An exemplary glycerol-3-phosphate dehydrogenase whose activity may be reduced or ablated includes the FAD-dependent glycerol-3-phosphate dehydrogenase GUT2 (SEQ ID NO:56) encoded by GUT2 (SEQ ID NO:55) from *L. starkeyi*.

Acyl-CoA oxidases include enzymes falling under EC number 1.3.3.6. An exemplary acyl-CoA oxidase whose activity may be reduced or ablated includes POX1 (SEQ ID NO:70) encoded by POX1 (SEQ ID NO:69) from *L. starkeyi*. Acyl-CoA oxidases catalyze the first step of beta oxidation.

Enoyl-CoA hydratases include enzymes falling under EC number 4.2.1.17. An exemplary enoyl-CoA hydratase whose activity may be reduced or ablated includes FOX1 (SEQ ID NO:72) encoded by FOX1 (SEQ ID NO:71) from *L. starkeyi*. Enoyl-CoA hydratases catalyze the third step of beta oxidation.

3-Hydroxyacyl-CoA dehydrogenases include enzymes falling under EC number 1.1.1.35. An exemplary 3-hydroxyacyl-CoA dehydrogenase whose activity may be reduced or ablated includes FOX1 (SEQ ID NO:72) encoded by FOX1 (SEQ ID NO:71) from *L. starkeyi*. 3-hydroxyacyl-CoA dehydrogenases catalyze the second step of beta oxidation.

Certain enzymes are multifunctional and have more than one enzymatic activity. Examples include the FOX1 (SEQ ID NO:72) encoded by FOX1 (SEQ ID NO:71) from *L. starkeyi*, which has both 3-hydroxyacyl-CoA dehydrogenase and enoyl-CoA hydratase activities, and is thereby considered to be both a 3-hydroxyacyl-CoA dehydrogenase and an enoyl-CoA hydratase.

Other suitable proteins whose activity may be reduced or ablated include those comprising amino acid sequences at least about 80%, at least about 85%, at least about 90%, at least about 95%, at least about 97%, or at least about 99% identical to the sequences listed above. Other suitable proteins whose activity may be reduced or ablated include orthologs and paralogs of the proteins listed above. Other suitable proteins whose activity may be reduced or ablated include those comprising amino acid sequences at least about 80%, at least about 85%, at least about 90%, at least about 95%, at least about 97%, or at least about 99% identical to orthologs and paralogs of the proteins listed above.

A modification that reduces or ablates the activity of a gene product such as a protein is referred to herein as a "functional deletion." "Functional deletion" or its grammatical equivalents refers to any modification to a microorganism that ablates, reduces, inhibits, or otherwise disrupts production of a gene product, renders a produced gene product non-functional, or otherwise reduces or ablates a produced gene product's activity. Accordingly, in some instances, a gene product that is functionally deleted means that the gene product is not produced by the microorganism at all. "Gene product" refers to a protein or polypeptide encoded and produced by a particular gene. "Gene" refers to a nucleic acid sequence capable of producing a gene product and may include such genetic elements as a coding sequence together with any other genetic elements required for transcription and/or translation of the coding sequence. Such genetic elements may include a promoter, an enhancer, and/or a ribosome binding site (RBS), among others.

One of ordinary skill in the art will appreciate that there are many well-known ways to functionally delete a gene product. For example, functional deletion can be accomplished by introducing one or more genetic modifications. As used herein, "genetic modifications" refer to any differences in the nucleic acid composition of a cell, whether in the cell's native chromosome or in endogenous or exogenous non-chromosomal plasmids harbored within the cell. Examples of genetic modifications that may result in a functionally deleted gene product include but are not limited to substitutions, partial or complete deletions, insertions, or other variations to a coding sequence or a sequence controlling the transcription or translation of a coding sequence, such as placing a coding sequence under the control of a less active promoter, etc. In some versions, a gene or coding sequence can be replaced with a selection marker or screenable marker. Various methods for introducing genetic modifications are well known in the art and include homologous recombination, among other mechanisms. See, e.g., Green et al., *Molecular Cloning: A laboratory manual*, 4$^{th}$ ed., Cold Spring Harbor Laboratory Press (2012) and Sambrook et al., *Molecular Cloning: A Laboratory Manual*, 3$^{rd}$ ed., Cold Spring Harbor Laboratory Press (2001). In some versions, functional deletion can be accomplished by expressing ribozymes or antisense sequences that target the mRNA of the gene of interest. Functional deletion can also be accomplished by inhibiting the activity of the gene product, for example, by chemically inhibiting a gene product with a small-molecule inhibitor, by expressing a protein that interferes with the activity of the gene product, or by other means. In some versions, the functional deletion may comprise an activity-reducing or activity-ablating mutation in the endogenous gene. The activity-reducing or activity-ablating mutation in the endogenous gene may comprise a nucleotide substitution in the endogenous gene, a nucleotide insertion in the endogenous gene, a partial deletion of the endogenous gene, and/or a complete deletion of the endogenous gene.

In certain versions of the invention, the functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the non-functionally deleted gene product.

In certain versions of the invention, a cell with a functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the gene product compared to a cell with the non-functionally deleted gene product.

In certain versions of the invention, the functionally deleted gene product may be expressed at an amount less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the amount of the non-functionally deleted gene product.

In certain versions of the invention, the functionally deleted gene product may result from a genetic modification in which at least 1, at least 2, at least 3, at least 4, at least 5, at least 10, at least 20, at least 30, at least 40, at least 50, or more nonsynonymous substitutions are present in the gene or coding sequence of the gene product.

In certain versions of the invention, the functionally deleted gene product may result from a genetic modification in which at least 1, at least 2, at least 3, at least 4, at least 5, at least 10, at least 20, at least 30, at least 40, at least 50, or more bases are inserted in the gene or coding sequence of the gene product.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of the gene product's gene or coding sequence is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a promoter driving expression of the gene product is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of an enhancer controlling transcription of the gene product's gene is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a sequence controlling translation of the gene product's mRNA is deleted or mutated.

In certain versions of the invention, the decreased activity or expression of the functionally deleted gene product is determined with respect to the activity or expression of the gene product in its unaltered state as found in nature. In certain versions of the invention, the decreased activity or expression of the functionally deleted gene product is determined with respect to the activity or expression of the gene product in its form in a corresponding microorganism. In certain versions, the genetic modifications giving rise to a functionally deleted gene product are determined with respect to the gene in its unaltered state as found in nature. In certain versions, the genetic modifications giving rise to a functionally deleted gene product are determined with respect to the gene in its form in a corresponding microorganism. As used herein, "corresponding microorganism" refers to a microorganism of the same species having the same or substantially same genetic and proteomic composition as a microorganism of the invention, with the exception of genetic and proteomic differences resulting from the manipulations described herein for the microorganisms of the invention.

The yeasts of the invention with the modifications described herein preferably exhibit a property selected from the group consisting of increased lipid production, increased lipid secretion, increased lipid production under nitrogen-rich conditions, increased lipid yield, increased lipid secretion under nitrogen-rich conditions, increased enzyme production, increased enzyme secretion, increased carbohydrase production, increased carbohydrase secretion, increased growth rates, and/or increased organic consumption, such as increased glycerol consumption and/or and increased disaccharide (cellobiose and/or trehalose) consumption relative to a non-recombinant control. "Carbohydrase" refers to any enzyme capable of breaking down a carbohydrate, such as amylases, cellulases, glucosidases, etc.

Nitrogen-rich conditions exist when the form, the amount, or form and amount of nitrogen biologically available to the cell exceeds the amount of carbon source necessary for balanced cell growth. The form of nitrogen refers to the chemical form in which it is supplied to the cells. An easily assimilated nitrogen source includes amino acids or extracts of yeast cells. These nitrogen sources require less metabolic energy for assimilation and provide carbon at the same time. A less readily assimilated nitrogen source includes inorganic salts of ammonium or nitrate or nitrogen supplied as urea. Elemental nitrogen or nitrogen bound in insoluble minerals are not generally considered biologically available to fungi. Nitrogen-rich conditions can exist when either readily assimilated or less-readily assimilated nitrogen sources are provided to a cell in excess of the amount of carbon required for protein, nucleic acid and cell wall synthesis.

Nitrogen-poor conditions can exist when the amount of readily available or less readily available nitrogen supplied is substantially less than the amount of available carbon source that can be assimilated. A nitrogen-poor or nitrogen-limiting condition could also exist when an easily assimilated nitrogen source is supplied slowly or in a slow-release formulation.

As in the case of the nitrogen supply, the carbon source can be readily assimilated, less readily assimilated, poorly assimilated or not assimilated. The cell can use readily assimilated carbon source such as glucose to rapidly generate metabolic energy. A carbon source such as glycerol, cellobiose or other oligosaccharides might or might not be readily assimilated depending on the enzymes available for its metabolism and the conditions of growth such as the supply of oxygen.

A nitrogen-rich condition in a native organism can be identified as a concentration above a nitrogen-limited concentration, wherein the nitrogen-limited concentration includes all concentrations at or below the concentration of nitrogen in which any decreases thereof increase the amount of lipid produced and/or accumulated by the organism.

Acetyl-CoA carboxylase and diacylglycerol acyltransferase are both preferred targets for increasing lipid production. Overexpression of acetyl-CoA carboxylase results in increased rates of fatty acid biosynthesis and fatty acid content. The Acct acetyl-CoA carboxylase of *L. starkeyi* has serine residues at positions corresponding to 639 and 1146 of SEQ ID NO2. The inventors have determined that the serine at position 1146 is responsible for downregulating ACC1 activity upon post-translational modification. Certain versions of this invention modify the serine at position 1146 to an amino acid other than serine or threonine, such as alanine or any other amino acid, to prevent this downregulation.

Overexpression of diacylglycerol acyltransferase leads to an increase in lipid production. This lipid production is increased even further following overexpression of acetyl-CoA carboxylase. The present inventors surmise that a sink for triglyceride synthesis, such as through high expression of diacylglycerol acyltransferase, should be present in order for overexpression of acetyl-CoA carboxylase to be fully effective.

One of the prerequisites of oleaginous organisms is the ability to produce a continuous supply of acetyl-CoA precursors in the cytosol. ATP citrate lyase acts as the primary source of cytosolic acetyl-CoA in these species, and is believed to be one of the rate limiting steps of lipid biosynthesis. The activity of ATP citrate lyase correlates well with the specific rate of lipid biosynthesis in *L. starkeyi*. In *Lipomyces* both intracellular and extracellular citrate levels rise in response to nitrogen limitation (Holdsworth et al. 1988). Citrate accumulation may represent a bottleneck, which could be overcome by increasing ATP citrate lyase activity in the cytosol or citrate synthase (CS) in the mitochondria.

NADPH, which is required for lipid biosynthesis, is largely supplied by the oxidative pentose phosphate pathway (PPP). Native lipogenic yeasts possess a highly active oxidative pentose phosphate pathway along with an enzyme system that exports citric acid to the cytosol where it is converted into acetyl-CoA and NADPH that feed into lipid synthesis. Modification of lipogenic enzymes or alteration of gene expression that boosts these systems can further increase lipid synthesis in native lipogenic yeasts. Overexpression of 6-phosphogluconate dehydrogenase (GND1) and/or glucose-6-phosphate dehydrogenase (ZWF1), for example, are predicted to increase the supply of NADPH for lipid synthesis, but since ZWF1 and (particularly) GND1 are subject to strong allosteric regulation by physiological levels of NADPH (Barcia-Vieitez et al. 2014, Rippa et al. 1998, Velasco et al. 1995), modification of the regulatory controls are predicted to be more effective. For example, substitution of the tyrosine at position 99 (i.e., Y99) of the ZWF1 of *L. starkeyi* represented by SEQ ID NO:44 can alter binding of NADPH and thereby render this enzyme resistant to allosteric regulation by NADPH. The tyrosine in ZWF1 can be substituted by any amino acid. The tyrosine in ZWF1 is preferably substituted with serine, threonine, glutamine asparagine, cysteine, alanine, proline, leucine, isoleucine, phenylalanine, valine, histidine, lysine, asparagine, aspartic, glutamic acid, or glycine; more preferably substituted with serine or threonine; and most preferably substituted with serine. An analogous substitution in GND1 can also or alternatively be performed to render GND1 resistant to allosteric regulation by NADPH.

The NADPH supplied by malic enzyme has a strong influence on lipid accumulation in lipogenic yeasts. Increasing malic enzyme activity is predicted to provide lipogenic yeasts with more NADPH for lipid synthesis.

Another approach to increasing the production of lipid is to reduce activity of the β-oxidation pathway. The β-oxidation pathway is responsible for consuming lipid after lipogenic yeasts exhaust their carbohydrate sources Eliminating the breakdown of lipids is therefore another target for developing yeasts with enhanced lipid production. Exemplary modifications in this regard include functional deletion of an acyl-CoA oxidase, a 3-hydroxyacyl-CoA dehydrogenase, and/or an enoyl-CoA hydratase. Acyl-CoA oxidases catalyze the first step in beta oxidation. Enoyl-CoA hydratases catalyze the second step in beta oxidation. 3-Hydroxyacyl-CoA dehydrogenases catalyze the third step in beta oxidation. POX1 is an exemplary acyl-CoA oxidase in *L. starkeyi*. FOX1 is a multifunctional enzyme in *L. starkeyi* that can be considered to be both a 3-hydroxyacyl-CoA dehydrogenase and an enoyl-CoA hydratase, as it has both 3-hydroxyacyl-CoA dehydrogenase and enoyl-CoA hydratase activities. Other modifications that inhibit lipid oxidation are acceptable.

Disruption of the gene for the regulatory protein CreA/Mig1 in *Y. lipolytica* increased the lipid content from 36% to 48.7% of its dry weight while increasing the $C_{18:1}$ content (Wang et al. 2013). A CreA homolog in the *L. starkeyi* genome is similar to the CreA transcriptional activator of *Y. lipolytica*, and could be a good target to determine whether disruption of the CREA/MIG1 homolog in *L. starkeyi* results in an increase in lipid production.

For *Mucor circinelloides* (Zhang et al. 2008), *Rhodotorula glutinis* (Li et al. 2012), and *Yarrowia lipolytica* (Tai et al. 2013), the basal lipid production contents of the parental strains are all considerably lower than what has been observed in native (non-engineered) *L. starkeyi* under nitrogen limiting conditions (≈65%), indicating that there is substantial room for improvement in these strains with the modifications described herein.

Genetic Engineering

The cells of the invention may be genetically altered to functionally delete, express, or overexpress any of the specific genes or gene products explicitly described herein or homologs thereof. Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Nucleic acid or gene product (amino acid) sequences of any known gene, including the genes or gene products described herein, can be determined by searching any sequence databases known in the art using the gene name or accession number as a search term. Common sequence databases include GenBank (www.ncbi.nlm.nih.gov), ExPASy (expasy.org), KEGG (www.genome.jp), among others. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologs of the genes or gene products described herein include genes or gene products having at least about 30%, 35%, 40%, 45%, 50%, 55%, 60%, 65%, 70%, 75%, 80%, 85%, 90%, 95%, or 99% identity to the genes or gene products described herein. Methods for determining sequence similarity percentages (e.g., BLASTP and BLASTN using default parameters) are described herein and are generally available. The homologous proteins should demonstrate comparable activities and, if an enzyme, participate in the same or analogous pathways. Homologs include orthologs and paralogs. "Orthologs" are genes and products thereof in different species that evolved from a common ancestral gene by speciation. Normally, orthologs retain the same or similar function in the course of evolution. Paralogs are genes and products thereof related by duplication within a genome. As used herein, "orthologs" and "paralogs" are included in the term "homologs."

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is a nucleic acid or amino acid sequence corresponding to the genes or gene products described herein.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al., J. Mol. Biol. 215:403-

410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The terms "identical" or "percent identity", in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The phrase "substantially identical" in the context of two nucleic acids or polypeptides refers to two or more sequences or subsequences that have at least about 60%, about 65%, about 70%, about 75%, about 80%, about 85%, about 90, about 95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous", without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

Terms used herein pertaining to genetic manipulation are defined as follows.

Deletion: The removal of one or more nucleotides from a nucleic acid molecule or one or more amino acids from a protein, the regions on either side being joined together.

Derived: When used with reference to a nucleic acid or protein, "derived" means that the nucleic acid or polypeptide is isolated from a described source or is at least 70%, 80%, 90%, 95%, 99%, or more identical to a nucleic acid or polypeptide included in the described source.

Endogenous: As used herein with reference to a nucleic acid molecule, genetic element (e.g., gene, promoter, etc.), or polypeptide in a particular cell, "endogenous" refers to a nucleic acid molecule, genetic element, or polypeptide that is in the cell and was not introduced into the cell or transferred within the genome of the cell using recombinant engineering techniques. For example, an endogenous genetic element is a genetic element that was present in a cell in its particular locus in the genome when the cell was originally isolated from nature. The term "native" is used herein interchangeably with "endogenous."

Exogenous: As used herein with reference to a nucleic acid molecule, genetic element (e.g., gene, promoter, etc.), or polypeptide in a particular cell, "exogenous" refers to any nucleic acid molecule, genetic element, or polypeptide that was introduced into the cell or transferred within the genome of the cell using recombinant engineering techniques. For example, an exogenous genetic element is a genetic element that was not present in its particular locus in the genome when the cell was originally isolated from nature. The term "heterologous" is used herein interchangeably with "exogenous."

Expression: The process by which a gene's coded information is converted into the structures and functions of a cell, such as a protein, transfer RNA, or ribosomal RNA. Expressed genes include those that are transcribed into mRNA and then translated into protein and those that are transcribed into RNA but not translated into protein (for example, transfer and ribosomal RNAs).

Introduce: When used with reference to genetic material, such as a nucleic acid, and a cell, "introduce" refers to the delivery of the genetic material to the cell in a manner such that the genetic material is capable of being expressed within the cell. Introduction of genetic material includes both transformation and transfection. Transformation encompasses techniques by which a nucleic acid molecule can be introduced into cells such as prokaryotic cells or non-animal eukaryotic cells. Transfection encompasses techniques by which a nucleic acid molecule can be introduced into cells such as animal cells. These techniques include but are not limited to introduction of a nucleic acid via conjugation, electroporation, lipofection, infection, and particle gun acceleration.

Isolated: An "isolated" biological component (such as a nucleic acid molecule, polypeptide, or cell) has been substantially separated or purified away from other biological components in which the component naturally occurs, such as other chromosomal and extrachromosomal DNA and RNA and proteins. Nucleic acid molecules and polypeptides that have been "isolated" include nucleic acid molecules and polypeptides purified by standard purification methods. The term also includes nucleic acid molecules and polypeptides prepared by recombinant expression in a cell as well as chemically synthesized nucleic acid molecules and polypeptides. In one example, "isolated" refers to a naturally-occurring nucleic acid molecule that is not immediately contiguous with both of the sequences with which it is immediately contiguous (one on the 5' end and one on the 3' end) in the naturally-occurring genome of the organism from which it is derived.

Nucleic acid: Encompasses both RNA and DNA molecules including, without limitation, cDNA, genomic DNA, and mRNA. Nucleic acids also include synthetic nucleic acid molecules, such as those that are chemically synthesized or recombinantly produced. The nucleic acid can be double-stranded or single-stranded. Where single-stranded, the nucleic acid molecule can be the sense strand, the antisense strand, or both. In addition, the nucleic acid can be circular or linear.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. An origin of replication is operably linked to a coding sequence if the origin of replication controls the replication or copy number of the nucleic acid in the cell. Operably linked nucleic acids may or may not be contiguous.

Operon: Configurations of separate genes that are transcribed in tandem as a single messenger RNA are denoted as operons. Thus, a set of in-frame genes in close proximity under the transcriptional regulation of a single promoter constitutes an operon. Operons may be synthetically generated using the methods described herein.

Overexpress: When a gene is caused to be transcribed at an elevated rate compared to the endogenous or basal transcription rate for that gene. In some examples, overexpression additionally includes an elevated rate of translation of the gene compared to the endogenous translation rate for that gene. Methods of testing for overexpression are well known in the art, for example transcribed RNA levels can be assessed using RT-PCR and protein levels can be assessed using SDS-PAGE gel analysis.

Recombinant: A recombinant nucleic acid molecule, genetic element (e.g., gene, promoter, etc.), or polypeptide is one that has a sequence that is not naturally occurring, is present in a different locus (e.g., genetic locus or on an extrachromosomal plasmid) within a particular cell than in a corresponding native cell, or both. A recombinant cell or microorganism is one that contains a recombinant nucleic acid molecule, genetic element, or polypeptide.

Vector or expression vector: An entity comprising a nucleic acid molecule that is capable of introducing the nucleic acid, or being introduced with the nucleic acid, into a cell for expression of the nucleic acid. A vector can include nucleic acid sequences that permit it to replicate in the cell, such as an origin of replication. A vector can also include one or more selectable marker genes and other genetic elements known in the art. Examples of suitable vectors are found below.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below.

Exogenous nucleic acids can be introduced stably or transiently into a cell using techniques well known in the art, including electroporation, lithium acetate transformation, calcium phosphate precipitation, DEAE-dextran mediated transfection, liposome-mediated transfection, conjugation, transduction, and the like. For stable transformation, a nucleic acid can further include a selectable marker. Suitable selectable markers include antibiotic resistance genes that confer, for example, resistance to nourseothricin, G418, hygromycin B, neomycin, tetracycline, chloramphenicol, or kanamycin, genes that complement auxotrophic deficiencies, and the like. (See below for more detail.)

Various embodiments of the invention use an expression vector that includes a recombinant nucleic acid encoding a protein involved in a metabolic or biosynthetic pathway. Suitable expression vectors include, but are not limited to viral vectors, phage vectors, bacteriophage vectors, plasmids, phagemids, cosmids, fosmids, bacterial artificial chromosomes, Pl-based artificial chromosomes, yeast plasmids, yeast artificial chromosomes, and any other vectors specific for cells of interest.

Useful vectors can include one or more selectable marker genes to provide a phenotypic trait for selection of transformed cells. The selectable marker gene encodes a protein necessary for the survival or growth of transformed cells grown in a selective culture medium. Cells not transformed with the vector containing the selectable marker gene will not survive in the culture medium. Typical selection genes encode proteins that (a) confer resistance to antibiotics or other toxins, e.g., nourseothricin, G418, hygromycin B, ampicillin, neomycin, methotrexate, or tetracycline, (b) complement auxotrophic deficiencies, or (c) supply critical nutrients not available from complex media. In alternative embodiments, the selectable marker gene is one that encodes orotidine 5'-phosphate decarboxylase, dihydrofolate reductase or confers neomycin resistance (for use in eukaryotic cell culture).

The coding sequence in the expression vector is operably linked to an appropriate expression control sequence (promoters, enhancers, and the like) to direct synthesis of the encoded gene product. Such promoters can be derived from endogenous or exogenous sources. Thus, the recombinant genes of the invention can comprise a coding sequence operably linked to a heterologous genetic element, such as a promoter, enhancer, ribosome binding site, etc. "Heterologous" in this context refers to a genetic element that is not operably linked to the coding sequence in nature. Depending on the cell/vector system utilized, any of a number of suitable transcription and translation control elements, including constitutive and inducible promoters, transcription enhancer elements, transcription terminators, etc. can be used in the expression vector (see e.g., Bitter et al. (1987) *Methods in Enzymology*, 153:516-544).

Non-limiting examples of suitable promoters for use within a eukaryotic cell are typically viral in origin and include the promoter of the mouse metallothionein I gene (Hamer et al. (1982) *J. Mol. Appl. Gen.* 1:273); the TK promoter of Herpes virus (McKnight (1982) *Cell* 31:355); the SV40 early promoter (Benoist et al. (1981) *Nature* (London) 290:304); the Rous sarcoma virus promoter; the cytomegalovirus promoter (Foecking et al. (1980) *Gene* 45:101); and the yeast gal4 gene promoter (Johnston et al. (1982) *PNAS* (USA) 79:6971; Silver et al. (1984) *PNAS* (USA) 81:5951.

Coding sequences can be operably linked to an inducible promoter. Inducible promoters are those wherein addition of an effector induces expression. Suitable effectors include proteins, metabolites, chemicals, or culture conditions capable of inducing expression.

Alternatively, a coding sequence can be operably linked to a repressible promoter. Repressible promoters are those wherein addition of an effector represses expression.

In some versions, the cell is genetically modified with a recombinant nucleic acid encoding a biosynthetic pathway gene product that is operably linked to a constitutive promoter. Suitable constitutive promoters are known in the art.

In some versions, the cell is genetically modified with an exogenous nucleic acid encoding a single protein. In other embodiments, a modified cell is one that is genetically modified with exogenous nucleic acids encoding two or more proteins. Where the cell is genetically modified to express two or more proteins, those nucleic acids can each be contained in a single or in separate expression vectors. When the nucleic acids are contained in a single expression vector, the nucleotide sequences may be operably linked to a common control element (e.g., a promoter), that is, the common control element controls expression of all of the coding sequences in the single expression vector.

When the cell is genetically modified with recombinant nucleic acids encoding two or more proteins, one of the nucleic acids can be operably linked to an inducible promoter, and one or more of the nucleic acids can be operably linked to a constitutive promoter. Alternatively, all can be operably linked to inducible promoters or all can be operably linked to constitutive promoters.

Nucleic acids encoding proteins desired to be expressed in a cell may be codon-optimized for that particular type of cell. Codon optimization can be performed for any nucleic acid by "OPTIMUMGENE"-brand gene design system by GenScript (Piscataway, N.J.).

Methods for transforming yeast cells with recombinant DNA and producing polypeptides therefrom are disclosed by Clontech Laboratories, Inc., Palo Alto, Calif., USA (in the product protocol for the "YEASTMAKER"-brand yeast transformation system kit); Reeves et al. (1992) *FEMS Microbiology Letters* 99:193-198; Manivasakam and Schiestl (1993) *Nucleic Acids Research* 21(18):4414-5; and Ganeva et al. (1994) *FEMS Microbiology Letters* 121:159-64. Expression and transformation vectors for transformation into many yeast strains are available. For example, expression vectors have been developed for the following yeasts: *Candida albicans* (Kurtz, et al. (1986) *Mol. Cell. Biol.* 6:142); *Candida maltosa* (Kunze et al. (1985) *J. Basic Microbiol.* 25:141); *Hansenula polymorpha* (Gleeson et al. (1986) *J. Gen. Microbiol.* 132:3459) and Roggenkamp et al. (1986) *Mol. Gen. Genet.* 202:302); *Kluyveromyces fragilis* (Das et al. (1984) *J. Bacteriol.* 158:1165); *Kluyveromyces lactis* (De Louvencourt et al. (1983) *J. Bacteriol.* 154:737) and Van den Berg et al. (1990) Bio/Technology 8:135); *Pichia quillerimondii* (Kunze et al. (1985) *J. Basic Microbiol.* 25:141); *Pichia pastoris* (Cregg et al. (1985) *Mol. Cell. Biol.* 5:3376; U.S. Pat. Nos. 4,837,148; and 4,929,555); *Saccharomyces cerevisiae* (Hinnen et al. (1978) *Proc. Natl. Acad. Sci. USA* 75:1929 and Ito et al. (1983) *J. Bacteriol.* 153:163); *Schizosaccharomyces pombe* (Beach et al. (1981) *Nature* 300:706); and *Yarrowia lipolytica* (Davidow et al. (1985) *Curr. Genet.* 10:380-471 and Gaillardin et al. (1985) *Curr. Genet.* 10:49). Genetic transformation systems for metabolic engineering have been developed specifically for a number of lipogenic yeasts including *Mucor circinelloides* (Zhang et al. 2007), *Yarrowia lipolytica* (Xuan et al. 1988), *Rhodotorula glutinis* (Li et al. 2012), *Rhodosporidium toruloides* (Zhu et al. 2012), *Lipomyces starkeyi* (Calvey et al. 2014, Oguro et al. 2015), and *Trichosporon oleaginosus* (Gorner et al. 2016).

Organic Substrate Conversion

An aspect of the invention includes methods of processing organics. The methods can be performed with the native, non-genetically modified yeasts or genetically modified yeasts such as those described herein. If non-genetically modified, the yeasts are preferably native lipogenic (oleaginous) yeasts, such as *Lipomyces starkeyi*.

The methods involve consuming certain organics while producing other organics. As used herein, "organic" refers to any organic compound, molecule, or polymer capable of being consumed or produced by a microorganism. Exemplary organics include but are not limited to carbohydrates (simple sugars, oligosaccharides, polysaccharides), nucleotides, nucleosides, nucleic acids, polypeptides, organic acids (including amino acids), and organic compounds. Specific examples of organics include glucose, glucan, xylose, xylan, arabinose, arabinan, lactic acid, glycerol, acetic acid, butanediol, ethanol, fatty acids, acylglycerols, enzymes (amylases, glucosidases, etc.), among others. As used herein, "consume" refers to the reduction of a certain component from a medium and can encompass direct uptake of the component for internal metabolic processing thereof or external processing of the component optionally followed by uptake of resulting products for internal metabolic processing.

The engineered yeasts of the invention and certain lipogenic yeasts are particularly effective at consuming certain organics that other microorganisms either cannot consume or cannot do so effectively. These organics include glycerol, cellobiose, xylose, lactic acid, trehalose, and oligosaccharides. Accordingly, an aspect of the methods of the invention includes the consumption of these and other organics from the medium. In certain versions of the invention, contacting the medium with the yeast reduces an amount of any one or more of these or other organics to less than about 80%, less than about 70%, less than about 60%, less than about 50%, less than about 45%, less than about 40%, less than about 35%, less than about 30%, less than about 25%, less than about 20%, less than about 15%, less than about 10%, less than about 5%, less than about 2.5%, or less than about 1% of the initial amount.

In some aspects of the invention, the medium comprises one or more components selected from glucose, glucan, trehalose, xylose, xylan, arabinose, arabinan, lactic acid, glycerol, acetic acid, butanediol, and ethanol. The medium, for example, may comprise glucose in an amount of from about 0.01 to about 100 g/L, from about 0.1 g/L to about 10 g/L, or about 1 g/L; glucan in an amount of from about 0.1 g/L to about 1000 g/L, from about 1 g/L to about 100 g/L, or about 10 g/L; trehalose in an amount of from about 0.01 to about 100 g/L or from about 0.1 g/L to about 10 g/L; xylose in an amount of from about 0.01 g/L to about 100 g/L, from about 0.1 g/L to about 10 g/L, or about 1 g/L; xylan in an amount of from about 0.05 g/L to about 500 g/L, from 0.5 g/L to about 50 g/L, or about 5 g/L; arabinose in an amount of from about 0.005 g/L to about 50 g/L; from about 0.05 g/L to about 5 g/L, or about 0.5 g/L; arabinan in an amount of from about 0.005 g/L to about 50 g/L, from about 0.05 g/L to about 5 g/L, or about 0.5 g/L; lactic acid in an amount of from about 0.15 g/L to about 1500 g/L, about 1.5 g/L to about 150 g/L, or about 15 g/L; glycerol in an amount of from about 0.15 g/L to about 1500 g/L, from about 1.5 g/L to about 150 g/L, or about 15 g/L; acetic acid in an amount of from about 0.005 g/L to about 50 g/L; from about 0.05 g/L to about 5 g/L, or about 0.5 g/L; butanediol in an amount of from about 0.02 g/L to about 200 g/L, from about 0.2 g/L to about 20 g/L, or about 2 g/L; and/or ethanol in an amount of from about 0.005 g/L to about 50 g/L, from about 0.05 g/L to about 5 g/L, or about 0.5 g/L. Contacting the medium with a yeast may reduce an amount of any one or more of these or other organics to less than about 80%, less than about 70%, less than about 60%, less than about 50%, less than about 45%, less than about 40%, less than about 35%, less than about 30%, less than about 25%, less than about 20%, less than about 15%, less than about 10%, less than about 5%, less than about 2.5%, or less than about 1% of the initial amount.

In certain versions of the invention, the medium comprises a grain ethanol distillation stillage or a processed grain ethanol distillation stillage. The processed grain ethanol distillation stillage may be made by centrifuging distiller's wet grain therefrom, removing oil, concentrating, and filtering, or other thin-stillage processing steps described elsewhere herein or known in the art. The concentrating may comprise evaporating. In some versions, the processed grain ethanol distillation stillage comprises thin stillage. The thin stillage may be further processed by removing oil and concentrating to generate the medium.

The medium may comprise various amounts of the grain ethanol distillation stillage or processed grain ethanol distillation stillage. In some versions, the medium may comprise at least about 5%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 97%, at least about 99%, or about 100% grain ethanol distillation stillage or processed grain ethanol distillation stillage. The grain ethanol distillation stillage or processed grain ethanol distillation stillage may be diluted with water or other solvents.

The engineered yeasts of the invention and certain lipogenic yeasts are particularly effective at producing certain organics that other microorganisms either cannot produce or cannot do so effectively. These organics include lipids (triacylglycerols, diacylglycerols, monoacylglycerols, fatty acids, etc.), enzymes (amylases, glucosidases, etc.), and other proteins. Particular enzymes include glycoside hydrolases, alpha-amylases (thermostable and secreted), dextranases (amylo-alpha-1,6-glycosidase), maltases, beta-1,4-glucosidases, endo-1,4-beta-D-glucanases (cellulases) or any other of the enzymes described elsewhere herein. Accordingly, an aspect of the methods of the invention includes the production of these and other organics.

The organic produced by the yeast may be separated or purified from any other component of the spent medium for downstream use in other applications. For example, enzymes produced by the yeast may be used in liquefaction of starch and/or saccharification of liquefaction-processed starch. Such enzymes may include any of the enzymes produced by the yeast as described above, such as carbohydrases. Lipid produced by the yeast may be used for producing biofuels therefrom or used as a replacement for palm or other oils in food applications or other applications. The yeast grown in the medium may themselves be harvested and processed to yield a source of protein as a replacement, for example, for soy protein or as a source of long-chain polyunsaturated fatty acids for fish grown in aquaculture.

The spent medium may also be mixed, either alone or with other liquids (such as thin stillage), with starch as a backset for liquefaction of the starch. The reduction in dissolved organics by virtue of the yeast consumption reduces the build-up of organics in grain ethanol production systems as a whole and in the liquefaction fermentation in particular.

EXAMPLES

Background and Overview

The existence of an annotated genome for *Lipomyces starkeyi* greatly facilitates cloning and homologous expression, but even with a complete or nearly-complete genome, various problems are encountered in cloning and expressing target genes.

One aspect of a suitable cloning strategy involves overexpressing endogenous genes involved in lipid production in *L. starkeyi* under constitutive promoters. Genomic DNA (gDNA) can be a preferable source for gene amplification, because all introns should be natively excised, and genomic DNA preparation is faster and cheaper than creating cDNA libraries. However, certain introns may have regulatory functions or their presence may impede or promote the post-transcriptional processing, subsequent protein translation, or stability of the transcript when overexpressed. Therefore, some gene targets are preferably cloned from cDNA and other targets are cloned from gDNA.

Another issue to consider in cloning involves possible alternate start codons present in the sequences of transcribed mRNA of certain gene targets. As an example, both GUT1 and DGA1 of *L. starkeyi* have two possible initiator methionine sites differing by a respective 15 and 156 base pairs upstream from the sequence annotated on the Joint Genome Institute site. Detailed sequence alignments with orthologs of these genes in yeast species with well-annotated sequences are inconclusive, owing to the large divergence of *L. starkeyi* from other yeast species and the high degree of variability at the N-terminus of these proteins. Hence, in such situations, both versions of these genes are cloned. As shown below, results sometimes demonstrate a large difference in lipid content, as in the case for the two DGA1 variants, whereas others, such as the two GUT1 variants, behave similarly.

It is not evident a priori whether genes from cDNA can be amplified under all conditions. For example, seven out of nine gene targets from cDNA could be amplified from cDNA derived from standard yeast cultures growing in liquid (yeast peptone dextrose) YPD media. However, one construct required gDNA as a cloning template. The exception was ACC1, which could not be amplified as a product from this cDNA library (as deemed by agarose gel electrophoresis) despite many PCR optimization efforts. Amplification of the gene was possible with the same primers when gDNA was used as the template. When *L. starkeyi* was cultivated under highly lipogenic conditions and a new cDNA library created from these cells, amplification of ACC1 was successful. Such evidence indicates that Acc1 is not constitutively expressed and that expression of ACC1 is inducible under lipogenic conditions. This finding emphasizes the importance of ACC1 as an important gene target for enhancing lipid biosynthesis.

Generation of vectors involves assembly of 4 to 6 fragments to create the desired gene cassettes using the well-established "Gibson" method for in vitro enzymatic assembly of DNA fragments (Gibson et al. 2009). Cloning attempts can be unsuccessful in producing any of the desired constructs. Gel purification methods to isolate amplified genes can introduce errors in DNA terminal regions. Therefore, gel extraction of DNA fragments and column PCR purification are preferred to improve the purity and concentration of the PCR products used in the assembly reaction.

Correct and complete constructs of the desired cassettes can be identified by colony PCR. This can be accomplished through colony PCR by amplifying either parts of the construct or the entire construct. During routine screening and sequencing, some of the construct candidates can contain partial cassettes (i.e. some will be missing part or all of one or more of the assembly components). To avoid selecting these partial constructs, it is preferable to use colony PCR for the entire cassette (instead of portions of the cassette). That way only candidates containing the appropriately sized insert are then sequenced.

*L. starkeyi* is cultivated under special conditions and genetic transformation is optimized in order to obtain transformants with genes integrated into the genome (Calvey et al. 2014). *L. starkeyi* can be transformed relatively easily with a base vector that contains only essential elements as well as a selectable marker. An exemplary base vector is represented by SEQ ID NO:91. Success depends upon having cells at an appropriate stage of development, at an appropriate cell density and with the correct ratio of cells to DNA. Transformation conditions are systematically evaluated for each method used to determine cell density, and for the activity and condition of critical reagents such as salmon sperm DNA.

In native strains of *L. starkeyi*, each DNA expression cassette integrates either randomly via non-homologous end joining (NHEJ) or in a targeted manner via homologous recombination to create a transformant. In native strains of *L. starkeyi*, NEHJ integration occurs much more frequently than homologous recombination. Even genes that normally increase lipid production when overexpressed from most integration sites can generate transformants with reduced lipid production relative to the wild-type when integrated randomly into various sites. Many strains are therefore screened under controlled conditions in order to obtain those with improved performance.

Nile Red fluorescence can be used as a rapid assay for cells or strains of cells showing greater relative lipid accumulation. However, the assay is highly variable, and it is important to conduct the trials under specific conditions. Selection of media that will enable identification of strains with the capacity for elevated lipid production on stillage is particularly critical. Some types of rich media used to cultivate *L. starkeyi*, such as YPD or those based on modified thin stillage (mTS), have intrinsic fluorescent properties that interfere with the proper quantification of the bona fide Nile Red fluorescent signal from the cells. Moreover, unmodified thin stillage contains significant amounts of corn oil and lipids from the hydrolysis of *Saccharomyces cerevisiae*. A partial solution to this problem is to perform a series of washes to remove the media from the cells, followed by suspension of the cells in $H_2O$. This treatment can eliminate interference due to media components that can be removed by washing. As described elsewhere herein, other methods can be used to reduce background fluorescence.

When examining cultures for increased lipid accumulation it is important to distinguish higher levels of lipid due to higher cell density from higher levels of lipid due to higher lipid content per cell. The fluorescence response is therefore normalized to the cell density.

Effects of Medium Components

The fluorescence assay is intended to identify transformants that overproduce lipid when cultivated on an industrial medium composed in part or in whole of thin stillage. Medium components can strongly affect the fluorescence assay for intracellular lipid by increasing or decreasing intracellular lipid production. When screening for a transformant with the capacity for increased lipid production, it is more difficult to identify improved mutants when the medium enables the cells to accumulate high levels of lipid than when native cells normally produce relatively little lipid under the growth conditions.

For example, wild-type, untransformed *L. starkeyi* cultivated in a defined minimal medium using an easily assimilated carbon source and a low amount of a poorly assimilated nitrogen source would produce a high level of lipid. The same organism cultivated with the same carbon source but an amount of readily assimilated nitrogen sufficient for cell growth would accumulate less lipid as illustrated by published studies (Calvey 2016).

It is easier to identify a transformant with increased capacity for lipid production when it is cultivated in a medium that allows lower lipid accumulation than in a medium that enables higher lipid accumulation.

As taught elsewhere in this disclosure, the relationship between the amount and the source of the carbon and the nitrogen provided to the cells can affect growth and lipid production in complex ways. Moreover, media used in certain commercial applications will include a complex mixture of glycerol, cellobiose, trehalose, xylose, xylitol, acetic acid residual corn oil and oligosaccharides derived from residual starch, hemicellulosic and cellulosic components from corn along with hydrolysis products from lysed yeast cells. In practice it is not reasonable to predict how strains or transformants will perform on a complex medium of such composition by screening their performance against simple or complex media composed of typical laboratory substrates such as glucose, yeast extract, peptone or other common medium constituents. For this reason, empirical testing is important to identify media that is representative of the industrial substrate and appropriate for strain screening. These considerations were addressed with various media as described below.

Six types of growth media were examined to determine how they influenced the native lipid accumulation of *L. starkeyi* over a 3-day fermentation period. The types of media included in the analysis were M1 (LN), M2 (LN), M3 (HN), M4 (HN), YPD, and mTS. M1 (LN) is a minimally defined low nitrogen media containing 1.72 g/L of yeast nitrogen base, 0.417 g/L ammonium sulfate 0.179 g/L urea, and 30 g/L of dextrose. The M1 (LN) formulation is nitrogen limiting and gives a C:N ratio of approximately 150:1. M2 (LN) is a low nitrogen media identical to YPD but containing only 3.64% of the amount of yeast extract that YPD contains and only 1.82% of the amount of peptone that YPD contains. Converted to grams/liter, M2 (LN) contains 0.364 g/L of yeast extract and 0.364 g/L of peptone. The amount of dextrose in M2 (LN) is the same as in traditional YPD (20 g/liter). The M2 (LN) formulation is nitrogen limiting and gives a C:N ratio of approximately 70:1. M3 (HN) and M4 (HN) are high nitrogen-containing versions of M1, with M4 HN containing peptone. More specifically, M3 (HN) contains 6.7 g/L yeast nitrogen base, 2.145 g/L urea, and 30 g/L dextrose. M4 HN media contains 6.7 g/L yeast nitrogen base, 2.145 g/L urea, 3.0 g/L peptone, and 30 g/L dextrose. YPD is yeast peptone dextrose media. mTS is modified thin stillage. The mTS was prepared by clarifying thin stillage to remove oil by skimming, boiling to concentrate the stillage, removing precipitates produced by the boiling, autoclaving, and removing precipitates generated during the autoclaving.

As shown in FIG. 4, the type of media greatly influences the basal lipid production of L. starkeyi NRRL Y-11557, even if nitrogen is not considered limiting. These wild-type cells appear to accumulate a moderate amount of lipids (≈30%) when cultivated in mTS during extended fermentation times, despite its nitrogen content. The mildly lipogenic property of mTS with L. starkeyi NRRL Y-11557 is likely due to the presence of glycerol and/or other compound(s).

The choice of a screening media should be done carefully. Choosing a media limiting in nitrogen could mask small lipogenic effects of certain genes, while media high in nitrogen or complexity may suppress those effects. Likewise, even media that is not nitrogen limiting can be slightly lipogenic, as seen in M3 (HN) media, because the lack of some nutrients can induce lipogenesis.

In light of these considerations, transformants of NRRL Y-11557 are screened using mTS medium to identify yeast strains that convert the soluble organics and sugars to other products. Evaluation on this medium also eliminates the possibility that some transformants perform well during screening on synthetic media but present significantly dampened or null effects when grown on a commercially relevant fermentation stream. Transformants are also screened using YPD to control for any possible variation in various sources of mTS.

Gene Cassette Selections and Primer Design

Gene cassette integration vectors are designed using a base vector as shown in FIG. 5 and having a sequence of SEQ ID NO:91. The base vector contains an origin of replication (Ori) and a kanamycin resistance cassette that permits maintenance and propagation in bacteria. In addition, it contains two multiple cloning sites (MCS) and two modified LoxP sites (RE and LE) that flank the strong constitutive LsTDH3 promoter coupled to a codon optimized nourseothricin (NAT) resistance gene and its respective transcription terminator region.

Measures are taken to ensure no antibiotic resistance gene is incorporated in the final yeast strain. The bacterial kanamycin resistance gene is not integrated into the yeast genome if it is interrupted by restriction digestion prior to transformation. The presence of the loxP sites enables excision of the NAT resistance gene after genome integration. The LoxP sites themselves are modified (i.e. dead) such that the product after one recombination event resists further recombination, thereby protecting the genomic integrity of the organism. The gene overexpression cassettes therefore include a constitutive promoter, the gene(s) of interest, and one or more transcription terminator regions inserted into one of the MCSs.

Genes are overexpressed to increase lipid production under nutrient-rich conditions. These include: acetyl-coenzyme-A carboxylase (LsACC1), delta-9 acyl-CoA desaturase (LsOLE1), ATP-citrate lyase alpha and beta subunits (LsACL1/LsACL2), two variants of glycerol kinase (LsGUT1-1602) and (LsGUT1-1617), two variants of diacylglycerol acyltransferase (LsDGA1-1233) and (LsDGA1-1389) having different start sites, and malic enzyme cloned from genomic DNA (LsgME) and cDNA (LscME), among other genes described herein. Precise promoter, gene, and terminator sequences are selected based on Illumina RNAseq data and knowledge of promoter strength and expression patterns in this organism. All contain a single promoter, gene, and terminator region, with exception to the LsAcl1/LsAcl2 construct, which involves a bidirectional promoter expressing the two genes with different transcription terminator regions. These sequences are then analyzed for the presence of specific restriction digest sites to determine into which one of two MCSs contained in the base vector they would be cloned. This step facilitates future subcloning into other vectors. For example, the diacylglycerol acyltransferase (LsDGA1) construct is capable of being inserted upstream of the loxP site using the Sbf1 restriction enzyme to linearize the vector. Other constructs are capable of being inserted downstream of the opposing loxP site, using RsrII and AvrII to linearize the vector. The desired sequence combinations and restriction enzyme sites are entered into the NEBuilder® assembly tool (nebuilder.neb.com/) with a minimum overlap setting of 20 base pairs to construct the primer sequences for performing the Gibson assembly reaction.

Schematic of the Pipeline for Creating and Characterizing Strains

An assembly line of sequential steps to create metabolically engineered yeast is shown in FIG. 6. These steps included target gene, promoter, and terminator selection, molecular biology techniques (PCR, Gibson assembly), yeast transformations, selection, cataloging and storage, Nile Red screening, and further validation assays.

gDNA Extraction and cDNA Library Creation:

A Masterpure™ Yeast DNA Purification Kit (Epicentre, Madison, Wis.) is used to extract L. starkeyi gDNA. Nitrogen rich (YPD) or nitrogen limited (YPD 70:1 (C:N)) cultures are used for RNA extraction. The YPD 70:1 media contain only 3.64% and 1.82% percent of the yeast extract and peptone as YPD, respectively. A freshly saturated 5 mL culture of L. starkeyi grown under constant agitation at 30° C. is pelleted by centrifugation, washed, suspended in 5 mL of sterile $H_2O$, then used to inoculate 50 mL of either YPD or YPD 70:1 media in a 125 mL shaker flask≈0.8 $OD_{600}$ and allowed to incubate overnight at 30° C. under 225 rpm. Cells are observed microscopically to determine lipid production in the YPD 70:1 media as compared to the YPD media, and the $OD_{600}$ is measured to calculate the quantity of cells to use in the RNA extraction protocol. RNA is extracted using an RNeasy Mini Kit (Qiagen), following enzymatic disruption. cDNA is synthesized from these RNA preparations using a QuantiTect® Reverse Transcription Kit (Qiagen), following the instructions of the manufacturer.

PCR of Fragments and Gibson Enzymatic Assembly:

The base vector (pXC301—FIG. 5—SEQ ID NO:91) linearized with the enzymes listed in Table 2 is used to clone L. starkeyi genes in conjunction with the "Gibson method" for in vitro enzymatic assembly of DNA fragments. All PCR amplifications are performed using Phusion High Fidelity Taq polymerase (NEB) and the manufacturer protocol in either 5× Phusion GC buffer (ACC1) or 5× Phusion buffer (all others) using the annealing temperatures in Table 2. Annealing steps are carried out using the lowest $T_m$ of the primer pair, or the experimentally optimized annealing temperature, where appropriate. The reaction products are analyzed by agarose gel electrophoresis containing ethidium bromide and subsequently visualized and photographed. Successful reactions of identical fragments are pooled and then all samples (including the digested base vector) are subjected to a PCR cleanup column (Qiagen), and then quantified on a Nanodrop 2000 instrument (Thermo Scientific). The vector and inserts are then added in equimolar quantities (0.1 pmoles/fragment) in a separate tube, and the final volume adjusted to 20 µL by the addition of 15 µL premade Gibson assembly reaction mix and water. All reactions are allowed to incubate at 50° C. for one hour, and then 5 µL of the assembly reaction is used to transform 20 µL of Endura™ DUO competent cells (Lucigen) using standard techniques. Transformants are selected on LB plates containing kanamycin, and positive candidates are identified by colony PCR and sent for sequencing confirmation.

TABLE 2

Summary of Gene Targets, Promoters, and Terminators with Cloning Information

| Target Gene | Full Name | Promoter and Terminator Pairings | PCR Annealing Temperature | Cloning Digest Enzymes | Enzymes for Yeast Transformation |
|---|---|---|---|---|---|
| ACC1 | Acetyl-coenzyme-A carboxylase | FBA1 Promoter | 55-64° C. | RsrII and AvrII | AsiSI |
| | | ACC1 | 67° C. | | |
| | | FBA1 Terminator | 55-64° C. | | |
| OLE1 | Delta-9 acyl-CoA desaturase | GLN1 Promoter | 60° C. | RsrII and AvrII | AsiSI |
| | | OLE1 | 63° C. | | |
| | | GLN1 Terminator | 60° C. | | |
| ACL1 and ACL2 | ATP-citrate lyase, alpha and beta subunits | ENO1 Promoter | 57° C. | RsrII and AvrII | AsiSI |
| | | ACL1 | 58° C. | | |
| | | ATPase Terminator | 64° C. | | |
| | | ACL2 | 58° C. | | |
| | | TPI Terminator | 65° C. | | |
| Glycerol Kinase 1602 | Glycerol Kinase 1602 Variant | ATPase (3900) Promoter | 55.3-61.2° C. | RsrII and AvrII | AsiSI |
| | | Glycerol Kinase 1602 | 63.9-67° C. | | |
| | | ATPase (3900) Terminator | 62.75-66.25° C. | | |
| Glycerol Kinase 1617 | Diacylglycerol acyltransferase 1617 Variant | ATPase (3900) Promoter | 58° C. | RsrII and AvrII | AsiSI |
| | | Glycerol Kinase 1617 | 65° C. | | |
| | | ATPase (3900) Terminator | 65° C. | | |
| DGA1 1233 | Diacylglycerol acyltransferase 1233 Variant | TEF1 Promoter | 60° C. | SbfI | XmaI/AvrII |
| | | DGA1 | 72° C. | | |
| | | TDH3 Terminator | 70° C. | | |
| DGA1 1389 | Diacylglycerol acyltransferase 1389 Variant | TEF1 Promoter | 60° C. | SbfI | XmaI/AvrII |
| | | DGA1 | 72° C. | | |
| | | TDH3 Terminator | 70° C. | | |
| gMalic Enzyme | Malic Enzyme (gDNA) | TDH3 Promoter | 60° C. | RsrII and AvrII | AsiSI |
| | | gMalic Enzyme | 60° C. | | |
| | | TDH3 Terminator | | | |
| eMalic Enzyme | Malic Enzyme (cDNA) | TPI (196787) Promoter) | 62° C. | RsrII and AvrII | AsiSI |
| | | cMalic Enzyme | 58° C. | | |
| | | TPI (196787) Terminator | 66° C. | | |

Vectors are linearized so the entire target gene cassette, including the loxP flanked region, randomly integrates into the *L. starkeyi* genome as one fragment. Table 2 lists restriction enzymes for linearization. Linearized DNA is ethanol precipitated and suspended in TE to increase its concentration (>160 nM) and purity. To transform the cells, a procedure based on the lithium acetate method was used (Calvey et al. 2014, Gietz et al. 2002). A near stationary phase culture of *L. starkeyi* is inoculated into 50 ml YPD to between 0.6 and 0.8 $OD_{600}$ and grown overnight to reach between 3.0 and 4.0 $OD_{600}$. The culture is harvested and washed twice with 25 mL sterile water, and resuspended to 1.5 mL in sterile water or 0.1M LiAc. Aliquots of 150 µL are dispensed into 1.5 mL tubes and centrifuged. The remaining cell pellet is then suspended in 360 µL transformation mix containing 240 µL 50% w/v PEG 3350, 50 µL boiled ssDNA, 36 µL 1.0 M LiAc, and 36 µL of the desired plasmid DNA (added last). Samples are incubated at 30° C. for 3 hours, heat shocked at 40° C. for 5 minutes, and then centrifuged to remove the transformation suspension. Cells are allowed to recover in 3 mL YPD for 4 hours before being plated onto appropriate selective media. After 6 days of growth, transformants are selected, catalogued by size, and streaked onto appropriate antibiotic selection plates for creating glycerol stocks until characterization.

Yeast Lipid Screening Using Nile Red:

Both YPD and mTS are used to screen for lipid accumulation in *L. starkeyi*. Starter cultures are inoculated with the desired transformants in 5 mL tubes containing YPD-NAT or YPD liquid media at 30° C. under constant agitation. This lipid screening protocol is based on Nile Red fluorescence adapted from a previous study (Sitepu et al. 2012). Samples and appropriate dilutions are then prepared in a 96-well black clear-bottomed plate to contain 100 µL in each well. Nile Red is prepared as a 2 mg/mL stock solution and then diluted to a 2× working concentration (8 µg/mL). Fluorescent signals and $OD_{630}$ readings are read independently from two plate readers (BioTek™ FLx800 and BioWhittaker™ ELx808, respectively). Data is analyzed by normalizing the fluorescent signal to the $OD_{630}$ of the culture. To enable comparisons between different runs, normalized fluorescence is standardized relative to the WT culture of each group.

Lipid Extraction Analysis:

An extraction protocol is used for crude gravimetric assessments of total lipid content based on the classic Bligh and Dyer method (Bligh et al. 1959) (20). First, 2 mL of cell culture is centrifuged at 3,000 rpm for 5 minutes in 15 mL falcon tubes, and the cell pellets frozen at −20° C. until lipid extraction analysis. Thawed cell pellets are suspended in 1 mL $H_2O$ containing 200 µL of concentrated HCl, and the suspension was heated to 90° C. for 1 hour to lyse cells. Lipids are then extracted by addition of 6 mL of a 2:1 (v:v) methanol:chloroform solution and 3 mL of 1M NaCl, followed by vortexing for 5 minutes. Tubes are then centrifuged at 3,000 rpm for 10 minutes to induce phase separation. The lipid-containing lower chloroform layer (≈2 mL) is then carefully removed using a glass Pasteur pipette, and transferred into a clean, pre-weighed, 5 mL glass vial. Finally, the extracted chloroform layer is completely evaporated by incubation in a 40° C. heat block under a constant stream of air for 1 hour. Vials are then re-weighed to determine the mass of extracted total lipids.

HPLC Analysis of Organics:

Concentrations of sugars and mTS metabolites (including glucose, xylose, cellobiose, arabinose, xylitol, ethanol, glycerol, lactic acid, and acetic acid) are determined by high performance liquid chromatography (HPLC) using an Agilent 1100 Series auto sampler, pump, and refractive index detector, with a Bio-Rad Aminex HPX-87H ion exclusion column (300×7.8 mm) held at 65° C. The mobile phase is 0.01N $H_2SO_4$ at a flow rate of 0.6 mL/min. Samples are diluted 1:10 prior to injection.

Selection of a Yeast Platform

The constituents of thin stillage obtained from a supplier were characterized in order to better monitor the consumption of organics during fermentation of engineered yeast strains. It was discovered that mTS contains between 18.6 to 20.5 g/L glycerol, among other components. To establish a yeast platform for bioprocessing of mTS and metabolic engineering, the growth performance of several strains of *L. starkeyi* on different media was monitored. All of them grew well on starch but the Y-11558 strain grew slightly faster (Table 3).

When challenged with glycerol as a carbon source, none of the South African strains (Y-27493, 27494 and 27495) grew, and Y-11558 was much slower ($\mu$=0.047; Td=21 h). See FIG. 7. However, mutagenesis and serial subculturing reduced the doubling time of Y-11557 to 9.9 h on glycerol. These findings established that *L. starkeyi* grows on glycerol, a major component of mTS, and that adaptation increases growth rates. Based on these results and given that the genome of *L. starkeyi* NRRL Y-11557 has been sequenced (Grigoriev et al. 2012 and DOEJGI 2011), this strain was selected as the exemplary platform yeast for metabolic engineering.

TABLE 3

Doubling Times of Different *Lipomyces starkeyi* Strains Grown on starch

| Strain | Doubling Time (Hrs) | μ |
|---|---|---|
| Y-1388 | 3.56 | 0.28 |
| Y-11557 | 3.60 | 0.28 |
| Y-11558 | 3.36 | 0.30 |
| Y-27493 | 3.52 | 0.28 |
| Y-27494 | 3.97 | 0.25 |
| Y-27495 | 4.28 | 0.23 |

Metabolic Engineering and Screening

The next objective was to modify the physiology of *L. starkeyi* so that it would generate lipids under high nitrogen conditions, such as those found in thin stillage (TS) and modified thin stillage (mTS). As described in Table 2, specific genes targets were selected with constitutive promoter and terminator pairings based on knowledge of the *L. starkeyi* genome, its lipid biochemistry, and gene expression profile under these conditions. These were all cloned into target vectors and transformed into *L. starkeyi*. Since the vector integrates at random within the genome, each transformant might display different lipid biosynthetic capabilities based simply upon the site of genomic integration, or on the number of copies introduced within the genome. It was hypothesized that although gene cassettes conferring genuine lipogenic effects could occasionally integrate into unfavorable regions that could mask their effect, the average normalized fluorescence of that particular transformant pool should be somewhat higher than the average of the WT and base vector transformed strains. In addition, there may also be more variation among the transformants of these genes than those with no effect, since each transformant could have different degrees of increased lipid biosynthesis, as opposed to genes with null effects. Following this logic, a total of 234 transformants were screened from the pool of metabolically engineered strains for Nile Red fluorescence when cultivated on YPD (234), mTS (11), or both (145). The screening was performed over the course of 2 (YPD) or 3 (mTS) days. The results of this preliminary screening are shown in FIG. 8A, which displays the top 50% performers of each gene. Three gene targets (DGA1-1233, DGA1-1389, and ACC1) had either large standard deviations, higher relative normalized fluorescence (1.5-2 times higher), or both when compared to the WT yeast transformed with the base vector. This behavior was independent of the screening medium for DGA1-1233 and ACC1. Additionally, DGA1-1389, GUT1-1617 and ACL1/ACL2 displayed moderate standard deviations when screened in mTS media. The complexity of mTS likely contributed to this phenomenon. In general, however, transformants that performed well in YPD media also performed well in mTS media. Considering the variability of thin stillage across ethanol plants, this is encouraging because it implies that the engineered strains have the flexibility to overproduce lipids in various types of media. In fact, a total of 12 transformants were identified that exhibited one full standard deviation higher normalized fluorescence compared to the empty vector transformed yeast at the end of the growth phase when cultivated on both YPD and mTS. Eight of these are DGA1-1233 transformants, while the other 4 are ACC1 transformed strains.

In order to obtain a more statistically significant analysis of these results, the top performers of each gene were rescreened in triplicate in mTS. The results of this analysis are shown in FIG. 8B, and clearly demonstrate increased normalized fluorescent signals relative to the WT in DGA1-1233 6L, GUT1-1602 6L, and GUT1-1617 2L. In these transformants, it was also confirmed that the entire cassette had integrated into the genome by PCR amplification from genomic DNA using primers specific to the cassette. All had the expected fragment (data not shown).

Effects of Overexpressing Glycerol Kinase in *L. starkeyi*

The presence of sugars or oligosaccharides can repress glycerol utilization in some yeasts, so overexpressing the glycerol kinase gene (GUT1) in *L. starkeyi* could increase glycerol utilization if that were the rate limiting step. When this hypothesis was tested, *L. starkeyi* transformants showed increased lipid content by Nile Red fluorescence, but presented lower growth rates. In screening about twelve GUT1-1602 and GUT1-1617 transformants for growth on thin stillage plates, one GUT1-1617 transformant, Ls-11, appeared to grow relatively faster than the others. This strain was selected to use in shake flask and 3-L bioreactor trials to compare against the WT strain. Ls-11 showed higher cell growth and glycerol utilization rates as compared to WT cells in shake flasks (FIG. 9). The cells from the 200 ml shake flasks were then used to inoculate 200 ml of medium in 3-L bioreactors. In the bioreactor studies glycerol utilization by the Ls-11 transformant was initially faster. Besides these characteristics, the Ls-11 transformant accumulated larger liposomes when examined microscopically, and formed pseudomycelia structures (FIG. 10B).

It was hypothesized that in the GUT1 transformant, glycerol kinase shunts glycerol directly towards triglyceride production via glycerol-3-phosphate, and that this accounts for higher lipid accumulation with lower growth rates. To increase the growth rate on glycerol glycerol-3-phosphate dehydrogenase (GUT2) can also be overexpressed, as described in subsequent sections. Overexpression of GUT1 alone has complex and differing effects on the growth and morphology of *L. starkeyi*. Different transformants of GUT1 alone show various rates of growth and increased lipid accumulation, some of which are superior to the WT or Ls-11.

Remarkably, *L. starkeyi* is capable of using cellobiose, trehalose, amylodextrins, cellulo-oligosaccharides, xylose, xylan oligosaccharides and glycerol—the primary carbohydrate sources present in thin stillage. The fact that *L. starkeyi* effectively consumes all of the oligosaccharide components and all of the glycerol in thin stillage highlights the importance and bioprocessing capabilities of this organism.

Evaluation of Other Cellular Features of DGA1-Transformed Strain

To gain further insight into the physiology of the metabolically engineered strains, a deeper evaluation into the DGA1-transformed strain (DGA1-1233 6L) was performed by evaluating its whole crude lipid content, dry cell weight, growth rate, consumption of organics, and cellular morphology relative to the WT when cultivated in mTS in a bioreactor. The DGA1-1233 6L strain grew slightly slower than the WT, leading to marginally reduced glycerol and cellobiose utilization rates (FIG. 11). Nevertheless, both strains consumed all of the available oligosaccharides and carbon sources present in mTS within five days, except for trace amounts of lactic acid (data not shown). When the cells were examined under the microscope, significantly more liposomes were observed in the DGA1-1233 transformant than the WT (FIG. 11). Remarkably, it was found that overexpression of DGA1 increased the final lipid content from 8.25 g/L to 22.7 g/L, which is an increase of about 14.5 g/L or 275%. This also correlates to an increase in the lipid content (g lipid/g dry cell weight) from approximately 30% to 85% (FIG. 12). It is hypothesized that overexpression of DGA1 is seeding liposome formation, and this in turn is increasing the lipid carrying capacity of the cells. Taken together, the present examples have demonstrated the creation of a DGA1-1233 engineered strain of *L. starkeyi* capable of efficiently converting mTS into cell mass with nearly 85% lipid content and 22.7 g/L lipids. This was also accomplished without optimization of culturing conditions (aeration, pH, temperature, etc.), which will surely lead to further improvements in lipid production and productivity.

Improved Screening by Substituting Bodipy Dye for Nile Red

Nile Red dye is useful in identifying engineered yeast strains that produce more lipid when cultivated on modified thin stillage (mTS), but it has several limitations: First, thin stillages from different plants vary greatly, and this variance can affect the response of the Nile Red assay. Stillages are altered by the method and extent of corn oil extraction, the extent of stillage backset, and whether clarification, and/or concentration is employed. Each of these factors affect cell growth, lipid production and the response of the Nile Red assay. Second, the mTS medium used in the screens can interfere with the Nile Red fluorescent signal, which necessitates washing cells prior to dye addition. Third, Nile Red dye itself is unstable, and signal loss occurs within several minutes following addition. Finally the number of handling steps reduces throughput in sample processing. All of these factors are exacerbated because random integration of genes into the chromosome requires examining many transformants in order to identify the top performers. An effective screening assay must be rapid, offer similar responses on many different stillages and effective in-situ without cell harvest or washing. We therefore modified our screening process to accommodate higher sample throughput by using a different fluorescent dye, Bodipy, which is superior to Nile Red in many aspects, and by standardizing the medium for screening.

Bodipy (boron-dipyrromethene) fluorescent dyes are much more sensitive and stable than Nile Red. They have been used successfully for conducting in vivo lipid trafficking and accumulation studies. One Bodipy variant (4,4-Difluoro-1,3,5,7,8-Pentamethyl-4-Bora-3a,4a-Diaza-s-Indacene) is ideal for detecting neutral lipids, such as those that accumulate in the liposomes of *L. starkeyi*. We established a new screening methodology in which Bodipy dye (0.6 µg/mL) is added directly to a synthetic thin stillage (sTS) to mimic cultivation in mTS under more consistent conditions. Synthetic thin stillage is composed of 6.7 g/L yeast nitrogen base with ammonium sulfate and amino acids, 20 g/L glycerol, and 6 g/L cellobiose. This method enables a 6.5 fold higher throughput in screening. It also requires fewer steps, as samples from actively growing cultures can be immediately assessed for fluorescence without washing off stillage prior to dye addition.

We also developed an improved automated method for ranking transformants based on their raw fluorescence with Bodipy. In short, samples are normalized by dilution to a target OD630 and then measured for fluorescence once a day for four days. An algorithm is then applied to rank the transformants for easy identification of prime performers. The data can be presented as bar graphs of either entire transformant pools or replicates of the same transformants. These graphs account for the dilution factor of the cells/dye, which we refer to as fluorescence in the figures for simplicity, even though it is fluorescence following correction for dilution. This approach streamlines the data analysis process with minimal manipulation. As proof of principle, many of the same transformants that had been selected manually in Nile Red assays were also identified by this approach, along with other high performing strains that might have been overlooked based on the previous method.

Investigating DGA1 Cassette Variants on Lipid Accumulation

One of the most lipogenic cassettes discussed above overexpresses diacylglycerol acyltransferase (DGA1-1233), which was cloned from cDNA (cDGA1-1233). It employs a NAT marker for resistance to the antibiotic nourseothricin to enable selection of transformed strains. In order to facilitate overexpression of cDGA1-1233-NAT in combination with other genes—either by sequential transformations or by mating—we constructed a second DGA1-1233 overexpression cassette using an alternate resistance marker. We then determined the conditions under which *L. starkeyi* transformants could be recovered on plates containing an antibiotic other than nourseothricin.

We next questioned whether overexpression of cDNA or genomic DNA (gDNA) of DGA1 (gDGA1-1233) resulted in better transformants. The principal difference between the gDNA and cDNA clones of DGA1-1233 is the presence or absence of introns. Introns are known to enable alternative splicing of mRNA so a single gene can create multiple proteins, and while introns do not encode protein products, they can be integral to the regulation of gene expression.

Little is known about how or whether introns regulate gene expression in *L. starkeyi*. To address this, we created sibling cDGA1-1233 and gDGA1-1233 cassettes cloned from cDNA and gDNA into a vector that confers resistance to Hygromycin B. These were then transformed into *L. starkeyi* and the Bodipy fluorescence of the resulting transformant pools were monitored in sTS over the course of four days. Although both versions yielded more fluorescence over the wild-type strain, the gDNA version did not induce as many liposomes as the cDNA version, which indicated that the presence of introns modulated cDGA1-1233 expression. Subsequent screening tests revealed that the top cDNA transformant (cDGA1-1233 154L) outperformed the top gDNA transformant (gDGA 163M). Moreover, cDGA 154L behaved similarly to strain 6L, the top performer from the Nile Red screen. See FIG. 13. Therefore, we selected cDGA1-1233 154L as our platform strain for further development.

Deregulated Acc1 Mutants

ACC1 expression is induced under lipogenic conditions in *L. starkeyi*, and when overexpressed, we identified four transformants that exhibited one full standard deviation higher normalized fluorescence when compared to yeast transformed with the empty vector. However, these transformants were clearly less prodigious at producing lipids compared to our DGA1 transformants. This was surprising, since ACC catalyzes the carboxylation of acetyl-CoA into malonyl-CoA, which is a regulated commitment step in fatty acid biosynthesis.

Enzyme activity can be regulated by more factors than gene expression alone. In fact, ACC activity in *S. cerevisiae* and other organisms is regulated by an AMP-activated protein kinase (Snf1), which phosphorylates certain serine residues. Mutation of these residues can prevent inhibition of ACC, and increase lipid yields.

To determine if ACC could also be deregulated in *L. starkeyi*, we identified two possible serine phosphorylation sites in the *L. starkeyi* ACC1 ortholog based on the AMPK phosphorylation target motif, and created three mutated versions of the ACC1 gene (S639A, S1146A, and the double mutant S639A/S1146A). These were made because it was unknown which mutations and in what combination could deregulate Acct activity. Following transformation and fluorescence screening in yeast, we discovered that constitutive expression of the single S1146A mutant (but not S639A nor the double mutant cassette), increased average fluorescence levels, as shown in FIG. 14.

Overexpression of Acyltransferases

Given the dramatic improvement in lipid accumulation that occurs in DGA1-1233 engineered strains, we hypothesized that expression of additional genes involved in the biosynthesis of triacylglycerols might coax cellular metabolism towards additional lipid production. The DGA1 gene product carries out the third and final acylation step in triacylglycerol synthesis, so we focused our attention on the two acyltransferases that catalyze the previous reactions, namely SCT1 and SLC1. The former (SCT1) is a glycerol-3-phosphate acyltransferase that carries out the first acylation step, whereas the latter (SLC1) is a lysophosphatidate acyltransferase, which catalyzes the second acylation step. To test these genes, we constructed SCT1 and SLC1 overexpression cassettes from gDNA under the control of the CIT1 promoter/terminator pair (SCT1) or the FBA1 promoter/terminator pair (SLC1), and generated over 200 transformants from each cassette to assay for increased lipid production. These strains were evaluated on sTS medium using our Bodipy screening methodology.

Data gathered from an exemplary screen of SCT1 transformants is shown in FIG. 15. Overexpression of SCT1 caused a moderate increase in lipid accumulation under these conditions. SCT1 transformants, on average, yielded 5-10% increased lipid content as measured by Bodipy fluorescence. However, some of the top performing SCT1 strains produced fluorescent readings approximately 30% higher than the wildtype across all time points tested. Taken together, these results demonstrate that SCT1 plays a critical role in initiating triacylglycerol biosynthesis in *L. starkeyi*. Additionally, SCT1 is an attractive target because it utilizes glycerol-3-phosphate as a substrate, and could potentially improve the rate of glycerol utilization in feedstocks with high glycerol content, such as thin stillage. SCT1 was also introduced into other genetic backgrounds by both mating and secondary transformations, as described below, to generate strains with further improvements.

In contrast to SCT1, overexpression of SLC1 did not result in any statistically significant improvements in lipid accumulation. On average the SLC1 strains performed no better, or perhaps slightly worse, than the wild-type in terms of Bodipy fluorescence readings (FIG. 16). Growth rates of all strains were approximately similar. However, there were a few strains that performed better than any wild-type replicates (e.g. SLC1-30L, FIG. 16), which could occur if multicopy integration or specific integration sites are required for SLC1 to have a measurable impact on lipid production.

Given that overexpression of SLC1 alone does not typically increase lipid production, this suggests that the second acylation reaction catalyzed by SLC1 is not a rate-limiting or highly regulated step during the accumulation of lipids in *Lipomyces*. Since we have demonstrated that overexpression of SCT1 (1st acylation) and DGA1/2 (3rd acylation) have such significant effects on improving lipid accumulation, it follows that these are the more significant bottlenecks than the SLC1 reaction.

However, it remains to be seen if combinatorial expression of SLC1 with other genes may synergistically increase lipid production. It is possible that overexpression of SLC1 in a SCT1 engineered strain could further improve lipid production if the bottleneck resolved by acceleration of the first acylation step (SCT1) subsequently leads to the creation of a new rate-limiting step at the second acylation (SLC1). Alternatively, overexpression of SLC1 in a DGA1 engineered strain could also improve lipid production by introducing a metabolic "pull" towards triacylglycerol production.

Combinatorial Expression of Lipogenic Cassettes

In order to evaluate the effects of overexpressing more than one lipogenic cassette in the same organism, we pursued two strategies. First, top strains with different resistance markers were mated together and subjected to sporulation, and progeny harboring both integrated cassettes were selected on double antibiotic plates. Alternatively, top strains were also used as a platform for a second round of transformations with another cassette, as long as the resistance markers were different. The resulting double transformed strains were then evaluated in our Bodipy screen against the progenitor transformant strain for enhanced lipid production. In this way, we screened over 70 mated strains of top performers and 200 double transformed strains.

We first evaluated mated transformants overexpressing DGA1-1233 and ACC1, ACC1(S639A), and ACC1 (S1146A). In some cases, the mated strains performed better than the parental strains. The biggest improvement was seen in the DGA1-1233/ACC1(S1146A) cross (FIG. 17). The DGA1-1233/ACC1(S639A) cross performed no better than the DGA1-1233/ACC1 cross and also no better than the parental DGA1-1233 strain, again suggesting that S639 plays no role in regulating ACC1. Hence, the combination of overexpressing DGA1-1233 and ACC1 in *L. starkeyi* enhances lipid production compared to independent overexpression of these proteins, but is particularly pronounced when ACC1 is mutated at the S1146 phosphorylation site.

We also evaluated mated transformants constitutively expressing DGA1-1233 and SCT1, and a strain with two DGA1-1233 overexpression cassettes. In both cases, each strain performed better than the parental strains. These are shown in FIG. 18, along with the wild-type and our previously identified top performer (cDGA NAT) for comparison purposes.

Combinatorial Expression of Lipogenic and Auxiliary Cassettes

We previously determined that certain cassettes resulted in no significant increase in lipid accumulation relative to control strains as deemed by Nile Red analysis in *Lipomyces starkeyi*. See FIG. 8. These included the dual overexpression of ATP citrate lyase subunits 1 and 2 (Acl1/Acl2), and the cDNA and gDNA versions of the malic enzyme (gME and cME). We re-evaluated these transformants in our sTS screening methodology using Bodipy and obtained similar results. We hypothesized that overexpressing these genes has little effect on lipid accumulation since they are not directly involved in the regulatory mechanisms that govern lipogenesis. However, their activities may synergistically enhance lipid accumulation in strains that have been deregulated from one or more of these mechanisms.

To test this hypothesis, we selected our top DGA1 transformant (cDGA1) to cross with select transformants overexpressing the cDNA version of the ATP citrate lyase cassette (cAcl1/2), or the cDNA and gDNA versions of the malic enzyme cassettes (cMalic Enzyme, gMalic Enzyme). After mating, the progeny and parental strains were evaluated in sTS containing Bodipy for lipid accumulation. As observed previously, the Acl1/Acl2 and malic enzyme sole transformants performed marginally better than the wild-type strain due to the presence of resistance marker integration and overexpression (FIG. 19). Sole overexpression of a resistance marker cassette can be marginally lipogenic due to a number of possibilities, including slower transformant growth and the position in which the cassette integrated in the genome. However, when coupled with overexpression of DGA1, the crossed strains performed significantly better than either of the parental strains, particularly on the third and fourth days of culture growth (FIG. 19). As a control, we also evaluated the parental DGA1 strain transformed with the empty base vector overexpressing the same resistance marker as the lipogenic transformants. The overall performance of these control strains was slightly worse than the parental DGA1 strain (FIG. 20), implying that the lipid accumulation observed in the mated strains could be synergistic, as the total improvement is the same if not higher than the individual improvements combined.

Enhanced glycerol utilization is another feature that is particularly important, due to the large amount of glycerol present in thin stillage. Glycerol Kinase (GUT1) catalyzes the phosphorylation of glycerol to glycerol-3-phosphate, and is the first step in glycerol utilization. However, when GUT1 was overexpressed in *L. starkeyi*, the cells presented with significantly lower growth rates, presumably due to the introduction of a metabolic bottleneck. To overcome this, we transformed a strain overexpressing GUT1 with an FAD dependent glycerol-3-phosphate dehydrogenase (GUT2), which catalyzes the second reaction in glycerol utilization by conversion of glycerol-6-phosphate to dihydroxyacetone phosphate (DHAP), and screened the resulting double transformants for growth on glycerol and lipid accumulation. Dual overexpression of GUT1 and GUT2 rescued the growth rates in approximately half of the transformants evaluated (FIG. 21), with some exhibiting superior lipid accumulation relative to the parental strains (FIG. 22). Importantly, overexpression of GUT2 alone did not significantly affect lipid accumulation (FIG. 22). One of the highly lipogenic strains (GUT1/GUT2 1L) was chosen for scale-up in shake flask experiments to better evaluate its glycerol utilization rate in media containing both glucose and glycerol as a carbon source (FIGS. 23A-23D). The results of this experiment demonstrate that the GUT1/GUT2 double transformant consumed glycerol at a faster rate than the wild-type, once glucose catabolite repression was alleviated.

The highly lipogenic nature of some of the double GUT1/GUT2 transformants was not anticipated, since enhanced glycerol utilization might diminish glycerol pools needed for triacylglyceride synthesis. One explanation for this is that only one molecule of glycerol is needed for every triacylglceride formed, and even though the wild-type strain uses glycerol as a substrate, expression of the assimilation pathway is not optimal. Biosynthesis of acyl carbon chains could be enhanced by increased metabolic carbon flux due to faster glycerol catabolism.

Overexpression of Glycerol-3-Phosphate Dehydrogenase (GPD1)

Intracellular production of glycerol involves the reduction of dihydroxyacetone phosphate (DHAP) into glycerol-3-phosphate by the NADH dependent enzyme glycerol-3-phosphate dehydrogenase (GPD1). Overexpression of GPD1 could alleviate a potential bottleneck in glycerol formation and introduce a metabolic "push" towards triacylglycerol production. Hence, we constructed a GPD1 overexpression cassette driven by a pyruvate kinase (PYK1) promoter and the cognate PYK1 terminator. This was transformed into *L. starkeyi* and several hundred transformants were obtained, of which a subset were selected for Bodipy analysis in sTS. The results of this are shown in FIG. 24. The transformant pool evaluated had moderately higher fluorescence over the wild-type, which became progressively more pronounced throughout the duration of the screen. In fact, by the last day the average fluorescence of the transformant pool was almost 13% higher than the wild-type. This is counterintuitive, since by this time the cells have consumed all of the cellobiose and most of the glycerol present in sTS. Lipogenic effects should be observed when the cells are consuming cellobiose and producing DHAP to convert into glycerol, not consuming glycerol. This could be explained if GPD1 favors conversion of glycerol-3-phosphate into DHAP during glycerol consumption. The DHAP could then enter the glycolytic pathway and be used to produce energy, which indirectly effects lipid levels and/or cell robustness. A similar Bodipy screen performed on media lacking glycerol but containing glucose could provide more insight into this phenomenon.

Engineering the Pentose Phosphate Pathway

To test our prediction that overexpression of 6-phosphogluconate dehydrogenase (GND1) and/or glucose-6-phosphate dehydrogenase (ZWF1) could improve lipid production via increasing the cytoplasmic pool of NADPH, we constructed a plasmid to simultaneously express both genes. The plasmid was transformed into *Lipomyces*, and several hundred transformants were obtained. Of these, 60 colonies were selected for further screening using our sTS and Bodipy methodology. The results of this screen are shown in FIG. 25.

We found that dual overexpression of GND1 and ZWF1 leads to moderately improved lipid accumulation in *Lipomyces* (FIG. 25). The average fluorescence readings of all transformants outperformed the wild-type by about 10-15% at each time point. Two exceptional strains, "GND1+ZWF1 37L" and "GND1+ZWF1 26L" had fluorescent values approximately 30% and 60% higher than the wild-type, respectively. These results suggest that when engineered cells are grown on sTS, overexpression of GND1 and ZWF1 helps to "pull" glucose (derived from cellobiose or amylodextrins) towards the pentose phosphate pathway. Catabolism of glucose via this pathway generates more NADPH than via glycolysis, which increases the availability of reducing power required for lipid biosynthesis.

Generation and Use of an NHEJ-Deficient (lig4Δ) Strain for Further Metabolic Engineering In *Lipomyces starkeyi*, genetic transformation occurs primarily via random integration into the genome, likely by a non-homologous end joining (NHEJ) mechanism. Previous attempts to disrupt genes of interest using homologous recombination with knockout constructs were unsuccessful. However, it is well known that disruption of the NHEJ pathway in a wide range of yeast species greatly increases homologous recombination efficiencies, and facilitates targeted deletion or insertion of genes. Knockouts of Ku70, Ku80, and/or Lig4 have all been commonly used to ablate NHEJ. Therefore, we sought to disrupt the DNA ligase LIG4 (PID_2300, SEQ ID NO:73 (nucleotide) and SEQ ID NO:74 (protein)), to generate an NHEJ-deficient strain of *Lipomyces*. A strain with improved homologous recombination could be used to knock out members of the beta-oxidation pathway, for example, to eliminate the ability of *Lipomyces starkeyi* to consume accumulated lipids.

A LIG4 knockout construct was compiled, using a LoxP-flanked NAT resistance construct bordered by 3 kb of cloned genomic DNA homologous to the upstream (promoter) and downstream (terminator) regions neighboring the LIG4 gene. The transformation rate was very low when introduced into *Lipomyces*, due to the large size of the construct (≈8.4 kb). A total of 22 colonies were selected for further examination to determine if they were truly LIG4 knockouts (lig4Δ). Following genomic DNA extraction and PCR genotyping, we found that only 1/22 transformants (4.5%) harbored a band consistent with replacement of the LIG4 gene by the NAT resistance construct (lig4::NAT). Thus, random integration elsewhere into the genome was the dominant mode of genetic transformation and that homologous recombination occurs only about 5% of the time even when very long flanking regions are used. Subsequent amplification and sequencing of the LIG4 locus in the putative knockout strain confirmed that gene replacement by homologous recombination occurred exactly as intended.

To determine the utility of this strain as a genetic tool, we designed two additional knockout constructs, targeting the acyl-CoA oxidase POX1 and multifunctional enzyme (3-hydroxyacyl-CoA dehydrogenase & enoyl-CoA hydratase) FOX1 in the lig4Δ strain. These constructs utilized a LoxP-flanked HPH resistance marker, bordered by only 1 kb of cloned genomic DNA homologous to the upstream/downstream regions neighboring each respective gene. Transformation of the lig4Δ strain with these constructs resulted in about 70 colonies each. From these, a total of 18 strains were selected for analysis by PCR genotyping. Of the POX1 transformants, we found that 7 out of 9 (78%) were confirmed as true knockouts. As for the FOX1 transformants, only 2 out of 9 (22%) were confirmed to be true knockouts. Regardless, these significantly improved homology recombination rates demonstrate that gene deletions are much easier to achieve in the lig4Δ::NAT background, and can be accomplished with shorter regions of homology.

Disruption of the β-Oxidation Pathway in *L. Starkeyi*

As described above, we generated a NHEJ-deficient *Lipomyces* strain by gene replacement of the DNA ligase LIG4 with a NAT resistance construct (lig4Δ::NAT). Using this strain as a platform, two additional transformations were carried out in order to subsequently knock out either the acyl-CoA oxidase POX1 or the multifunctional enzyme FOX1 by homologous recombination mediated gene replacement with a LoxP-flanked HPH construct. The resulting strains were knockouts for both LIG4 and either POX1 or FOX1 (ligΔ::NAT, pox1Δ::HPH), (lig4Δ::NAT, fox1Δ::HPH).

To test our prediction that disruption of the β-oxidation pathway could improve lipid accumulation, we subjected several replicates of validated pox1Δ or fox1Δ knockouts to our standard Bodipy screening methodology in sTS medium (FIG. 26). We found that deletion of either POX1 or FOX1 mildly enhances lipid accumulation when cells are incubated under aerobic conditions. Average fluorescent readings of these knockout strains ranged from about 5-15% higher values that the wildtype controls. These results suggest that, in addition to overexpressing lipogenic genes, eliminating lipid consumption by the β-oxidation pathway is another viable route for improving lipid accumulation in *Lipomyces starkeyi*.

Overexpression of DGA2—A Second Diacylglycerol Acyltransferase

Overexpression of diacylglycerol acyltransferases, alone or in combination with other lipogenic genes, is predicted to increase lipid accumulation. Unlike *Saccharomyces cerevisiae*, some oleaginous yeast species (e.g. *Yarrowia lipolytica*) possess two or more protein encoding genes with diacylglycerol acyltransferase activity. Upon searching the genome for additional putative DGA genes, we discovered that *Lipomyces starkeyi* contains a second, previously unknown, diacylglycerol acyltransferase gene (DGA2, PID_6231, SEQ ID NOS: 57 and 58). The sequences of DGA1 and DGA2 are quite divergent, as DGA2 is a member of the MBOAT family (Membrane Bound O-Acyl Transferase), and possesses several transmembrane domains. DGA1 is most likely localized to liposomes, while we predict DGA2 resides in the endoplasmic reticulum.

It is unknown whether DGA1 and DGA2 might have differing metabolic roles, activities, or regulation. We therefore tested whether overexpression of the DGA2 gene was capable of increasing lipid production. A plasmid was designed to overexpress DGA2 under the control of the native *Lipomyces* TPI1 promoter and PGK1 terminator. Hundreds of transformants were obtained and subjected to the Bodipy screening methodology described previously. In an exemplary screen, 87 individual DGA2 transformant strains were grown and assessed for lipid accumulation as compared to wild-type replicates. We found that overexpression of DGA2 leads to significantly improved lipid accumulation in *Lipomyces* (FIG. 27). The average of all DGA2 transformants, which includes poor performers, still outperformed the wild-type by 5-10% on each time point. Some of the most promising strains, such as "DGA2-20L" and "DGA2-70L," had fluorescent values 20-30% higher than the wildtype (FIG. 27). Therefore, we have identified a second diacylglycerol acyltransferase as an engineering target for increasing lipid accumulation in Lipomyces starkeyi.
Presence of Trehalose in Thin Stillage and its Utilization in Lipomyces Starkeyi Thin stillage is a complex mixture containing a variety of short-chain oligosaccharides that are difficult to distinguish from each other using typical analytical methods (e.g. HPLC). For example, disaccharides of glucose include cellobiose, maltose, and trehalose, which differ only in the location of their glycosidic bonds. For simplicity, our synthetic thin stillage medium (sTS) includes cellobiose as the sole analog for all disaccharides which might be present. However, trehalose accumulates in Saccharomyces cerevisiae in response to many environmental stress conditions, particularly as an adaptation mechanism to ethanol tolerance. Consequently, in the yeast ethanol industry, trehalose is found among the residual sugars at the termination of fermentation. Trehalose makes up a significant portion of the remaining disaccharide fraction, referred to as the "DP2 peak" in reference to the degree of polymerization of the oligosaccharides eluted together during HPLC analysis.

Therefore, complete conversion of the organics present in thin stillage requires either addition of a trehalase enzyme or use of organisms capable of naturally utilizing trehalose as a carbon source. We have observed nearly complete disappearance of the "DP2 peak" when Lipomyces is cultured on thin stillage, which suggests that this species natively possesses the ability to consume the residual trehalose. We discovered two trehalases in L. starkeyi, which are categorized based on their predicted pH optimum: the "neutral" trehalase NTH1 (PID_4858, SEQ ID NOS: 59 and 60), and the "acidic" trehalase ATH1 (PID_4583, SEQ ID NOS: 61 and 62). Interestingly, the L. starkeyi ATH1 has a strong secretion signal, which indicates its usefulness in engineering strains for hyper-secretion of trehalase, or other glycoside hydrolases. If spent Lipomyces broth were recycled back into primary fermentation vessels, secreted trehalases would reduce the residual sugars present in the DP2 peak, resulting in increased ethanol yields and plant profitability.
Targeting Glycerol Transporters in Lipomyces starkeyi for Enhanced Glycerol Utilization There are multiple potential routes for glycerol assimilation in yeast. The phosphorylative pathway, which involves the glycerol kinase GUT1 and the mitochondrial FAD-dependent glycerol 3-phosphate dehydrogenase GUT2, ultimately generates DHAP for glycolysis. Simultaneous overexpression of GUT1 and GUT2 improves the rate of glycerol utilization, as described elsewhere. Another strategy for improving glycerol utilization is the overexpression of transporters involved in the uptake of glycerol into the cell. Several glycerol transporters have been identified in yeast.

The primary route for glycerol uptake in Saccharomyces is through active transport via STL1, a glycerol/H+ symporter. STL1 is a member of the major facilitator superfamily, a broad group of transporters for many substrates, which can make identification of specific genes difficult. We have identified two a glycerol/H+ symporters in Lipomyces starkeyi, referred to as STL1 (PID_114515, SEQ ID NOS:63 and 64 and STL2 (PID_201837, SEQ ID NOS:65 and 66).

A secondary route for glycerol uptake in Saccharomyces is through passive transport by FPS1, a glycerol facilitator, which is mainly used for controlled export of glycerol during osmoregulation. However, FPS1 homologs in other species with superior glycerol utilization rates (such as Pachysolen tannophilus) have been shown to be the main route of glycerol import. We have identified a FPS1 homolog in L. starkeyi (PID_67294, SEQ ID NOS:67 and 68). Interestingly, the L. starkeyi FPS1 is more similar to the Pachysolen FPS1 than the Saccharomyces FPS1, so it may function as a passive glycerol transporter by facilitated diffusion.

We have observed that when Lipomyces is grown in the presence of both glucose and glycerol, glucose is preferentially utilized first due to the effects of carbon catabolite repression. One of the methods for controlling this response arises from transcriptional regulation of glycerol transporters, which are not highly expressed while glucose is present. Transporters unconstrained by transcriptional regulation could help to improve glycerol uptake and enable simultaneous utilization of glucose and glycerol. Therefore, the STL1, STL2, and FPS1 can be overexpressed with constitutive promoters to overcome carbon catabolite repression and improve glycerol utilization rates in L. starkeyi.
Engineering Constitutive Glucoamylase Secretion Alpha-amylase and glucoamylases are major expenses in ethanol plants, required for the hydrolysis of starch polysaccharides into fermentable glucose monomers. Interestingly, L. starkeyi is known to synthesize both dextranases and amylases. We found evidence of inducible extracellular glucoamylase activity in the supernatant of cells cultured in media containing starch, but not dextrose. This activity was also eliminated by boiling, indicating that it is the result of one or more secreted enzymes, induced by the presence of complex carbohydrates (FIG. 28 (A)). If one or more of these secreted enzymes could be engineered for high levels of secretion in L. starkeyi, then it could serve as a valuable co-product during the production of lipid. To demonstrate the feasibility of this strategy, we identified a secreted α-amylase in L. starkeyi and engineered it for constitutive expression. The supernatant of the resulting transformants exhibited glucoamylase activity independent of the culture medium, and this activity was retained following incubation for 1 hour at 70° C. (FIG. 28, (B)). Thus, we have achieved constitutive secretion of a relatively thermostable α-amylase in L. starkeyi. Optimally, this will result in a spent culture broth rich in a collection of starch degrading enzymes with exceptional processivity and substrate diversity that could be used in ethanol plants to reduce operating costs, or other related industries.
Consolidation of Transformed Traits Combinations of gene cassettes from the top lipid producing strains described above further enhance lipid accumulation, and can be done through yeast mating. Mating techniques for Lipomyces starkeyi and isolation of spores for screening progeny enables identification of crossed strains with more than one cassette integrated in the genome without needing to create cassettes with alternate resistance markers and repeat the screening process. Nonetheless, integration vectors that confer resistance to G418 and Hygromycin B that are functional in L. starkeyi can be used. Lastly, a Lipomyces starkeyi strain that constitutively secretes a native α-amylase and could be mated to the DGA1-1233 transformant to obtain a strain that converts mTS to lipids and α-amylase. Lipids and α-amylase are products of much higher value than the mTS substrate, which currently presents a disposal cost.

REFERENCES

Anon, Edn. Jul. 29, 2016 (U.S. Energy Information Administration, 2016).
Athenstaedt, K. YALI0E32769g (DGA1) and YALI0E16797g (LRO1) encode major triacylglycerol synthases of the oleaginous yeast Yarrowia lipolytica.

Biochimica Et Biophysica Acta-Molecular and Cell Biology of Lipids 1811, 587-596 (2011).

Barcia-Vieitez, R. & Ramos-Martinez, J. I. The Regulation of the Oxidative Phase of the Pentose Phosphate Pathway: New Answers to Old Problems. *Iubmb Life* 66, 775-779 (2014).

Becker, J. et al. Metabolic flux engineering of L-lysine production in *Corynebacterium glutamicum*—overexpression and modification of G6P dehydrogenase. *Journal of Biotechnology* 132, 99-109 (2007).

Beopoulos, A. et al. Identification and characterization of DGA2, an acyltransferase of the DGAT1 acyl-CoA:diacylglycerol acyltransferase family in the oleaginous yeast *Yarrowia lipolytica*. New insights into the storage lipid metabolism of oleaginous yeasts. *Applied Microbiology and Biotechnology* 93, 1523-1537 (2012).

Bignell, G. R., Bruce, I. J. & Evans, I. H. Amylolytic enzymes of *Lipomyces starkeyi*: purification and size-determination. *Biotechnology Letters* 22, 1713-1718 (2000).

Bligh and Dyer. A rapid method of total lipid extraction and purification. *Canadian Journal of Biochemistry and Physiology* 37(8):911-7 (1959).

Boulton, C. A. & Ratledge, C. Use of transition studies in continuous cultures of *Lipomyces starkeyi*, an oleaginous yeast, to investigate the physiology of lipid accumulation. *Journal of general microbiology* 129, 2871-2876 (1983).

Calvey, C. H., Willis, L. B. & Jeffries, T. W. An optimized transformation protocol for *Lipomyces starkeyi*. *Current Genetics* 60, 223-230 (2014).

Calvey, C. H., Su, Y. K., Willis, L. B., McGee, M. & Jeffries, T. W. Nitrogen limitation, oxygen limitation, and lipid accumulation in *Lipomyces starkeyi*. *Bioresource Technology* 200, 780-788 (2016).

Cannella, D. & Jorgensen, H. Do New Cellulolytic Enzyme Preparations Affect the Industrial Strategies for High Solids Lignocellulosic Ethanol Production? *Biotechnology and Bioengineering* 111, 59-68 (2014).

Cardenas, J. & Da Silva, N. A. Engineering cofactor and transport mechanisms in *Saccharomyces cerevisiae* for enhanced acetyl-CoA and polyketide biosynthesis. *Metabolic Engineering* 36, 80-89 (2016).

Chen, L., Zhou, X. S., Fan, W. M. & Zhang, Y. X. Expression, purification and characterization of a recombinant *Lipomyces starkeyi* dextranase in *Pichia pastoris*. *Protein Expression and Purification* 58, 87-93 (2008).

Choi, J. W. & Da Silva, N. A. Improving polyketide and fatty acid synthesis by engineering of the yeast acetyl-CoA carboxylase. *Journal of Biotechnology* 187, 56-59 (2014).

Collett, J. R., Meyer, S. & Jones, S. Preliminary economics for hydrocarbon fuel production from cellulosic sugars. (2014).

Courchesne, N. M. D., Parisien, A., Wang, B. & Lan, C. Q. Enhancement of lipid production using biochemical, genetic and transcription factor engineering approaches. *J Biotechnol* 141, 31-41 (2009).

Evans, C. T. & Ratledge, C. Possible regulatory roles of ATP-citrate lyase, malic enzyme and AMP deaminate in lipid accumulation by *Rhodosporidium toruloides* CBS-14. *Canadian Journal of Microbiology* 31, 1000-1005 (1985).

Flores, C. L., and Gancedo, C. *Yarrowia lipolytica* mutants devoid of pyruvate carboxylase activity show an unusual growth phenotype, *Eukaryot. Cell* 4 (2005) 356-364.

Gallagher, A. M., Kelly, C. T. & Fogarty, W. M. A novel extracellular carbohydrase produced by *Lipomyces tetrasporus*. *Applied Microbiology and Biotechnology* 35, 455-460 (1991).

Garay, L. A. et al. Eighteen new oleaginous yeast species. *Journal of industrial microbiology & biotechnology* 43, 887-900 (2016).

Gibson, D. G. et al. Enzymatic assembly of DNA molecules up to several hundred kilobases. *Nature Methods* 6, 343-U341 (2009).

Gietz, R. D., and R. A. Woods, Transformation of yeast by lithium acetate/single stranded carrier DNA/polyethylene glycol method. *Methods in Enzymology* 350:87-96 (2002).

Gomma, A. E., Lee, S. K., Sun, S. M., Yang, S. H. & Chung, G. Improvement in Oil Production by Increasing Malonyl-CoA and Glycerol-3-Phosphate Pools in *Scenedesmus quadricauda*. *Indian Journal of Microbiology* 55, 447-455 (2015).

Gong, Z. W. et al. Co-fermentation of cellobiose and xylose by *Lipomyces starkeyi* for lipid production. *Bioresource Technology* 117, 20-24 (2012).

Gorner, C. et al. Genetic engineering and production of modified fatty acids by the non-conventional oleaginous yeast *Trichosporon oleaginosus* ATCC 20509. *Green Chemistry* 18, 2037-2046 (2016).

Hamid, A. A., Mokhtar, N. F., Taha, E. M., Omar, O. & Yusoff, W. M. W. The role of ATP citrate lyase, malic enzyme and fatty acid synthase in the regulation of lipid accumulation in *Cunninghamella* sp 2A1. *Annals of Microbiology* 61, 463-468 (2011).

Hammond, E. G., Johnson, L. A., Su, C., Wang, T. & White, P. J. Soybean oil. Bailey's Industrial Oil and Fat Products (2005).

Holdsworth, J. E. & Ratledge, C. Lipid turnover in oleaginous yeasts. *Journal of General Microbiology* 134, 339-346 (1988).

Holdsworth, J. E., Veenhuis, M. & Ratledge, C. Enzyme activities in oleaginous yeasts accumulating and utilizing exogenous or endogenous lipids. *Journal of General Microbiology* 134, 2907-2915 (1988).

Jeffries, T. W. *Lipomyces starkeyi* NRRL Y-11557 Genome Sequencing Project. *European Nucleotide Archive* (2013).

Kang, H. K. et al. Cloning and characterization of a dextranase gene from *Lipomyces starkeyi* and its expression in *Saccharomyces cerevisiae*. *Yeast* 22, 1239-1248 (2005).

Kildegaard, K. R. et al. Engineering and systems-level analysis of *Saccharomyces cerevisiae* for production of 3-hydroxypropionic acid via malonyl-CoA reductase-dependent pathway. *Microbial Cell Factories* 15 (2016).

Kim, Y. et al. Composition of corn dry-grind ethanol by-products: DDGS, wet cake, and thin stillage. *Bioresource Technology* 99, 5165-5176 (2008).

Lee, S. Y. et al. Demonstration of two independent dextranase and amylase active sites on a single enzyme elaborated by *Lipomyces starkeyi* KSM 22. *Journal of Microbiology and Biotechnology* 13, 313-316 (2003).

Li, Z. et al. Overexpression of malic enzyme (ME) of *Mucor circinelloides* improved lipid accumulation in engineered *Rhodotorula glutinis*. *Appl Microbiol Biotechnol* (2012).

Lodder, J., Acomina & Kreger-Van Rij, N. J. W. The yeasts-a taxonomic study. (1952).

Moritz, B., Striegel, K., De Graaf, A. A. & Sahm, H. Kinetic properties of the glucose-6-phosphate and 6-phosphogluconate dehydrogenases from *Corynebacterium glutamicum* and their application for predicting pentose phosphate pathway flux in vivo. *European journal of biochemistry/FEBS* 267, 3442-3452 (2000).

Naganuma, T., Uzuka, Y., Tanaka, K. & Iizuka, H. Differences in enzyme activities of *Lipomyces starkeyi* between cells accumulating lipid and proliferating cells. *Journal of basic microbiology* 27, 35-42 (1987).

Oguro, Y. et al. Multicopy integration and expression of heterologous genes in the oleaginous yeast, *Lipomyces starkeyi*. *Bioscience Biotechnology and Biochemistry* 79, 512-515 (2015).

Ohnishi, J., Katahira, R., Mitsuhashi, S., Kakita, S. & Ikeda, M. A novel gnd mutation leading to increased L-lysine production in *Corynebacterium glutamicum*. *FEMS Microbiology Letters* 242, 265-274 (2005).

Pan, L.-X. et al. Isolation of the oleaginous yeasts from the soil and studies of their lipid-producing capacities. *Food Technol. Biotechnol* 47, 215-220 (2009).

Papanikolaou, S., Chevalot, I., Komaitis, M., Aggelis, G. & Marc, I. Kinetic profile of the cellular lipid composition in an oleaginous *Yarrowia lipolytica* capable of producing a cocoa-butter substitute from industrial fats. *Antonie Van Leeuwenhoek International Journal of General and Molecular Microbiology* 80, 215-224 (2001).

Punpeng, B., Nakata, Y., Goto, M., Teramoto, Y. & Hayashida, S. A novel raw-starch digesting yeast alpha amylase from *Lipomyces starkeyi*. *Journal of Fermentation and Bioengineering* 73, 108-111 (1992).

Rangasamy, D. & Ratledge, C. Genetic Enhancement of Fatty Acid Synthesis by Targeting Rat Liver ATP:Citrate Lyase into Plastids of Tobacco. *Plant Physiology* 122, 1231-1238 (2000).

Ratledge, C. Lipid biotechnology—a wonderland for the microbial physiologist. *Journal of the American Oil Chemists Society* 64, 1647-1656 (1987).

Ratledge, C. Regulation of lipid accumulation in oleaginous micro-organisms. *Biochemical Society Transactions* 30, 1047-1050 (2002).

Ratledge, C. Fatty acid biosynthesis in microorganisms being used for Single Cell Oil production. *Biochimie* 86, 807-815 (2004).

Ratledge, C. The role of malic enzyme as the provider of NADPH in oleaginous microorganisms: a reappraisal and unsolved problems. *Biotechnol. Lett.* 36, 1557-1568 (2014).

Riley R, et al. (2016) Comparative genomics of biotechnologically important yeasts. *Proceedings of the National Academy of Sciences* 113(35):9882-9887.

Rippa, M., Giovannini, P. P., Barrett, M. P., Dallocchio, F. & Hanau, S. 6-phosphogluconate dehydrogenase: the mechanism of action investigated by a comparison of the enzyme from different species. *Biochimica Et Biophysica Acta-Protein Structure and Molecular Enzymology* 1429, 83-92 (1998).

Ruenwai, R., Cheevadhanarak, S. & Laoteng, K. Overexpression of acetyl-CoA carboxylase gene of *Mucor rouxii* enhanced fatty acid content in *Hansenula polymorpha*. *Mol Biotechnol* 42, 327-332 (2009).

Ryu, S. J. et al. Purification and partial characterization of a novel glucanhydrolase from *Lipomyces starkeyi* KSM 22 and its use for inhibition of insoluble glucan formation. *Bioscience Biotechnology and Biochemistry* 64, 223-228 (2000).

Saenge, C., Cheirsilp, B., Suksaroge, T. T. & Bourtoom, T. Potential use of oleaginous red yeast *Rhodotorula glutinis* for the bioconversion of crude glycerol from biodiesel plant to lipids and carotenoids. *Process Biochemistry* 46, 210-218 (2011).

Sitepu, et al. An improved high-throughput Nile red fluorescence assay for estimating intracellular lipids in a variety of yeast species. *Journal of Microbiological Methods* 91:321-328 (2012).

Shi, S. B., Chen, Y., Siewers, V. & Nielsen, J. Improving Production of Malonyl Coenzyme A-Derived Metabolites by Abolishing Snf1-Dependent Regulation of Acc1. *Mbio* 5 (2014).

Steyn, A. J. C., Marmur, J. & Pretorius, I. S. Cloning, sequence analysis and expression in yeasts of a cDNA-containing a *Lipomyces kononenkoae* alpha-amylase encoding gene. *Gene* 166, 65-71 (1995).

Tai, M. & Stephanopoulos, G. Engineering the push and pull of lipid biosynthesis in oleaginous yeast *Yarrowia lipolytica* for biofuel production. *Metabolic Engineering* 15, 1-9 (2013).

Tang, W., Zhang, S., Wang, Q., Tan, H. & Zhao, Z. K. The isocitrate dehydrogenase gene of oleaginous yeast *Lipomyces starkeyi* is linked to lipid accumulation. *Can J Microbiol* 55, 1062-1069 (2009).

Tang, X. L., Feng, H. X. & Chen, W. N. Metabolic engineering for enhanced fatty acids synthesis in *Saccharomyces cerevisiae*. *Metabolic Engineering* 16, 95-102 (2013).

Tang, X. L. & Chen, W. N. Investigation of fatty acid accumulation in the engineered *Saccharomyces cerevisiae* under nitrogen limited culture condition. *Bioresource Technology* 162, 200-206 (2014).

van Rossum, H. M., Kozak, B. U., Pronk, J. T. & van Maris, A. J. A. Engineering cytosolic acetyl-coenzyme A supply in *Saccharomyces cerevisiae*: Pathway stoichiometry, free-energy conservation and redox-cofactor balancing. *Metabolic Engineering* 36, 99-115 (2016).

Velasco, P., Sieiro, A. M., Ibarguren, I., Ramosmartinez, J. I. & Barcia, R. The Modulation of the Oxidative Phase of the Pentose-Phosphate Pathway in Mouse Liver. *International Journal of Biochemistry & Cell Biology* 27, 1015-1019 (1995).

Vicente, G. et al. Direct transformation of fungal biomass from submerged cultures into biodiesel. *Energy & Fuels* 24, 3173-3178 (2010).

Wang, Z. P., Xu, H. M., Wang, G. Y., Chi, Z. & Chi, Z. M. Disruption of the MIG1 gene enhances lipid biosynthesis in the oleaginous yeast *Yarrowia lipolytica* ACA-DC 50109. *Biochimica Et Biophysica Acta-Molecular and Cell Biology of Lipids* 1831, 675-682 (2013).

Wang, J. C., Xu, R. H., Wang, R. L., Hague, M. E. & Liu, A. Z. Overexpression of ACC gene from oleaginous yeast *Lipomyces starkeyi* enhanced the lipid accumulation in *Saccharomyces cerevisiae* with increased levels of glycerol 3-phosphate substrates. *Bioscience Biotechnology and Biochemistry* 80, 1214-1222 (2016).

Wei, T., Sufang, Z., Qian, W., Haidong, T. & Zongbao Kent, Z. The isocitrate dehydrogenase gene of oleaginous yeast *Lipomyces starkeyi* is linked to lipid accumulation. *Canadian Journal of Microbiology* 55, 1062-1069 (2009).

Wilkie, A. C., Riedesel, K. J. & Owens, J. M. Stillage characterization and anaerobic treatment of ethanol stillage from conventional and cellulosic feedstocks. *Biomass & Bioenergy* 19, 63-102 (2000).

Wynn, J. P., bin Abdul Hamid, A. & Ratledge, C. The role of malic enzyme in the regulation of lipid accumulation in filamentous fungi. *Microbiology* 145 (Pt 8), 1911-1917 (1999).

Wynn, J. P., Hamid, A. B. A. & Ratledge, C. The role of malic enzyme in the regulation of lipid accumulation in filamentous fungi. *Microbiology-Uk* 145, 1911-1917 (1999).

Xuan, J. W., Fournier, P. & Gaillardin, C. Cloning of the Lys5 gene encoding saccharopine dehydrogenase from the yeast *Yarrowia lipolytica*. *Current Genetics* 14, 15-21 (1988).

Yen, H.-W., Yang, Y.-C. & Yu, Y.-H. Using crude glycerol and thin stillage for the production of microbial lipids through the cultivation of *Rhodotorula glutinis*. *Journal of Bioscience and Bioengineering* 114, 453-456 (2012).

Zha, J., Shen, M. H., Hu, M. L., Song, H. & Yuan, Y. J. Enhanced expression of genes involved in initial xylose metabolism and the oxidative pentose phosphate pathway in the improved xylose-utilizing *Saccharomyces cerevisiae* through evolutionary engineering. *Journal of Industrial Microbiology & Biotechnology* 41, 27-39 (2014).

Zhang, Y., Adams, I. P. & Ratledge, C. Malic enzyme: the controlling activity for lipid production? Overexpression of malic enzyme in *Mucor circinelloides* leads to a 2.5-fold increase in lipid accumulation. *Microbiology-Sgm* 153, 2013-2025 (2007).

Zhang, Y., Wang, Z. Y., He, X. P., Liu, N. & Zhang, B. R. New industrial brewing yeast strains with ILV2 disruption and LSD1 expression. *International Journal of Food Microbiology* 123, 18-24 (2008).

Zhang, M., Galdieri, L. & Vancura, A. The Yeast AMPK Homolog SNF1 Regulates Acetyl Coenzyme A Homeostasis and Histone Acetylation. *Molecular and Cellular Biology* 33, 4701-4717 (2013).

Zhao, X., Kong, X. L., Hua, Y. Y., Feng, B. & Zhao, Z. B. Medium optimization for lipid production through co-fermentation of glucose and xylose by the oleaginous yeast *Lipomyces starkeyi*. *European Journal of Lipid Science and Technology* 110, 405-412 (2008).

Zhou, Y. J. J. et al. Production of fatty acid-derived oleochemicals and biofuels by synthetic yeast cell factories. *Nature Communications* 7 (2016).

Zhu, Z. W. et al. in *Nature Communications*, Vol. 3 (2012).

EXEMPLARY EMBODIMENTS OF THE INVENTION

Exemplary embodiments of the invention are as follows:

Embodiment 1

A recombinant yeast comprising one or more recombinant nucleic acids configured to express one or more proteins selected from the group consisting of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme.

Embodiment 2

The recombinant yeast of embodiment 1, wherein the one or more recombinant nucleic acids comprises one or more recombinant genes configured to express the one or more proteins.

Embodiment 3

The recombinant yeast of any prior embodiment, wherein the one or more recombinant nucleic acids comprises one or more recombinant genes configured to express a glycerol kinase and a glycerol-3-phosphate dehydrogenase.

Embodiment 4

The recombinant yeast of any prior embodiment, wherein the one or more recombinant nucleic acids comprises one or more recombinant genes configured to express a diacylglycerol acyltransferase and at least one of an ATP citrate lyase and a malic enzyme.

Embodiment 5

The recombinant yeast of any prior embodiment, wherein the one or more recombinant nucleic acids comprises one or more recombinant genes configured to express an acetyl-CoA carboxylase comprising a sequence at least about 90% identical to SEQ ID NO:2.

Embodiment 6

The recombinant yeast of any prior embodiment, wherein the one or more recombinant nucleic acids comprises one or more recombinant genes configured to express an acetyl-CoA carboxylase comprising a sequence at least about 90% identical to SEQ ID NO:2, wherein the sequence comprises a residue other than serine and threonine at a position corresponding to position 1146 of SEQ ID NO:2.

Embodiment 7

The recombinant yeast of any prior embodiment, wherein the one or more recombinant nucleic acids comprises one or more recombinant genes configured to express an acetyl-CoA carboxylase comprising a sequence at least about 90% identical to SEQ ID NO:2, wherein the sequence comprises a serine or threonine at a position corresponding to position 639 of SEQ ID NO:2 a residue other than serine and threonine at a position corresponding to position 1146 of SEQ ID NO:2.

Embodiment 8

The recombinant yeast of any prior embodiment, wherein the one or more recombinant nucleic acids comprises one or more recombinant genes configured to express one or more alpha-amylases comprising a sequence selected from the group consisting of a sequence at least about 90% identical to SEQ ID NO:4, a sequence at least about 90% identical to SEQ ID NO:6, and a sequence at least about 90% identical to SEQ ID NO:8.

Embodiment 9

The recombinant yeast of any prior embodiment, wherein the one or more recombinant nucleic acids comprises one or more recombinant genes configured to express an ATP citrate lyase comprising a sequence selected from the group consisting of a sequence at least about 90% identical to SEQ ID NO:10 and a sequence at least about 90% identical to SEQ ID NO:12.

Embodiment 10

The recombinant yeast of any prior embodiment, wherein the one or more recombinant nucleic acids comprises one or more recombinant genes configured to express a diacylglycerol acyltransferase comprising a sequence selected from the group consisting of a sequence at least about 90% identical to SEQ ID NO:14, a sequence at least about 90% identical to SEQ ID NO:16, and a sequence at least about 90% identical to SEQ ID NO:58.

Embodiment 11

The recombinant yeast of any prior embodiment, wherein the one or more recombinant nucleic acids comprises one or more recombinant genes configured to express a diacylglycerol acyltransferase comprising a sequence at least about 90% identical to SEQ ID NO:14 and devoid of a sequence corresponding to positions 1-52 of SEQ ID NO:16.

Embodiment 12

The recombinant yeast of any prior embodiment, wherein the one or more recombinant nucleic acids comprises one or more recombinant genes configured to express a fatty acid synthase comprising a sequence selected from the group consisting of a sequence at least about 90% identical to SEQ ID NO:18, a sequence at least about 90% identical to SEQ ID NO:20, a sequence at least about 90% identical to SEQ ID NO:22, and a sequence at least about 90% identical to SEQ ID NO:24.

Embodiment 13

The recombinant yeast of any prior embodiment, wherein the one or more recombinant nucleic acids comprises one or more recombinant genes configured to express a glycerol kinase comprising a sequence selected from the group consisting of a sequence at least about 90% identical to SEQ ID NO:26 and a sequence at least about 90% identical to SEQ ID NO:28.

Embodiment 14

The recombinant yeast of any prior embodiment, wherein the one or more recombinant nucleic acids comprises one or more recombinant genes configured to express a glycerol kinase comprising a sequence at least about 90% identical to SEQ ID NO:26 and devoid of a sequence corresponding to positions 1-5 of SEQ ID NO:28.

Embodiment 15

The recombinant yeast of any prior embodiment, wherein the one or more recombinant nucleic acids comprises one or more recombinant genes configured to express a 6-phosphogluconate dehydrogenase comprising a sequence at least about 90% identical to SEQ ID NO:30.

Embodiment 16

The recombinant yeast of any prior embodiment, wherein the one or more recombinant nucleic acids comprises one or more recombinant genes configured to express a glycerol-3-phosphate dehydrogenase comprising a sequence selected from the group consisting of a sequence at least about 90% identical to SEQ ID NO:32 and a sequence at least about 90% identical to SEQ ID NO:56.

Embodiment 17

The recombinant yeast of any prior embodiment, wherein the one or more recombinant nucleic acids comprises one or more recombinant genes configured to express a glycerol kinase comprising a sequence selected from the group consisting of a sequence at least about 90% identical to SEQ ID NO:26 and a sequence at least about 90% identical to SEQ ID NO:28 and a glycerol-3-phosphate dehydrogenase comprising a sequence at least about 90% identical to SEQ ID NO:56.

Embodiment 18

The recombinant yeast of any prior embodiment, wherein the one or more recombinant nucleic acids comprises one or more recombinant genes configured to express a malic enzyme comprising a sequence at least about 90% identical to SEQ ID NO:34.

Embodiment 19

The recombinant yeast of any prior embodiment, wherein the one or more recombinant nucleic acids comprises one or more recombinant genes configured to express a diacylglycerol acyltransferase comprising a sequence selected from the group consisting of a sequence at least about 90% identical to SEQ ID NO:14, a sequence at least about 90% identical to SEQ ID NO:16, and a sequence at least about 90% identical to SEQ ID NO:58, in combination with at least one of an ATP citrate lyase comprising a sequence selected from the group consisting of a sequence at least about 90% identical to SEQ ID NO:10 and a sequence at least about 90% identical to SEQ ID NO:12 and a malic enzyme comprising a sequence at least about 90% identical to SEQ ID NO:34.

Embodiment 20

The recombinant yeast of any prior embodiment, wherein the one or more recombinant nucleic acids comprises one or more recombinant genes configured to express a fatty acyl-CoA reductase comprising a sequence at least about 90% identical to SEQ ID NO:36.

Embodiment 21

The recombinant yeast of any prior embodiment, wherein the one or more recombinant nucleic acids comprises one or more recombinant genes configured to express a delta-9 acyl-CoA desaturase comprising a sequence at least about 90% identical to SEQ ID NO:38.

Embodiment 22

The recombinant yeast of any prior embodiment, wherein the one or more recombinant nucleic acids comprises one or more recombinant genes configured to express a glycerol-3-phosphate acyltransferase comprising a sequence at least about 90% identical to SEQ ID NO:40.

Embodiment 23

The recombinant yeast of any prior embodiment, wherein the one or more recombinant nucleic acids comprises one or more recombinant genes configured to express a lysophosphatidate acyltransferase comprising a sequence at least about 90% identical to SEQ ID NO:42.

Embodiment 24

The recombinant yeast of any prior embodiment, wherein the one or more recombinant nucleic acids comprises one or more recombinant genes configured to express a glucose-6-phosphate dehydrogenase comprising a sequence at least about 90% identical to SEQ ID NO:44.

Embodiment 25

The recombinant yeast of any prior embodiment, wherein the one or more recombinant nucleic acids comprises one or more recombinant genes configured to express a beta-glucosidase comprising a sequence at least about 90% identical to SEQ ID NO:46.

Embodiment 26

The recombinant yeast of any prior embodiment, wherein the one or more recombinant nucleic acids comprises one or more recombinant genes configured to express a hexose transporter comprising a sequence at least about 90% identical to SEQ ID NO:48.

Embodiment 27

The recombinant yeast of any prior embodiment, wherein the one or more recombinant nucleic acids comprises one or more recombinant genes configured to express a glycerol transporter comprising a sequence selected from the group consisting of a sequence at least about 90% identical to SEQ ID NO:66, a sequence at least about 90% identical to SEQ ID NO:66, and a sequence at least about 90% identical to SEQ ID NO:68.

Embodiment 28

The recombinant yeast of any prior embodiment, wherein the one or more recombinant nucleic acids comprises one or more recombinant genes configured to express one or more glycoside hydrolase family 5 enzymes comprising a sequence selected from the group consisting of a sequence at least about 90% identical to SEQ ID NO:50 and a sequence at least about 90% identical to SEQ ID NO:52.

Embodiment 29

The recombinant yeast of any prior embodiment, wherein the one or more recombinant nucleic acids comprises one or more recombinant genes configured to express a trehalase comprising a sequence selected from the group consisting of a sequence at least about 90% identical to SEQ ID NO:60 and a sequence at least about 90% identical to SEQ ID NO:62.

Embodiment 30

The recombinant yeast of any prior embodiment, wherein the one or more recombinant nucleic acids comprises one or more recombinant genes configured to express an auxiliary activity family 9 enzyme comprising a sequence at least about 90% identical to SEQ ID NO:54.

Embodiment 31

The recombinant yeast of any prior embodiment, wherein at least one of the one or more recombinant nucleic acids comprises a recombinant gene comprising a constitutive promoter or an inducible promoter.

Embodiment 32

The recombinant yeast of any prior embodiment, wherein at least one of the one or more recombinant nucleic acids comprise a recombinant gene comprising a promoter operably linked to a coding sequence of at least one of the one or more enzymes, wherein the promoter has a sequence selected from the group consisting of a sequence at least about 90% identical to any one of SEQ ID NOS:75-84.

Embodiment 33

The recombinant yeast of any prior embodiment, wherein at least one of the one or more recombinant nucleic acids comprise a recombinant gene comprising a terminator operably linked to a coding sequence of at least one of the one or more enzymes, wherein the terminator has a sequence selected from the group consisting of a sequence at least about 90% identical to any one of SEQ ID NOS:85-90.

Embodiment 34

The recombinant yeast of any prior embodiment, wherein the yeast exhibits increased expression of at least one of the one or more enzymes relative to a non-recombinant control.

Embodiment 35

The recombinant yeast of any prior embodiment, wherein the yeast comprises a modification that reduces or ablates the activity of one or more native enzymes in the yeast selected from the group consisting of a delta-9 acyl-CoA desaturase, a glycerol-3-phosphate dehydrogenase, an acyl-CoA oxidase, a 3-hydroxyacyl-CoA dehydrogenase, and an enoyl-CoA hydratase.

Embodiment 36

The recombinant yeast of any prior embodiment, wherein the yeast comprises a modification that reduces or ablates the activity of a native delta-9 acyl-CoA desaturase comprising a sequence at least about 90% identical to SEQ ID NO:38.

Embodiment 37

The recombinant yeast of any prior embodiment, wherein the yeast comprises a modification that reduces or ablates the activity of a native glycerol-3-phosphate dehydrogenase comprising a sequence at least about 90% identical to SEQ ID NO:56.

Embodiment 38

The recombinant yeast of any prior embodiment, wherein the yeast comprises a modification that reduces or ablates the activity of a native acyl-CoA oxidase comprising a sequence at least about 90% identical to SEQ ID NO:70.

Embodiment 39

The recombinant yeast of any prior embodiment, wherein the yeast comprises a modification that reduces or ablates the activity of a native 3-hydroxyacyl-CoA dehydrogenase comprising a sequence at least about 90% identical to SEQ ID NO:72.

Embodiment 40

The recombinant yeast of any prior embodiment, wherein the yeast comprises a modification that reduces or ablates the activity of a native enoyl-CoA hydratase comprising a sequence at least about 90% identical to SEQ ID NO:72.

Embodiment 41

The recombinant yeast of any prior embodiment, wherein the yeast exhibits a property selected from the group consisting of increased lipid production, increased lipid secretion, increased carbohydrase production, increased carbohydrase secretion, increased growth rate, increased glycerol consumption, increase trehalose consumption, and increased cellobiose consumption relative to a non-recombinant control.

Embodiment 42

The recombinant yeast of any prior embodiment, wherein the yeast is a recombinant lipogenic yeast.

Embodiment 43

The recombinant yeast of any prior embodiment, wherein the yeast is a recombinant *Lipomyces starkeyi*.

Embodiment 44

A method of processing comprising: contacting a medium comprising a first organic with a yeast, wherein the yeast consumes the first organic and produces a second organic.

Embodiment 45

The method of embodiment 44, wherein the first organic is selected from the group consisting of glycerol, cellobiose, xylose, lactic acid, trehalose, and an oligosaccharide.

Embodiment 46

The method of any one of embodiments 44-45, wherein the contacting reduces an amount of the first organic to less than 25% of an initial amount in the medium.

Embodiment 47

The method of any one of embodiments 44-46, wherein the second organic is selected from the group consisting of a lipid and a protein.

Embodiment 48

The method of any one of embodiments 44-47, wherein the second organic is an enzyme.

Embodiment 49

The method of any one of embodiments 44-48, further comprising, after the contacting, separating at least a portion of a component selected from the group consisting of lipid produced by the yeast, enzymes produced by the yeast, and the yeast from at least a portion of one other component of spent medium resulting from the contacting.

Embodiment 50

The method of any one of embodiments 44-49, further comprising, after the contacting, conducting a process selected from the group consisting of liquefaction of starch and saccharification of liquified starch with enzymes produced by the yeast.

Embodiment 51

The method of any one of embodiments 44-50, further comprising, after the contacting, mixing spent medium resulting from the contacting with starch and conducting liquefaction of the starch in the presence of the spent medium.

Embodiment 52

The method of any one of embodiments 44-51, wherein the medium comprises a component selected from the group consisting of glucose, glucan, trehalose, xylose, xylan, arabinose, arabinan, lactic acid, glycerol, acetic acid, butanediol, and ethanol.

Embodiment 53

The method of any one of embodiments 44-52, wherein the medium comprises a component selected from the group consisting of glucose in an amount of from about 0.1 g/L to about 10 g/L, glucan in an amount of from about 1 g/L to about 100 g/L, xylose in an amount of from about 0.1 g/L to about 10 g/L, trehalose in an amount of from about 0.01 g/L to about 100 g/L, xylan in an amount of from 0.5 g/L to about 50 g/L, arabinose in an amount of from about 0.05 g/L to about 5 g/L, arabinan in an amount of from about 0.05 g/L to about 5 g/L, lactic acid in an amount of from about 1.5 g/L to about 150 g/L, glycerol in an amount of from about 1.5 g/L to about 150 g/L, acetic acid in an amount of from about 0.05 g/L to about 5 g/L, butanediol in an amount of from about 0.2 g/L to about 20 g/L, and ethanol in an amount of from about 0.05 g/L to about 5 g/L.

Embodiment 54

The method of any one of embodiments 44-53, wherein the medium comprises a grain ethanol distillation stillage or a processed grain ethanol distillation stillage.

Embodiment 55

The method of any one of embodiments 44-45, wherein the medium comprises a processed grain ethanol distillation stillage made by processing grain ethanol distillation stillage with a step selected from the group consisting of centrifuging, removing oil, and concentrating.

Embodiment 56

The method of any one of embodiments 44-54, wherein the yeast is a lipogenic yeast.

Embodiment 57

The method of any one of embodiments 44-55, wherein the yeast is a non-genetically modified lipogenic yeast.

Embodiment 58

The method of any one of embodiments 44-56, wherein the yeast is non-genetically modified *Lipomyces starkeyi*.

Embodiment 59

The method of any one of embodiments 44-57, wherein the yeast is a recombinant yeast as recited in any one of embodiments 1-43.

We claim:

1. A recombinant yeast comprising one or more recombinant genes, wherein the one or more recombinant genes are configured to express:
   - a diacylglycerol acyltransferase;
   - a protein selected from the group consisting of a malic enzyme and a glycerol-3-phosphate acyltransferase; and
   - at least one of:
     - an acetyl-CoA carboxylase, wherein the acetyl-CoA carboxylase comprises a sequence at least about 90% identical to SEQ ID NO:2 and the acetyl-CoA carboxylase comprises a residue other than serine and threonine at a position corresponding to position 1146 of SEQ ID NO:2;
     - a glycerol-3-phosphate dehydrogenase comprising a sequence at least about 90% identical to SEQ ID NO:32;
     - a glucose-6-phosphate dehydrogenase and a 6-phosphogluconate dehydrogenase, wherein the glucose-6-phosphate dehydrogenase comprises a sequence at least about 90% identical to SEQ ID NO:44 and the 6-phosphogluconate dehydrogenase comprises a sequence at least about 90% identical to SEQ ID NO:30;
     - a fatty acid synthase, wherein the fatty acid synthase comprises a first subunit comprising a sequence at least about 90% identical to SEQ ID NO:22 and a second subunit comprising a sequence at least about 90% identical to SEQ ID NO:24;
     - an ATP citrate lyase, wherein the ATP citrate lyase comprises a first subunit comprising a sequence at least about 90% identical to SEQ ID NO:10 and a second subunit comprising a sequence at least about 90% identical to SEQ ID NO:12; and
     - a glycerol kinase and a glycerol-3-phosphate dehydrogenase, wherein the glycerol kinase comprises a sequence at least about 90% identical to SEQ ID NO:26 and the glycerol-3-phosphate dehydrogenase comprises a sequence at least about 90% identical to SEQ ID NO:56.

2. The recombinant yeast of claim 1, wherein the diacylglycerol acyltransferase comprises a sequence at least about 90% identical to SEQ ID NO:14 and is devoid of a sequence corresponding to positions 1-52 of SEQ ID NO:16.

3. The recombinant yeast of claim 2, wherein the one or more recombinant genes are further configured to express a second diacylglycerol acyltransferase, wherein the second diacylglycerol acyltransferase comprises a sequence at least about 90% identical to SEQ ID NO:58.

4. The recombinant yeast of claim 1, wherein the malic enzyme comprises a sequence at least about 90% identical to SEQ ID NO:34 and the glycerol-3-phosphate acyltransferase comprises a sequence at least about 90% identical to SEQ ID NO:40.

5. The recombinant yeast of claim 1, wherein the one or more recombinant genes are configured to express the acetyl-CoA carboxylase.

6. The recombinant yeast of claim 5, wherein the acetyl-CoA carboxylase comprises a serine or threonine at a position corresponding to position 639 of SEQ ID NO:2.

7. The recombinant yeast of claim 1, wherein the one or more recombinant genes are configured to express the glycerol-3-phosphate dehydrogenase.

8. The recombinant yeast of claim 1, wherein the one or more recombinant genes are configured to express the glucose-6-phosphate dehydrogenase and the 6-phosphogluconate dehydrogenase.

9. The recombinant yeast of claim 1, wherein the one or more recombinant genes are configured to express the fatty acid synthase.

10. The recombinant yeast of claim 1, wherein the one or more recombinant genes are configured to express the ATP citrate lyase.

11. The recombinant yeast of claim 1, wherein the one or more recombinant genes are configured to express the glycerol kinase and the glycerol-3-phosphate dehydrogenase.

12. The recombinant yeast of claim 1, wherein the yeast is a recombinant lipogenic yeast.

13. The recombinant yeast of claim 1, wherein the yeast is a recombinant *Lipomyces starkeyi*.

14. A recombinant yeast comprising one or more recombinant genes, wherein:

the one or more recombinant genes are configured to express a diacylglycerol acyltransferase, wherein the diacylglycerol acyltransferase comprises a sequence at least 95% identical to SEQ ID NO:14 and is devoid of a sequence corresponding to positions 1-52 of SEQ ID NO:16;

the one or more recombinant genes are configured to express a second diacylglycerol acyltransferase, wherein the second diacylglycerol acyltransferase comprises a sequence at least 95% identical to SEQ ID NO:58;

the one or more recombinant genes are configured to express a malic enzyme comprising a sequence at least 95% identical to SEQ ID NO:34;

the one or more recombinant genes are configured to express a glycerol-3-phosphate acyltransferase comprising a sequence at least 95% identical to SEQ ID NO:40; and the yeast is a recombinant *Lipomyces starkeyi*.

\* \* \* \* \*